US011142584B2

(12) United States Patent
Poma et al.

(10) Patent No.: US 11,142,584 B2
(45) **Date of Patent: *Oct. 12, 2021**

(54) CD20-BINDING PROTEINS COMPRISING SHIGA TOXIN A SUBUNIT EFFECTOR REGIONS FOR INDUCING CELLULAR INTERNALIZATION AND METHODS USING SAME

(71) Applicant: MOLECULAR TEMPLATES, INC., Austin, TX (US)

(72) Inventors: Eric Poma, New York, NY (US); Jason Kim, Austin, TX (US); Jack Higgins, Georgetown, TX (US); Erin Willert, Round Rock, TX (US); Sangeetha Rajagopalan, Round Rock, TX (US)

(73) Assignee: Molecular Templates, Inc., Austin, TX (US)

( * ) Notice: Subject to any disclaimer, the term of this patent is extended or adjusted under 35 U.S.C. 154(b) by 263 days.

This patent is subject to a terminal disclaimer.

(21) Appl. No.: 14/643,619

(22) Filed: Mar. 10, 2015

(65) Prior Publication Data

US 2015/0259428 A1 Sep. 17, 2015

Related U.S. Application Data

(63) Continuation-in-part of application No. PCT/US2014/023198, filed on Mar. 11, 2014.

(51) Int. Cl.

| | |
|---|---|
| *C07K 16/28* | (2006.01) |
| *C07K 14/25* | (2006.01) |
| *G01N 33/68* | (2006.01) |
| *A61K 39/12* | (2006.01) |
| *A61K 47/68* | (2017.01) |
| *A61K 39/00* | (2006.01) |
| *G01N 33/574* | (2006.01) |

(52) U.S. Cl.

CPC .......... *C07K 16/2887* (2013.01); *A61K 39/12* (2013.01); *A61K 47/6829* (2017.08); *A61K 47/6849* (2017.08); *C07K 14/25* (2013.01); *G01N 33/6872* (2013.01); *A61K 2039/505* (2013.01); *A61K 2039/6056* (2013.01); *C07K 2317/622* (2013.01); *C07K 2317/73* (2013.01); *C07K 2317/77* (2013.01); *C07K 2317/92* (2013.01); *C07K 2319/22* (2013.01); *C07K 2319/30* (2013.01); *C07K 2319/55* (2013.01); *C12N 2760/16134* (2013.01); *G01N 33/57426* (2013.01); *G01N 2333/70596* (2013.01)

(58) Field of Classification Search

CPC .......................... C07K 16/00; C07K 16/2887; C07K 2317/56; C07K 2319/55; C07K 14/25; C07K 2319/30; C07K 2317/77; C07K 2317/622; C07K 2317/73; A61K 47/6829; A61K 47/6849; A61K 2039/505

See application file for complete search history.

(56) References Cited

U.S. PATENT DOCUMENTS

| | | | | |
|---|---|---|---|---|
| 5,080,898 | A | 1/1992 | Murphy | |
| 5,135,736 | A | 8/1992 | Anderson et al. | |
| 5,635,384 | A * | 6/1997 | Walsh | C07K 14/415 435/199 |
| 5,668,255 | A | 9/1997 | Murphy | |
| 5,858,682 | A * | 1/1999 | Gruenwald | C07K 16/3061 435/325 |
| 6,022,950 | A | 2/2000 | Murphy | |
| 6,080,400 | A | 6/2000 | Williams | |
| 6,492,498 | B1 | 12/2002 | Vallera et al. | |
| 6,652,857 | B2 | 11/2003 | Williams | |
| 6,770,456 | B1 | 8/2004 | Coulie et al. | |

(Continued)

FOREIGN PATENT DOCUMENTS

| | | | |
|---|---|---|---|
| CN | 105713087 | A | 1/2016 |
| EP | 1654287 | A2 | 5/2006 |

(Continued)

OTHER PUBLICATIONS

Yu et al., Investigative Ophthalmology & Visual Science 49(2): 522-527 (Year: 2008).*

(Continued)

*Primary Examiner* — Phuong Huynh

(74) *Attorney, Agent, or Firm* — Cooley LLP

(57) ABSTRACT

The present invention provides CD20-binding proteins that bind to and rapidly internalize in a CD20-mediated fashion from a cell surface location to the interior of the cell. CD20-binding proteins of the invention comprise a CD20 binding region and a Shiga toxin effector region. Certain of the disclosed CD20-binding proteins kill cells that express CD20 on their surface. Further, the presently disclosed CD20-binding proteins can comprise additional exogenous materials, such as, e.g., antigens, and are capable of targeted delivery of these additional exogenous materials into the interior of CD20 expressing cells. These CD20-binding proteins have uses in methods such as, e.g., methods involving the efficient cellular internalization of CD20, targeted killing of CD20 expressing cells, delivering exogenous materials inside CD20 expressing cells, detecting CD20 expressing cells, and treating a variety of conditions involving CD20 expressing cells including cancers, tumors, growth abnormalities, and immune disorders.

18 Claims, 4 Drawing Sheets

Specification includes a Sequence Listing.

(56) References Cited

U.S. PATENT DOCUMENTS

| | | | |
|---|---|---|---|
| 7,144,991 B2 * | 12/2006 | Goshorn | B82Y 5/00 |
| | | | 530/391.7 |
| 7,267,973 B2 | 9/2007 | Backer | |
| 7,527,787 B2 | 5/2009 | Chang et al. | |
| 7,700,557 B2 | 4/2010 | Backer | |
| 7,713,915 B1 | 5/2010 | Gariepy et al. | |
| 7,799,900 B2 | 9/2010 | Adams | |
| 7,834,258 B2 | 11/2010 | Choe et al. | |
| 7,887,801 B2 | 2/2011 | Wels et al. | |
| 8,048,985 B2 | 11/2011 | Harrison et al. | |
| 8,147,832 B2 * | 4/2012 | Carr | A61P 37/00 |
| | | | 424/133.1 |
| 8,337,844 B2 | 12/2012 | Carr et al. | |
| 8,470,314 B2 | 6/2013 | Davis | |
| 8,530,637 B2 | 9/2013 | Wels et al. | |
| 8,865,866 B2 | 10/2014 | Harrison et al. | |
| 8,895,006 B2 | 11/2014 | Tumer et al. | |
| 8,969,529 B2 | 3/2015 | O'Brien et al. | |
| 9,175,059 B2 | 11/2015 | Pieczykolan et al. | |
| 9,364,557 B2 | 6/2016 | Neville et al. | |
| 2002/0012658 A1 | 1/2002 | Williams et al. | |
| 2002/0168370 A1 | 11/2002 | McDonald | |
| 2003/0166196 A1 | 9/2003 | Better | |
| 2004/0141982 A1 | 7/2004 | Lust et al. | |
| 2004/0166565 A1 | 8/2004 | Backer | |
| 2005/0054835 A1 | 3/2005 | Better | |
| 2005/0069545 A1 * | 3/2005 | Carr | C07K 16/2887 |
| | | | 424/144.1 |
| 2007/0140966 A1 * | 6/2007 | Chang | A61K 47/48746 |
| | | | 424/1.49 |
| 2009/0023649 A1 | 1/2009 | Backer | |
| 2009/0092578 A1 * | 4/2009 | Su | C07K 16/1203 |
| | | | 424/85.2 |
| 2009/0156417 A1 | 6/2009 | Gariepy et al. | |
| 2009/0156502 A1 | 6/2009 | Harrison et al. | |
| 2010/0093563 A1 | 4/2010 | Williamson et al. | |
| 2011/0189209 A1 | 8/2011 | Neville et al. | |
| 2011/0280913 A1 | 11/2011 | Byrd et al. | |
| 2012/0039908 A1 | 2/2012 | Combs et al. | |
| 2012/0149650 A1 | 6/2012 | Harrison et al. | |
| 2012/0251542 A1 | 10/2012 | Tumer | |
| 2013/0071325 A1 | 3/2013 | Sahin et al. | |
| 2013/0189271 A1 | 7/2013 | De Goeij et al. | |
| 2013/0196928 A1 | 8/2013 | Gariepy et al. | |
| 2015/0044210 A1 | 2/2015 | Mechaly et al. | |
| 2015/0259428 A1 | 9/2015 | Poma | |
| 2016/0017047 A1 | 1/2016 | Poma et al. | |
| 2016/0017784 A1 | 1/2016 | Kumar | |
| 2016/0068577 A1 | 1/2016 | Poma et al. | |
| 2016/0177284 A1 | 6/2016 | Poma et al. | |
| 2016/0340394 A1 | 11/2016 | Poma et al. | |
| 2016/0347798 A1 | 12/2016 | Poma et al. | |
| 2016/0355803 A1 | 12/2016 | Poma et al. | |
| 2016/0376328 A1 | 12/2016 | Poma et al. | |
| 2017/0002046 A1 | 1/2017 | Poma et al. | |
| 2017/0101636 A1 | 4/2017 | Poma et al. | |
| 2017/0143814 A1 | 5/2017 | Poma et al. | |
| 2017/0275382 A1 | 9/2017 | Poma et al. | |
| 2018/0057544 A1 | 3/2018 | Poma et al. | |
| 2018/0243432 A1 | 8/2018 | Poma et al. | |
| 2018/0258143 A1 | 9/2018 | Poma et al. | |
| 2018/0258144 A1 | 9/2018 | Poma et al. | |
| 2018/0291359 A1 | 10/2018 | Poma et al. | |
| 2019/0100597 A1 | 4/2019 | Keyt et al. | |
| 2019/0153044 A1 | 5/2019 | Poma et al. | |
| 2019/0153471 A1 | 5/2019 | Paul et al. | |
| 2019/0249145 A1 | 8/2019 | Jang et al. | |
| 2019/0359657 A1 | 11/2019 | Poma et al. | |
| 2020/0002387 A1 | 1/2020 | Poma et al. | |

FOREIGN PATENT DOCUMENTS

| | | |
|---|---|---|
| EP | 3265575 A2 | 1/2018 |
| EP | 3448874 A1 | 3/2019 |
| GB | 2519786 | 5/2015 |
| JP | 1993-502880 | 5/1993 |
| JP | 2011-507389 A | 6/1999 |
| JP | 2001500730 | 1/2001 |
| JP | 2002-521019 A | 7/2002 |
| JP | 2002544173 | 12/2002 |
| JP | 2003531588 | 10/2003 |
| JP | 2007-536905 A | 12/2007 |
| JP | 2008533977 | 8/2008 |
| JP | 2009502936 | 1/2009 |
| JP | 2012044997 | 3/2012 |
| JP | 2012070737 | 4/2012 |
| KR | 2011-0033233 | 3/2011 |
| KR | 2011-0119725 | 11/2011 |
| WO | WO-1991009871 | 7/1991 |
| WO | WO-1994026910 | 11/1994 |
| WO | 1996030043 A1 | 10/1996 |
| WO | WO 96/040200 A1 | 12/1996 |
| WO | WO-1998011229 | 3/1998 |
| WO | 1999040185 A1 | 8/1999 |
| WO | WO-2000004926 | 2/2000 |
| WO | WO-2000067795 | 11/2000 |
| WO | WO-2001070945 | 9/2001 |
| WO | 2001/077342 | 10/2001 |
| WO | WO 03/066854 | 8/2003 |
| WO | WO-2004056312 | 7/2004 |
| WO | WO-2004058158 | 7/2004 |
| WO | 2005000902 A1 | 1/2005 |
| WO | WO-2005016969 | 2/2005 |
| WO | WO-2005017148 A1 * | 2/2005 ............. A61P 37/00 |
| WO | 2005052129 A2 | 6/2005 |
| WO | WO 2005/052006 A2 | 6/2005 |
| WO | WO-2005092917 | 10/2005 |
| WO | WO-2006099875 | 9/2006 |
| WO | 2007005874 A2 | 1/2007 |
| WO | WO-2007014238 | 2/2007 |
| WO | WO-2007033497 | 3/2007 |
| WO | 2007071061 A1 | 6/2007 |
| WO | WO-2008080218 | 8/2008 |
| WO | 2009017823 A2 | 2/2009 |
| WO | WO-2009032954 | 3/2009 |
| WO | 2007098201 A2 | 4/2009 |
| WO | 2009014835 A3 | 5/2009 |
| WO | WO-2009064815 | 5/2009 |
| WO | 2009088403 A2 | 7/2009 |
| WO | 2009110944 A1 | 9/2009 |
| WO | WO-2010011697 | 1/2010 |
| WO | WO-2010085539 | 7/2010 |
| WO | WO-2011009624 | 1/2011 |
| WO | WO-2012022985 | 2/2012 |
| WO | WO-2012093158 | 7/2012 |
| WO | WO-2012101235 | 8/2012 |
| WO | WO-2012104344 | 8/2012 |
| WO | WO-2012154530 | 11/2012 |
| WO | 2013080147 A1 | 6/2013 |
| WO | WO-2013080147 | 6/2013 |
| WO | WO 2014/143807 A2 | 9/2014 |
| WO | 2015063187 A1 | 10/2014 |
| WO | WO-2014164680 | 10/2014 |
| WO | WO-2014164693 | 10/2014 |
| WO | WO-2015113005 | 7/2015 |
| WO | WO-2015113007 | 7/2015 |
| WO | WO-2015120058 | 8/2015 |
| WO | WO-2015138435 | 9/2015 |
| WO | WO-2015138452 | 9/2015 |
| WO | 2015191764 A1 | 12/2015 |
| WO | 2015193411 | 12/2015 |
| WO | 2016126950 A1 | 8/2016 |
| WO | 2016196344 A1 | 12/2016 |
| WO | 2017019623 A2 | 2/2017 |
| WO | 2018080812 A1 | 5/2018 |
| WO | 2018106895 A1 | 6/2018 |
| WO | 2018140427 A1 | 8/2018 |

(56) References Cited

FOREIGN PATENT DOCUMENTS

| WO | 2018162749 | 9/2018 |
|---|---|---|
| WO | WO 2018/183182 A1 | 10/2018 |

OTHER PUBLICATIONS

Paul, Fundamental Immunology, (textbook), pp. 292-295 (Year: 1993).*
Rudikoff et al., Proc. Natl. Acad. Sci. USA 1982 vol. 79: 1979-1983 (Year: 1982).*
Wargalla et al., Proc Natl. Acad. Sci. USA 86: 5146-5150 (Year: 1989).*
Haisma et al., Blood 92(1): 184-190 (Year: 1998).*
Jubala et al., Vet Pathol 42: 468-476 (Year: 2005).*
LaPointe et al., J Biol Chem 290(24): 23310-23318 (Year: 2005).*
Lev et al., PNAS 101(24): 9051-9056 (Year: 2004).*
U.S. Appl. No. 14/965,882, Molecular Templates, Inc., filed Dec. 10, 2015.
Jackson, ME et al., "The KDEL retrieval system is exploited by Pseudomonas exotoxin A, but not by Shiga-like toxin-1, during retrograde transport from the Golgi complex to the endoplasmic reticulum", Journal of Cell Science, 112(4), (1999), 467-475.
Johannes, L et al., "Retrograde Transport of KDEL-bearing B-fragment of Shiga Toxin", Journal of Biological Chemistry, 272(31), (1997), 19554-19561.
Sandvig, K, et al., "Protein toxins: mode of action and cell entry", Endocytosis, Toxins, Immunotoxins and Viruses, Biochemical Society Transactions, 20(4), (1992), 724-727.
Wales, R et al., "Addition of an endoplasmic reticulum retrieval sequence to ricin A chain significantly increases its cytotoxicity to mammalian cells", Journal of Biological Chemistry, 268(32), (1993), 23986-23990.
Gannon, VP, et al., "Molecular cloning and nucleotide sequence of another variant of the *Escherichia coli* Shiga-like toxin II family", Journal of General Microbiology 136(6), (1990), 1125-1135.
Casalini, P., et al., "Use of Combination of Monoclonal Antibodies Directed Against Three Distinct Epitopes of a Tumor-Associated Antigen: Analysis of Cell Binding and Internalization", International Journal of Cancer 48 (2), (1991), 284-290.
Ewers, H., and Helenius, A., "Lipid-Mediated Endocytosis", Cold Spring Harbor Perspectives in Biology 3 (8), (2011), 1-14.
Cao, Y, et al., "Design optimization and characterization of Her2/neu-targeted immunotoxins: comparative in vitro and in vivo efficacy studies", Oncogene, 33(4), (2014), 429-439.
Hexham, JM, et al., "Influence of relative binding affinity on efficacy in a panel of anti-CD3 scFv immunotoxins", Molecular Immunology, 38(5), (2001), 397-408.
Lyu, MA, et al., Cell-Targeting Fusion Constructs Containing Recombinant Gelonin, Methods in Enzymology, 502, (2012), 167-214.
Beers, SA, et al., "CD20 as a Target for Therapeutic Type I and II Monoclonal Antibodies", Seminars in Hematology, 47(2), (2010), 107-114.
Ackerman, R, et al., "SLT-VEGF Reduces Lung Metastases, Decreases Tumor Recurrence, and Improves Survival in an Orthotopic Melanoma Model", Toxins (Basel), 2(9), (2010), 224-257.
Al-Jaufy, AY, et al., "Cytotoxicity of a Shiga Toxin A Subunit-CD4 Fusion Protein to Human Immunodeficiency Virus-Infected Cells", Infection and Immunity, 62(3), (1994), 956-960.
Al-Jaufy, AY, et al., "Purification and Characterization of a Shiga Toxin A Subunit-CD4 Fusion Protein Cytotoxic to Human Immunodeficiency Virus-Infected Cells", Infection and Immunity, 63(8), (1995), 3073-3078.
Backer, MV, et al., "Shiga-like toxin-VEGF fusion proteins are selectively cytotoxic to endothelial cells overexpressing VEGFR-2", Journal of Controlled Release, 74(1-3), (2001), 349-355.
Backer, MV, Backer JM, "Targeting Endothelial Cells Overexpressing VEGFR-2: Selective Toxicity of Shiga-like Toxin-VEGF Fusion Proteins", Bioconjugate Chemistry, 12(6), (2001), 1066-1073.

Beers, SA, et al., "Type II (tositumomab) anti-CD20 monoclonal antibody out performs type I (rituximab-like) reagents in B-cell depletion regardless of complement activation", Blood, 112, (2008), 4170-4177.
Beers, SA, et al., "Antigenic modulation limits the efficacy of anti-CD20 antibodies: implications for antibody selection", Blood, 115(25), (2010), 5191-5201.
Beum, PV, et al., "The Shaving Reaction: Rituximab/CD20 Complexes Are Removed from Mantle Cell Lymphoma and Chronic Lymphocytic Leukemia Cells by THP-1 Monocytes", Journal of Immunology, 176(4), (2006), 2600-2609.
Beum, PV, et al., "Loss of CD20 and Bound CD20 Antibody from Opsonized B Cells Occurs More Rapidly Because of Trogocytosis Mediated by Fc Receptor-Expressing Effector Cells Than Direct Internalization by the B Cells", Journal of Immunology, 187(6), (2011), 3438-3447.
Boross, P, et al., "Both activating and inhibitory Fc gamma receptors mediate rituximab-induced trogocytosis of CD20 in mice", Immunology Letters, 143(1), (2012), 44-52.
Boross, P, et al., "Mechanisms of action of CD20 antibodies", American Journal of Cancer Research, 2(6), (2012), 676-690.
Braslawsky, GR, et al., "Adriamycin(hydrazone)-antibody conjugates require internalization and intracellular acid hydrolysis for antitumor activity", Cancer Immunology, Immunotherapy 33, (1991), 367-374.
Cheung, MC, et al., "An evolved ribosome-inactivating protein targets and kills human melanoma cells in vitro and in vivo", Molecular Cancer, 9(28), (2010).
Cizeau, JPA, et al., "8th Fabisch-Symposium, 3rd Targeted Tumor Therapies, Berlin 2012", Mar. 21, 2012.
Cragg, MS, et al., "Apparent modulation of CD20 by rituximab: an alternative explanation", Blood, 103(10), (2004), 3989-3990.
Goulet, AC, et al., "Conjugation of Blocked Ricin to an Anti-CD19 Monoclonal Antibody Increases Antibody-Induced Cell Calcium Mobilization and CD19 Internalization", Blood, 90(6), (1995), 2364-2375.
Hiraga, J, et al., "Down-regulation of CD20 expression in B-cell lymphoma cells after treatment with rituximab-containing combination chemotherapies: its prevalence and clinical significance", Blood, 113(20), (2009), 4885-4893.
Hotz, B, et al., "Specific Targeting of Tumor Endothelial Cells by a Shiga-like Toxin-Vascular Endothelial Growth Factor Fusion Protein as a Novel Treatment Strategy for Pancreatic Cancer", Neoplasia, 12(10), (2010), 797-806.
"International Application Serial No. PCT/US2014/023198, International Search Report dated Sep. 18, 2014 and published Oct. 9, 2014", 5 pgs.
"International Application Serial No. PCT/US2014/023198, Written Opinion dated Sep. 18, 2014", 6 pgs.
"International Application Serial No. PCT/US2014/023198, Written Opinion dated Feb. 12, 2015", 7 pgs.
"International Application Serial No. PCT/US2014/023231, International Search Report dated Oct. 24, 2014 and published Dec. 4, 2014", 3 pgs.
"International Application Serial No. PCT/US2014/023231, Written Opinion dated Oct. 24, 2014", 4 pgs.
Jilani, I, et al., "Transient down-modulation of CD20 by rituximab in patients with chronic lymphocytic leukemia", Blood, 102(10), (2003), 3514-3520.
Jilani, I, et al., "Anti-idiotype versus anti-mouse Ig for detecting rituximab", Blood, 103(10), (2004), 3990.
Lambert, J, et al., "Purified Immunotoxins That Are Reactive with Human Lymphoid Cells: Monoclonal antibodies conjugated to the ribosome-inactivating proteins gelonin and the pokeweed antiviral proteins", Journal of Biological Chemistry, 260(22), (1985), 12035-12041.
Law, CL, et al., "Efficient Elimination of B-Lineage Lymphomas by Anti-CD20-Auristatin Conjugates", Clinical Cancer Research, 10(23), (2004), 7842-7851.
Li, H, et al., "The CD20 Calcium Channel Is Localized to Microvilli and Constitutively Associated with Membrane Rafts: Antibody binding increases the affinity of the association through an epitope-

(56) References Cited

OTHER PUBLICATIONS dependent cross-linking-independent mechanism", Journal of Biological Chemistry, 279(19), (2004), 19893-19901.
Lim, SH, et al., "Fc gamma receptor IIb on target B cells promotes rituximab internalization and reduces clinical efficacy", Blood, 118(9), (2011), 2530-2540.
Luqman, M, et al., "The antileukemia activity of a human anti-CD40 antagonist antibody, HCD122, on human chronic lymphocytic leukemia cells", Blood, 112(3), (2008), 711-720.
Michel, RB, et al., "Intracellular Accumulation of the Anti-CD20 Antibody 1F5 in B-Lymphoma cells", Clinical Cancer Research, 8(8), (2002), 2701-2713.
Noakes, K, et al., "Exploiting retrograde transport of Shiga-like toxin 1 for the delivery of exogenous antigens into the MHC class I presentation pathway", FEBS Letters 543, (1999) 95-99.
Oloomi, M, et al., "In vivo Characterization of Fusion Protein Comprising of A1 Subunit of Shiga Toxin and Human GM-CSF: Assessment of Its Immunogenicity and Toxicity", Iranian Biomedical Journal, 14(4), (2010), 136-141.
Pastan, I, et al., "Immunotoxin Treatment of Cancer", Annual Review of Medicine 58, (2007), 221-237.
Pirie, CM, et al., "Convergent Potency of Internalized Gelonin Immunotoxins across Varied Cell Lines, Antigens, and Targeting Moieties", Journal of Biological Chemistry, 286(6), (2011), 4165-4172.
Polito, L, et al., "The conjugate Rituximab/saporin-S6 completely inhibits clonogenic growth of CD20-expressing cells and produces a synergistic toxic effect with Fludarabine", Leukemia, 18(7), (2004), 1215-1222.
Polson, AG, et al., "Antibody-Drug Conjugates for the Treatment of Non-Hodgkin's Lymphoma: Target and Linker-Drug Selection", Cancer Research, 69(6), (Jan. 1, 2009), 2358-2364.
Poma, Eric, "Proteins Comprising Binding Regions, Shiga Toxin A Subunit Effector Regions, and Carboxy-Terminal, Endoplasmic Reticulum Localization Signal Motifs", International Application Serial No. PCT/US2015/019684, Filed on Mar. 10, 2015.
Poma, Eric, "Proteins Comprising Amino-Terminal Proximal Shiga Toxin A Subunit Effector Regions and Cell-Targeting Immunoglobulin-Type Binding Regions", International Application Serial No. PCT/US2015/019708, Filed Mar. 10, 2015.
Poma, Eric, "Protease-Cleavage Resistant, Shiga Toxin A Subunit Effector Polypeptides and Cell-Targeted Molecules Comprising the Same", International Application Serial No. PCT/US2015/035179, Filed on Jun. 10, 2015.
Press, OW, et al., "Endocytosis and Degradation of Monoclonal Antibodies Targeting Human B-Cell Malignancies", Cancer Research, 49(17), (1989), 4906-4912.
Press, OW, et al., "Retention of B-Cell-Specific Monoclonal Antibodies by Human Lymphoma Cells", Blood, 83(5), (1994), 1390-1397.
Protein ID ABM97743, European Molecular Biology Laboratory (EMBL), Oloomi, M, et al., "synthetic construct partial A1-GMCSF chimeric protein", Sep. 10, 2007.
Rajagopalan, S, et al., "CD20-Specific Engineered Toxin Body Demonstrates Direct Cell Kill of Multiple B-Cell Non-Hodgkin's Lymphoma Types", Blood, 122(21), (2013), 5152.
Rajagopalan, S, et al., "CD20-specific Engineered Toxin Body demonstrates direct cell kill of multiple B-cell Non-Hodgkin's lymphoma types", Proceedings: American Association for Cancer Research (AACR) Annual Meeting 2014, Abstract #647, (Apr. 5-9, 2014).
Roudkenar, MH, et al., "Selective cytotoxicity of recombinant STXA1-GM-CSF protein in hematopoetic cancer cells", Cell Biology and Toxicology, 22(3), (2006), 213-219.
Sieber, T, et al., "Selective internalization of monoclonal antibodies by B-cell chronic lymphocytic leukaemia cells", 121(3), (2003), 458-461.
Su, H, et al., "Clinical grade production and characterization of a fusion protein comprised of the chemokine CCL2-ligand genetically fused to a mutated and truncated form of the Shiga A1 subunit", Protein Expression and Purification, 66(2), (Jan. 1, 2009), 149-157.
Vallera, DA, et al., "Bioengineering a Unique Deimmunized Bispecific Targeted Toxin That Simultaneously Recognizes Human CD22 and CD19 Receptors in a Mouse Model of B-Cell Metastases", Molecular Cancer Therapeutics, 9(6), (2010), 1872-1883.
Wirth, R, et al., "Engineered Toxin Body demonstrating CD20-specific binding and cell kill in B-Cell Non-Hodgkin lymphoma vells", Proceedings: American Association for Cancer Research (AACR) 104th Annual Meeting 2013, Abstract #5477, (Apr. 6-10, 2013).
Burgess, BJ, et al., "Proteolytic cleavage at arginine residues within the hydrophilic disulphide loop of the *Escherichia coli* Shiga-like toxin I A subunit is not essential for cytotoxicity", Molecular Microbiology, 10(1), (1993), 171-179.
Lea, N, et al., "Proteolytic cleavage of the A subunit is essential for maximal cytotoxicity of *Escherichia coli* O157:H7 Shiga-like toxin-1", Microbiology, 145(5), (1999), 999-1004.
Bevan, N., et al., Real-time 96-well antibody internalization assays using IncuCyte® FabFluor Red Antibody Labeling Reagent, Application Note, Sartorius, 2017 Essen BioScience.
International Application Serial No. PCT/US2015/035179, Written Opinion dated Sep. 9, 2015, 10 pgs.
International Application Serial No. PCT/US2015/035179, Written Opinion dated May 18, 2016, 9 pgs.
International Application Serial No. PCT/US2015/035179, Preliminary Report on Patentability dated Aug. 12, 2016, 8 pgs.
International Application Serial No. PCT/US2016/016580, International Search Report dated Apr. 22, 2016 and published Aug. 11, 2016, 4 pgs.
International Application Serial No. PCT/US2016/016580, Written Opinion, dated Apr. 22, 2016 dated Mar. 28, 2016, 5 pgs.
International Application Serial No. PCT/US2016/043902, International Search Report dated Jan. 30, 2017 and published Mar. 9, 2017, 6 pgs.
International Application Serial No. PCT/US2016/043902, Written Opinion dated Jan. 30, 2017, 9 pgs.
International Application Serial No. PCT/US2016/043902, Preliminary Report on Patentability dated Oct. 10, 2017, 7 pgs.
Ishikawa et al., Protection against Shiga Toxin I Challenge by Immunization of Mice with Purified Mutant Shiga Toxin 1., Infection and Immunity 71(6) 3235-3239 (2003).
Jackson et al., "Mutational analysis of the Shiga Toxin and Shiga-like toxin II enzymatic subunits", Journal of Bacteriology 172(6) 3346-3350 (1990).
Jain, RK, "Barriers to Drug Delivery in Solid Tumors", Scientific American 271(1), (1994), 58-65.
Johannes et al., "Shiga toxins—from cell biology to biomedical applications" Nature Reviews Microbiology 8(2) 105-116 (2010).
Johannes, L, Decaudin, D, "Protein toxins: intracellular trafficking for targeted therapy" Gene Therapy, 12(18), (2005), 1360-1368.
Johnson, N, et al., "Construction of an epitope vector utilizing the diphtheria toxin B-subunit", FEMS Microbiology Letters, 146(1), (1997), 91-96.
Jones "Critically Assessing the State-of-the-art in Protein Structure Prediction", The Pharmacogenomics Journal, 1(2): 126-134 (2001).
Jubala et al., "CD20 Expression in Normal Canine B cells and in Canine non-Hodgkin Lymphoma", Veterinary Pathology 42:4 468-476 (2005).
Karanikas et al., "Antibody and T Cell Responses of Patients with Adenocarcinoma Immunized with Mannan-MUC1 Fusion Protein", Journal of Clinical Investigation, 100(11): 2783-2792 (1997).
Kelland, LR, "'Of mice and men': values and liabilities of the athymic nude mouse model in anticancer drug development", European Journal of Cancer 40(6), (2004), 827-836.
Kim et al., "A fold-back single chain diabody format enhances the bioactivity of an anti-monkey CD3 recombinant diphtheria toxin-based immunotoxin", Protein Engineering 20(9) 425-432 (2007).
Kotera et al., "Humoral Immunity against a Tandem Repeat Epitope of Human Mucin MUC-1 in Sera from Breast, Pancreatic, and Colon Cancer Patients", Cancer Research 54(11): 2856-2860 (1994).

(56) References Cited

OTHER PUBLICATIONS

Kurmanova et al., "Structural requirements for furin-induced cleavage and activation of Shiga toxin", Biochemical and Biophysical Research Communications 357(1) 144-149 (2007).
Kyu, E, "Characterization of the A subunit mutants of Stx1 and Stx2 in *Saccharomyces cerevisiae*", thesis, Rutgers, The State University of New Jersey, New Brunswick, retrieved from http://dx.doi.org/doi:10.7282/T34F1QWJ (2009).
Lapointe et al., "A Role for the Protease-sensitive Loop Region of Shiga-like Toxin 1 in the Retrotranslocation of its A Domain from the Endoplasmic Reticulum Lumen", Journal of Biological Chemistry 280(24): 23310-23318 (2005).
Laske et al., "Intraventricular Immunotoxin Therapy for Leptomeningeal Neoplasia", Neurosurgery, 41(5): 1039-1051 (1997).
Lazar et al., "Transforming Growth Factor alpha: Mutation of Aspartic Acid 47 and Leucine 48 Results in Different Biological Activities", Molecular and Cellular Biology, 8(3): 1247-1252 (1988).
Lee, RS, et al., "Major histocompatibility complex class I presentation of exogenous soluble tumor antigen fused to the B-fragment of Shiga toxin", European Journal of Immunology, 28, (1998), 2726-2737.
Lehmann, CHK, et al., "Direct Delivery of Antigens to Dendritic Cells via Antibodies Specific for Endocytotic Receptors as a Promising Strategy for Future Therapies", Vaccines, 4(2):1-32 (2016).
Li et al., "Development of Novel Tetravalent Anti-CD20 Antibodies with Potent Antitumor Activity", Cancer Research 68(7) 2400-2408 (2008).
Ling et al., "Structure of the Shiga-like Toxin I B-Pentamer Complexed with an Analogue of Its Receptor Gb3", Biochemistry, 37(7): 1777-1788 (1998).
Giansanti et al., "Strategies to Improve the Clinical Utility of Saporin-Based Targeted Toxins" Toxins 10(82): 1-32 (2018).
Harwerth et al., Monoclonal Antibodies against the Extracellular Domain of the erbB-2 Receptor Function as Partial Ligand Agonists, Journal of Biol. Chem 267(21):15160-15167 (1992).
Li et al., "Clinical targeting recombinant immunotoxins for cancer therapy", Onco Targets and Therapy 10:3645-3665 (2017).
Maak, M, et al., "Tumor-Specific Targeting of Pancreatic Cancer with Shiga Toxin B-Subunit", Molecular Cancer Therapeutics, 10(10), (2011), 1918-1928.
Mallard, F, et al., "Direct Pathway from Early/Recycling Endosomes to the Golgi Apparatus Revealed through the Study of Shiga Toxin B-fragment Transport", The Journal of Cell Biology, 143(4), (1998), 973-990.
Mascarell, L, et al., "Induction of Neutralizing Antibodies and Th1-Polarized and CD4-Independent CD8+ T-Cell Responses following Delivery of Human Immunodeficiency Virus Type 1 Tat Protein by Recombinant Adenylate Cyclase of Bordetella pertussis", Journal of Virology, 79(15), (2005), 9872-9884.
Mazor et al., "chFRP5-ZZ-PE38, a large IgG-toxin immunoconjugate outperforms the corresponding smaller FRP5 (Fv)-ETA immunotoxin in eradicating ErbB2-expressing tumor xenografts", Cancer Letters, 257(1) 124-135: (2007).
Mazor, R, et al., "Identification and elimination of an immunodominant T-cell epitope in recombinant immunotoxins based on Pseudomonas exotoxin A", Proceedings of the National Academy of Sciences U.S.A., 109(51), (2012), E3597-E3603.
McCluskey et al., "Charged and hydrophobic surfaces on the A chain of Shiga-like Toxin 1 recognize the C-terminal Domain of Ribosomal Stalk Proteins," PLoS One 7(2): (2012).
McCluskey et al., "Shiga-like Toxin 1: Molecular Mechanism of Toxicity and Discovery of Inhibitors", thesis University of Toronto (2010).
McCluskey, AJ, et al., "The Catalytic Subunit of Shiga-like Toxin 1 Interacts with Ribosomal Stalk Proteins and is Inhibited by Their Conserved C-Terminal Domain", Journal of Molecular Biology, 378(2), (2008), 375-386.
McKenzie, J, et al., "Passage through the Golgi is necessary for Shiga toxin B subunit to reach the endoplasmic reticulum", The FEBS Journal, 276(6), (2009), 1581-1595.
Miller et al., "Design, Construction, and In-Vitro analyses of Multivalent Antibodies", Journal of Immunology 170(9) 4854-4861 (2003).
Minckwitz et al., "Phase I clinical study of the recombinant antibody toxin scFv(FRP5)-ETA specific for the ErbB2/HER2 receptor in patients with advanced solid malignomas" Breast Cancer Research 7(5): 617-626 (2005).
Newland et al., "Cloning of Genes for Production of *Escherichia coli* Shiga-Like Toxin Type II", Infection and Immunity, 55(11): 2675-2680 (1987).
Ninkovic, T, et al., "Identification of O-glycosylated decapeptides within the MUC1 repeat domain as potential MHC class I (A2) binding epitopes", Molecular Immunology 47(1), (2009), 131-140.
Ohmura et al., "Characterization of non-toxic mutant toxins of Vero toxin I that were constructed by replacing amino acids in the A subunit", Microbial Pathogenesis 15(3): 169-176 (1993).
Olafsen et al., "ImmunoPET imaging of B-cell lymphoma using anti-CD20 scFv dimers (diabodies)", Protein Engineering, Design & Selection 23(4): 243-249 (2010).
Olafsen et al., "Recombinant Anti-CD20 Antibody fragments for Small-Animal PET Imaging of B-Cell Lymphomas", Journal of Nuclear Medicine 50(9): 1500-1508 (2009).
Onda, M, et al., "An immunotoxin with greatly reduced immunogenicity by identification and removal of B cell epitopes", Proceedings of the National Academy of Sciences U.S.A., 105(32), (2008), 11311-11316.
Osicka, R, et al., "Delivery of CD8+ T-cell epitopes into major histocompatibility complex class I antigen presentation", Infection and Immunity, 68(1), (2000), 247-256.
Pai-Scherf, LH, et al., "Hepatotoxicity in Cancer Patients Receiving erb-38, a Recombinant Immunotoxin that Targets the erbB2 Receptor", Clinical Cancer Research, 5(9), (1999), 2311-2315.
Paul "Fundamental Immunology" 3rd Edition Raven Press 292-295 (1993).
Peng, KW, et al., "Oncolytic measles viruses displaying a single-chain antibody against CD38, a myeloma cell marker", Blood, 101(7), (2003), 2557-2562.
Perampalam, S et al., "Designing combinatorial protein libraries based on a protein toxin template", Molecular and Cellular Proteomics, 2(9), (2003), 825-915.
Perampalam, S et al., "Designing combinatorial protein libraries based on a protein toxin template", HUPO 2nd Annual & IUBMB IXI World Congress, Oct. 8-11, Montreal, Poster Session 28 Proteomics & Biotechnology, 80.16 (Oct. 2003).
Perampalam et al., "Cell-targeted Ribsosome-Inactivating Proteins derived from Protein Combinatorial Libraries", Thesis—University of Toronto (2008).
Peterson, JK, et al., "Integrating pharmacology and in vivo cancer models in preclinical and clinical drug development", European Journal of Cancer 40(6), (2004), 837-844.
Pisarev, VM, et al., "T cells recognize PD(N/T)R motif common in a variable number of tandem repeat and degenerate repeat sequences of MUC1", International Immunopharmacology 5(2), (2005), 315-330.
Polito et al., "Saporin-S6: A Useful Tool in Cancer Therapy", Toxins 5: 1698-1722 (2013).
Promega, Technical Reference, Amino Acids (2018).
Preville, X, et al., "Eradication of Established Tumors by Vaccination With Recombinant Bordetella pertussis Adenylate Cyclase Carrying the Human Papillomavirus 16 E7 Oncoprotein", Cancer Research, 65(2), (2005), 641-649.
Ramos et al., "The safety and efficacy profile of a PD-L1 directed Engineered Toxin Body, as a novel targeted direct-cell kill approach for the treatment of PD-L1 expressing cancers" Proceedings: American Association for Cancer Research (AACR) Annual Meeting 2019, Poster #3900, (2019).
Rajagopalan, S, et al., "A novel targeted engineered toxin body for treatment of HER2 positive breast cancer", Proceedings: Thirty-Seventh Annual CTRC-AACR San Antonio Breast Cancer Symposium, Poster, #P4-15-17, (Dec. 9-13, 2014).
Rajagopalan, S, et al., "CD38-specific engineered toxin body: Therapeutic potential for multiple myeloma", The Journal of Cancer

(56) References Cited

OTHER PUBLICATIONS

Research, 74(19 Suppl): Abstract #671, (Oct. 1, 2014) from American Association for Cancer Research (AACR) Annual Meeting 2014, (Apr. 5-9, 2014).
Rajagopalan, S, et al., "HER2-targeted engineered toxin body demonstrates selective binding and cell kill of HER2-overexpressing breast cancer", Proceedings: American Association for Cancer Research (AACR) Annual Meeting 2013, Poster, (Apr. 6-10, 2013).
Rajagopalan, S, et al., "HER2-targeted engineered toxin body demonstrates selective binding and cell kill of HER2-overexpressing breast cancer", The Journal of Cancer Research, 73(8 Suppl): Abstract #868, (Apr. 15, 2013).
Rajagopalan, S, et al., "Next-generation engineered toxin bodies: CD38, PD-L1 and HER2 targeted ETBs", The Journal of Cancer Research, 76(14 Suppl), (Jul. 15, 2016), Abstract nr 595 from American Association for Cancer Research (AACR) Annual Meeting 2016, (Apr. 16-20, 2016).
Ramakrishnan, S, and Houston, L, "Comparison of the Selective Cytotoxic Effects of Immunotoxins Containing Ricin A Chain or Pokeweed Antiviral Protein and Anti-Thy 1.1. Monoclonal Antibodies", Cancer Research, 44(1), (1984), 201-208.
Robinson, GL, et al., "In vivo efficacy of a CD38-specific engineered toxin body", Clinical Cancer Research, 21(17 Suppl), (Sep. 1, 2015), Abstract A15.
Robinson, GL, et al., "In vivo efficacy of a CD38-specific engineered toxin body", Proceedings: American Association for Cancer Research (AACR) Special Conference on Hematologic Malignancies: Translating Discoveries to Novel Therapies, Poster A15 (Sep. 21, 2015).
Robinson, GL, et al., "MT-3724, an engineered toxin body targeting CD20 for non-Hodgkin's lymphoma", Proceedings of the 107th Annual Meeting of the American Association for Cancer Research, Cancer Research, Jul. 15, 2016, 76(14 Suppl), Abstract 1483.
Robinson, GL, et al., "MT-4019: a de-immunized engineered toxin body targeting CD38 for multiple myeloma", Proceedings: American Association for Cancer Research (AACR) Annual Meeting 2017, Poster, Abstract 2659 (Apr. 1-5, 2017).
Romaniuk, SI, et al., "Recombinant Diphtheria toxin derivatives: Perspectives of application", Russian Journal of Bioorganic Chemistry, 38(6), (2012), 565-577.
Rossi et al., "Novel Designs of Multivalent Anti-CD20 Humanized Antibodies as Improved Lymphoma Therapeutics", Cancer Research 68(20) 8384-8392 (2008).
Rudikoff et al., "Single amino acid substitution altering antigen-binding specificity", Proceedings of the National Academy of Sciences of the USA 79:6 1979-1983 (1982).
Saijo, N, "What are the reasons for negative phase III trials of molecular-target-based drugs?", Cancer Science 95(10), (2004), 772-776.
Sandvig et al., "Entry of Shiga Toxin into Cells", Zentralblatt fur Bakteriologie 278(2-3): 296-305 (1993).
Saron, MF, et al., "Anti-viral protection conferred by recombinant adenylate cyclase toxins from Bordetella pertussis carrying a CD8+ T cell epitope from lymphocytic choriomeningitis virus", Proceedings of the National Academy of Sciences U.S.A., 94(7), (1997), 3314-3319.
Schindler et al., "A Phase I Study of a Combination of anti-CD19 and anti-CD22 Immunotoxins (Combotox) in Adult Patients with Refractory B-Lineage Acute Lymphoblastic Leukaemia", British Journal of Haematology, 154(4): 1-11 (2011).
Schlecht, G, et al., "Antigen Targeting to CD11b Allows Efficient Presentation of CD4+ and CD8+ T Cell Epitopes and In Vivo Th1-Polarized T Cell Priming", The Journal of Immunology, 173(10), (2004), 6089-6097.
Schuh, JC, "Trials, Tribulations, and Trends in Tumor Modeling in Mice", Toxicologic Pathology 32 (Suppl. 1), (2004), 53-66.
Schultz et al., "A Tetravalent Single-chain Antibody-Streptavidin Fusion Protein for Pretargeted Lymphoma Therapy", Cancer Research 60(23): 6663-6669 (2000).
Sebo, P, et al., "Cell-Invasive Activity of Epitope-Tagged Adenylate Cyclase of Bordetella pertussis allows In Vitro Presentation of a Foreign Epitope to CD8+ Cytotoxic T Cells", Infection and Immunity, 63(10), (1995), 3851-3857.
Sebo, P, et al., "In vivo induction of CTL responses by recombinant adenylate cyclase of Bordetella pertussis carrying multiple copies of a viral CD8+ T-cell epitope", FEMS Immunology & Medical Microbiology, 26(2), (1999), 167-173.
Shan et al., "Characterization of scFV-Ig Constructs Generated from the Anti-CD20 mAb 1F5 Using Linker Peptides of Varying Lengths", Journal of Immunology 162(11): 6589-6595 (1999).
Shaw, CA, et al., "Stimulation of CD8+ T Cells following Diphtheria Toxin-Mediated Antigen Delivery into Dendritic Cells", Infection and Immunity, 74(2), (2006), 1001-1008.
Shen et al., "Evaluation of four CD22 Antibodies as Ricin A Chain-Containing Immunotoxins for the In Vivo Therapy of Human B-Cell Leukemias and Lymphomas", International Journal of Cancer 42(5): 792-797 (1988).
Shete, V, "Generation and Characterization of Random Site-directed Mutatns of Shiga-like Toxin by *Escherichia coli* O157:H7 in *Saccharomyces Cerevisiae*", thesis, Rutgers, The State University of New Jersey, New Brunswick, (2009), retrieved from http://dx.doi.org/doi:10.7282/T300029Z.
Shiba, Y, et al., "AGAP2 regulates retrograde transport between early endosomes and the TGN", Journal of Cell Science 123(Pt 14), (2010), 2381-2390.
Simsova, M, et al., "The adenylate cyclase toxin from Bordetella pertussis—a novel promising vehicle for antigen delivery to dendritic cells", International Journal of Medical Microbiology, 239, (2004), 571-576.
Sivam, G, et al., "Immunotoxin to a Human Melanoma-associated Antigen: Comparison of Gelonin with Ricin and Other A Chain Conjugates", Cancer Research, 47(12), (1987), 3169-3173.
Skinner et al., "Inhibition of prokaryotic translation by the Shiga toxin enzymatic subunit", Microbial Pathogenesis 24(2) 117-122 (1998).
Skinner et al., "Investigation of ribosome binding by the Shiga Toxin A1 subunit, using competition and site-directed mutagenesis", Journal of Bacteriology 179(4): 1368-1374 (1997).
Smith, DC, et al., "Exogenous Peptides Delivered by Ricin Require Processing by Signal Peptidase for Transporter Associated with Antigen Processing-Independent MHC Class I-Restricted Presentation", The Journal of Immunology, 169(1), (2002), 99-107.
Stenmark, H, et al., "Peptides fused to the amino-terminal end of Diphtheria toxin are translocated to the cytosol", The Journal of Cell Biology, 113(5), (1991), 1025-1032.
Suh, JK., et al., "Shiga Toxin Attacks Bacterial Ribosomes as Effectively as Eucaryotic Ribosomes", Biochemistry, 37(26), (1998), 9394-9398.
Suhan et al., "Disruption of an Internal Membrane-Spanning Region in Shiga Toxin I Reduces Cytotoxicity", Infection and Immunity 66(11): 5252-5259 (1998).
Tacken, PJ, et al., "Effective induction of naive and recall T-cell responses by targeting antigen to human dendritic cells via a humanized anti-DC-SIGN antibody", Blood, 106(4), (2005), 1278-85.
Tesh et al., "Comparison of the Relative Toxicities of Shiga-Like Toxins Type I and Type II for Mice", Infection and Immunity, 61(8): 3392-3402 (1993).
Thompson et al., "Improved binding of a bivalent single-chain immunotoxin results in increased efficacy for in vivo T-cell depletion", Protein Engineering 14(12): 1035-1041 (2001).
Aatsinki et al. "An alternative use of basic pGEX vectors for producing both N- and C-terminal fusion proteins for production and affinity purification of antibodies", Protein Expression and Purification, 40(2), (2005), 287-291.
Adotevi et al., "B Subunit of Shiga Toxin-Based Vaccines Synergize with α-Galactosylceramide to Break Tolerance against Self Antigen and Elicit Antiviral Immunity", The Journal of Immunology, 179(5), (2007), 3371-3379.
Antignani "Immunotoxins: The Role of the Toxin", Toxins, 5(8), (2013), 1486-1502.

(56) References Cited

OTHER PUBLICATIONS

Apostolpoulos et al., "MUC1 peptide epitopes associated with five different H-2 class I molecules", European Journal of Immunology, 27(10), (1997), 2579-2587.
Baker et al., "Immunogenicity of Protein Therapeutics: the Key Causes, Consequences and Challenges", Self/Nonself 1(4): 314-322 (2010).
Ballard, JD, et al., "Anthrax Toxin as a Molecular Tool for Stimulation of Cytotoxic T Lymphocytes: Disulfide-Linked Epitopes, Multiple Injections, and Role of CD4+ Cells", Infection and Immunity, 66(10), (1998), 4696-4699.
Ballard, JD, et al., "Anthrax Toxin-Mediated Delivery In Vivo and In Vitro of a Cytotoxic T-Lymphocyte Epitope from Ovalbumin", Infection and Immunity, 66(2), (1998), 615-619.
Barnd et al., "Specific, Major Histocompatibility Complex-Unrestricted Recognition of Tumor-Associated Mucins by Human Cytotoxic T cells", Proceedings of the National Academy of Sciences U.S.A., 86(18): 7159-7163 (1989).
Barratt-Boyes, SM, et al., "Immunization of Chimpanzees with Tumor Antigen MUC1 Mucin Tandem Repeat Peptide Elicits Both Helper and Cytotoxic T-cell Responses", Clinical Cancer Research 5(7), (1999), 1918-1924.
Bera et al., "Pharmacokinetics and Antitumor Activity of a Bivalent Disulfide-stabilized Fv Immunotoxin with improved Antigen Binding to erbB2", Cancer Research 59(16): 4018-4022 (1999).
Bibby "Orthotopic models of cancer for preclinical drug evaluation: advantages and disadvantages", European Journal of Cancer 40(6), (2004), 852-857.
Bolognesi, A, et al., "A comparison of anti-lymphocyte immunotoxins containing different ribosome-inactivating proteins and antibodies", Clinical & Experimental Immunology, 89(3), (1992), 341-346.
Bonifaz et al., "Efficient Targeting of Protein Antigen to the Dendritic Cell Receptor DEC-205 in the Steady State Leads to Antigen Presentation on Major Histocompatibility Complex Class I Products and Peripheral CD8+ T Cell Tolerance", Journal of Experimental Medicine, 196(12), (2002), 1627-1638.
Bray et al., "Probing the surface of eukaryotic cells using combinatorial toxin libraries", Current Biology 11(9) 697-701 (2001).
Brieschke, B, et al., "Antigen Seeding Technology by Engineered Toxin Bodies Provides a Targeted Immuno-Oncology Approach for Treatment of Cancers", Proceedings: American Association for Cancer Research (AACR) Annual Meeting 2018, Poster 2777, Abstract #4912, (2018).
Brieschke, B, et al., "Targeted Engineered Toxin Bodies provide a novel mechanism of action against HER2 positive cancers", Cancer Research, 78 (13 Suppl), (Jul. 2018), Abstract 5769.
Brieschke, B, et al., "Targeted Engineered Toxin Bodies provide a novel mechanism of action against HER2 positive cancers", Proceedings: American Association for Cancer Research (AACR) Annual Meeting 2018, Poster #5769, (Apr. 18, 2018).
Brieschke, B, et al., "Identification and Functional Profiling of PD-L1 Targeted Engineered Toxin Bodies for Antigen Seeding Technology (AST) and Redirection of T cell Response to Tumors", 33rd Annual Meeting of the Society for Immunotherapy of Cancer (SITC), Washington, D.C., Poster # 11078, (Nov. 7-11, 2018).
Brieschke, B, et al., "Identification and functional profiling of PD-L1 targeted engineered toxin bodies for antigen seeding technology and redirection of T cell response to tumors", Journal of ImmunoTherapy of Cancer, 6(Suppl 1): 114, (Nov. 6, 2018), Abstract P9.
Brigotti, M, et al., "Damage to Nuclear DNA Induced by Shiga Toxin 1 and Ricin in Human Endothelial Cells", The FASEB Journal, 16(3), (2002), 365-372.
Brigotti et al., Change in Conformation with Reduction of a-Helix Content Causes Loss of Neutrophil Binding Activity in Fully Cytotoxic Shiga Toxin 1, The Journal of Biological Chemistry 286(40) 34514-34521 (2011).
Bujny et al., "The retromer component sorting nexin-1 is required for efficient retrograde transport of Shiga toxin from early endosome to the trans Golgi network", Journal of Cell Science, 120(Pt 12), (2007), 2010-2021.
Cao et al., "Construction of mutant genes for a non-toxic verotoxin 2 variant (VT2vp1) of *Escherichia coli* and characterization of purified mutant toxins", Microbiology and Immunology, 38(6) 441-447 (1994).
Carbonetti, NH, "Pertussis toxin and adenylate cyclase toxin: key virulence factors of Bordetella pertussis and cell biology tools", Future Microbiology 5, (2010), 455-469.
Carbonetti, NH, et al., "Intracellular Delivery of a Cytolytic T-Lymphocyte Epitope Peptide by Pertussis Toxin to Major Histocompatibility Complex Class I without Involvement of the Cytosolic Class I Antigen Processing Pathway", Infection and Immunity, 67(2), (1999), 602-607.
Carbonetti, NH, et al., "Stimulation of HIV gp120-specific cytolytic T lymphocyte responses in vitro and in vivo using a detoxified pertussis toxin vector", AIDS Research and Human Retroviruses, 17(9), (2001), 819-827.
Cheung et al., "A Ribosome-inactivating Protein Toxin as a Template for Cancer Drug Discovery", thesis, University of Toronto, (2012), retrieved from http://hdl.handle.net/1807/33952.
Cizeau, J, et al., "Fusogenics: A Recombinant Immunotoxin-Based Screening Platform to Select Internalizing Tumor-Specific Antibody Fragments", Journal of Biomolecular Screening 16(1), (2011), 90-100.
Cleton-Jansen et al., "A Single Amino Acid Substitution Changes the Substrate Specificity of Quinoprotein Glucose Dehydrogenase in Gluconobacter oxydans", Molecular and General Genetics, 229(2): 206-212 (1991).
Dadaglio, G, et al., "Induction of a Polarized Th1 Response by Insertion of Multiple Copies of a Viral T-Cell Epitope into Adenylate Cyclase of Bordetella pertussis", Infection and Immunity, 68(7), (2000), 3867-3872.
Dadaglio, G, et al., "Recombinant adenylate cyclase toxin of Bordetella pertussis induces cytotoxic T lymphocyte responses against HLA*0201-restricted melanoma epitopes", International Immunology, 15(12), (2003), 1423-1430.
Dekker et al., "Engineered Toxin Bodies delivering immunogenic MHC class I peptides to tumor cells summon polyfunctional and relevant CTL responses against cancers", Presented at: Immunology 2019™, Annual Meeting of the American Association of Immunologists, May 10, 2019, The American Association of Immunologists, Inc., San Diego, Abstract 1791.
Deresiewicz et al., "Identification of amino acids critical for the cytotoxicity of Shiga Toxin I A-chain", Biochemistry 31(12) 3272-3280 (1992).
Doling, AM, et al., "Cytotoxic T-Lymphocyte Epitopes Fused to Anthrax Toxin Induce Protective Antiviral Immunity", Infection and Immunity, 67(7), (1999), 3290-3296.
Donnelly, JJ, et al., "Targeted delivery of peptide epitopes to class I major histocompatibility molecules by a modified Pseudomonas exotoxin", Proceedings of the National Academy of Sciences U.S. A., 90, (1993), 3530-3534.
Engedal, N, et al., "Shiga toxin and its use in targeted cancer therapy and imaging", Microbial Biotechnology, 4(1), (2011), 32-46.
EP 14720298.0, Office Action dated Oct. 21, 2016, 6 pgs.
EP 14720298.0, Office Action dated Jun. 23, 2017, 6 pgs.
Eriksson, K, et al., "Coupling of antigen to cholera toxin for dendritic cell vaccination promotes the induction of MHC class I-restricted cytotoxic T cells and the rejection of a cognate antigen-expressing model tumor", European Journal of Immunology, 34(5), (2004), 1272-1281.
Fanale, MA, et al., "Phase I/Ib study of the novel CD20-targeted immunotoxin MT-3724 in relapsed/refractory non-Hodgkin's B-cell lymphoma", Proceedings of the 107th Annual Meeting of the American Association for Cancer Research (AACR), Poster, Abstract # CT049, (Apr. 16-20, 2016).
Fanale, MA, et al., "Phase I/Ib study of the novel CD20-targeted immunotoxin MT-3724 in relapsed/refractory non-Hodgkin's B-cell lymphoma", Cancer Research, 76(14 Suppl), (Jul. 2016), Abstract nr CT049.

(56) References Cited

OTHER PUBLICATIONS

Fayolle, C, et al., "Therapy of Murine Tumors with Recombinant Bordetella pertussis Adenylate Cyclase Carrying a Cytotoxic T Cell Epitope", The Journal of Immunology, 162(7), (1999), 4157-4162.
Filpula, D, "Releasable PEGylation of Mesothelin Targeted Immunotoxin SSIP Achieves Single Dosage Complete Regression of a Human Carcinoma in Mice", Bioconjugate Chemistry, 18(3): 773-784 (2007).
Freshney, RI, "Culture of Animal Cells: A Manual of Basic Technique", Alan R. Liss, Inc., 1983, New York, pp. 3-4.
Garred et al., "Furin-induced cleavage and activation of Shiga toxin", Journal of Biological Chemistry, 270(18), (1995), 10817-10821.
Garred et al., "Role of processing and intracellular transport for optimal toxicity of Shiga toxin and toxin mutants", Experimental Cell Research 218(1) 39-49 (1995).
Gavrilov et al., "Effects of Glycosylation on Antigenicity and Immunogenicity of Classical Swine Fever Virus Envelope Proteins", Virology, 420(2):135-145 (2011).
Gendler et al., "A Highly Immunogenic Region of a Human Polymorphic Epithelial Mucin Expressed by Carcinomas is Made Up of Tandem Repeats", Journal of Biological Chemistry, 263(26): 12820-12823 (1988).
Ghetie et al., "Homodimers but not monomers of Rituxan (chimeric anti-CD20) induce apoptosis in human B-lymphoma cells and synergize with a chemotherapeutic agent and an immunotoxin", Blood 97(5) 1392-1398 (2001).
Gilliland, DG, et al., "Antibody-directed cytotoxic agents: use of monoclonal antibody to direct the action of toxin A chains to colorectal carcinoma cells", Proceedings of the National Academy of Sciences of the United States of America, 77(8), (1980), 4539-43.
Glennie et al., "Mechanisms of killing by anti-CD20 monoclonal antibodies", Molecular Immunology 44(16) 3823-3837 (2007).
Gong, J, et al., "Selection and characterization of MUC1-specific CD8+ T cells from MUC1 transgenic mice immunized with dendritic-carcinoma fusion cells", Immunology, 101(3), (2000), 316-324.
Gordon et al., "An enzymatic Mutant of Shiga-like Toxin II Variant is a vaccine Candidate for Edema Disease of Swine", Infection and Immunity 60(2): 485-490 (1992).
Grant, K, et al., "Abstract 1380: Engineered toxin bodies with specific activity against EGFR and HER2 expressing cells" Proceedings of the 102nd Annual Meeting of the American Association for Cancer Research (AACR); Apr. 2-6, 2011; The Journal of Cancer Research, 71 (8 Suppl): Abstract #1380, (Apr. 2011).
Guermonprez, P, et al., "Les Toxines Bacteriennes Recombinantes: De Nouveaux Vecteurs Pour La Vaccination?", M/S Medecine Sciences, Societe Des Periodiques Flammarion, 16(5), (2000), 653-662.
Guermonprez, P, et al., "The Adenylate Cyclase Toxin of Bordetella pertussis Binds to Target Cells via the αMβ2 Integrin (CD11b/CD18)", Journal of Experimental Medicine, 193(9), (2001), 1035-1044.
Güssow, D, Seemann, G, "Humanization of Monoclonal Antibodies", Methods in Enzymology, 203, (1991), 99-121.
Haddad et al., "Minimum Domain of the Shiga Toxin A subunit Required for Enzymatic Activity", Journal of Bacteriology 175(16) 4970-4978 (1993).
Haicheur, N, et al., "The B Subunit of Shiga Toxin Fused to a Tumor Antigen Elicits CTL and Targets Dendritic Cells to Allow MHC Class I-Restricted Presentation of Peptides Derived from Exogenous Antigens", The Journal of Immunology, 165(6), (2000), 3301-3308.
Haisma et al., "Construction and Characterization of a Fusion Protein Single-Chain Anti-CD20 Antibody and Human beta-glucuronidase for Antibody-Directed Enzyme Prodrug Therapy", Blood 92:1 184-190 (1998).
Harris "Exploiting antibody-based technologies to manage environmental pollution", Trends in Biotechnology, Diagram figure taken from 17(7): 290-296 (1999).
Head et al., Preparation of VT1 and VT2 Hybrid Toxins from Their Purified Dissociated Subunits. Evidence for B Subunit Modulation of a Subunit Function, Journal of Biological Chemistry, 266(6): 3617-3621 (1991).
Higgins, JP, et al., "Engineered toxin bodies with specific cell kill activity against mesenchymal cells", Cancer Research, 71(8 Suppl), (Apr. 2011), Abstract #1751.
Holubova, J, et al., "Delivery of Large Heterologous Polypeptides across the Cytoplasmic Membrane of Antigen-Presenting Cells by the Bordetella RTX Hemolysin Moiety Lacking the Adenylyl Cyclase Domain", Infection and Immunity, 80(3), (2012), 1181-1192.
Hovde et al., "Evidence that glutamic acid 167 is an active-site residue of Shiga-like toxin-I," Proceedings of the National Academy of Sciences of the United States of America, 85(8) 2568-2572 (1988).
Huang, S, et al., "The CD20-specific engineered toxin antibody MT-3724 exhibits lethal effects against mantle cell lymphoma", Blood Cancer Journal, 8(3), (2018), 33.
Huang et al. "Abstract 3651: Preclinical examination of the effects of MT-3724, an engineered toxin body targeting CD20, in mantle cell lymphoma" AACR Annual Meeting Abstract (2017).
Huang et al. "AACR 2017 | Poster 3651/24—Preclinical examination of the effects of a CD20-specific engineered toxin body, MT-3724, in Mantle Cell Lymphoma" AACR Annual Meeting, Poster 3651/24 (2017).
Iberg, A, et al., "Design and Characterization of Bispecific Engineered Toxin Bodies for Targeted Cancer Therapy", Proceedings: American Association for Cancer Research (AACR) Annual Meeting 2019, Poster #2984, (2019).
International Application Serial No. PCT/US2014/023198, Preliminary Report on Patentability dated Jan. 9, 2015 and dated Jul. 15, 2015, 8 pgs.
International Application Serial No. PCT/US2014/023231, Preliminary Report on Patentability, dated Sep. 15, 2015, 7 pgs.
International Application Serial No. PCT/US2015/012968, International Search Report dated Jul. 13, 2015 and published Jul. 30, 2015, 8 pgs.
International Application Serial No. PCT/US2015/012968, Written Opinion dated Jan. 11, 2016, 15 pgs.
International Application Serial No. PCT/US2015/012968, Preliminary Report on Patentability, dated Apr. 20, 2016 10 pgs.
International Application Serial No. PCT/US2015/012970, International Search Report dated Jun. 26, 2015 and published Jul. 30, 2015, 5 pgs.
International Application Serial No. PCT/US2015/012970, Written Opinion dated Jun. 26, 2015, 7 pgs.
International Application Serial No. PCT/US2015/012970, Preliminary Report on Patentability, dated Nov. 24, 2015 and dated Apr. 20, 2016, 10 pgs.
International Application Serial No. PCT/US2015/019684, International Search Report dated Jun. 29, 2015 and published Jul. 30, 2015, 6 pgs.
International Application Serial No. PCT/US2015/019684, Written Opinion dated Jun. 29, 2015, 8 pgs.
International Application Serial No. PCT/US2015/019708, International Search Report dated Jun. 29, 2015 and published Sep. 17, 2015, 5 pgs.
International Application Serial No. PCT/US2015/019708, Written Opinion, dated Jan. 2015, 8 pgs.
International Application Serial No. PCT/US2015/019708, Preliminary Report on Patentability, dated Sep. 13, 2016, 9 pgs.
International Application Serial No. PCT/US2015/035179, International Search Report dated Sep. 9, 2015 and published Dec. 17, 2015, 5 pgs.
Bera, TK, et al., "A Bivalent Disulfide-stabilized Fv with Improved Antigen Binding to erbB2", Journal of Molecular Biology, 281(3), (1998), 475-483.
Cuesta, AM, et al., "Multivalent antibodies: when design surpasses evolution", Trends in Biotechnology, 28(7), (2010), 355-362.
Hamlin, PA, et al., "Safety and Efficacy of Anti-CD20 Immunotoxin MT-3724 in Relapsed/Refractory B-cell Non-Hodgkin Lymphoma (NHL) in a Phase 1 Study", 2018 American Society of Clinical Oncology Annual Meeting, Abstract 7580, (Jun. 4, 2018).

(56) References Cited

OTHER PUBLICATIONS

Hooijberg, E, et al., "Characterization of a Series of Isotype Switch Variants of a New CD20 Monoclonal Antibody", Hybridoma 15(1), (1996), 23-31.
Vervoordeldonk, SF, et al., "Preclinical Studies with Radiolabeled Monoclonal Antibodies for Treatment of Patients with B-Cell Malignancies", Cancer 73(3), (1994), 1006-1011.
Torgersen, ML, et al., "The A-subunit of surface-bound Shiga toxin stimulates clathrin-dependent uptake of the toxin", The FEBS Journal, 272(16), (2005), 4103-4013.
Tosatto et al. "Large-Scale Prediction of Protein Structure and Function from Sequence", Current Pharmaceutical Design, 12(17): 2067-2086 (2006).
Varner et al., "Recent Advances in Engineering Polyvalent Biological Interactions", Biomacromolecules 16(1): 43-55 (2014).
Vingert, B, et al., "The Shiga toxin B-subunit targets antigen in vivo to dendritic cells and elicits anti-tumor immunity", European Journal of Immunology 36(5), (2006) 1124-1135.
Voskoglou-Nomikos, T, et al., "Clinical Predictive Value of the In Vitro Cell Line, Human Xenograft, and Mouse Allograft Preclinical Cancer Models", Clinical Cancer Research 9(11), (2003), 4227-4239.
Wang, E, et al., "T-cell-directed cancer vaccines: the melanoma model", Expert Opinion on Biological Therapy 1(2), (2001), 277-290.
Wargalla et al., "Rate of internalization of an immunotoxin correlates with cytotoxic activity against human tumor cells", Proceedings of the National Academy of Sciences of the USA 86:13 5146-5150 (1989).
Willert et al., "TAK-169, an exceptionally potent CD38 targeted engineered toxin body, as a novel direct cell kill approach for the treatment of multiple myeloma", Proceedings: American Association for Cancer Research (AACR) Annual Meeting 2019, Poster #2384, (Apr. 1, 2019).
Willert, EK, et al., "Engineered toxin bodies: A next-generation immunotoxin scaffold with novel immuno-oncology functionality", Proceedings: American Association for Cancer Research (AACR) Annual Meeting 2015, Poster, Abstract #2477 (Apr. 18, 2015).
Willert, EK, et al., "Engineered toxin bodies: A next-generation immunotoxin scaffold with novel immuno-oncology functionality", The Journal of Cancer Research, 75(15 Suppl): Abstract #2477, (Aug. 1, 2015).
Windschiegl, B, et al., "Lipid Reorganization Induced by Shiga Toxin Clustering on Planar Membranes", PLoS One, 4(7), (2009), e6238.
Wirth, R, et al., "Engineered Toxin Body demonstrating CD20-specific binding and cell kill in B-Cell Non-Hodgkin lymphoma cells", [abstract]. In: Proceedings of the 104th Annual Meeting of the American Association for Cancer Research, Cancer Research, Apr. 15, 2013, 73(8 Suppl), Abstract #5477.
Wu et al., "Humanization of a murine monoclonal antibody by simultaneous optimization of framework and CDR residues", J. Mol. Biol. 294: 151-162 (1999).
Wu et al., "Multimerization of a chimeric anti-CD20 single chain Fv-Fc fusion protein is mediated through variable domain exchange", Protein Engineering 14(12):1025-1033 (2001).
Yamasaki et al., "Importance of arginine at position 170 of the A subunit of Vero toxin 1 produced by enterohemorrahagic *Escherichia coli* for toxin activity" Microbial Pathogenesis 11(1) (1991).
Yu et al., "Interaction between Bevacizumab and Murine VEGF-A: A Reassessment", Investigative Ophthamology & Visual Science 49(2) 522-527 (2008).
Zacny et al., "Novel toxin library for the discovery of oncology therapeutics", Cancer Research, (Apr. 2010), 70(8 Suppl), Abstract #5506.
Zapata, G, et al., "Engineering linear F(ab')2 fragments for efficient production in *Escherichia coli* and enhanced antiproliferative activity", Protein Engineering, 8(10), (1995), 1057-1062.
Stepanov et al., "Design of Targeted B Cell Killing Agents", PLoS One 6(6) e20991 (2011).

U.S. Appl. No. 14/643,619, Office Action dated Jun. 27, 2018, 48 pgs.
U.S. Appl. No. 14/774,130, Office Action dated Feb. 27, 2017, 19 pgs.
U.S. Appl. No. 14/774,130, Office Action dated Aug. 24, 2017, 20 pgs.
U.S. Appl. No. 14/774,130, Office Action dated Oct. 25, 2016, 5 pgs.
U.S. Appl. No. 14/965,882, Office Action dated Mar. 22, 2018, 12 pgs.
U.S. Appl. No. 14/965,882, Office Action dated Jun. 6, 2017, 19 pgs.
U.S. Appl. No. 15/114,474, Office Action dated Jun. 18, 2018, 20 pgs.
U.S. Appl. No. 15/114,474, Office Action dated Aug. 24, 2017, 11 pgs.
U.S. Appl. No. 15/114,474, Office Action dated Oct. 26, 2017, 24 pgs.
U.S. Appl. No. 15/125,126 Office Action dated Dec. 5, 2018, 20 pgs.
U.S. Appl. No. 15/290,266, Office Action dated Jun. 27, 2018, 32 pgs.
U.S. Appl. No. 15/317,892, Office Action dated Mar. 5, 2018, 22 pgs.
U.S. Appl. No. 15/421,758, Office Action dated Apr. 17, 2017, 22 pgs.
UniProtKB/Swiss-Prot P09385 (STXA_BP933), Shiga-like toxin 2 subunit A, retrieved from https://www.ncbi.nlm.nih.gov/protein/P09385.2 on Jan. 10, 2018.
Weinstein et al., "In Vivo Formation of Hybrid Toxins Comprising Shiga Toxin and the Shiga-Like Toxins and Role of the B Subunit in Localization and Cytotoxic Activity", Infection and Immunity, 57(12): 3743-3750 (1989).
Weldon et al. "A guide to Taming a Toxin: Recombinant Immunotoxins Constructed from Pseudomonas Exotoxin A for the Treatment of Cancer", The FEBS Journal, 278(23): 4683-4700 (2011).
EP Application No. 182078113.1 Extended European Search Report dated Jun. 17, 2019, 10 pgs.
IL Application No. 240433 Office Action Translation dated May 30, 2019, 2 pgs.
IL Application No. 246701 Office Action Translation dated May 16, 2019, 5 pgs.
IL Application No. 247298 Office Action Translation dated May 21, 2019, 4 pgs.
IL Application No. 246632 Office Action Translation dated May 16, 2019, 5 pgs.
Thorpe, PE, et al., "Cytotoxicity Acquired by Conjugation of an Anti-Thy1.1 Monoclonal Antibody and the Ribosome-Inactivating Protein, Gelonin", European Journal of Biochemistry, 116(3), (1981), 447-454.
Dermer, GB, "Another Anniversary for the War on Cancer", Bio/Technology 12, (1994), 320.
Di et al., "Identification of amino acids critical for the cytotoxicity of Shiga toxin 1 and 2 in *Saccharomyces cerevisiae*", Toxicon 57(4) 525-539 (2011).
Boes et al., "Affinity Purification of a Framework 1 Engineered Mouse/Human Chimeric IgA2 Antibody From Tobacco", Biotechnology Bioengineering, 108(12): 2804-2814 (2011).
Lakhrif et al., "A method to confer protein L binding ability to any antibody fragment" MAbs, 8(2): 379-388 (2016).
Zahid et al., "Design and reshaping of an scFv directed against human platelet glycoprotein VI with diagnostic potential", Analytical Biochemistry, 417(2): 274-282 (2011).
Lee et al., "Molecular mechanism of PD-1/PD-L1 blockade via anti-PD-L1 antibodies atezolizumab and durvalumab", Scientific Reports 7(1):5532 (2017).
Rudikoff et al. "Single amino acid substitution altering antigen-binding specificity." Proceedings of the National Academy of Sciences 79(6): 1979-1983 (1982).
Pascalis et al., "Grafting of "abbreviated" complementarity-determining regions containing specificity-determining residues essential for ligand contact to engineer a less immunogenic humanized monoclonal antibody." The Journal of Immunology 169(6): 3076-3084 (2002).

(56) References Cited

OTHER PUBLICATIONS

Casset et al., "A peptide mimetic of an anti-CD4 monoclonal antibody by rational design." Biochemical and Biophysical Research Communications 307(1): 198-205 (2003).
Lee et al.,"Phylogenetic analysis of Shiga toxin 1 and Shiga toxin 2 genes associated with disease outbreaks." BMC Microbiology 7(1): 109 (2007).
Cao et al. "Construction and characterization of novel, recombinant immunotoxins targeting the Her2/neu oncogene product: in vitro and in vivo studies." Cancer Research 69(23): 8987-8995 (2009).
U.S. Appl. No. 61/777,130, filed Mar. 12, 2013, Poma et al.
U.S. Appl. No. 62/112,314, filed Feb. 5, 2015, Poma et al.
U.S. Appl. No. 62/249,193, filed Oct. 31, 2015, Poma et al.
Anderson, K. C. et al., "Expression of Human B Cell-Associated Antigens on Leukemias and Lymphomas: A Model of Human B Cell Differentiation," Blood, 63(6): 1424-1433 (1984).
Aqel, N. et al., "*In-situ*mantle cell lymphoma—a report of two cases," Histopathology, 52:239-262 (2008).
Brigotti, M. et al., "Shiga toxin 1: damage to DNA in vitro," Toxicon, 39:341-348 (2001).
Burnett, C. et al., "A Phase 2a Open-Label Study to Investigate Safety and Tolerability (including the MTD), Efficacy, Pharmacokinetics, Pharmacodynamics and Immunogenicity of MT-3724 in Combination with Gemcitabine and Oxaliplatin in Subjects with Relapsed or Refractory B-Cell Non-Hodgkin Lymphoma," Blood, 134 (Supplement 1 ):5322 (2019), 3 pages.
Burnett, C. et al., "A Phase 2a Open-Label Study to Investigate Safety and Tolerability (including the MTD), Efficacy, Pharmacokinetics, Pharmacodynamics and Immunogenicity of MT-3724 in Combination with Lenalidomide in Subjects with Relapsed or Refractory B-Cell Non-Hodgkin Lymphoma," Blood, 134 (Supplement 1): 1597 (2019), 3 pages.
Chen, Z. et al., "Prospective isolation of clonogenic mantle cell lymphoma-initiating cells," Stem Cell Research, 5:212-225 (2010).
Chomel, J. -C. et al., "Leukemic stem cell persistence in chronic myeloid leukemia patients with sustained undetectable molecular residual disease," Blood, 118(13):3657-3660 (2011).
Corbin, A. S. et al., "Human chronic myeloid leukemia stem cells are insensitive to imatinib despite inhibition of BCR-ABL activity," J Clin Invest., 121 (1):396-409 (2011); doi:10.1172/JCI35721.
Deret, S. et al., "SUBIM: a program for analysing the Kabat database and determining the variability subgroup of a new immunoglobulin sequence," CABIOS, 11(4):435-439 (1995).
Gerber, J. M et al., "A clinically relevant population of leukemic CD34+ CD38- cells in acute myeloid leukemia," Blood, 119(15):3571-3577 (2012).
Higgins, J. P et al., "Abstract 2060: Combination of CD20 targeted engineered toxin body, MT-3724, with chemotherapy or IMiDs for the treatment of non Hodgkin's lymphoma," In: Proceedings of the American Association for Cancer Research Annual Meeting 2019, March 29-Apr. 3, 2019, Atlanta, GA, Cancer Res 2019; 79(13 Suppl): Abstract nr 2060, 2 pages.
Higgins, J. P et al., "Abstract 1644: Combination of MT-3724 with sirolimus reduces anti-drug antibody response and prolongs drug exposure," In: Proceedings of the American Association for Cancer Research Annual Meeting 2017, Apr. 1-5, 2017, Washington, DC. Cancer Res 2017; 77(13 Suppl): Abstract nr 1644, 2 pages.
Hope, K. J. et al., "Acute myeloid leukemia originates from a hierarchy of leukemic stem cell classes that differ in self-renewal capacity," Nature Immunology, 5(7):738-743 (2004).
Ishikawa, F. et al., "Chemotherapy-resistant human AML stem cells home to and engraft within the bone-marrow endosteal region," Nature Biotechnology, 25(11):1315-1321 (2007).
Jones, R. J et al., "Circulating clonotypic B cells in classic Hodgkin lymphoma," Blood, 113:5920-5926 (2009).
Lim, S. H et al., "Anti-CD20 monoclonal antibodies: historical and future perspectives," Haematologica, 95:135-143 (2010).
Limpens, J et al., "Bc/-2/Jh rearrangements in benign tissues with follicular hyperplasia," Oncogene, 6:2271 -2276 (1991).

Liu, H et al., "Resistance of t(11; 18) positive gastric mucosa-associated lymphoid tissue lymphoma to *Helicobacter pylori*eradication therapy," The Lancet, 357:39-40 (2001).
Manches, 0 et al., "In vitro mechanisms of action of rituximab on primary non-Hodgkin lymphomas," Blood, 101:949-954 (2003).
Marti, G et al., "Overview of monoclonal B-cell lymphocytosis," British Journal of Haematology, 139:701 -708 (2007).
Martin, B et al., "Primary cutaneous CD20-positive T-cell lymphoma," J Cutan Pathol, 38:663-669 (2011).
Molecular Templates Corporate Presentation, Nov. 2019, 26 pages.
Muller, P. Y. & Brennan, F. R., "Safety Assessment and Dose Selection for First-in-Human Clinical Trials With Immunomodulatory Monoclonal Antibodies," Clinical Pharmacology & Therapeutics, 85(3):247-258 (2009).
Muzard, J et al., "Grafting of protein L-binding activity onto recombinant antibody fragments," Analytical Biochemistry, 388:331-338 (2009).
Natarajan, A et al., "A Novel Engineered Anti-CD20 Tracer Enables Early Time PET Imaging in a Humanized Transgenic Mouse Model of B-cell Non-Hodgkins Lymphoma," Clin Cancer Res, 19(24):6820-6829 (2013).
Nilson, B. H. K et al., "Protein L from Peptostreptococcus magnus Binds to the k Light Chain Variable Domain," The Journal of Biological Chemistry, 267(4):2234-2239 (1992).
Nilson, B. H. K et al., "Purification of antibodies using protein L-binding framework structures in the light chain variable domain," Journal of Immunological Methods, 164:33-40 (1993).
O'Brien, A. D et al., "Shiga Toxin: Biochemistry, Genetics, Mode of Action, and Role in Pathogenesis," Current Topics in Microbiology and Immunology, 180:65-94 (1992).
Press Release Molecular Molecular Templates' Presentations at the American Association of Cancer Research (AACR) Annual Meeting 2019 Highlight Evolution of ETB Platform, Apr. 2, 2019, 3 pages.
Press Release New Data on Molecular Templates' Engineered Toxin Bodies to be Presented at the American Association of Cancer Research (AACR) Annual Meeting 2019, Feb. 27, 2019, 4 pages.
Press Release Molecular Templates Announces Presentations Featuring Engineered Toxin Bodies at the 2017 American Association for Cancer Research (AACR) Annual Meeting, Mar. 30, 2017, 2 pages.
Rawstron, A. C. et al., "Monoclonal B-Cell Lymphocytosis and Chronic Lymphocytic Leukemia," N Engl J Med, 359:575-583 (2008).
Richard, P. et al., "'In situ-like' mangle cell lymphoma: a report of two cases," J Clin Pathol, 69:995-996 (2006); doi: 10.1136/jcp. 2005.030783.
Rosenthal, A. et al., "A phase 2 study of lenalidomide, rituximab, cyclophosphamide, and dexamethasone (LR-CD) for untreated low-grade non-Hodgkin lymphoma requiring therapy," Am J Hematol., 92(5):467-472 (2017).
Roulland, S. et al., "Follicular lymphoma-like B cells in healthy individuals: a novel intermediate step in early lymphomagenesis," JEM, 203(11):2425-2431 (2006).
Sarantopoulos, S. et al., "B Cells in Chronic Graft-versus-Host Disease," Biol Blood Marrow Transplant, 21:16-23 (2015).
Scheutz, F. et al., "Multicenter Evaluation of a Sequence-Based Protocol for Subtyping Shiga Toxins and Standardizing Stx Nomenclature," Journal of Clinical Microbiology, 50(9):2951 -2963 (2012).
Strop, P. et al., "Location Matters: Site of Conjugation Modulates Stability and Pharmacokinetics of Antibody Drug Conjugates," Chemistry & Biology, 20:161-167 (2013).
Tam, P. J. & Lingwood, C. A., "Membrane-cytosolic translocation of verotoxin Ai subunit in target cells," Microbiology, 153:2700-2710 (2007).
Teeling, J. L et al., "The Biological Activity of Human CD20 Monoclonal Antibodies Is Linked to Unique Epitopes on CD20," The Journal of Immunology, 177:362-371 (2006).
Van Meerten, T. et al., "Complement-Induced Cell Death by Rituximab Depends on CD20 Expression Level and Acts Complementary to Antibody-Dependent Cellular Cytotoxicity," Clin Cancer Res, 12(13):4027-4035 (2006).
Wang, J. C. Y. & Dick, J. E., "Cancer stem cells: lessons from leukemia," Trends in Cell Biology, 15(9):494-501 (2005).

(56) References Cited

OTHER PUBLICATIONS

Mateos, M. -V. et al., "Lenalidomide plus Dexamethasone for High-Risk Smoldering Multiple Myeloma," The New England Journal of Medicine, 369(5):438-447 (2013).
Press Release Molecular Templates Announces FDA Acceptance of IND Application for MT-5111, An Engineered Toxin Body Targeting HER2, Austin Texas, Apr. 22, 2019, 2 pages.
Von Minckwitz, G. et al., "Phase I clinical study of the recombinant antibody toxin scFv(FRP5)-ETA specific for the ErbB2/HER2 receptor in patients with advanced solid malignomas," Breast Cancer Research, 7(5):R617-R626 (2005).
Wels, W. et al., "Selective Inhibition of Tumor Cell Growth by a Recombinant Single-Chain Antibody-Toxin Specific for the erbB-2 Receptor," Cancer Research, 52:6310-6317 (1992).

* cited by examiner

Figure 1. Schematic Drawing of the General Architecture of Exemplary CD20-Binding Proteins

Figure 2. Disseminated Tumor Xenograft Results: Exemplary CD20-binding proteins reduced disseminated tumor volumes *in vivo*
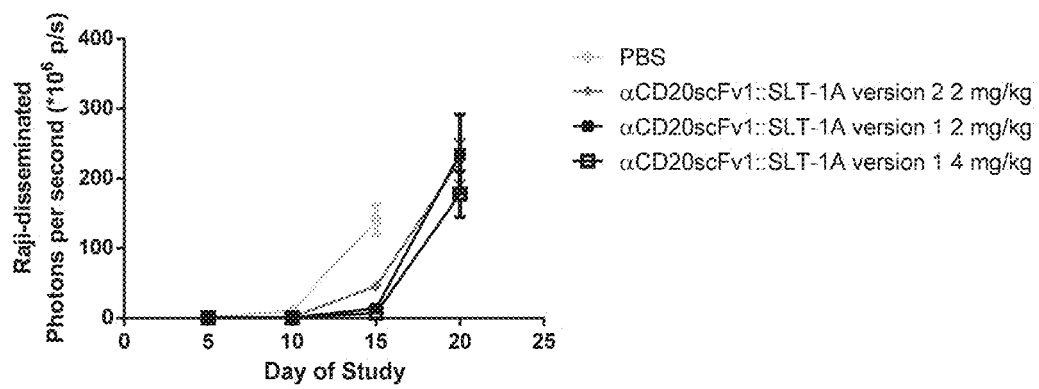
Figure 3. Disseminated Tumor Xenograft Results: Exemplary CD20-binding proteins extended lifespan
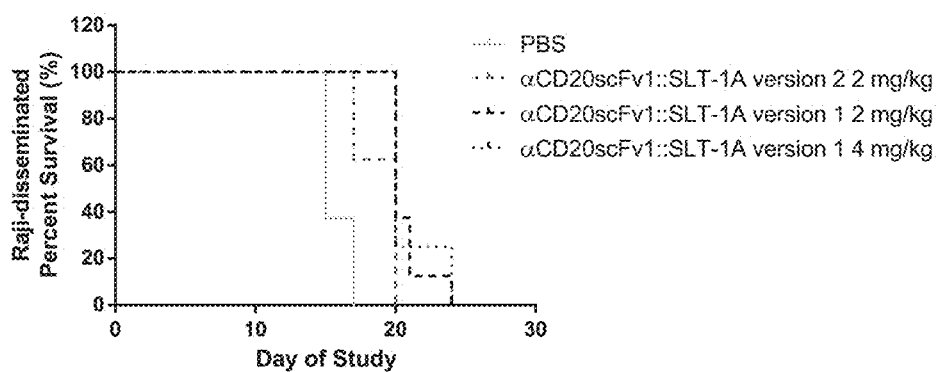

Figure 4. Subcutaneous Xenograft Results: the majority of mice displayed complete regression of tumor volume by day 54
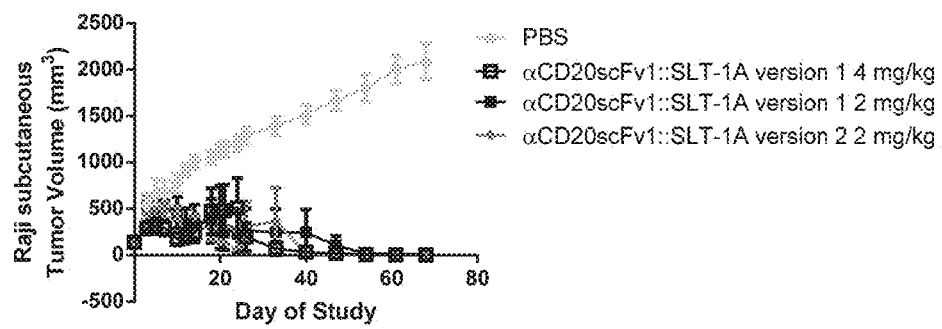
Figure 5. Non-Human Primate Results: Following parenteral administration of an exemplary CD20-binding protein, dose-dependent depletion of peripheral blood B-cells was observed over time
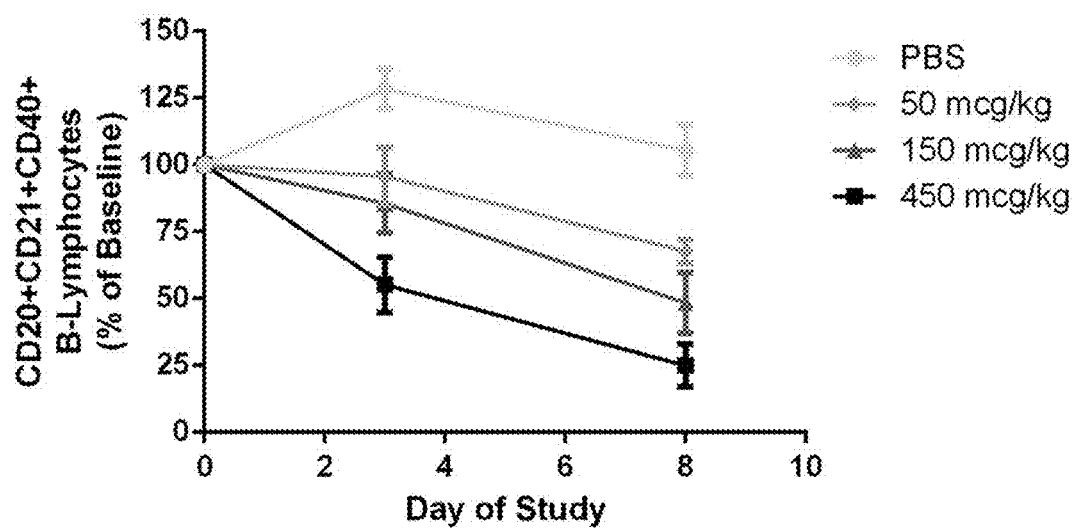

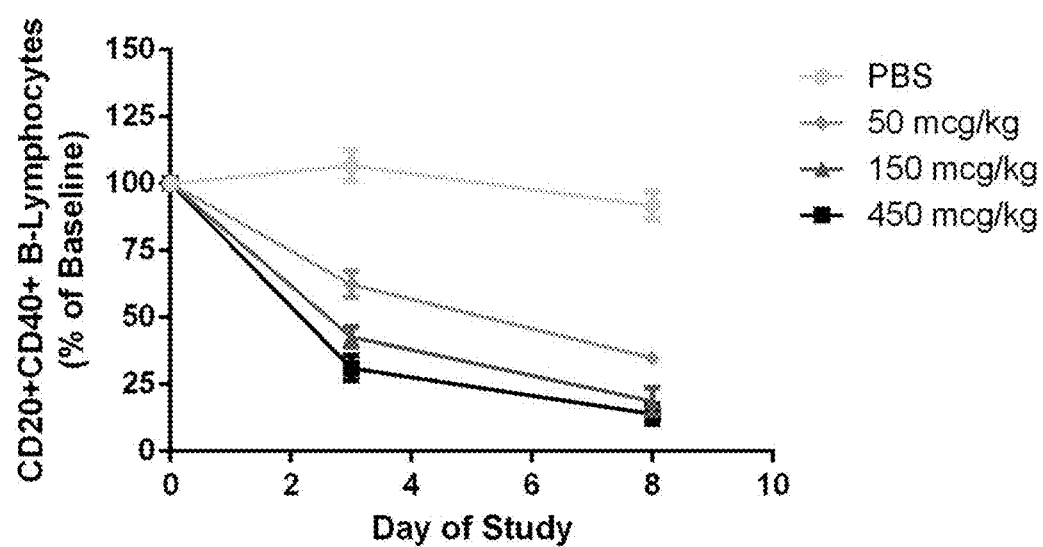
Figure 6. Non-Human Primate Results: Following parenteral administration of an exemplary CD20-binding protein, dose-dependent depletion of peripheral blood B-cells was observed over time ics and Methods Using Same

CD20-BINDING PROTEINS COMPRISING SHIGA TOXIN A SUBUNIT EFFECTOR REGIONS FOR INDUCING CELLULAR INTERNALIZATION AND METHODS USING SAME

SEQUENCE LISTING

The instant application contains a Sequence Listing which has been submitted electronically in ASCII format and is hereby incorporated by reference in its entirety. Said ASCII copy, created on May 7, 2018, is named 13-03PCT-CIP_SL.txt and is 379,631 bytes in size.

FIELD OF THE INVENTION

The present invention relates to CD20-binding proteins capable of binding to and inducing the rapid internalization of CD20 antigens from a cell surface location to the cell interior. These CD20-binding proteins have uses, e.g., for the selective killing of specific cell types, delivering exogenous materials inside CD20 expressing cells, detecting CD20 expressing cells, and as therapeutic molecules for treatment of a variety of diseases, including cancers, tumors, growth abnormalities, and immune disorders.

BACKGROUND OF THE INVENTION

An immunotoxin is a chimeric cytotoxic protein which combines a cell surface binding region that confers specificity, such as from an immunoglobulin domain, and a toxin region that mediates target cell killing, typically derived from a naturally occurring protein toxin, such as those found in bacteria or plants (Pastan I et al., *Nat Rev Cancer* 6: 559-65 (2006); Pastan I et al., *Annu Rev Med* 58: 221-37 (2007)). The potency of an immunotoxin greatly depends on its efficiency in transiting from the cell surface to the cytosol, a process that begins with cell internalization (see Pirie C et al., *J Biol Chem* 286: 4165-72 (2011)).

CD20 is a member of a family of polypeptides known as the membrane-spanning 4A (MS4A) family that includes at least 26 proteins in humans and mice (Ishibashi K et al., *Gene* 264: 87-93 (2001)). As with all MS4A members, the CD20 sequence predicts three hydrophobic regions forming a transmembrane molecule that spans the membrane four times, a structural characteristic believed central to its function. Also predicted is a single extracellular loop between the proposed third and fourth transmembrane domains and intracellular amino- and carboxy-terminal regions (Tedder T et al., *Proc Natl Acad Sci* 85: 208-12 (1988)). It is within this extracellular loop of approximately 40 amino acids that the majority of anti-CD20 monoclonal antibodies (mAbs), such as rituximab, are believed to bind with alanine-170 and proline-172 being the most critical residues. A crystal structure of an antibody binding a peptide fragment of CD20 using amino acids 163-187 of CD20 has confirmed amino acids 170 (alanine) through amino acids 173 (serine) as antigen-antibody interaction points for rituximab and CD20 (Du J et al., *J Biol Chem* 282: 15073-80 (2007)).

CD20 is believed to be present on the cell surface as a homo-multimer, likely a tetramer, and electron microscopy has shown that 90% of complexed CD20 is present in the membrane in lipid rafts and microvilli (Li H et al., *J Biol Chem* 279: 19893-901 (2004)). Lipid rafts are micro-domains found in the plasma membrane which have high polypeptide, sphingolipid, and cholesterol concentrations (Brown D, London E, *Annu Rev Cell Dev Biol* 14: 111-36 (1998)). Microvilli, or microvillar channels, are cell extensions from the plasma membrane surface (Reaven E et al., *J Lipid Res* 30: 1551-60 (1989)). Some antibodies to CD20 are known to bind only when the molecule is present in lipid rafts, such as FMC7 (Polyak M et al., *Leukemia* 17:1384-89 (2003)) and others, such as rituximab, are known to increase association of CD20 to rafts (Cragg M et al., *Blood* 101: 1045-52 (2003); Li H et al, *J Biol Chem* 279: 19893-901 (2004)). It is hypothesized that raft association is important to the proposed function of CD20 as an amplifier of calcium signals that are transduced through the B-cell antigen receptor (BCR), another protein commonly located within lipid rafts and found associated with CD20 multimers (Polyak M et al., *J Biol Chem* 283: 18545-52 (2008)).

There is an unsolved problem in designing therapeutics that require cell internalization for efficacy and that target extracellular CD20 antigens, which is—how to efficiently drive the therapeutic agents bound to cell surface CD20 molecules inside target cells. CD20 is a particularly attractive target for antibody-based therapies based on mechanisms in which it is desirable for a therapeutic agent to remain on the cell surface because CD20 does not internalize after being bound by antibodies (Anderson K et al., *Blood* 63: 1424-33 (1984); Press O et al., *Blood* 69: 584-91 (1987); Glennie M et al., *Mol Immunol* 44: 3823-37 (2007)). Although the lack of CD20 internalization was later proven to be both cell-type and antibody-type specific, in general, CD20 appears to internalize at a much lower rate than do other cell surface antigens and is generally considered a non-internalizing, extracellular target (Beers S et al., *Sem Hematol* 47: 107-14 (2010)). CD20 is "resistant to internalization and remains on the cell surface with its bound mAb for extended periods of hours and perhaps days" (Glennie M et al., *Mol Immunol* 44: 3823-37 (2007); see e.g. Press O et al., *Cancer Res* 49: 4906-12 (1989); McLaughlin P et al., *J Clin Oncol* 16: 2825-33 (1998); Johnson P, Glennie M, *Semin Oncol* 30: 3-8 (2003)).

Although antibody-based therapies targeting extracellular CD20 antigens are numerous, they are all based on extracellular mechanisms (see Cheson B, Leonard J, *N Engl J Med* 359: 613-26 (2008); Boross P, Leusen J, *Am J Cancer Res* 2: 676-90 (2012)). Thus, there is a question in the art as to the utility of CD20 as an extracellular target for therapies whose effectiveness requires a therapeutic agent to reach the intracellular space of a target cell in a CD20-mediated fashion because of the general finding that CD20 does not readily internalize (Anderson K et al., *Blood* 63: 1424-33 (1984); Press O et al., *Blood* 69: 584-91 (1987); Press O et al., *Cancer Res* 49: 4906-12 (1989); Press O et al., *Blood* 83: 1390-7 (1994); Countouriotis A et al., *Stem Cells* 20: 215-29 (2002): Beers S et al., *Sem Hematol* 47: 107-14 (2010)).

The effectiveness of therapies relying on cellular internalization of a therapeutic, such as, e.g., immunotoxins, ligand-toxin fusions, and immuno-RNases, depends on both the quantity of their target on the surface of target cells (see e.g. Decket T et al., *Blood* 103: 2718-26 (2004); Du X et al., *Blood* 111: 338-43 (2008); Baskar S et al., *mAbs* 4: 349-61 (2012)) and the rate of cellular internalization of surface-bound therapeutic complexed with its target (see e.g. Du X et al., *Cancer Res* 68: 6300-5 (2008); de Virgilio M et al., *Toxins* 2: 2699-737 (2011)). For CD20 in particular, there is an unsolved problem in targeting extracellular CD20 with internalizing therapeutics—how to efficiently drive the therapeutic agents bound to cell surface CD20 molecules into the interior of target cells. The general lack of CD20 internalization means that the unsolved problem of driving efficient CD20 internalization applies even to target cells that express relatively high quantities and/or densities of CD20 on their surfaces as well as to other target cells which do not.

There is a need in the art to develop effective compositions, therapeutics, and therapeutic methods which target cells expressing CD20 that do not efficiently internalize CD20 after binding, such as, e.g., by an immunoglobulin-type domain. In particular, there is a need in the art to develop CD20-targeted compositions that trigger rapid and efficient cellular internalization of cell surface CD20 molecules. For example, it would be desirable to have immunotoxins which (a) robustly induce cellular internalization of cell surface expressed CD20 molecules, (b) intracellularly route toxin regions to the cytosol, and (c) are capable of killing cells (in which they have internalized) for the development of effective anti-neoplastic and immunomodulatory therapeutics targeting CD20 expressing malignant cells. B lymphocytes (B-cells), and T lymphocytes (T-cells). New therapies are especially needed for patients who are insensitive or develop resistance to current CD20-targeted therapies relying on extracellular mechanisms such as, e.g., Fc region effector functions of anti-CD20 monoclonal antibodies (Alduaij W. Illidge T, *Blood* 117: 2993-3001 (2011)).

SUMMARY OF THE INVENTION

The present invention provides various CD20-binding proteins for inducing cellular internalization of CD20, which comprise 1) a CD20 binding region, such as an immunoglobulin domain, and 2) a Shiga toxin effector region, such as a truncation of SLT-1A. Upon binding a CD20 antigen on the surface of a cell, the CD20-binding proteins of the invention are capable of entering the interior of the cell in a CD20-mediated. The linking of CD20 binding regions with Shiga-toxin-Subunit-A-derived polypeptides enables the engineering of cytotoxic Shiga-toxin based molecules that are capable of inducing rapid cellular internalization of cell-surface CD20, as well as capable of delivering additional exogenous materials into the interior of CD20 expressing cells. The CD20-binding proteins of the invention have uses, e.g., for targeted killing of CD20 positive cell types, delivering exogenous materials, as diagnostic agents, and as therapeutics for the treatment of a variety of conditions in patients such as, e.g., cancers, tumors, and immune disorders related to B-cell lineages like hematologic and rheumatic diseases.

A CD20-binding protein of the invention comprises (a) a CD20 binding region capable of specifically binding an extracellular part of CD20; and (b) a Shiga toxin effector region comprising a polypeptide derived from the amino acid sequence of the A Subunit of at least one member of the Shiga toxin family; and whereby administration of CD20-binding protein to one or more cells which express CD20 at a cellular surface, CD20-binding protein is internalized into one or more of said cells within five hours at 37 degrees Celsius (° C.). In certain further embodiments, the CD20-binding protein of the invention is internalized into one or more of said cells within one hour at 37° C.

In certain embodiments, the CD20-binding protein of the invention comprises (a) a CD20 binding region capable of specifically binding an extracellular part of CD20; and (b) a Shiga toxin effector region comprising a polypeptide derived from the amino acid sequence of the A Subunit of at least one member of the Shiga toxin family; and whereby administration of CD20-binding protein to one or more CD20 positive cells. CD20-binding protein is internalized into one or more of said CD20 positive cells within five hours at 37 degrees Celsius. In certain further embodiments, the CD20-binding protein of the invention is internalized into one or more of said CD20 positive cells within one hour at 37 degrees Celsius.

For certain embodiments of the CD20-binding proteins of the present invention, whereby administration of a plurality of the CD20-binding protein to a plurality of CD20-expressing cells at a concentration equivalent to 5-50% cell surface CD20 occupancy, the majority of the CD20-binding protein is internalized into said CD20-expressing cells within five hours at 37 degrees Celsius. In certain further embodiments, the majority of the CD20-binding protein of the invention is internalized into said CD20-expressing cells within one hour at 37 degrees Celsius.

For certain embodiments of the CD20-binding proteins of the present invention, whereby administration of a plurality of the CD20-binding protein to a plurality of CD20 positive cells at a concentration equivalent to 38-50% cell surface CD20 occupancy, the majority of the CD20-binding protein is internalized into said CD20 positive cells within five hours at 37 degrees Celsius. In certain further embodiments, the majority of the CD20-binding protein of the invention is internalized into said CD20 positive cells within one hour at 37 degrees Celsius.

In certain embodiments, the CD20-binding protein of the invention comprises (a) a CD20 binding region comprising an immunoglobulin-type binding region and capable of specifically binding an extracellular part of CD20; and (b) a Shiga toxin effector region comprising a polypeptide derived from the amino acid sequence of the A Subunit of at least one member of the Shiga toxin family; and whereby administration of CD20-binding protein to one or more CD20 positive cells expressing CD20 at a cellular surface, CD20-binding protein is internalized into one or more of said CD20 positive cells within five hours at 37 degrees Celsius (° C.). In certain further embodiments, the CD20-binding protein of the invention is internalized into one or more of said CD20 positive cells within one hour at 37 degrees Celsius (° C.). For certain further embodiments of the CD20-binding proteins of the present invention, whereby administration of a plurality of the CD20-binding protein to a plurality of CD20 positive cells at a concentration equivalent to 5% to 50% cell surface CD20 occupancy, the majority of the CD20-binding protein is internalized into one or more of said CD20 positive cells within one hour at 37 degrees Celsius.

In certain embodiments of the CD20-binding proteins of the present invention, the CD20 binding region comprises an immunoglobulin-type binding region comprising a polypeptide selected from the group consisting of: single-domain antibody (sdAb) fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronection-derived 10$^{th}$ fibronectin type III domain (10Fn3), tenacsin type III domain, ankyrin repeat motif domain, low-density-lipoprotein-receptor-derived A-domain (LDLR-A), lipocalin (anticalins), Kunitz domain, Protein-A-derived Z domain, gamma-B crystalline-derived domain, ubiquitin-derived domain, Sac7d-derived polypeptide (affitins), Fyn-derived SH2 domain, miniprotein, C-type lectin-like domain scaffold, engineered antibody mimic, and any genetically manipulated counterparts of any of the foregoing which retain binding functionality.

The CD20-binding proteins of the present invention may lack any Fc region or comprises only those Fc region effector domains which lack Fc effector function. In certain embodiments of the CD20-binding proteins of the present invention, the CD20-binding protein does not comprise an Fc region (lacks an Fc region). In certain embodiments of the CD20-binding proteins of the present invention, the CD20-binding protein does not comprise any Fc region effector domain which retains Fc effector function. Certain CD20-binding proteins of the present invention may comprise an Fc region or Fc region effector domain as long as it lacks Fc effector functions.

For certain embodiments of the CD20-binding proteins of the present invention, whereby administration of CD20-binding protein to said one or more CD20 positive cells, the CD20 positive cell or cells is a descendant or member of a B-cell lineage.

For certain embodiments of the CD20-binding proteins of the present invention, whereby administration of CD20-binding protein to said one or more CD20 positive cells, the CD20 positive cell or cells is selected from the group consisting of: malignant B-cell, B-cell leukemia cell. B-cell lymphoma cell, B-cell myeloma cell, acute myeloid leukemia cell, acute non-lymphocytic leukemia cell, B-cell chronic lymphocytic leukemia cell, B-cell lymphoma cell, B-cell non-Hodgkin's lymphoma cell, B-cell precursor acute lymphoblastic leukemia cell, B-cell prolymphocytic leukemia cell, Burkitt's lymphoma cell, chronic lymphocytic leukemia cell, chronic myeloid leukemia cell, diffuse large B-cell lymphoma cell, follicular lymphoma cell, hairy cell leukemia cell, Hodgkin's lymphoma cell, immunoblastic large cell lymphoma cell, mantle cell lymphoma cell, melanoma cell, multiple myeloma cell, neoplastic plasma cell, nodular lymphocyte predominant Hodgkin's lymphoma cell, non-Hodgkin's lymphoma cell, plasmablastic lymphoma cell, plasma cell myeloma cell, precursor B-lymphoblastic lymphoma cell, small lymphocytic lymphoma cell, malignant T-cell, T-cell leukemia cell, T-cell lymphoma cell, T-cell large granular lymphocyte leukemia cell, T-cell prolymphocytic leukemia, healthy B-cell lineage cell, and healthy T-cell.

For certain embodiments of the CD20-binding proteins of the present invention, whereby administration of the CD20-binding protein to one or more CD20 positive cells at a physiological temperature appropriate for the cell results in one or more of the following behaviors in said one or more CD20 positive cells: (i) internalizing CD20-binding protein inside the cell within one hour, (ii) subcellular routing at least one Shiga toxin effector region polypeptide to the cell's cytosol, (iii) disrupting the cell's ribosome function, and (iv) killing of the cell.

For certain embodiments, administration of the CD20-binding protein to a cell which expresses CD20 at a cellular surface, e.g. a CD20 positive cell, the CD20-binding proteins are capable of causing the death of the cell, i.e. killing the cell. In certain other embodiments, the CD20-binding proteins of the invention comprise Shiga toxin effector regions that lack catalytic activity and are not capable of causing the death of a cell through a Shiga toxin effector mediated, ribosome inactivation mechanism. In certain embodiments, the CD20-binding proteins of the invention are capable of causing the death of a CD20-expressing cell via the action of an additional exogenous material despite lacking any Shiga toxin effector region catalytic activity.

For certain embodiments of the CD20-binding proteins of the present invention, whereby administration of the CD20-binding protein to a first population of CD20 positive cells, and a second population of cells whose members do not express a significant amount of a CD20 target of the CD20-binding protein at a cellular surface, the cytotoxic effect of the CD20-binding protein to members of the first population of cells relative to members of the second population of cells is at least 3-fold greater. A CD20 target of a CD20-binding protein of the invention is a CD20 molecule comprising an extracellular part bound specifically and with high-affinity by the CD20 binding region of that CD20-binding protein of the invention.

For certain embodiments of the CD20-binding proteins of the present invention, the CD20-binding proteins comprise the Shiga toxin effector region comprising or consisting essentially of amino acids 75 to 251 of SEQ ID NO:1, SEQ ID NO:2, or SEQ ID NO:3. Further embodiments are CD20-binding proteins in which the Shiga toxin effector region comprises or consists essentially of amino acids 1 to 241 of SEQ ID NO:1, SEQ ID NO:2, or SEQ ID NO:3; amino acids 1 to 251 of SEQ ID NO:1, SEQ ID NO:2, or SEQ ID NO:3; and/or amino acids 1 to 261 of SEQ ID NO:1, SEQ ID NO:2, or SEQ ID NO:3.

In certain embodiments of the CD20-binding proteins of the present invention, the CD20-binding proteins comprise the CD20 binding region comprising at least one heavy-chain variable ($V_H$) domain polypeptide and at least one light-chain variable domain polypeptide selected from the group consisting of: (a) a heavy chain variable domain comprising i) HCDR1, HCDR2, and HCDR3 amino acid sequences as shown in SEQ ID NO:5, SEQ ID NO:6, and SEQ ID NO:7, respectively; ii) HCDR1, HCDR2, and HCDR3 amino acid sequences as shown in SEQ ID NO:11, SEQ ID NO:12, or SEQ ID NO:13, respectively; iii) HCDR1, HCDR2, and HCDR3 amino acid sequences as shown in SEQ ID NO:17, SEQ ID NO:18, and SEQ ID NO:19, respectively; iv) HCDR1, HCDR2, and HCDR3 amino acid sequences as shown in SEQ ID NO:23, SEQ ID NO:24, and SEQ ID NO:25, respectively; v) HCDR1, HCDR2, and HCDR3 amino acid sequences as shown in SEQ ID NO:29, SEQ ID NO:30, and SEQ ID NO:31, respectively; and vi) HCDR1, HCDR2, and HCDR3 amino acid sequences as shown in SEQ ID NO:35, SEQ ID NO:36, and SEQ ID NO:37, respectively; and (b) a light chain variable ($V_L$) domain comprising i) LCDR1, LCDR2, and LCDR3 amino acid sequences as shown in SEQ ID NO:8, SEQ ID NO:9, and SEQ ID NO:10, respectively; ii) LCDR1, LCDR2, and LCDR3 amino acid sequences as shown in SEQ ID NO:14, SEQ ID NO:15, and SEQ ID NO:16, respectively; iii) LCDR1, LCDR2, and LCDR3 amino acid sequences as shown in SEQ ID NO:20, SEQ ID NO:21, and SEQ ID NO:22, respectively; iv) LCDR1, LCDR2, and LCDR3 amino acid sequences as shown in SEQ ID NO:26, SEQ ID NO:27, and SEQ ID NO:28, respectively; v) LCDR1, LCDR2, and LCDR3 amino acid sequences as shown in SEQ ID NO:32. SEQ ID NO:33, and SEQ ID NO:34, respectively; and vi) LCDR1, LCDR2, and LCDR3 amino acid sequences as shown in SEQ ID NO:38, SEQ ID NO:39, and SEQ ID NO:40, respectively. Further embodiments are CD20-binding proteins comprising the immunoglobulin-type binding region comprising or consisting essentially of amino acids 2-245 of any one of the amino acid sequences shown in SEQ ID NOs: 46-87. Further embodiments are CD20-binding proteins comprising the immunoglobulin-type binding region comprising or consisting essentially of amino acids 2-245 of any one of the amino acid sequences shown in SEQ ID NOs: 46-87 linked with the Shiga toxin effector region comprising or consisting essentially of amino acids 75-251 of SEQ ID NO:1. Further embodiments are CD20-binding proteins comprising the immunoglobulin-type binding region comprising or consisting essentially of amino acids 2-245 of any one of the amino acid sequences shown in SEQ ID NOs: 46-87 linked with the Shiga toxin effector region comprising or consisting essentially of the amino acid sequence shown in SEQ ID NO:4.

For certain embodiments, the CD20-binding protein comprises or consists essentially of the polypeptide shown in any one of SEQ ID NOs: 46-112.

In certain embodiments, the CD20-binding proteins comprise Shiga toxin effector regions which comprise a mutation relative to a naturally occurring A Subunit of a member of the Shiga toxin family which changes the enzymatic activity of the Shiga toxin effector region, the mutation selected from at least one amino acid residue deletion or substitution. In certain further embodiments, the mutation reduces or eliminates cytotoxicity of the Shiga toxin effector region.

For certain embodiments of the CD20-binding proteins of the present invention, the CD20-binding protein is cytotoxic. In certain embodiments, a cytotoxic CD20-binding protein of the invention comprises (a) a Shiga toxin effector region comprising a polypeptide derived from the amino acid sequence of the A Subunit of at least one member of the Shiga toxin family and (b) a CD20 binding region capable of specifically binding an extracellular part of CD20; and whereby administration of CD20-binding protein to one or more cells which express CD20 at a cellular surface, CD20-binding protein is internalized into one or more of said cells within five hours at 37 degrees Celsius (° C.) and kills one or more of said cells. In certain further embodiments, the cytotoxic CD20-binding protein of the invention comprises (a) a Shiga toxin effector region comprising a polypeptide derived from the amino acid sequence of the A Subunit of at least one member of the Shiga toxin family and (b) a CD20 binding region capable of specifically binding an extracellular part of CD20; and whereby administration of CD20-binding protein to one or more CD20 positive cells, CD20-binding protein is internalized into one or more of said CD20 positive cells within five hours at 37 degrees Celsius (° C.) and kills one or more of said CD20 positive cells.

In certain embodiments of the cytotoxic CD20-binding proteins of the present invention, whereby administration of a plurality of the cytotoxic CD20-binding protein of the invention to a plurality of cells expressing CD20 at a cellular surface, cytotoxic CD20-binding protein is internalized into and kills one or more of said cells. In certain further embodiments of the cytotoxic CD20-binding proteins of the present invention, whereby administration of a plurality of the cytotoxic CD20-binding protein of the invention to a plurality of CD20 positive cells, cytotoxic CD20-binding protein is internalized into and kills one or more of said CD20 positive cells.

For certain embodiments of the cytotoxic CD20-binding proteins of the present invention, whereby administration of a plurality of the CD20-binding protein to a plurality of CD20-expressing cells at a concentration equivalent to 5% to 50% cell surface CD20 occupancy, the majority of the CD20-binding protein is internalized into said CD20-expressing cells within five hours at 37 degrees Celsius. In certain further embodiments, the majority of the CD20-binding protein of the invention is internalized into said CD20-expressing cells within one hour at 37 degrees Celsius. For certain further embodiments of the cytotoxic CD20-binding proteins of the present invention, whereby administration of a plurality of the CD20-binding protein to a plurality of CD20 positive cells at a concentration equivalent to 5% to 50% cell surface CD20 occupancy, the majority of the CD20-binding protein is internalized into one or more of said CD20 positive cells within one hour at 37 degrees Celsius.

For certain embodiments of the cytotoxic CD20-binding proteins of the present invention, whereby administration of the CD20-binding protein to a first population of CD20 positive cells, and a second population of cells whose members do not express a significant amount of a CD20 target of the CD20-binding protein at a cellular surface, the cytotoxic effect of the CD20-binding protein to members of the first population of cells relative to members of the second population of cells is at least 3-fold greater.

In certain further embodiments of the cytotoxic CD20-binding proteins of the invention, the CD20 binding region comprises an immunoglobulin-type binding region. In certain further embodiments of the cytotoxic CD20-binding proteins of the present invention, the CD20 binding region comprises an immunoglobulin-type binding region comprising a polypeptide selected from the group consisting of: single-domain antibody (sdAb) fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronectin-derived 10$^{th}$ fibronectin type III domain (10Fn3), tenacsin type III domain, ankyrin repeat motif domain, low-density-lipoprotein-receptor-derived A-domain (LDLR-A), lipocalin (anticalins), Kunitz domain, Protein-A-derived Z domain, gamma-B crystalline-derived domain, ubiquitin-derived domain, Sac7d-derived polypeptide (affitins), Fyn-derived SH2 domain, miniprotein. C-type lectin-like domain scaffold, engineered antibody mimic, and any genetically manipulated counterparts of any of the foregoing which retain binding functionality.

In certain embodiments, the cytotoxic CD20-binding proteins of the present invention lack any Fc region or comprise only those Fe region effector domains which lack Fc effector function. In certain embodiments of the cytotoxic CD20-binding proteins of the present invention, the CD20-binding protein does not comprise any Fc region (lacks any Fe region). In certain embodiments of the CD20-binding proteins of the present invention, the CD20-binding protein does not comprise any Fc region effector domain which retains Fc effector function. Certain cytotoxic CD20-binding proteins of the present invention may comprise an Fc region or Fc region effector domain as long as it lacks Fc effector functions.

In certain embodiments, the cytotoxic CD20-binding protein of the present invention comprises (a) a Shiga toxin effector region comprising a polypeptide derived from the amino acid sequence of the A Subunit of at least one member of the Shiga toxin family and (b) a CD20 binding region capable of specifically binding an extracellular part of CD20 and comprising an immunoglobulin-type binding region comprising a polypeptide selected from the group consisting of: single-domain antibody (sdAb) fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronectin-derived 10$^{th}$ fibronectin type III domain (10Fn3), tenacsin type III domain, ankyrin repeat motif domain, low-density-lipoprotein-receptor-derived A-domain (LDLR-A), lipocalin (anticalins), Kunitz domain, Protein-A-derived Z domain, gamma-B crystalline-derived domain, ubiquitin-derived domain, Sac7d-derived polypeptide (affitins), Fyn-derived SH2 domain, miniprotein. C-type lectin-like domain scaffold, engineered antibody mimic, and any genetically manipulated counterparts of any of the foregoing which retain binding functionality; and wherein the CD20-binding protein does not comprise an Fc region or Fc effector domain which retains Fc function; and whereby administration of CD20-binding protein to one or more CD20 positive cells, CD20-binding protein is internalized into one or more of said CD20 positive cells within five hours at 37 degrees Celsius and kills one or more of said CD20 positive cells.

For certain embodiments of the cytotoxic CD20-binding proteins of the present invention, whereby administration of cytotoxic CD20-binding protein to said one or more CD20 positive cells, the CD20 positive cell or cells is a descendant or member of a B-cell lineage.

For certain embodiments of the cytotoxic CD20-binding proteins of the present invention, whereby administration of cytotoxic CD20-binding protein to said one or more CD20 positive cells, the CD20 positive cell or cells is selected from the group consisting of: malignant B-cell, B-cell leukemia cell, B-cell lymphoma cell, B-cell myeloma cell, acute myeloid leukemia cell, acute non-lymphocytic leukemia cell, B-cell chronic lymphocytic leukemia cell, B-cell lymphoma cell, B-cell non-Hodgkin's lymphoma cell, B-cell precursor acute lymphoblastic leukemia cell. B-cell prolymphocytic leukemia cell, Burkitt's lymphoma cell, chronic lymphocytic leukemia cell, chronic myeloid leukemia cell, diffuse large B-cell lymphoma cell, follicular lymphoma cell, hairy cell leukemia cell, Hodgkin's lymphoma cell, immunoblastic large cell lymphoma cell, mantle cell lymphoma cell, melanoma cell, multiple myeloma cell, neoplastic plasma cell, nodular lymphocyte predominant Hodgkin's lymphoma cell, non-Hodgkin's lymphoma cell, plasmablastic lymphoma cell, plasma cell myeloma cell, precursor B-lymphoblastic lymphoma cell, small lymphocytic lymphoma cell, malignant T-cell, T-cell leukemia cell, T-cell lymphoma cell, T-cell large granular lymphocyte leukemia cell. T-cell prolymphocytic leukemia, healthy B-cell lineage cell, and healthy T-cell.

For certain embodiments of the cytotoxic CD20-binding proteins of the present invention, whereby administration of the cytotoxic CD20-binding protein to a first population of CD20 positive cells, and a second population of cells whose members do not express a significant amount of a CD20 target of the CD20-binding protein at a cellular surface, the cytotoxic effect of the CD20-binding protein to members of the first population of cells relative to members of the second population of cells is at least 3-fold greater.

For certain embodiments of the cytotoxic CD20-binding proteins of the present invention, the CD20-binding proteins comprise the Shiga toxin effector region comprising or consisting essentially of amino acids 75 to 251 of SEQ ID NO:1, SEQ ID NO:2, or SEQ ID NO:3. Further embodiments are cytotoxic CD20-binding proteins in which the Shiga toxin effector region comprises or consists essentially of amino acids 1 to 241 of SEQ ID NO:1, SEQ ID NO:2, or SEQ ID NO:3; amino acids 1 to 251 of SEQ ID NO:1, SEQ ID NO:2, or SEQ ID NO:3; and/or amino acids 1 to 261 of SEQ ID NO:1, SEQ ID NO:2, or SEQ ID NO:3.

In certain embodiments of the cytotoxic CD20-binding proteins of the present invention, the CD20-binding proteins comprise the CD20 binding region comprising at least one heavy-chain variable ($V_H$) domain polypeptide and at least one light-chain variable domain polypeptide selected from the group consisting of: (a) a heavy chain variable domain comprising i) HCDR1, HCDR2, and HCDR3 amino acid sequences as shown in SEQ ID NO:5, SEQ ID NO:6, and SEQ ID NO:7, respectively; ii) HCDR1, HCDR2, and HCDR3 amino acid sequences as shown in SEQ ID NO:11, SEQ ID NO:12, or SEQ ID NO:13, respectively; iii) HCDR1, HCDR2, and HCDR3 amino acid sequences as shown in SEQ ID NO:17, SEQ ID NO: 18, and SEQ ID NO:19, respectively; iv) HCDR1, HCDR2, and HCDR3 amino acid sequences as shown in SEQ ID NO:23, SEQ ID NO:24, and SEQ ID NO:25, respectively; v) HCDR1, HCDR2, and HCDR3 amino acid sequences as shown in SEQ ID NO:29, SEQ ID NO:30, and SEQ ID NO:31, respectively; and vi) HCDR1, HCDR2, and HCDR3 amino acid sequences as shown in SEQ ID NO:35, SEQ ID NO:36, and SEQ ID NO:37, respectively; and (b) a light chain variable ($V_L$) domain comprising i) LCDR1, LCDR2, and LCDR3 amino acid sequences as shown in SEQ ID NO:8, SEQ ID NO:9, and SEQ ID NO:10, respectively; ii) LCDR1, LCDR2, and LCDR3 amino acid sequences as shown in SEQ ID NO:14, SEQ ID NO:15, and SEQ ID NO:16, respectively; iii) LCDR1, LCDR2, and LCDR3 amino acid sequences as shown in SEQ ID NO:20, SEQ ID NO:21, and SEQ ID NO:22, respectively; iv) LCDR1, LCDR2, and LCDR3 amino acid sequences as shown in SEQ ID NO:26, SEQ ID NO:27, and SEQ ID NO:28, respectively; v) LCDR1, LCDR2, and LCDR3 amino acid sequences as shown in SEQ ID NO:32. SEQ ID NO:33, and SEQ ID NO:34, respectively; and vi) LCDR1, LCDR2, and LCDR3 amino acid sequences as shown in SEQ ID NO:38, SEQ ID NO:39, and SEQ ID NO:40, respectively.

Further embodiments are cytotoxic CD20-binding proteins comprising the immunoglobulin-type binding region comprising or consisting essentially of amino acids 2-245 of any one of the amino acid sequences shown in SEQ ID NOs: 46-87. Further embodiments are cytotoxic CD20-binding proteins comprising the immunoglobulin-type binding region comprising or consisting essentially of amino acids 2-245 of any one of the amino acid sequences shown in SEQ ID NOs: 46-87 linked with the Shiga toxin effector region comprising or consisting essentially of amino acids 75-251 of SEQ ID NO:1. Further embodiments are CD20-binding proteins comprising the immunoglobulin-type binding region comprising or consisting essentially of amino acids 2-245 of any one of the amino acid sequences shown in SEQ ID NOs: 46-87 linked with the Shiga toxin effector region comprising or consisting essentially of the amino acid sequence shown in SEQ ID NO:4.

For certain embodiments, the cytotoxic CD20-binding protein comprises or consists essentially of the polypeptide shown in any one of SEQ ID NOs: 46-112.

In certain embodiments, the cytotoxic CD20-binding proteins comprise Shiga toxin effector regions which comprise a mutation relative to a naturally occurring A Subunit of a member of the Shiga toxin family which changes the enzymatic activity of the Shiga toxin effector region, the mutation selected from at least one amino acid residue deletion or substitution. In certain further embodiments, the mutation reduces or eliminates the cytotoxicity of the Shiga toxin effector region.

Certain embodiments of the CD20-binding proteins can also be utilized for the delivery of an additional exogenous material into a cell that expresses CD20 at a cellular surface. The CD20-binding proteins for the delivery of additional exogenous material each comprise (a) a CD20 binding region capable of specifically binding an extracellular part of a CD20 molecule, (b) a Shiga toxin effector region comprising a polypeptide derived from the amino acid sequence of at least one member of the Shiga toxin family, and (c) an additional exogenous material; and whereby administration of CD20-binding protein to one or more cells expressing CD20 at a cellular surface, the CD20-binding protein is internalized into said one or more cells and capable of delivering the additional exogenous material into the interior of the cell. In certain further embodiments of the CD20-binding protein for the delivery of additional exogenous material, whereby administration of CD20-binding protein to one or more cells expressing CD20 at a cellular surface, the CD20-binding protein is internalized into one or more of said cells and capable of delivering the additional exogenous material into the interior of one or more of said cells within five hours at 37 degrees Celsius. In certain further embodiments of the CD20-binding protein for the delivery of additional exogenous material, the CD20-binding protein is internalized into one or more of said cells within one hour at 37 degrees Celsius. In certain further embodiments of the CD20-binding protein for the delivery of additional exogenous material, whereby administration of CD20-binding protein to one or more CD20 positive cells, the CD20-binding protein is internalized into one or more of said CD20 positive cells and capable of delivering the additional exogenous material into the interior of one or more of said CD20 positive cells within five hours at 37 degrees Celsius. In certain further embodiments of the CD20-binding protein for the delivery of additional exogenous material, the CD20-binding protein and additional exogenous material is internalized into one or more of said CD20 positive cells within one hour at 37 degrees Celsius.

In certain embodiments of the CD20-binding protein for the delivery of additional exogenous material, whereby administration of a plurality of the CD20-binding protein of the invention to a plurality of cells expressing CD20 at a cellular surface, CD20-binding protein and the additional exogenous material is internalized into one or more of said cells. In certain further embodiments of the CD20-binding protein for the delivery of additional exogenous material, whereby administration of a plurality of the CD20-binding protein of the invention to a plurality of CD20 positive cells, CD20-binding protein and the additional exogenous material is internalized into one or more of said CD20 positive cells.

For certain embodiments of the CD20-binding proteins of the present invention for delivery of additional exogenous material, whereby administration of a plurality of the CD20-binding protein to a plurality of said CD20 positive cells at a concentration equivalent to 38-50% cell surface CD20 occupancy, the majority of the CD20-binding protein and the exogenous material is internalized into one or more of said CD20 positive cells within one hour at 37 degrees Celsius.

In certain embodiments of the CD20-binding proteins of the present invention for delivery of additional exogenous material, the CD20 binding region comprises an immunoglobulin-type binding region comprising a polypeptide selected from the group consisting of: single-domain antibody (sdAb) fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronection-derived $10^{th}$ fibronectin type III domain (10Fn3), tenacsin type III domain, ankyrin repeat motif domain, low-density-lipoprotein-receptor-derived A-domain (LDLR-A), lipocalin (anticalins), Kunitz domain, Protein-A-derived Z domain, gamma-B crystalline-derived domain, ubiquitin-derived domain, Sac7d-derived polypeptide (affitins), Fyn-derived SH2 domain, miniprotein, C-type lectin-like domain scaffold, engineered antibody mimic, and any genetically manipulated counterparts of any of the foregoing which retain binding functionality.

In certain embodiments of the CD20-binding proteins of the present invention for delivery of additional exogenous material, the CD20-binding protein comprises (a) a Shiga toxin effector region comprising a polypeptide derived from the amino acid sequence of at least one member of the Shiga toxin family; (b) a CD20 binding region capable of specifically binding an extracellular part of CD20 and comprising an immunoglobulin-type binding region comprising a polypeptide selected from the group consisting of: single-domain antibody (sdAb) fragment, single-chain variable fragment (scFv), antibody variable fragment (Fv), a complementary determining region 3 (CDR3) fragment, constrained FR3-CDR3-FR4 (FR3-CDR3-FR4) polypeptide, Fd fragment, antigen-binding fragment (Fab), fibronection-derived $10^{th}$ fibronectin type 111 domain (10Fn3), tenacsin type III domain, ankyrin repeat motif domain, low-density-lipoprotein-receptor-derived A-domain (LDLR-A), lipocalin (anticalins), Kunitz domain. Protein-A-derived Z domain, gamma-B crystalline-derived domain, ubiquitin-derived domain. Sac7d-derived polypeptide (affitins), Fyn-derived SH2 domain, miniprotein, C-type lectin-like domain scaffold, engineered antibody mimic, and any genetically manipulated counterparts of any of the foregoing which retain binding functionality; and an additional exogenous material; and whereby administration of CD20-binding protein to one or more CD20 positive cells, the CD20-binding protein is internalized into one or more of said CD20 positive cells and capable of delivering the additional exogenous material into the interior of one or more of said CD20 positive cells within five hours at 37 degrees Celsius. In certain further embodiments of the CD20-binding protein for delivery of additional exogenous material, the CD20-binding protein is internalized into one or more of said CD20 positive cells and capable of delivering the additional exogenous material into the interior of one or more of said CD20 positive cells within one hour at 37 degrees Celsius.

In certain embodiments of the CD20-binding proteins of the present invention for delivery of additional exogenous material, the CD20-binding proteins lack any Fc region or comprise only those Fc region effector domains which lack Fc effector function. In certain embodiments of the CD20-binding proteins of the present invention for delivery of additional exogenous material, the CD20-binding protein does not comprise any Fc region (lacks any Fc region). In certain embodiments of the CD20-binding proteins of the present invention for delivery of additional exogenous material, the CD20-binding protein does not comprise any Fc region effector domain which retains Fc effector function.

For certain embodiments of the CD20-binding proteins of the present invention for delivery of additional exogenous material, whereby administration of CD20-binding protein to said one or more CD20 positive cells, the CD20 positive cell or cells is a descendant or member of a B-cell lineage.

For certain embodiments of the CD20-binding proteins of the present invention for delivery of additional exogenous material, whereby administration of CD20-binding protein to said one or more CD20 positive cells, the CD20 positive cell or cells is selected from the group consisting of: malignant B-cell, B-cell leukemia cell, B-cell lymphoma cell, B-cell myeloma cell, acute myeloid leukemia cell, acute non-lymphocytic leukemia cell, B-cell chronic lymphocytic leukemia cell, B-cell lymphoma cell, B-cell non-Hodgkin's lymphoma cell, B-cell precursor acute lymphoblastic leukemia cell, B-cell prolymphocytic leukemia cell, Burkitt's lymphoma cell, chronic lymphocytic leukemia cell, chronic myeloid leukemia cell, diffuse large B-cell lymphoma cell, follicular lymphoma cell, hairy cell leukemia cell, Hodgkin's lymphoma cell, immunoblastic large cell lymphoma cell, mantle cell lymphoma cell, melanoma cell, multiple myeloma cell, neoplastic plasma cell, nodular lymphocyte predominant Hodgkin's lymphoma cell, non-Hodgkin's lymphoma cell, plasmablastic lymphoma cell, plasma cell myeloma cell, precursor B-lymphoblastic lymphoma cell, small lymphocytic lymphoma cell, malignant T-cell, T-cell leukemia cell, T-cell lymphoma cell, T-cell large granular lymphocyte leukemia cell, T-cell prolymphocytic leukemia, healthy B-cell lineage cell, and healthy T-cell.

For certain embodiments of the CD20-binding proteins of the present invention for delivery of additional exogenous material, whereby administration of the CD20-binding protein to one or more CD20 positive cells expressing CD20 at a cellular surface results in one or more of the following behaviors in said one or more CD20 positive cells: (i) internalizing CD20-binding protein inside the cell within one hour, (ii) subcellular routing at least one Shiga toxin effector region polypeptide to the cell's cytosol, (iii) delivering the exogenous material to the cell's cytosol, (iv) disrupting the cell's ribosome function, and (v) killing of the cell.

For certain embodiments of the CD20-binding proteins of the present invention for delivery of additional exogenous material, whereby administration of the CD20-binding protein to a first population of CD20 positive cells, and a second population of cells whose members do not express a significant amount of a CD20 target of the CD20-binding protein at a cellular surface, the cytotoxic effect of the CD20-binding protein to members of the first population of cells relative to members of the second population of cells is at least 3-fold greater.

In certain embodiments of the CD20-binding proteins of the present invention for delivery of additional exogenous material, the additional exogenous material is a cytotoxic agent, such as, e.g., a chemotherapeutic agent, cytotoxic antibiotic, alkylating agent, antimetabolite, topoisomerase inhibitor, and/or tubulin inhibitor.

In certain embodiments of the CD20-binding proteins of the present invention for delivery of additional exogenous material, the additional exogenous material is selected from the group consisting of peptides, polypeptides, proteins, and polynucleotides. In certain embodiments of the CD20-binding proteins of the present invention for delivery of additional exogenous material, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA).

In certain embodiments of the CD20-binding proteins of the present invention for delivery of additional exogenous material, the additional exogenous material is a peptide and the peptide is an antigen. In certain embodiments of the CD20-binding proteins of the present invention for delivery of additional exogenous material, the additional exogenous material is an antigen derived from a bacterial protein. In certain other embodiments of the CD20-binding proteins of the present invention for delivery of additional exogenous material, the antigen is derived from a protein mutated in cancer. Further embodiments are ones in which the antigen is derived from a protein aberrantly expressed in cancer. Still further embodiments are ones in which the antigen is derived from a T-cell complementary determining region. In certain embodiments of the CD20-binding proteins of the present invention for delivery of additional exogenous material, the additional exogenous material is an antigen derived from a viral protein. In certain further embodiments, the antigen comprises or consists essentially of the amino acid sequence shown in SEQ ID NO:44. In certain further embodiments, the CD20-binding protein comprises or consists essentially of the amino acid sequence shown in SEQ ID NO:50, SEQ ID NO:54. SEQ ID NO:55, SEQ ID NO:59. SEQ ID NO:62, SEQ ID NO:67. SEQ ID NO:71, SEQ ID NO:74. SEQ ID NO:78, SEQ ID NO:89, and SEQ ID NO: 110.

For certain embodiments of the CD20-binding proteins of the present invention for delivery of additional exogenous material, the CD20-binding proteins comprise the Shiga toxin effector region comprising or consisting essentially of amino acids 75 to 251 of SEQ ID NO:1, SEQ ID NO:2, or SEQ ID NO:3. Further embodiments are CD20-binding proteins in which the Shiga toxin effector region comprises or consists essentially of amino acids 1 to 241 of SEQ ID NO:1, SEQ ID NO:2, or SEQ ID NO:3; amino acids 1 to 251 of SEQ ID NO:1, SEQ ID NO:2, or SEQ ID NO:3; and/or amino acids 1 to 261 of SEQ ID NO:1, SEQ ID NO:2, or SEQ ID NO:3.

In certain embodiments of the CD20-binding proteins of the present invention for delivery of additional exogenous material, the CD20-binding proteins comprise the CD20 binding region comprising at least one heavy-chain variable ($V_H$) domain polypeptide and at least one light-chain variable domain polypeptide selected from the group consisting of: (a) a heavy chain variable domain comprising i) HCDR1, HCDR2, and HCDR3 amino acid sequences as shown in SEQ ID NO:5, SEQ ID NO:6, and SEQ ID NO:7, respectively; ii) HCDR1, HCDR2, and HCDR3 amino acid sequences as shown in SEQ ID NO:11, SEQ ID NO:12, or SEQ ID NO:13, respectively; iii) HCDR1, HCDR2, and HCDR3 amino acid sequences as shown in SEQ ID NO:17, SEQ ID NO:18, and SEQ ID NO:19, respectively; iv) HCDR1, HCDR2, and HCDR3 amino acid sequences as shown in SEQ ID NO:23, SEQ ID NO:24, and SEQ ID NO:25, respectively; v) HCDR1, HCDR2, and HCDR3 amino acid sequences as shown in SEQ ID NO:29, SEQ ID NO:30, and SEQ ID NO:31, respectively; and vi) HCDR1, HCDR2, and HCDR3 amino acid sequences as shown in SEQ ID NO:35, SEQ ID NO:36, and SEQ ID NO:37, respectively; and (b) a light chain variable ($V_L$) domain comprising i) LCDR1, LCDR2, and LCDR3 amino acid sequences as shown in SEQ ID NO:8, SEQ ID NO:9, and SEQ ID NO:10, respectively; ii) LCDR1, LCDR2, and LCDR3 amino acid sequences as shown in SEQ ID NO:14, SEQ ID NO:15, and SEQ ID NO: 16, respectively; iii) LCDR1, LCDR2, and LCDR3 amino acid sequences as shown in SEQ ID NO:20, SEQ ID NO:21, and SEQ ID NO:22, respectively; iv) LCDR1, LCDR2, and LCDR3 amino acid sequences as shown in SEQ ID NO:26, SEQ ID NO:27, and SEQ ID NO:28, respectively; v) LCDR1, LCDR2, and LCDR3 amino acid sequences as shown in SEQ ID NO:32, SEQ ID NO:33, and SEQ ID NO:34, respectively; and vi) LCDR1, LCDR2, and LCDR3 amino acid sequences as shown in SEQ ID NO:38, SEQ ID NO:39, and SEQ ID NO:40, respectively. Further embodiments are CD20-binding proteins for delivery of additional exogenous material comprising the immunoglobulin-type binding region comprising or consisting essentially of amino acids 2-245 of any one of SEQ ID NOs: 46-87. Further embodiments are CD20-binding proteins for delivery of additional exogenous material comprising the immunoglobulin-type binding region comprising or consisting essentially of amino acids 2-245 of any one of SEQ ID NOs: 46-87 and the Shiga toxin effector region comprising or consisting essentially of amino acids 75-251 of SEQ ID NO:1. In certain further embodiments, the antigen comprises or consists essentially the amino acid sequence shown in SEQ ID NO:44. In certain further embodiments, the CD20-binding protein comprises or consists essentially of the amino acid sequence of any one shown in SEQ ID NO:50, SEQ ID NO:54, SEQ ID NO:55, SEQ ID NO:59, SEQ ID NO:62, SEQ ID NO:67, SEQ ID NO:71, SEQ ID NO:74, SEQ ID NO:78, SEQ ID NO:89, and SEQ ID NO:110.

In certain embodiments of the CD20-binding proteins of the present invention for delivery of additional exogenous material, the antigen is included within the CD20-binding protein as part of a polypeptide fusion in which the peptide antigen is located between the CD20 binding region and the Shiga toxin effector region of a single-chain protein. In certain further embodiments, the antigen comprises or consists essentially the amino acid sequence shown in SEQ ID NO:44. In certain further embodiments, the CD20-binding protein comprises or consists essentially of the amino acid sequence shown in any one of SEQ ID NO:50, SEQ ID NO:54, SEQ ID NO:55, SEQ ID NO:59, SEQ ID NO:62, SEQ ID NO:67, SEQ ID NO:71, SEQ ID NO:74, SEQ ID NO:78, SEQ ID NO:89, and SEQ ID NO:110.

In certain embodiments of the CD20-binding proteins of the present invention for delivery of additional exogenous material, the CD20-binding proteins comprise Shiga toxin effector regions which comprise a mutation relative to a naturally occurring A Subunit of a member of the Shiga toxin family which changes the enzymatic activity of the Shiga toxin effector region, the mutation selected from at least one amino acid residue deletion or substitution. In certain further embodiments, the mutation reduces or eliminates the cytotoxicity of the Shiga toxin effector region.

The present invention also provides pharmaceutical compositions comprising a CD20-binding protein of the present invention and at least one pharmaceutically acceptable excipient or carrier; and the use of such a protein or a composition comprising it in methods of the present invention as further described herein.

Among certain embodiments of the present invention is a diagnostic composition comprising a CD20-binding protein of the present invention further comprising a detection promoting agent for the collection of information about a cell type, tissue, organ, disease, disorder, condition, and/or patient.

Beyond the proteins of the present invention, polynucleotides capable of encoding a protein of the present invention are within the scope of the present invention, as well as expression vectors which comprise a polynucleotide of the present invention and host cells comprising an expression vector of the present invention. Host cells comprising an expression vector may be used, e.g., in methods for producing a CD20-binding protein of the present invention or a polypeptide component or fragment thereof by recombinant expression.

Additionally, the present invention provides methods of killing a cell(s) expressing CD20 at a cellular surface, the method comprising the step of contacting a cell(s) with a CD20-binding protein or a pharmaceutical composition of the present invention. In certain further embodiments, the method is for killing a CD20 positive cell(s) and the method comprises the step of contacting a CD20 positive cell(s) with a CD20-binding protein or a pharmaceutical composition of the present invention. In certain embodiments of the cell killing methods, the step of contacting the cell(s) occurs in vitro. In certain other embodiments of the cell killing methods, the step of contacting the cell(s) occurs in vivo.

In addition, the present invention provides a method of inducing cellular internalization of a CD20-binding protein into a CD20 positive cell(s) expressing CD20 at a cellular surface, the method comprising the step of contacting the cell(s) with a CD20-binding protein of the present invention or a pharmaceutical or diagnostic composition thereof. In certain embodiments, the step of contacting the cell(s) occurs in vitro. In certain other embodiments, the step of contacting the cell(s) occurs in vivo. In certain further embodiments of the inducing cellular internalization method, the cellular internalization of the CD20-binding protein occurs within five hours at 37 degrees Celsius. For certain further embodiments of the inducing cellular internalization method, the cellular internalization of the CD20-binding protein occurs within one hour at 37 degrees Celsius. For certain further embodiments of the inducing cellular internalization method, the administration of a plurality of the CD20-binding protein to a plurality of said CD20 expressing cells at a concentration equivalent to 5-50% cell surface CD20 occupancy, cellular internalization occurs for the majority of the CD20-binding protein is internalized into one or more of said CD20 expressing cells within one hour at 37 degrees Celsius.

Similarly, the present invention provides a method of internalizing a cell surface localized CD20 bound by a CD20-binding protein in a patient, the method comprising the step of administering to the patient a CD20-binding protein, or a pharmaceutical or diagnostic composition of the present invention. In certain further embodiments of the internalizing method, the cellular internalization of said cell surface localized CD20 bound by a CD20-binding protein occurs within five hours at 37 degrees Celsius. In certain further embodiments of the internalizing method, the cellular internalization of said cell surface localized CD20 bound by a CD20-binding protein occurs within one hour at a physiological temperature.

Additionally, the present invention provides a method for delivering an exogenous material to the inside of a cell expressing CD20 at a cellular surface, the method comprising contacting the cell(s), either in vitro or in vivo, with a CD20-binding protein or pharmaceutical composition of the present invention. In certain embodiments, the present invention provides a method for delivering an exogenous material to the inside of a CD20 positive cell(s), the method comprising contacting the cell(s), either in vitro or in vivo, with a CD20-binding protein or pharmaceutical composition of the present invention.

In certain embodiments, the additional exogenous material is selected from the group consisting of peptides, polypeptides, proteins, and polynucleotides. In certain embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA). In certain embodiments, the additional exogenous material is a peptide and the peptide is an antigen. In certain embodiments, the additional exogenous material is an antigen derived from a bacterial protein. In certain other embodiments, the antigen is derived from a protein mutated in cancer. Further embodiments are ones in which the antigen is derived from a protein aberrantly expressed in cancer. Still further embodiments are ones in which the antigen is derived from a T-cell complementary determining region.

The present invention further provides methods of treating diseases, disorders, and/or conditions in patients comprising the step of administering to a patient in need thereof a therapeutically effective amount of a CD20-binding protein or a pharmaceutical composition of the present invention. In certain embodiments of these treating methods of the present invention, the disease, disorder, or condition to be treated using a method of the present invention involves the cancer cell, tumor cell, and/or immune cell which express CD20 at a cellular surface. In certain embodiments of these treating methods of the present invention, the disease, disorder, or condition to be treated using a method of the present invention involves a CD20 positive cancer cell, tumor cell, and/or immune cell. In certain embodiments of these treating methods of the present invention, the disease to be treated is selected from the group consisting of: hematologic cancer, leukemia, lymphoma, melanoma, and myeloma. In certain embodiments of these treating methods of the present invention, the immune disorder to be treated is selected from the group consisting of: amyloidosis, ankylosing spondylitis, asthma, Crohn's disease, diabetes, graft rejection, graft-versus-host disease, Graves' disease, Graves' ophthalmopathy, Hashimoto's thyroiditis, hemolytic uremic syndrome, HIV-related diseases, lupus erythematosus, multiple sclerosis, neuromyelitis optica spectrum disorders, N-methyl D-aspartate (NMDA) receptor encephalitis, opsoclonus myoclonus syndrome (OMS), paroxysmal nocturnal hemoglobinuria, polyarteritis nodosa, polyarthritis, psoriasis, psoriatic arthritis, rheumatoid arthritis, scleritis, scleroderma, septic shock, Sjorgren's syndrome, ulcerative colitis, and vasculitis. In certain embodiments of these treating methods of the present invention, the cancer to be treated is selected from the group consisting of: acute myeloid leukemia (acute myelogenous leukemia or AML), acute non-lymphocytic leukemia, B-cell chronic lymphocytic leukemias (B-cell CLL), B-cell lymphoma, B-cell non-Hodgkin's lymphoma (B-cell NHL), B-cell precursor acute lymphoblastic leukemia (BCP-ALL or B-ALL), B-cell prolymphocytic leukemia (B-PLL), Burkitt's lymphoma (BL), chronic lymphocytic leukemia (CLL), chronic myeloid leukemia (CML), diffuse large B-cell lymphoma (DLBCL or DLBL), follicular lymphoma (FL), hairy cell leukemia (HCL), Hodgkin's lymphoma (HL or HD), immunoblastic large cell lymphoma, mantle cell lymphoma (MCL), multiple myeloma (MM), nodular lymphocyte predominant Hodgkin's lymphoma (NLPHL), non-Hodgkin's lymphoma (NHL), plasmablastic lymphoma, plasma cell neoplasma, plasma cell myeloma, precursor B-lymphoblastic lymphoma (B-LBL), small lymphocytic lymphoma (SLL), T-cell large granular lymphocyte leukemia (T-LGLL), T-cell lymphoma (TCL), T-cell prolymphocytic leukemia (T-PLL), and Waldenström's macroglobulinemia (WM).

Among certain embodiments of the present invention is the use of one or more compositions of matter of the present invention in the treatment or prevention (e.g. a pharmaceutical composition) of a cancer, tumor, or immune disorder. Among certain embodiments of the present invention is the use of one or more compositions of matter of the present invention (e.g. a pharmaceutical composition) in the manufacture of a medicament for the treatment or prevention of a cancer, tumor, or immune disorder.

Among certain embodiments of the present invention is a method of producing a CD20-binding protein, the method comprising the step of purifying a CD20-binding protein or polypeptide component of the CD20-binding protein using a chitin binding interaction. In certain further embodiments, the purifying step of the method involves the protein comprising or consisting essentially of any one of the polypeptides shown in SEQ ID NOs: 90-102.

Certain embodiments of the CD20-binding proteins of the present invention may be utilized for the delivery of additional exogenous material into a cell physically coupled with an extracellular CD20 target biomolecule of the CD20-binding protein of the present invention. Additionally, the present invention provides a method for delivering exogenous material to the inside of a CD20+ cell(s) comprising contacting the cell(s), either in vitro or in vivo, with a CD20-binding protein, pharmaceutical composition, and/or diagnostic composition of the present invention. The present invention further provides a method for delivering exogenous material to the inside of a CD20+ cell(s) in a patient in need thereof, the method comprising the step of administering to the patient a CD20-binding protein of the present invention (with or without cytotoxic activity), wherein the target cell(s) is physically coupled with an extracellular CD20 target biomolecule of the CD20-binding protein.

Among certain embodiments of the present invention is a method of using a CD20-binding protein of the present invention comprising a detection promoting agent for the collection of information useful in the diagnosis, prognosis, or characterization of a disease, disorder, or condition. Among certain embodiments of the present invention is a method of detecting a cell using a CD20-binding protein and/or diagnostic composition of the present invention comprising the steps of contacting a cell with the CD20-binding protein and/or diagnostic composition of the present invention and detecting the presence of the CD20-binding protein and/or diagnostic composition. In certain embodiments, the step of contacting the cell(s) occurs in vitro and/or ex vivo. In certain embodiments, the step of contacting the cell(s) occurs in vivo. In certain embodiments, the step of detecting the cell(s) occurs in vitro and/or ex vivo. In certain embodiments, the step of detecting the cell(s) occurs in vivo.

Among certain embodiments of the present invention are kits comprising a composition of matter of the present invention, and optionally, instructions for use, additional reagent(s), and/or pharmaceutical delivery device(s).

These and other features, aspects and advantages of the present invention will become better understood with regard to the following description, appended claims, and accompanying figures. The aforementioned elements of the present invention may be combined or removed freely in order to make other embodiments, without any statement to object such combination or removal hereinafter.

BRIEF DESCRIPTION OF THE FIGURES

FIG. 1 shows the general architecture of exemplary CD20-binding proteins of the present invention.

FIG. 2 graphically shows the change in total body luminescence over time with the administration of different dosages of αCD20scFv1::SLT-1A version 1 and αCD20scFv1::SLT-1A version 2 in a disseminated Raji-luc xenograft model. Administration of buffer-only samples was used as a negative control group.

FIG. 3 graphically shows the increased survival of Raji-luc xenograft model mice with the administration of different dosages of αCD20scFv1::SLT-1A version 1 and αCD20scFv1::SLT-1A version 2 as compared to a buffer-only negative control.

FIG. 4 graphically shows the change in tumor volume with the administration of different dosages of αCD20scFv1::SLT-1A version 1 and αCD20scFv1::SLT-1A version 2 in a Raji subcutaneous xenograft model over time.

FIG. 5 shows dose-dependent B-cell depletion over time in a non-human primate study using different dosages of αCD20scFv1::SLT-1A version 1. Specifically, the subsets of CD20+ B-cells that expressed CD21 were analyzed.

FIG. 6 shows dose-dependent B-cell depletion over time in a non-human primate study using different dosages of αCD20scFv1::SLT-1A version 1. Specifically, the subsets of CD20+ B-cells that did not express CD21 were analyzed.

DETAILED DESCRIPTION OF THE INVENTION

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope of the invention to those skilled in the art.

In order that the present invention may be more readily understood, certain terms are defined below. Additional definitions may be found within the detailed description of the invention.

As used in the specification and the appended claims, the terms "a" "an" and "the" include both singular and the plural referents unless the context clearly dictates otherwise.

As used in the specification and the appended claims, the term "and/or" when referring to two species, A and B, means at least one of A and B. As used in the specification and the appended claims, the term "and/or" when referring to greater than two species, such as A, B, and C, means at least one of A, B, or C, or at least one of any combination of A, B, or C (with each species in singular or multiple possibility).

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout this specification, the term "including" is used to mean "including but not limited to." "Including" and "including but not limited to" are used interchangeably.

The term "amino acid residue" or "amino acid" includes reference to an amino acid that is incorporated into a protein, polypeptide, or peptide. The term "polypeptide" includes any polymer of amino acids or amino acid residues. The term "polypeptide sequence" refers to a series of amino acids or amino acid residues which physically comprise a polypeptide. A "protein" is a macromolecule comprising one or more polypeptides or polypeptide "chains." A "peptide" is a small polypeptide of sizes less than a total of 15-20 amino acid residues. The term "amino acid sequence" refers to a series of amino acids or amino acid residues which physically comprise a peptide or polypeptide depending on the length. Unless otherwise indicated, polypeptide and protein sequences disclosed herein are written from left to right representing their order from an amino terminus to a carboxy terminus.

The terms "amino acid," "amino acid residue," "amino acid sequence," or polypeptide sequence include naturally occurring amino acids (including L and D isosteriomers) and, unless otherwise limited, also include known analogs of natural amino acids that can function in a similar manner as naturally occurring amino acids, such as, e.g., selenocysteine, pyrrolysine, N-formylmethionine, gamma-carboxyglutamate, hydroxyprolinehypusine, pyroglutamic acid, and selenomethionine. The amino acids referred to herein are described by shorthand designations as follows in Table A:

TABLE A

| Amino Acid Nomenclature | | |
|---|---|---|
| Name | 3-letter | 1-letter |
| Alanine | Ala | A |
| Arginine | Arg | R |
| Asparagine | Asn | N |
| Aspartic Acid or Aspartate | Asp | D |
| Cysteine | Cys | C |
| Glutamic Acid or Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The phrase "conservative substitution" with regard to a polypeptide, refers to a change in the amino acid composition of the polypeptide that does not substantially alter the function and structure of the overall polypeptide (see Creighton, *Proteins: Structures and Molecular Properties* (W. H. Freeman and Company, New York (2nd ed., 1992)).

As used herein, the term "expressed," "expressing" or "expresses" refers to translation of a polynucleotide or nucleic acid into a polypeptide or protein. The expressed polypeptides or proteins may remain intracellular, become a component of the cell surface membrane or be secreted into an extracellular space.

As used herein, cells which express a significant amount of CD20 at least one cellular surface are "CD20 positive cells" or "CD20+ cells" and are cells physically coupled to significant amounts of the extracellular target biomolecule CD20. A significant amount of CD20 is defined below in Section III-C.

As used herein, the symbol "α" is shorthand for an immunoglobulin-type binding region capable of binding to the biomolecule following the symbol. The symbol "α" is used to refer to the functional characteristic of an immunoglobulin-type binding region based on its capability of binding to the biomolecule following the symbol.

The symbol "::" means the polypeptide regions before and after it are physically linked together to form a continuous polypeptide.

The term "selective cytotoxicity" with regard to the cytotoxic activity of a CD20-binding protein refers to the relative levels of cytotoxicity between a targeted cell population and a non-targeted bystander cell population, which can be expressed as a ratio of the half-maximal cytotoxic concentration ($CD_{50}$) for a targeted cell type over the $CD_{50}$ for an untargeted cell type to show preferentially of cell killing of the targeted cell type.

For purposes of the present invention, the term "effector" means providing a biological activity, such as cytotoxicity, biological signaling, enzymatic catalysis, subcellular routing, and/or intermolecular binding resulting in the recruit of a factors and/or allosteric effects.

For purposes of the present invention, the phrase "derived from" means that the polypeptide region comprises amino acid sequences originally found in a protein and which may now comprise additions, deletions, truncations, or other alterations from the original sequence such that overall function and structure are substantially conserved.

For purposes of the present invention, a Shiga toxin effector function is a biological activity conferred by a polypeptide region derived from a Shiga toxin A Subunit. Non-limiting examples of Shiga toxin effector functions include cellular internalization, subcellular routing, catalytic activity, and cytotoxicity. Shiga toxin catalytic activities include, for example, ribosome inactivation, protein synthesis inhibition, N-glycosidase activity, polynuclcotide:adenosine glycosidase activity, RNAase activity, and DNAase activity. Shiga toxins are ribosome inactivating proteins (RIPs). RIPs can depurinate nucleic acids, polynucleosides, polynucleotides, rRNA, ssDNA, dsDNA, mRNA (and polyA), and viral nucleic acids (Barbieri L et al., *Biochem J* 286: 1-4 (1992); Barbieri L et al., *Nature* 372: 624 (1994); Ling J et al., *FEBS Lett* 345: 143-6 (1994); Barbieri L et al., *Biochem J* 319: 507-13 (1996); Roncuzzi L, Gasperi-Campani A, *FEBS Lett* 392: 16-20 (1996); Stirpe F et al., *FEBS Lett* 382: 309-12 (1996); Barbieri L et al., Nucleic Acids Res 25: 518-22 (1997); Wang P, Turner N, *Nucleic Acids Res* 27: 1900-5 (1999); Barbieri L et al., *Biochim Biophys Acta* 1480: 258-66 (2000); Barbieri L et al., *J Biochem* 128: 883-9 (2000); Bagga S et al., *J Biol Chem* 278: 4813-20 (2003); Picard D et al., *J Biol Chem* 280: 20069-75 (2005)). Some RIPs show antiviral activity and superoxide dismutase activity (Erice A et al., *Antimicrob Agents Chemother* 37: 835-8 (1993); Au T et al., *FEBS Lett* 471: 169-72 (2000); Parikh B. Tumer N. *Mini Rev Med Chem* 4: 523-43 (2004); Sharma N et al., *Plant Physiol* 134: 171-81 (2004)). Shiga toxin catalytic activities have been observed both in vitro and in vivo. Assays for Shiga toxin effector activity can measure various activities, such as, e.g., protein synthesis inhibitory activity, depurination activity, inhibition of cell growth, cytotoxicity, supercoiled DNA relaxation activity, and nuclease activity.

As used herein, the retention of Shiga toxin effector function refers to a level of Shiga toxin functional activity, as measured by an appropriate quantitative assay with reproducibility comparable to a wild-type Shiga toxin effector region control. For ribosome inhibition, Shiga toxin effector function is exhibiting an $IC_{50}$ of 10,000 picomolar (pM) or less. For cytotoxicity in a target positive cell kill assay, Shiga toxin effector function is exhibiting a $CD_{50}$ of 1,000 nanomolar (nM) or less, depending on the cell type and its expression of an extracellular CD20 target bound specifically by that CD20-binding protein of the invention.

INTRODUCTION

The present invention provides CD20-binding proteins that bind to extracellular CD20 antigens present on a cellular surface and internalize from a cell membrane location to the interior of the cell. The present invention solves problems for engineering therapeutics targeting CD20 whose effectiveness require an efficient CD20-mediated cell internalization mechanism because Shiga toxin derived effector regions are capable of inducing the cellular internalization of CD20. Certain of the disclosed CD20-binding proteins induce the rapid cellular internalization of cell-surface CD20. Certain of the disclosed CD20-binding proteins potently kill cells which express CD20 on their surface. In addition, certain of the disclosed CD20-binding proteins are capable of precisely delivering additional exogenous material in the form of molecular cargos to the interior of cells which express CD20 on their surface. Thus, the present invention expands the universe of immunotoxin-drugable targets to include CD20 and provides a novel modality for treating diseases, disorders, and conditions involving CD20 positive cells, such as, e.g., malignancies involving cells derived from B-cell lineages and autoimmune diseases resulting from B-cell dysregulation.

The General Structure of the CD20-Binding Protein

The present invention provides various CD20-binding proteins for targeted cellular internalization into CD20 expressing cell types. A CD20-binding protein of the invention comprises 1) a CD20 binding region capable of specifically binding an extracellular part of CD20 and 2) a Shiga toxin effector region comprising a polypeptide derived from the amino acid sequence of the A Subunit of at least one member of the Shiga toxin family. The CD20 binding regions of the CD20-binding proteins of the invention are capable of specifically binding to at least one extracellular part of a CD20 molecule physically coupled to a eukaryotic cell. The Shiga toxin effector regions of the CD20-binding proteins of the invention may be cytotoxic and non-toxic. In addition, the CD20-binding proteins of the present invention may optionally comprise one or more additional exogenous materials. This general structure is modular in that various CD20 binding regions can be directly linked to Shiga-toxin-Subunit-A derived effector regions and additional exogenous materials at various positions or with different linkers between them to produce variations of the same general structure (see e.g. FIG. 1).

CD20 Binding Regions Capable of Specifically Binding an Extracellular Part of CD20

The CD20-binding proteins of the invention each comprise a CD20 binding region capable of specifically binding to an extracellular part of CD20. The CD20 binding region may comprise one or more various peptidic or polypeptide moieties, such as randomly generated peptide sequences, naturally occurring ligands or derivatives thereof, immunoglobulin derived domains, synthetically engineered scaffolds as alternatives to immunoglobulin domains, and the like. In certain embodiments, a CD20-binding protein of the invention comprises a CD20 binding region comprising an immunoglobulin-type binding region comprising one or more polypeptides capable of selectively and specifically binding an extracellular part of CD20.

For purposes of the present invention, the term "CD20 binding region" refers to a peptide or polypeptide region capable of specifically binding an extracellular part of a CD20 molecule. While the name CD20 might refer to multiple proteins with related structures and polypeptide sequences from various species, for the purposes of the present invention the term "CD20" refers to the B-lymphocyte antigen CD20 proteins present in mammals whose exact sequence might vary slightly based on the isoform and from individual to individual. Alternative names for CD20, as recognized in the art, include B-lymphocyte surface antigen B1, Leu-16 and Bp35. For example, in humans CD20 refers to the protein represented by the predominant polypeptide sequence UnitProt P11836 and NCBI accession NP 690605.1; however, different isoforms and variants may exist. The polypeptide sequences of certain CD20 proteins from various species have been described, such as from bats, cats, cattle, dogs, mice, marmosets, and rats, and can be predicted by bioinformatics in numerous other species based on genetic homology (e.g. CD20 has been predicted in various primates, including baboons, macaques, gibbons, chimpanzees, and gorillas) (see Zuccolo J et al., PLoS One 5: e9369 (2010) and NCBI protein database (National Center for Biotechnology Information, U.S.). A skilled worker will be able to identify a CD20 protein in mammals, even if it differs from the referenced sequences.

CD20 is expressed by B-cells within certain cell developmental stages that give rise to non-Hodgkin's lymphoma (NHL) and chronic lymphocytic leukemia (CLL); however CD20 is not expressed on hematopoietic stem cells or on mature plasma cells (van Meerten T et al., *Clin Cancer Res* 12: 4027-35 (2006)). An attractive characteristic of CD20 for therapeutic purposes is that it represents a quasi-universal target of lymphoma cells for being expressed on approximately 90% of B-cell non-Hodgkin's lymphomas (Anderson K et al., *Blood* 63: 2825-33 (1984); Press O et al., *Cancer Res* 49: 4906-12 (1989); Press O et al., *Blood*. 83: 1390-7 (1994); Manches O et al., *Blood* 101: 949-54 (2003)). Additional attractive characteristics of CD20 are its high expression on the plasma membrane of lymphoma cells and its multiple, extracellular, antigenic epitopes in close proximity to the plasma membrane (Teeling J et al., *J Immunol* 177: 362-71 (2006); Lim S et al., *Haemalologica* 95: 135-43 (2010)).

An extracellular part of a CD20 molecule refers to a portion of its structure exposed to the extracellular environment when the CD20 molecule is present in a cell membrane, such as, e.g., CD20 molecules natively expressed by a cell at a cellular surface. In this context, exposed to the extracellular environment means that part of the CD20 molecule is accessible by, e.g., an antibody or at least a binding moiety smaller than an antibody such as a single-domain antibody domain, a nanobody, a heavy-chain antibody domain derived from camelids or cartilaginous fishes, a single-chain variable fragment, or any number of engineered alternative scaffolds to immunoglobulins (see below). The exposure of a part of CD20 may be empirically determined by the skilled worker using methods known in the art. Note that some portion of CD20, which was predicted not to be accessible to an antibody in the extracellular space based on its location within CD20, was empirically shown to be accessible by a monoclonal antibody (Teeling J et al., *J. Immunol*. 177: 362-71 (2006)).

CD20 binding regions may be derived from antibody or antibody-like structures; however, alternative scaffolds from other sources are contemplated as a source of CD20 binding regions within the scope of the present invention. In certain embodiments, the CD20 binding region is derived from an immunoglobulin-derived binding region, such as an antibody paratope. In certain other embodiments, the CD20 binding region comprises an immunoglobulin-type binding region that is an engineered polypeptide not derived from any immunoglobulin domain.

According to one specific, but non-limiting aspect, the CD20 binding region may comprise an immunoglobulin-type binding region. The term "immunoglobulin-type binding region" as used herein refers to a polypeptide region capable of binding one or more target biomolecules, such as an antigen or epitope. Immunoglobulin-type binding regions are functionally defined by their ability to bind to target molecules, and all the immunoglobulin-type binding regions of the present invention are capable of binding CD20. Immunoglobulin-type binding regions are commonly derived from antibody or antibody-like structures; however, alternative scaffolds from other sources are contemplated within the scope of the term.

Immunoglobulin (Ig) proteins have a structural domain known as an Ig domain. Ig domains range in length from about 70-110 amino acid residues and possess a characteristic Ig-fold, in which typically 7 to 9 antiparallel beta strands arrange into two beta sheets which form a sandwich-like structure. The Ig fold is stabilized by hydrophobic amino acid interactions on inner surfaces of the sandwich and highly conserved disulfide bonds between cysteine residues in the strands. Ig domains may be variable (IgV or V-set), constant (IgC or C-set) or intermediate (IgI or I-set). Some Ig domains may be associated with a complementarity determining region or complementary determining region (CDR), also referred to as antigen binding region (ABR), which is important for the specificity of antibodies binding to their epitopes. Ig-like domains are also found in non-immunoglobulin proteins and are classified on that basis as members of the Ig superfamily of proteins. The HUGO Gene Nomenclature Committee (HGNC) provides a list of members of the Ig-like domain containing family.

An immunoglobulin-type binding region may be a polypeptide sequence of antibody or antigen-binding fragment thereof wherein the amino acid sequence has been varied from that of a native antibody or an Ig-like domain of a non-immunoglobulin protein, for example by molecular engineering or library screening. Because of the relevance of recombinant DNA techniques and in vitro library screening in the generation of immunoglobulin-type binding regions, antibodies can be redesigned to obtain desired characteristics, such as smaller size, cell entry, or other therapeutic improvements. The possible variations are many and may range from the changing of just one amino acid to the complete redesign of, for example, a variable region. Typically, changes in the variable region will be made in order to improve the antigen-binding characteristics, improve variable region stability, or reduce the potential for immunogenic responses.

There are numerous immunoglobulin-type binding regions that bind an extracellular part of CD20 contemplated according to the present invention. In certain embodiments, the immunoglobulin-type binding region is derived from an immunoglobulin binding region, such as an antibody paratope capable of binding an extracellular part of CD20. In certain other embodiments, the immunoglobulin-type binding region comprises an engineered polypeptide not derived from any immunoglobulin domain but that functions like an immunoglobulin binding region by providing high-affinity binding to an extracellular part of CD20. This engineered polypeptide may optionally include polypeptide scaffolds comprising or consisting essentially of complementary determining regions from immunoglobulins as described herein.

There are numerous immunoglobulin-derived binding regions and non-immunoglobulin engineered polypeptides in the prior art that are useful for targeting the CD20-binding proteins of the invention to CD20 expressing cells. In certain embodiments, the immunoglobulin-type binding region of the present CD20-binding proteins is selected from the group which includes single-domain antibody domains (sdAb) fragments, nanobodies, heavy-chain antibody domains derived from camelids ($V_H H$ fragments), bivalent nanobodies, heavy-chain antibody domains derived from cartilaginous fishes, immunoglobulin new antigen receptors (IgNARs), $V_{NAR}$ fragments, single-chain variable (scFv) fragments, bispecific tandem scFv fragments, disulfide stabilized antibody variable (Fv) fragments, disulfide stabilized antigen-binding (Fab) fragments consisting of the $V_L$, $V_H$, $C_L$ and $C_H 1$ domains, divalent F(ab')2 fragments, Fd fragments consisting of the heavy chain and $C_H 1$ domains, single chain Fv-$C_H 3$ minibodies, bispecific minibodies, dimeric $C_H 2$ domain fragments ($C_H 2D$), Fc antigen binding domains (Fcabs), isolated complementary determining region 3 (CDR3) fragments, constrained framework region 3, CDR3, framework region 4 (FR3-CDR3-FR4) polypeptides, small modular immunopharmaceutical (SMIP) domains, and any genetically manipulated counterparts of the foregoing that retain its paratope and binding function (see, Weiner L, *Cell* 148: 1081-4 (2012); Ahmad Z et al., *Clin Dev Immunol* 2012: 980250 (2012), for reviews).

In accordance with certain other embodiments, the immunoglobulin-type binding region of the CD20-binding proteins of the invention comprises an immunoglobulin-derived binding region that does not comprise an Fc region or any Fc region effector domain which retains an Fc region effector function. For certain embodiments of the CD20-binding proteins of the present invention, the CD20-binding protein does not comprise an Fc region or Fc region effector domain which retains an Fc function.

As used herein, the phrase "Fe region" refers to the fragment crystallizable region or Fc (Fragment, crystallizable region) which is a polypeptide domain present in immunoglobulins, such as, e.g., the immunoglobulin isotypes IgA, IgD. IgE, IgG, and IgM. Fc regions interact with the complement system of the immune system and/or Fc receptors present on immune cells, such as, e.g., T-cells, basophils, eosinophils, macrophagocytes (macrophages), mast cells, neutrophils, and natural killer cells (NK cells) (see e.g. van der Kolk L et al., *Br J Haematol* 115: 807-11 (2001); Cartron G et al., *Blood* 99: 754-8 (2002); Smith M, *Oncogene* 22: 7359-68 (2003): Lands L et al., *Pediatr Nephrol* 25: 1001-3 (2010)). Fc region effector functions include activating T-cells, stimulating the release of inflammatory mediators such as cytokines like TNF-alpha, initiating complement dependent cytotoxicity (CDC), antibody-dependent cytotoxicity (ADCC), eventual phagocytosis, and possible immunization effects (Selenko N, et al., *Leukemia* 15: 1619-26 (2001); Cartron G et al., *Blood* 99:754-8 (2002); Hainsworth J et al., *J Clin Oncol* 20: 4261-7 (2002); Weng W, Levy R, *J Clin Oncol* 21: 3940-7 (2003); Cartron G et al., *Blood* 104: 2635-42 (2004); Glennie M et al., *Mol Immunol* 44: 3823-37 (2007); Hilchey S et al., *Blood* 113: 3809-12 (2009); Abe's R et al., *Blood* 116: 926-34 (2010); Lim S et al., *Haemalologica* 95: 135-43 (2010)).

Fc regions may be engineered into recombinant polypeptides and proteins, such as, e.g., fusions of antigen-binding fragments and Fc regions in synthetic F(ab')2 and Fcabs.

The CD20-binding proteins of the invention that do not comprise any Fc region or Fc region effector domain which retains an Fc region effector function may function equally well in patients with impaired Fc-FcyR-dependent mechanisms, such as immunocompromised patients, as in other patients, such as immunocompetent patients.

In accordance with certain other embodiments, the immunoglobulin-type binding region of the CD20-binding proteins of the invention may include engineered, alternative scaffolds to immunoglobulin domains that exhibit similar functional characteristics, such as high-affinity and specific binding to CD20, and enable the engineering of improved characteristics, such as greater stability or reduced immunogenicity. For certain embodiments of the CD20-binding proteins of the invention, the immunoglobulin-type binding region is selected from the group which includes engineered, fibronection-derived, $10^{th}$ fibronectin type III (10Fn3) domain (monobodies, AdNectins™, or AdNexins™); engineered, tenacsin-derived, tenacsin type III domain (Centryns™); engineered, ankyrin repeat motif containing polypeptide (DARPins™); engineered, low-density-lipoprotein-receptor-derived, A domain (LDLR-A) (Avimers™); lipocalin (anticalins); engineered, protease inhibitor-derived, Kunitz domain; engineered, Protein-A-derived. Z domain (Affibodies™); engineered, gamma-B crystalline-derived scaffold or engineered, ubiquitin-derived scaffold (Affilins); Sac7d-derived polypeptides (Nanoffitins® or affitins); engineered, Fyn-derived, SH2 domain (Fynomers®); and engineered antibody mimic and any genetically manipulated counterparts of the foregoing that retains its binding functionality (Wörn A, Plückthun A, *J Mol Biol* 305: 989-1010 (2001); Xu L et al., *Chem Biol* 9: 933-42 (2002); Wikman M et al., *Protein Eng Des Sel* 17: 455-62 (2004); Binz H et al., *Nat Biotechnol* 23: 1257-68 (2005); Holliger P, Hudson P, *Nat Biotechnol* 23: 1126-36 (2005); Gill D, Damle N, *Curr Opin Biotech* 17: 653-8 (2006); Koide A, Koide S, *Methods Mol Biol* 352: 95-109 (2007)). For example, the engineered Fn3(CD20) is an engineered, alternative scaffold CD20 binding region which exhibits high affinity binding to CD20 expressing cells (Natarajan A et al., *Clin Cancer Res* 19: 6820-9 (2013)).

Any of the above CD20 binding regions may be used as a component of the present invention so long as the CD20 binding region component has a dissociation constant of $10^{-5}$ to $10^{-12}$ moles/liter, preferably less than 200 nanomolar (nM), towards an extracellular part of CD20 as described herein.

It will be appreciated by the skilled worker that any CD20 binding region of an immunoglobulin type capable of binding an extracellular part of CD20 may be used to design or select an immunoglobulin-type binding region to be linked to the Shiga toxin effector region to produce a CD20-binding protein of the invention.

B. Shiga Toxin Effector Regions Derived from a Subunits of Members of the Shiga Toxin Family For purposes of the present invention, the phrase "Shiga toxin effector region" refers to a polypeptide region derived from a Shiga toxin A Subunit of a member of the Shiga toxin family that is capable of exhibiting at least one Shiga toxin function. Shiga toxin functions include, e.g., cell entry, lipid membrane deformation, directing subcellular routing, avoiding degradation, catalytically inactivating ribosomes, effectuating cytotoxicity, and effectuating cytostatic effects.

A member of the Shiga toxin family refers to any member of a family of naturally occurring protein toxins which are structurally and functionally related, notably toxins isolated from *S. dysenteriae* and *E. coli* (Johannes, *Nat Rev Microbiol* 8: 105-16 (2010)). For example, the Shiga toxin family encompasses true Shiga toxin (Stx) isolated from *S. dysenteriae* serotype 1, Shiga-like toxin 1 variants (SLT1 or Stx1 or SLT-1 or Slt-I) isolated from serotypes of enterohemorrhagic *E. coli*, and Shiga-like toxin 2 variants (SLT2 or Stx2 or SLT-2) isolated from scrotypes of enterohemorrhagic *E. coli*. SLT1 differs by only one residue from Stx, and both have been referred to as Verocytotoxins or Verotoxins (VTs) (O'Brien, *Curr Top Microbiol Immunol* 180: 65-94 (1992)). Although SLT1 and SLT2 variants are only about 53-60% similar to each other at the amino acid sequence level, they share mechanisms of enzymatic activity and cytotoxicity common to the members of the Shiga toxin family (Johannes, *Nat Rev Microbiol* 8: 105-16 (2010)). Over 39 different Shiga toxins have been described, such as the defined subtypes Stx1a, Stx1c, Stx1d, and Stx2a-g (Scheutz F et al., *J Clin Microbiol* 50: 2951-63 (2012)). Members of the Shiga toxin family are not naturally restricted to any bacterial species because Shiga-toxin-encoding genes can spread among bacterial species via horizontal gene transfer (Strauch E et al., *Infect Immun* 69: 7588-95 (2001); Zhaxybayeva O, Doolittle W, *Curr Biol.* 21: R242-6 (2011)). As an example of interspecies transfer, a Shiga toxin was discovered in a strain of *A. haemolyticus* isolated from a patient (Grotiuz G et al., *J Clin Microbiol* 44: 3838-41 (2006)). Once a Shiga toxin encoding polynucleotide enters a new subspecies or species, the Shiga toxin amino acid sequence is presumed to be capable of developing slight sequence variations due to genetic drift and/or selective pressure while still maintaining a mechanism of cytotoxicity common to members of the Shiga toxin family (see Scheutz, *J Clin Microbiol* 50: 2951-63 (2012)).

Shiga toxin effector regions of the invention comprise or consist essentially of a polypeptide derived from a Shiga toxin A Subunit dissociated from any form of its native Shiga toxin B Subunit. In addition, the CD20-binding proteins of the present invention do not comprise any polypeptide comprising or consisting essentially of a functional binding domain of a Shiga toxin B subunit. Rather, the Shiga toxin A Subunit derived regions are functionally associated with heterologous CD20 binding regions to effectuate cell targeting to CD20 expressing cells.

For purposes of the present invention, the phrase "Shiga toxin effector region" refers to a polypeptide region derived from a Shiga toxin A Subunit of a member of the Shiga toxin family that is capable of exhibiting at least one Shiga toxin function. Shiga toxin functions include, e.g., cell entry, lipid membrane deformation, directing subcellular routing, avoiding degradation, catalytically inactivating ribosomes, effectuating cytotoxicity, and effectuating cytostatic effects.

As used herein, the retention of "significant" Shiga toxin effector function refers to a level of Shiga toxin functional activity, as measured by an appropriate quantitative assay with reproducibility comparable to a wild-type Shiga toxin effector polypeptide control. For in vitro ribosome inhibition, significant Shiga toxin effector function is exhibiting an $IC_{50}$ of 300 pM or less depending on the source of the ribosomes (e.g. bacteria, archaea, or eukaryote (algae, fungi, plants, or animals)). This is significantly greater inhibition as compared to the approximate $IC_{50}$ of 100,000 pM for the catalytically inactive SLT-1A 1-251 double mutant (Y77S/E167D). For cytotoxicity in a target positive cell kill assay in laboratory cell culture, significant Shiga toxin effector function is exhibiting a $CD_{50}$ of 100, 50, or 30 nM or less, depending on the cell line and its expression of the appropriate extracellular CD20 target. This is significantly greater cytotoxicity to the appropriate target cell line as compared to SLT-1A alone, without a cell targeting binding region, which has a $CD_{50}$ of 100-10,000 nM, depending on the cell line.

For some samples, accurate values for either $IC_{50}$ or $CD_{50}$ might be unobtainable due to the inability to collect the required data points for an accurate curve fit. Inaccurate $IC_{50}$ and/or $CD_{50}$ values should not be considered when determining significant Shiga toxin effector function activity. Data insufficient to accurately fit a curve as described in the analysis of the data from exemplary Shiga toxin effector function assays, such as, e.g., assays described in the Examples, should not be considered as representative of actual Shiga toxin effector function. For example, theoretically, neither an $IC_{50}$ nor $CD_{50}$ can be determined if greater than 50% ribosome inhibition or cell death, respectively, does not occur in a concentration series for a given sample.

The failure to detect activity in Shiga toxin effector function may be due to improper expression, polypeptide folding, and/or polypeptide stability rather than a lack of cell entry, subcellular routing, and/or enzymatic activity. Assays for Shiga toxin effector functions may not require much polypeptide of the invention to measure significant amounts of Shiga toxin effector function activity. To the extent that an underlying cause of low or no effector function is determined empirically to relate to protein expression or stability, one of skill in the art may be able to compensate for such factors using protein chemistry and molecular engineering techniques known in the art, such that a Shiga toxin functional effector activity may be restored and measured. As examples, improper cell-based expression may be compensated for by using different expression control sequences; improper polypeptide folding and/or stability may benefit from stabilizing terminal sequences, or compensatory mutations in non-effector regions which stabilize the three dimensional structure of the protein, etc. When new assays for individual Shiga toxin functions become available, Shiga toxin effector polypeptides may be analyzed for any level of those Shiga toxin effector functions, such as for being within a certain-fold activity of a wild-type Shiga toxin effector polypeptide. Examples of meaningful activity differences are, e.g., Shiga toxin effector regions that have 1000-fold or 100-fold or less the activity of a wild-type Shiga toxin effector polypeptide; or that have 3-fold to 30-fold or more activity compared to a functional knock-down or knockout Shiga toxin effector polypeptide.

Certain Shiga toxin effector functions are not easily measurable, e.g. subcellular routing functions. Currently there is no routine, quantitative assay to distinguish whether the failure of a Shiga toxin effector polypeptide to be cytotoxic is due to improper subcellular routing, but at a time when tests are available, Shiga toxin effector polypeptides may be analyzed for any significant level of subcellular routing as compared to the appropriate wild-type Shiga toxin effector region.

It should be noted that even if the cytotoxicity of a Shiga toxin effector polypeptide is reduced relative to wild-type, in practice, applications using attenuated Shiga toxin effector polypeptides may be equally or more effective than those using wild-type Shiga toxin effector polypeptides because the highest potency variants might exhibit undesirable effects which are minimized in reduced potency variants. Wild-type Shiga toxin effector polypeptides are very potent, being able to kill with only one molecule reaching the cytosol or perhaps 40 molecules being internalized. Shiga toxin effector polypeptides with even considerably reduced Shiga toxin effector functions, such as, e.g., subcellular routing or cytotoxicity, as compared to wild-type Shiga toxin effector polypeptides may still be potent enough for practical applications involving targeted cell killing and/or specific cell detection.

In certain embodiments, a Shiga toxin effector region of the invention may comprise or consist essentially of a full length Shiga toxin A Subunit (e.g. SLT-1A (SEQ ID NO:1), StxA (SEQ ID NO:2), or SLT-2A (SEQ ID NO:3)), noting that naturally occurring Shiga toxin A Subunits may comprise precursor forms containing signal sequences of about 22 amino acids at their amino-terminals which are removed to produce mature Shiga toxin A Subunits and are recognizable to the skilled worker. One specific example of a "toxin effector region" is one that is derived from the A chain of Shiga-like toxin 1 (SLT-1) (SEQ ID NO:1). The A chain of SLT-1 is composed of 293 amino acids with the enzymatic (toxic) domain spanning residues 1 to 239. In other embodiments, the Shiga toxin effector region of the invention comprises or consists essentially of a truncated Shiga toxin A Subunit which is shorter than a full-length Shiga toxin A Subunit.

Shiga-like toxin 1 A Subunit truncations are catalytically active, capable of enzymatically inactivating ribosomes in vitro, and cytotoxic when expressed within a cell (LaPointe, *J Biol Chem* 280: 23310-18 (2005)). The smallest Shiga toxin A Subunit fragment exhibiting full enzymatic activity is a polypeptide composed of residues 1-239 of Slt1A (LaPointe, *J Biol Chem* 280: 23310-18 (2005)). Although the smallest fragment of the Shiga toxin A Subunit reported to retain substantial catalytic activity was residues 75-247 of StxA (Al-Jaufy, *Infect Immun* 62: 956-60 (1994)), a StxA truncation expressed de novo within a eukaryotic cell requires only up to residue 240 to reach the cytosol and exert catalytic inactivation of ribosomes (LaPointe, *J Biol Chem* 280: 23310-18 (2005)).

Shiga toxin effector regions may commonly be less than the full length A subunit. It is preferred that the Shiga toxin effector region maintain the polypeptide region from amino acid position 77 to 239 (SLT-1A SEQ ID NO:1, StxA SEQ ID NO:2, or SLT-2A SEQ ID NO:3) or the equivalent in other A Subunits of members of the Shiga toxin family. For example, in certain embodiments of the invention, the Shiga toxin effector regions derived from SLT-1A may comprise or consist essentially of amino acids 75 to 251 of SEQ ID NO:1, 1 to 241 of SEQ ID NO:1, 1 to 251 of SEQ ID NO:1, or amino acids 1 to 261 of SEQ ID NO:1. Similarly, the Shiga toxin effector regions derived from Stx may comprise or consist essentially of amino acids 75 to 251 of SEQ ID NO:2, 1 to 241 of SEQ ID NO:2, 1 to 251 of SEQ ID NO:2, or amino acids 1 to 261 of SEQ ID NO:2. Additionally, the Shiga toxin effector regions derived from SLT-2 may comprise or consist essentially of amino acids 75 to 251 of SEQ ID NO:3, 1 to 241 of SEQ ID NO:3, 1 to 251 of SEQ ID NO:3, or amino acids 1 to 261 of SEQ ID NO:3.

The invention further provides variants of the CD20-binding proteins of the invention, wherein the Shiga toxin effector region differs from a naturally occurring Shiga toxin A Subunit by up to 1, 2, 3, 4, 5, 6, 7, 8, 9, 10, 15, 20, 25, 30, 35, 40 or more amino acid residues (but by no more than that which retains at least 85%, 90%, 95%, 99% or more amino acid sequence identity). Thus, a polypeptide region derived from an A Subunit of a member of the Shiga toxin family may comprise additions, deletions, truncations, or other alterations from the original sequence so long as at least 85%, 90%, 95%, 99% or more amino acid sequence identity is maintained to a naturally occurring Shiga toxin A Subunit.

Accordingly, in certain embodiments, the Shiga toxin effector region comprises or consists essentially of amino acid sequences having at least 55%, 60%, 65%, 70%, 75%, 80%, 85%, 90%, 95%, 97%, 98%, 99%, 99.5% or 99.7% overall sequence identity to a naturally occurring Shiga toxin A Subunit, such as SLT-1A (SEQ ID NO:1), Stx (SEQ ID NO:2), and/or SLT-2A (SEQ ID NO:3).

Optionally, either a full length or a truncated version of the Shiga toxin A Subunit may comprise one or more mutations (e.g. substitutions, deletions, insertions or inversions). In certain embodiments that are potently cytotoxic, the Shiga toxin effector region has sufficient sequence identity to retain cytotoxicity after entry into a cell, either by well-known methods of host cell transformation, transfection, infection or induction, or by internalization mediated by targeting immunoglobulin-type binding region linked with the Shiga toxin effector region. The most critical residues for enzymatic activity and/or cytotoxicity in the Shiga toxin A Subunits have been mapped to the following residue-positions: aspargine-75, tyrosine-77, glutamate-167, arginine-170, and arginine-176 among others (Di, *Toxicon* 57: 535-39 (2011)). In any one of the embodiments of the present invention, the Shiga toxin effector region may preferably but not necessarily maintain one or more conserved amino acids at positions, such as those found at positions 77, 167, 170, and 203 in StxA, SLT-1A, or the equivalent conserved position in other members of the Shiga toxin family which are typically required for cytotoxic activity. The capacity of a CD20-binding protein of the invention to cause cell death, e.g. its cytotoxicity, may be measured using any one or more of a number of assays well known in the art.

In certain embodiments of the invention, one or more amino acid residues may be mutated, inserted, or deleted in order to increase the enzymatic activity of the Shiga toxin effector region. For example, mutating residue-position alanine-231 in Stx1A to glutamate increased its enzymatic activity in vitro (Suhan M, Hovde C, *Infect Immun* 66: 5252-9 (1998)).

In certain embodiments of the invention, one or more amino acid residues may be mutated or deleted in order to reduce or eliminate cytotoxic activity of the Shiga toxin effector region. The cytotoxicity of the A Subunits of members of the Shiga toxin family may be abrogated or eliminated by mutation or truncation. The positions labeled tyrosine-77, glutamate-167, arginine-170, tyrosine-114, and tryptophan-203 have been shown to be important for the catalytic activity of Stx. Stx1, and Stx2 (Hovde C et al., *Proc Natl Acad Sci USA* 85: 2568-72 (1988); Deresiewicz R et al., *Biochemisty* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Slt-I A1 in a cell-free ribosome inactivation assay (LaPointe, *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe, *J Biol Chem* 280: 23310-18 (2005)).

This system is modular, in that various, diverse immunoglobulin-type CD20 binding regions can be used with the same Shiga toxin effector region to target different extracellular epitopes of CD20. In the above embodiments of CD20-binding proteins, the CD20 binding regions and Shiga toxin effector regions (which may be cytotoxic and/or harbor one or more mutations reducing or eliminating catalytic activity and/or cytotoxicity) may be directly linked to each other and/or suitably linked to each other via one or more intervening polypeptide sequences, such as with one or more linkers well known in the art and/or described herein. Optionally, a protein of the invention may further comprise a carboxy-terminal endoplasmic retention/retrieval signal motif, such as KDEL (SEQ ID NO:113).

For the purposes of the present invention, the specific order or orientation is not fixed for the Shiga toxin effector region and the CD20 binding region in relation to each other or the entire CD20-binding protein's N-terminal(s) and C-terminal(s) (see e.g. FIG. 1). The components of the CD20-binding proteins of the invention may be arranged in any order provided that the desired activities of the CD20 binding region and the Shiga toxin effector region are not eliminated. Desired activities include providing the CD20-binding protein with the ability, e.g., to bind CD20 expressing cells, induce cellular internalization, cause cytostasis, cause cytotoxicity, and/or deliver exogenous materials to the interiors of cells.

C. Endoplasmic Reticulum Retention/Retrieval Signal Motif of a Member of the KDEL Family In certain embodiments, the CD20-binding protein of the invention comprises a carboxy terminal endoplasmic reticulum retention/retrieval signal motif. For purposes of the present invention, the phrase "endoplasmic reticulum retention/retrieval signal motif," KDEL-type signal motif, or signal motif refers to any member of the KDEL family capable of functioning within a eukaryotic cell to promote subcellular localization of a protein to the endoplasmic reticulum via KDEL receptors.

The carboxy-terminal lysine-asparagine-glutamate-leucine (KDEL (SEQ ID NO:113)) sequence is a canonical, endoplasmic reticulum retention and retrieval signal motif for soluble proteins in eukaryotic cells and is recognized by KDEL receptors (see, Capitani M, Sallese M, *FEBS Lett* 583: 3863-71 (2009), for review). The KDEL family of signal motifs includes many KDEL-like motifs, such as HDEL (SEQ ID NO:114), RDEL (SEQ ID NO:115), WDEL (SEQ ID NO:116), YDEL (SEQ ID NO:117), HEEL (SEQ ID NO:118), KEEL (SEQ ID NO:119), REEL (SEQ ID NO:120), KFEL (SEQ ID NO:121), KIEL (SEQ ID NO:122), DKEL (SEQ ID NO:123), KKEL (SEQ ID NO:124), HNEL (SEQ ID NO:125), HTEL (SEQ ID NO:126), KTEL (SEQ ID NO:127), and HVEL (SEQ ID NO:128), all of which are found at the carboxy-terminals of proteins which are known to be residents of the lumen of the endoplasmic reticulum of organisms throughout multiple phylogenetic kingdoms (Munro S, Pelham H, *Cell* 48: 899-907 (1987); Raykhel I et al., *J Cell Biol* 179: 1193-204 (2007)). The KDEL signal motif family includes at least 46 polypeptide variants shown using synthetic constructs (Raykhel, *J Cell Biol* 179: 1193-204 (2007)). Additional KDEL signal motifs include ALEDEL (SEQ ID NO:129), HAEDEL (SEQ ID NO:130), HLEDEL (SEQ ID NO:131), KLEDEL (SEQ ID NO:132), IRSDEL (SEQ ID NO:133), ERSTEL (SEQ ID NO:134), and RPSTEL (SEQ ID NO:135) (Alanen H et al., *J Mol Biol* 409: 291-7 (2011)). A generalized consensus motif representing the majority of KDEL signal motifs has been described as [KRHQSA]-[DENQ]-E-L (SEQ ID NO:136) (Hulo N et al., *Nucleic Acids Res* 34: D227-30 (2006)).

Proteins containing KDEL family signal motifs are bound by KDEL receptors distributed throughout the Golgi complex and transported to the endoplasmic reticulum by a microtubule-dependent mechanism for release into the lumen of the endoplasmic reticulum (Griffiths G et al., *J Cell Biol* 127: 1557-74 (1994); Miesenböck G. Rothman J, *J Cell Biol* 129: 309-19 (1995)). KDEL receptors dynamically cycle between the Golgi complex and endoplasmic reticulum (Jackson M et al., *EMBO. J.* 9: 3153-62 (1990); Schutze M et al., *EMBO J.* 13: 1696-1705 (1994)).

For purposes of the present invention, the members of the KDEL family include synthetic signal motifs able to function within a eukaryotic cell to promote subcellular localization of a protein to the endoplasmic reticulum via KDEL receptors. In other words, some members of the KDEL family might not occur in nature or have yet to be observed in nature but have or may be constructed and empirically verified using methods known in the art; see e.g., Raykhel I et al., *J Cell Biol* 179: 1193-204 (2007).

As a component of the CD20-binding proteins of the invention, the KDEL-type signal motif is physically located, oriented, or arranged within the CD20-binding protein such that it is on a carboxy-terminal.

D. Linkages Connecting Polypeptide Components of the CD20-Binding Proteins of the Invention and/or their Subcomponents Individual polypeptide and/or protein components of the invention, e.g., the CD20 binding regions and Shiga toxin effector regions (which may be cytotoxic and/or harbor one or more mutations altering, reducing, or eliminating catalytic activity and/or cytotoxicity), may be suitably linked to each other via one or more linkers well known in the art and/or described herein. Individual polypeptide subcomponents of the CD20 binding regions, e.g. heavy chain variable regions ($V_H$), light chain variable regions ($V_L$), CDR, and/or ABR regions, may be suitably linked to each other via one or more linkers well known in the art and/or described herein (see e.g. Weisser N, Hall J, *Biotechnol Adv* 27: 502-20 (2009); Chen X et al., *Adv Drug Deliv Rev* 65: 1357-69 (2013)). Protein components of the invention, e.g., multi-chain, CD20 binding regions, may be suitably linked to each other or other polypeptide components of the invention, e.g., Shiga toxin effector polypeptides, via one or more linkers, such as a proteinaceous linker, which are well known in the art.

Suitable linkers are generally those which allow each polypeptide component of the invention to fold with a three-dimensional structure very similar to the polypeptide components produced individually without any linker or other component. Suitable linkers include single amino acids, peptides, polypeptides, and linkers lacking any of the aforementioned such as various non-proteinaceous carbon chains, whether branched or cyclic (see e.g. Chen X et al., *Adv Drug Deliv Rev* 65: 1357-69 (2013)).

Suitable linkers may be proteinaceous and comprise one or more amino acids, peptides, and/or polypeptides. Proteinaceous linkers are suitable for both recombinant fusion proteins and chemically linked conjugates. A proteinaceous linker typically has from about 2 to about 50 amino acid residues, such as, e.g., from about 5 to about 30 or from about 6 to about 25 amino acid residues. The length of the linker selected will depend upon a variety factors, such as, e.g., the desired property or properties for which the linker is being selected (see e.g. Chen X et al., *Adv Drug Deliv Rev* 65: 1357-69 (2013)).

Suitable linkers may be non-proteinaceous, such as, e.g. chemical linkers (see e.g. Dosio F et al., *Toxins* 3: 848-83 (2011); Feld J et al., *Oncotarget* 4: 397-412 (2013)). Various non-proteinaceous linkers known in the art may be used to link CD20 binding regions to the Shiga toxin effector regions, such as linkers commonly used to conjugate immunoglobulin-derived polypeptides to heterologous polypeptides. For example, polypeptide regions of the CD20-binding proteins of the present invention may be linked using the functional side chains of their amino acid residues and carbohydrate moieties such as, e.g., a carboxy, amine, sulfhydryl, carboxylic acid, carbonyl, hydroxyl, and/or cyclic ring group. For example, disulfide bonds and thioether bonds may be used to link two or more polypeptides (see e.g. Fitzgerald D et al., *Bioconjugate Chem* 1: 264-8 (1990); Pasqualucci L et al., *Haematologica* 80: 546-56 (1995)). In addition, non-natural amino acid residues may be used with other functional side chains, such as ketone groups (see e.g. Sun S et al., *Chembiochem Jul.* 18 (2014); Tian F et al., *Proc Natl Acad Sci USA* 111: 1766-71 (2014)). Examples of non-proteinaceous chemical linkers include but are not limited to N-succinimidyl(4-iodoacetyl)-aminobenzoate, S—(N-succinimidyl)thioacetate (SATA), N-succinimidyl-oxycarbonyl-cu-methyl-a-(2-pyridyldithio) toluene (SMPT), N-succinimidyl 4-(2-pyridyldithio)-pentanoate (SPP), succinimidyl 4-(N-maleimidomethyl)cyclohexane carboxylate (SMCC or MCC), sulfosuccinimidyl(4-iodoacetyl)-aminobenzoate, 4-succinimidyl-oxycarbonyl-α-(2-pyridyldithio) toluene, sulfosuccinimidyl-6-(α-methyl-α-(pyridyldithiol)-toluamido) hexanoate, N-succinimidyl-3-(-2-pyridyldithio)-proprionate (SPDP), succinimidyl 6(3(-(-2-pyridyldithio)-proprionamido) hexanoate, sulfosuccinimidyl 6(3(-(-2-pyridyldithio)-propionamido) hexanoate, maleimidocaproyl (MC), maleimidocaproyl-valine-citrulline-p-aminobenzyloxycarbonyl (MC-vc-PAB), 3-maleimidobenzoic acid N-hydroxysuccinimide ester (MBS), alpha-alkyl derivatives, sulfoNHS-ATMBA (sulfo-succinimidyl N-[3-(acetylthio)-3-methylbutyryl-beta-alanine]), sulfodicholorphenol, 2-iminothiolane, 3-(2-pyridyl-dithio)-propionyl hydrazide, Ellman's reagent, dichlorotriazinic acid, and S-(2-thiopyridyl)-L-cysteine (see e.g. Thorpe P et al., *Eur J Biochem* 147: 197-206 (1985); Thorpe P et al., *Cancer Res* 47: 5924-31 (1987); Thorpe P et al., *Cancer Res* 48: 6396-403 (1988); Grossbard M et al., *Blood* 79: 576-85 (1992); Lui C et al., *Proc Natl Acad Sci USA* 93: 8618-23 (1996); Doronina S et al., *Nat Biotechnol* 21: 778-84 (2003); Feld J et al., *Oncotarget* 4: 397-412 (2013)).

Suitable linkers, whether proteinaceous or non-proteinaceous, may include, e.g., protease sensitive, environmental redox potential sensitive, pH sensitive, acid cleavable, photocleavable, and/or heat sensitive linkers (see e.g. Dosio F et al., *Toxins* 3: 848-83 (2011); Chen X et al., *Adv Drug Deliv Rev* 65: 1357-69 (2013); Feld J et al., *Oncotarget* 4: 397-412 (2013)).

Proteinaceous linkers may be chosen for incorporation into CD20-binding proteins of the invention. For example, the component polypeptides of the CD20-binding proteins invention or their subcomponents may be joined by one or more linkers comprising one or more amino acids, peptides, and/or polypeptides. For fusion CD20-binding proteins of the invention, linkers typically comprise about 2 to 50 amino acid residues, preferably about 5 to 30 amino acid residues (Argos P, *J Mol Biol* 211: 943-58 (1990); Williamson M, *Biochem J* 297: 240-60 (1994); George R, Heringa J, *Protein Eng* 15: 871-9 (2002); Kreitman R, *AAPS J* 8: E532-51 (2006)). Commonly, proteinaceous linkers comprise a majority of amino acid residues with polar, uncharged, and/or charged residues, such as, e.g., threonine, proline, glutamine, glycine, and alanine (see e.g. Huston J et al. *Proc Natl Acad Sci U.S.A.* 85: 5879-83 (1988); Pastan I et al., *Annu Rev Med* 58: 221-37 (2007); Li J et al., *Cell Immunol* 118: 85-99 (1989); Cumber A et al. *Bioconj Chem* 3: 397-401 (1992); Friedman P et al., *Cancer Res* 53: 334-9 (1993); Whitlow M et al., *Protein Engineering* 6: 989-95 (1993); Siegall C et al., *J Immunol* 152: 2377-84 (1994); Newton et al. *Biochemistry* 35: 545-53 (1996); Ladurner et al. *J Mol Biol* 273: 330-7 (1997); Kreitman R et al., *Leuk Lymphoma* 52: 82-6 (2011); U.S. Pat. No. 4,894,443). Non-limiting examples of proteinaceous linkers include alanine-serine-glycine-glycine-proline-glutamate (ASGGPE) (SEQ ID NO:137), valine-methionine (VM), alanine-methionine (AM), AM(G$_{2\ to\ 4}$S)$_x$AM (SEQ ID NO:138) where G is glycine, S is serine, and x is an integer from 1 to 10.

Proteinaceous linkers may be selected based upon the properties desired. Proteinaceous linkers may be chosen by the skilled worker with specific features in mind, such as to optimize one or more of the fusion molecule's folding, stability, expression, solubility, pharmacokinetic properties, pharmacodynamic properties, and/or the activity of the fused domains in the context of a fusion construct as compared to the activity of the same domain by itself. For example, proteinaceous linkers may be selected based on flexibility, rigidity, and/or cleavability (see e.g. Chen X et al., *Adv Drug Deliv Rev* 65: 1357-69 (2013)). The skilled worker may use databases and linker design software tools when choosing linkers. Certain linkers may be chosen to optimize expression (see e.g. Turner D et al., *J Immunol Methods* 205: 43-54 (1997)). Certain linkers may be chosen to promote intermolecular interactions between identical polypeptides or proteins to form homomultimers or different polypeptides or proteins to form heteromultimers. For example, proteinaceous linkers may be selected which allow for desired non-covalent interactions between polypeptide components of the CD20-binding proteins of the invention, such as, e.g., interactions related to the formation dimers and other higher order multimers (see e.g. U.S. Pat. No. 4,946,778).

Flexible proteinaceous linkers are often greater than 12 amino acid residues long and rich in small, non-polar amino acid residues, polar amino acid residues, and/or hydrophilic amino acid residues, such as, e.g., glycines, serines, and threonines (see e.g. Bird R et al., *Science* 242: 423-6 (1988); Friedman P et al., *Cancer Res* 53: 334-9 (1993); Siegall C et al., *J Immunol* 152: 2377-84 (1994)). Flexible proteinaceous linkers may be chosen to increase the spatial separation between components and/or to allow for intramolecular interactions between components. For example, various "GS" linkers are known to the skilled worker and are composed of multiple glycines and/or one or more serines, sometimes in repeating units, such as, e.g., $(G_xS)_n$ (SEQ ID NO:139), $(S_xG)_n$ (SEQ ID NO:140), $(GGGGS)_n$ (SEQ ID NO:141), and $(G)_n$ (SEQ ID NO:142). in which x is 1 to 6 and n is 1 to 30 (see e.g. WO 96/06641). Non-limiting examples of flexible proteinaceous linkers include GKSSGSGSESKS (SEQ ID NO:143), GST-SGSGKSSEGKG (SEQ ID NO:144), GST-SGSGKSSEGSGSTKG (SEQ ID NO:145), GST-SGSGKSSEGKG (SEQ ID NO:144), GSTSGSGKPGSGEGSTKG (SEQ ID NO:147), EGKSSGSGSESKEF (SEQ ID NO:148), SRSSG (SEQ ID NO:149), and SGSSC (SEQ ID NO:150).

Rigid proteinaceous linkers are often stiff alpha-helical structures and rich in proline residues and/or one or more strategically placed prolines (see Chen X et al., *Adv Drug Deliv Rev* 65: 1357-69 (2013)). Rigid linkers may be chosen to prevent intramolecular interactions between linked components.

Suitable linkers may be chosen to allow for in vivo separation of components, such as, e.g., due to cleavage and/or environment-specific instability (see Dosio F et al., *Toxins* 3: 848-83 (2011); Chen X et al., *Adv Drug Deliv Rev* 65: 1357-69 (2013)). In vivo cleavable proteinaceous linkers are capable of unlinking by proteolytic processing and/or reducing environments often at a specific site within an organism or inside a certain cell type (see e.g. Doronina S et al., *Bioconjug Chem* 17: 144-24 (2006); Erickson H et al., *Cancer Res* 66: 4426-33 (2006)). In vivo cleavable proteinaceous linkers often comprise protease sensitive motifs and/or disulfide bonds formed by one or more cysteine pairs (see e.g. Pietersz G et al., *Cancer Res* 48: 4469-76 (1998); The J et al., *J Immunol Methods* 110: 101-9 (1998); see Chen X et al., *Adv Drug Deliv Rev* 65: 1357-69 (2013)). In vivo cleavable proteinaceous linkers can be designed to be sensitive to proteases that exist only at certain locations in an organism, compartments within a cell, and/or become active only under certain physiological or pathological conditions (such as, e.g., proteases with abnormally high levels, proteases overexpressed at certain disease sites, and proteases specifically expressed by a pathogenic microorganism). For example, there are proteinaceous linkers known in the art which are cleaved by proteases present only intracellularly, proteases present only within specific cell types, and proteases present only under pathological conditions like cancer or inflammation, such as, e.g., R-x-x-R motif (SEQ ID NO:151) and AMGRSGGGCAGNRVGSSLSCG-GLNLQAM (SEQ ID NO:152).

In certain embodiments of the CD20-binding proteins of the invention, a linker may be used which comprises one or more protease sensitive sites to provide for cleavage by a protease present within a target cell. In certain embodiments of the CD20-binding proteins of the invention, a linker may be used which is not cleavable to reduce unwanted toxicity after administration to a vertebrate organism (see e.g. Polson et al., *Cancer Res* 69: 2358-(2009)).

Suitable linkers may include, e.g., protease sensitive, environmental redox potential sensitive, pH sensitive, acid cleavable, photocleavable, and/or heat sensitive linkers, whether proteinaceous or non-proteinaceous (see Chen X et al., *Adv Drug Deliv Rev* 65: 1357-69 (2013)).

Suitable cleavable linkers may include linkers comprising cleavable groups which are known in the art such as, e.g., linkers noted by Zarling D et al., *J Immunol* 124: 913-20 (1980); Jung S, Moroi M, *Biochem Biophys Acta* 761: 152-62 (1983); Bouizar Z et al., *Eur J Biochem* 155: 141-7 (1986); Park L et al., *J Biol Chem* 261: 205-10 (1986); Browning J, Ribolini A, *J Immunol* 143: 1859-67 (1989); Joshi S, Burrows R, *J Biol Chem* 265: 14518-25 (1990)).

Suitable linkers may include pH sensitive linkers. For example, certain suitable linkers may be chosen for their instability in lower pH environments to provide for dissociation inside a subcellular compartment of a target cell. For example, linkers that comprise one or more trityl groups, derivatized trityl groups, bismaleimideothoxy propane groups, adipic acid dihydrazide groups, and/or acid labile transferrin groups, may provide for release of components of the CD20-binding proteins of the invention, e.g. a polypeptide component, in environments with specific pH ranges (see e.g. Welhöner H et al., *J Biol Chem* 266: 4309-14 (1991); Fattom A et al., *Inject Immun* 60: 584-9 (1992)). Certain linkers may be chosen which are cleaved in pH ranges corresponding to physiological pH differences between tissues, such as, e.g., the pH of tumor tissue is lower than in healthy tissues (see e.g. U.S. Pat. No. 5,612,474).

Photocleavable linkers are linkers that are cleaved upon exposure to electromagnetic radiation of certain wavelength ranges, such as light in the visible range (see e.g. Goldmacher V et al., *Bioconj Chem* 3: 104-7 (1992)). Photocleavable linkers may be used to release a component of a CD20-binding protein of the invention, e.g. a polypeptide component, upon exposure to light of certain wavelengths. Non-limiting examples of photocleavable linkers include a nitrobenzyl group as a photocleavable protective group for cysteine, nitrobenzyloxycarbonyl chloride cross-linkers, hydroxypropylmethacrylamide copolymer, glycine copolymer, fluorescein copolymer, and methylrhodamine copolymer (Hazum E et al., *Pept Proc Eur Pept Symp*, 16th, Brunfeldt K, ed., 105-110 (1981); Senter et al., *Photochem Photobiol* 42: 231-7 (1985); Yen et al., *Makromol Chem* 190: 69-82 (1989); Goldmacher V et al., *Bioconj Chem* 3: 104-7 (1992)). Photocleavable linkers may have particular uses in linking components to form CD20-binding proteins of the invention designed for treating diseases, disorders, and conditions that can be exposed to light using fiber optics.

In certain embodiments of the CD20-binding proteins of the invention, a CD20 binding region is linked to a Shiga toxin effector region using any number of means known to the skilled worker, including both covalent and noncovalent linkages (see e.g. Chen X et al., *Adv Drug Deliv Rev* 65: 1357-69 (2013); Behrens C, Liu B, *MAbs* 6: 46-53 (2014).

In certain embodiments of the CD20-binding proteins of the invention, the protein comprises a CD20 binding region which is a scFv with a linker connecting a heavy chain variable ($V_H$) domain and a light chain variable ($V_L$) domain. There are numerous linkers known in the art suitable for this purpose, such as, e.g., GGS, GGGS (Gly3Ser or G3S) (SEQ ID NO:153), GGGGS (Gly4Ser or G4S) (SEQ ID NO:154), GGGGSGGG (SEQ ID NO:155), GGSGGGG (SEQ ID NO:156), the 15-residue $(Gly4Ser)_3$ peptide (SEQ ID NO:157), GSTSGGGSGGGSGGGGSS (SEQ ID NO:158), and GSTSGSGKPGSSEGSTKG (SEQ ID NO:159) (Plückthun A, Pack P, *Immunotechnology* 3: 83-105 (1997); Atwell J et al., *Protein Eng* 12: 597-604 (1999); Wu A et al., *Protein Eng* 14: 1025-33 (2001); Yazaki P et al., J Immunol Methods 253: 195-208 (2001); Carmichael J et al., *J Mol Biol* 326: 341-51 (2003); Arndt M et al., *FEBS Lett* 578: 257-61 (2004); Bie C et al., *World J Hepatol* 2: 185-91 (2010)).

Suitable methods for linkage of components of the CD20-binding proteins of the invention may be by any method presently known in the art for accomplishing such, so long as the attachment does not substantially impede the binding capability of the CD20 binding region, the cellular internalization of the protein, and/or desired toxin effector function(s) of the Shiga toxin effector region as measured by an appropriate assay, including assays described herein.

II. Examples of Specific Structural Variations of the CD20-Binding Protein

A CD20-binding protein of the invention comprises 1) a CD20 binding region capable of specifically binding an extracellular part of CD20 and 2) a Shiga toxin effector region comprising a polypeptide derived from the amino acid sequence of the A Subunit of at least one member of the Shiga toxin family. Among certain embodiments of the present invention, the CD20-binding proteins comprise the Shiga toxin effector region comprising or consisting essentially of amino acids 75 to 251 of SLT-1A (SEQ ID NO:1), StxA (SEQ ID NO:2), or SLT-2A (SEQ ID NO:3). Further embodiments are CD20-binding proteins in which the Shiga toxin effector region comprises or consists essentially of amino acids 1 to 241 of SLT-1A (SEQ ID NO:1), StxA (SEQ ID NO:2), and/or SLT-2A (SEQ ID NO:3). Further embodiments are CD20-binding proteins in which the Shiga toxin effector region comprises or consists essentially of amino acids 1 to 251 of SLT-1A SLT-1A (SEQ ID NO:1), StxA (SEQ ID NO:2), and/or SLT-2A (SEQ ID NO:3). Further embodiments are CD20-binding proteins in which the Shiga toxin effector region comprises or consists essentially of amino acids 1 to 261 of SLT-1A (SEQ ID NO:1), StxA (SEQ ID NO:2), and/or SLT-2A (SEQ ID NO:3).

In certain embodiments, the CD20-binding protein comprises a CD20 binding region comprising an immunoglobulin-type polypeptide selected for specific and high-affinity binding to certain CD20 antigen(s) and/or the cellular surface of a CD20+ cell (see Table 7, infra).

As used herein, the term "heavy chain variable ($V_H$) domain" or "light chain variable ($V_L$) domain" respectively refer to any native antibody $V_H$ or VL domain (e.g. a human $V_H$ or $V_L$ domain) as well as any derivative thereof retaining at least qualitative antigen binding ability of the corresponding native antibody (e.g. a humanized $V_H$ or $V_L$ domain derived from a native murine $V_H$ or $V_L$ domain). A $V_H$ or $V_L$ domain consists of a "framework" region interrupted by the three CDRs. The framework regions serve to align the CDRs for specific binding to an epitope of an antigen. From amino-terminus to carboxyl-terminus, both $V_H$ and $V_L$ domains comprise the following framework (FR) and CDR regions: FR1, CDR1, FR2, CDR2, FR3, CDR3, FR4. For camelid $V_H$H fragments, IgNARs of cartilaginous fish, $V_{NAR}$ fragments, and derivatives thereof, there is a single heavy chain variable domain comprising the same basic arrangement: FR1, CDR1, FR2, CDR2, FR3, CDR3, and FR4. The assignment of amino acids to each domain is in accordance with the definitions of Kabat, *Sequences of Proteins of Immunological Interest* (5th ed., National Institutes of Health, Bethesda, Md., 1991), or Chothia and Lesk, *J. Mol. Biol.* 196: 901-17 (1987); Chothia et al., *Nature* 342:878-83, (1989). CDRs 1, 2, and 3 of a $V_H$ domain are also referred to herein, respectively, as HCDR1, HCDR2, and HCDR3; CDRs 1, 2, and 3 of a $V_L$ domain are also referred to herein, respectively, as LCDR1, LCDR2, and LCDR3.

In some embodiments of the present invention, the CD20 binding region comprises an antibody or an antibody-derived sequence that comprises a specific set of complementarity determining regions, or CDRs. CDRs are defined sequence regions within the variable domains of antibodies that are necessary for specific binding of the antibody to its antigenic determinants. In one embodiment of the invention, the CDRs comprise three CDRs derived from the heavy chain of the antibody and three CDRs derived from light chain of the antibody. In certain embodiments of the CD20-binding proteins of the present invention, the CD20-binding proteins comprise the CD20 binding region comprising at least one heavy-chain variable ($V_H$) domain polypeptide and at least one light-chain variable domain polypeptide selected from the group consisting of: (a) a heavy chain variable domain comprising i) HCDR1, HCDR2, and HCDR3 amino acid sequences as shown in SEQ ID NO:5. SEQ ID NO:6, and SEQ ID NO:7, respectively; ii) HCDR1, HCDR2, and HCDR3 amino acid sequences as shown in SEQ ID NO:11, SEQ ID NO:12, or SEQ ID NO:13, respectively; iii) HCDR1, HCDR2, and HCDR3 amino acid sequences as shown in SEQ ID NO:17, SEQ ID NO:18, and SEQ ID NO:19, respectively; iv) HCDR1, HCDR2, and HCDR3 amino acid sequences as shown in SEQ ID NO:23, SEQ ID NO:24, and SEQ ID NO:25, respectively; v) HCDR1, HCDR2, and HCDR3 amino acid sequences as shown in SEQ ID NO:29, SEQ ID NO:30, and SEQ ID NO:31, respectively; and vi) HCDR1, HCDR2, and HCDR3 amino acid sequences as shown in SEQ ID NO:35, SEQ ID NO:36, and SEQ ID NO:37, respectively; and (b) a light chain variable ($V_L$) domain comprising i) LCDR1, LCDR2, and LCDR3 amino acid sequences as shown in SEQ ID NO:8, SEQ ID NO:9, and SEQ ID NO:10, respectively; ii) LCDR1, LCDR2, and LCDR3 amino acid sequences as shown in SEQ ID NO:14, SEQ ID NO:15, and SEQ ID NO: 16, respectively; iii) LCDR1, LCDR2, and LCDR3 amino acid sequences as shown in SEQ ID NO:20, SEQ ID NO:21, and SEQ ID NO:22, respectively; iv) LCDR1, LCDR2, and LCDR3 amino acid sequences as shown in SEQ ID NO:26, SEQ ID NO:27, and SEQ ID NO:28, respectively; v) LCDR1, LCDR2, and LCDR3 amino acid sequences as shown in SEQ ID NO:32, SEQ ID NO:33, and SEQ ID NO:34, respectively; and vi) LCDR1, LCDR2, and LCDR3 amino acid sequences as shown in SEQ ID NO:38, SEQ ID NO:39, and SEQ ID NO:40, respectively. Further embodiments are CD20-binding proteins comprising the immunoglobulin-type binding region comprising or consisting essentially of amino acids 2-245 of any one of the amino acid sequences shown in SEQ ID NOs: 46-87. Further embodiments are CD20-binding proteins comprising the immunoglobulin-type binding region comprising or consisting essentially of amino acids 2-245 of any one of the amino acid sequences shown in SEQ ID NOs: 46-87 linked with the Shiga toxin effector region comprising or consisting essentially of amino acids 75-251 of SEQ ID NO:1. Further embodiments are CD20-binding proteins comprising the immunoglobulin-type binding region comprising or consisting essentially of amino acids 2-245 of any one of the amino acid sequences shown in SEQ ID NOs: 46-87 linked with the Shiga toxin effector region comprising or consisting essentially of the amino acid sequence shown in SEQ ID NO:4.

For certain embodiments, the CD20-binding protein comprises or consists essentially of the polypeptide shown in any one of SEQ ID NOs: 46-112.

It is within the scope of the invention to use fragments, variants, and/or derivatives of the polypeptides of the proteins of the invention which contain a functional CD20 binding site, and even more preferably capable of binding an extracellular part of CD20 with high affinity (e.g. as shown by K). For example, while the invention provides polypeptide sequences that can bind to CD20, any binding region comprising a polypeptide that binds to extracellular CD20 expressed at a cell surface, with a dissociation constant of $10^{-5}$ to $10^{-12}$ moles per liter, preferably less than 200 nM, may be substituted for use in making proteins of the invention.

Among certain embodiments of the present invention, the immunoglobulin-type binding region is derived from a nanobody or single domain immunoglobulin-derived region $V_H$ H. Generally, nanobodies are constructed from fragments of naturally occurring single, monomeric variable domain antibodies (sdAbs) of the sort found in camelids and cartilaginous fishes (Chondrichthyes). Nanobodies are engineered from these naturally occurring antibodies by truncating the single, monomeric variable domain to create a smaller and more stable molecule. Due to their small size, nanobodies are able to bind to antigens that are not accessible to whole antibodies. Among certain embodiments of the present invention, the immunoglobulin-type binding region is derived from a nanobody or single domain immunoglobulin-derived region $V_H$H which exhibits high affinity binding specifically to an extracellular part of a CD20 protein.

It is within the scope of the invention to use fragments, variants, and/or derivatives of the polypeptides of the CD20-binding proteins of the invention which contain a functional CD20 binding site to any extracellular part of CD20, and even more preferably capable of binding CD20 with high affinity (e.g. as shown by $K_D$). For example, the invention provides immunoglobulin-derived polypeptide sequences that can bind to CD20. Any polypeptide may be substituted for this region which binds an extracellular part of CD20 with a dissociation constant ($K_D$) of $10^{-5}$ to $10^{-12}$ moles/liter, preferably less than 200 nM, may be substituted for use in making proteins of the invention and methods of the invention.

Thus it is within the scope of the invention to alter the immunoglobulin-type binding site of a disclosed exemplary CD20-binding protein so long as at least one polypeptide sequence is chosen from the group consisting of the CDR1 sequences, CDR2 sequences, and CDR3 sequences that are described. In particular, but without limitation, the polypeptide sequences of the invention may consist essentially of 4 framework regions (FR1 to FR4) and three complementary determining regions (CDR1 to CDR3 respectively); or any suitable fragment of such amino acid sequence that exhibits CD20 binding functionality based on the presence of one or more CDRs.

III. The General Function of the CD20-Binding Protein

The present invention provides various CD20-binding proteins for the targeted internalization into CD20 expressing cells and, optionally, the killing of certain CD20 expressing cells. A CD20-binding protein of the invention comprises 1) a CD20 binding for cell targeting and 2) a Shiga toxin effector region for efficiently inducing CD20-mediated cellular internalization, directing intracellular routing, and/or effectuating cell killing. Certain embodiments are cytotoxic and others are not, such as, e.g., for labeling the interiors of CD20 expressing cells. Certain embodiments can deliver into CD20 expressing cells additional exogenous materials which may or may not result in cytotoxicity independent of the catalytic activity of the Shiga toxin effector region. The present invention provides certain embodiments of CD20-binding proteins of the invention for the selective killing of CD20+ cells in the presence of other cell types.

The linking of CD20 binding regions with Shiga-toxin-Subunit-A-derived regions enables the targeting of the potent Shiga toxin cytotoxicity specifically and selectively to CD20 positive cells. In preferred embodiments, the CD20-binding proteins of the invention are capable of binding CD20 expressed at a cellular surface and entering the cell within one hour at an appropriate physiological temperature for the cell. Once internalized within a CD20+ cell, certain embodiments of the CD20-binding proteins of the invention are capable of routing a cytotoxic Shiga toxin effector polypeptide fragment into the cytosol of the target cell. Once in the cytosol of a targeted cell type, certain embodiments of the CD20-binding proteins of the invention are capable of enzymatically inactivating ribosomes, interfering with cell homeostasis, and eventually killing the cell. Alternatively, non-toxic variants may be used to deliver additional exogenous materials and/or label the interiors of CD20 expressing cells for diagnostic purposes.

For certain embodiments of the CD20-binding proteins of the present invention, whereby administration of the CD20-binding protein to one or more CD20 positive cells at a physiological temperature appropriate for the cell results in one or more of the following behaviors in said one or more CD20 positive cells: (i) CD20-mediated cellular internalization of the CD20-binding protein within 6, 5, 4, 3, 2, 1 hour(s) or less, (ii) intracellular localization of an exogenous material linked to the CD20-binding protein, (iii) subcellular routing of at least one Shiga toxin effector region polypeptide to the cell's cytosol, (iv) disrupting the cell's ribosome function, (v) inhibiting cell proliferation, and (vi) killing of the cell.

Various types of cells that express CD20 at a cellular surface may be targeted by the CD20-binding proteins of the invention for killing and/or receiving exogenous materials, such as, e.g. cancer cells, tumor cells, and immune cells, whether healthy or malignant.

Among the CD20 expressing cell types anticipated to efficiently internalize the CD20-binding proteins of the invention are cells descendant from or members of a B-cell lineage. "B-cell lineage" is a term used to describe those cells that are identified, such as by cytological methods known in the art, e.g., through cell surface markers, such as 1) progenitors of B-cells, 2) B-cells, or 3) cells that were once or presently derived from B-cells. The term "B-cell lineage" includes neoplastic and malignant cells derived from the B-cell lineage or precursors to the B-cell lineage.

Among the CD20 expressing cell types that may be targeted by CD20-binding proteins of the invention are dysplastic or neoplastic cells of cell lineages which do not normally express CD20, e.g. melanoma cells. In particular, the CD20 expressing cells to be targeted with the CD20-binding proteins of the invention include neoplastic and malignant cells of B-cell lineages or non-B-cell lineages, such as neoplastic cells derived from a hematopoietic lineage that are not usually categorized as B-cells but which express CD20, e.g. neoplastic T-cells. Among the CD20 expressing cell types that may be targeted by CD20-binding proteins of the invention are healthy immune cells such as, e.g., B-cell lineage cells, mature B-cells, and mature T-cells. Such CD20 expressing cells described herein may be targeted for killing and/or for receiving the delivery of exogenous materials.

A. CD20-Binding Proteins Capable of Inducing Rapid Internalization of CD20

The Shiga toxin effector regions of the present invention provide a CD20-mediated cellular internalization function to efficiently move from the external surface of a target cell into the cytoplasm of the target cell. This cellular internalization function is capable of forcing, inducing, accelerating, or otherwise promoting CD20 internalization, such as, e.g., compared to CD20 internalization upon anti-CD20 antibody binding which has been observed to be very inefficient. This efficient cellular internalization function arises from the structure Shiga toxin effector regions of the CD20-binding proteins of the present invention and is capable of driving efficient, CD20-mediated, cellular internalization of entire CD20-binding proteins of the invention.

CD20 is considered a non-internalizing, extracellular target (Beers S et al., *Sem Hematol* 47: 107-14 (2010) based on the general finding that CD20 does not readily internalize (Anderson K et al., *Blood* 63: 1424-33 (1984); Press O et al., *Blood* 69: 584-91 (1987); Press O et al., *Cancer Res* 49: 4906-12 (1989); Press O et al., *Blood* 83: 1390-7 (1994); Countouriotis A et al., *Stem Cells* 20: 215-29 (2002)). CD20 is "resistant to internalization and remains on the cell surface with its bound mAb for extended periods of hours and perhaps days" (Glennie M et al., *Mol Immunol* 44: 3823-37 (2007); see e.g. Press O et al., *Cancer Res* 49: 4906-12 (1989); McLaughlin P et al., *J Clin Oncol* 16: 2825-33 (1998); Johnson P, Glennie M. *Semin Oncol* 30: 3-8 (2003)).

As used in the specification and the claims herein, the phrase "rapid cellular internalization" refers to the ability of a CD20-binding protein of the invention to decrease the time on average for cellular internalization of an extracellular CD20 antigen or cell surface localized CD20 molecules as compared to the time on average required for cellular internalization of an extracellular CD20 antigen or cell surface localized CD20 molecule, as measured by any one of a number of cell internalization assays known in the art or described herein.

As used in the specification and the claims herein, the phrase "rapid internalization" includes internalization which may be assayed as compared to a basal CD20 internalization rate and/or molecular binding induced internalization rate for CD20 after administration of an immunoglobulin-type binding molecule (e.g. a monoclonal antibody) known in the art to bind an extracellular part of CD20. The phrase "rapid cellular internalization" is intended to encompass internalization rates, on average, faster than those observed when testing a CD20-specific antibody or immunoglobulin-derived protein molecule with an Fc region. In general, an internalization rate constant may be defined as the time after administration of a protein of interest to CD20 positive cells at which 50% of cell surface CD20 antigens, CD20 molecules, and/or a high-affinity CD20-specific binding protein is internalized at a given administered protein concentration, to a particular cell type, and at a particular temperature. Cell-surface CD20 internalization, whether basally or in response to administration of a CD20-binding immunoglobulin-type protein, may be assayed by various methods known to the skilled worker (see e.g. Press O et al., *Blood*. 83: 1390-7 (1994); Golay J et al., *Blood* 98: 3383-9 (2001);

Goulet A et al., *Blood* 90: 2364-75 (1997); Manches O et al., *Blood* 101: 949-54 (2003); Hess G et al., *Biochim Biophys Acta* 1773: 1583-8 (2007); Baskar S et al., *Clin Cancer Res* 14: 396-404 (2008); Luqman M et al., *Blood* 112: 711-20 (2008)).

In certain embodiments, an internalization rate may be measured as the time after administration (on average) at which the CD20-binding protein is observed inside cell(s). For example, the monoclonal antibody rituximab typically reaches maximal internalization after 16 to 18 hours at 37° C., and thus, in the context of the present invention, a "rapid internalization" would indicate internalization rates several hours faster than that observed for the αCD20 antibody rituximab, on average at the same temperature and receptor occupancy level.

In certain embodiments, an internalization rate may be measured as the time after administration (on average) at which the amount of CD20 observed in the cell interior reaches a maximum.

In certain embodiments, an internalization rate may be measured as the time after administration (on average) at which the amount of CD20 observed on the surface reaches its minimum.

For the purposes of certain embodiments of the present invention, cellular internalization is considered rapid if the time for internalization to occur due to the binding of the CD20-binding protein is reduced as compared to the time for internalization of the target CD20 molecule with the binding of a well-characterized antibody recognizing a CD20 antigen, such as the αCD20 monoclonal antibody 1H4 (Haisma H et al., *Blood* 92: 184-90 (1999)). For example, internalization timing for the CD20 antigen, although variable for cell type and antibody type, does not typically begin to reach maximal levels until approximately six hours after binding. Thus the term "rapid" as used throughout the present description is intended to indicate that a CD20-binding protein of the invention enters one or more CD20 expressing and/or CD20 positive cells in less than this six hour standard internalization window. In certain embodiments, rapid can be as quickly as less than about one hour, but can also encompass a range of from about 1 hour to about 2 hours, to about 3 hours, to about 4 hours, to about 5 hours; a range of about 2 hours to about 3 hours, to about 4 hours, to about 5 hours; a range of about 3 hours to about 4 hours, to about 5 hours; and a range of about 4 hours to about 5 hours.

For the purposes of certain embodiments of the present invention, cellular internalization is considered rapid if the time for internalization to occur due to the binding of the CD20-binding protein is reduced as compared to the time for internalization of a prior art reference molecule at the same percent CD20 occupancy as determined by the same assay using the same cell type at the same temperature. In certain embodiments, the reference molecule is the monoclonal antibody selected from the group consisting of: 1FS, 1H4, 1K1791, 2B8, Leu16, Leuδ, 2F2, 2H7, 7D8, 8E4, 11B8, AME-133v, LY2469298, B9E9, BM-ca, C2B8, and GA110 (see Table 7, infra).

For purposes of certain embodiments of the present invention, the phrase "in less than about one hour" means that the maximal (or half-maximal in certain contexts) observed amount of intracellular CD20, CD20 antigen, and/or high-affinity CD20-binding protein during an internalization assay time course is observed at or before one hour from the step of contacting CD20 positive cell(s) with the CD20-binding protein of the invention as determined by an appropriate assay at conditions similar to 37° C. and 50 nM of CD20-binding protein. The time of maximal or half-maximal intracellular accumulation may be determined by comparing intracellular accumulation at different times to find a peak or plateau. If a plateau is observed, then the maximal intracellular accumulation may be determined to be the first time the plateau reaches its highest point.

The extracellular CD20 cell surface density and the $K_D$ of a CD20-binding protein may be used to calculate the percent occupancy for a given concentration of CD20-binding protein, such as a CD20-binding protein of the invention or a CD20 binding molecule comprising an immunoglobulin-type domain (e.g. monoclonal antibody) known to the skilled worker. For example, CD20 receptor occupancy for a given CD20-binding protein of the invention may be determined as a function of the 1) binding interaction between the extracellular CD20 receptor and CD20-binding protein, 2) amount of extracellular CD20 receptor available for binding, and 3) the amount of CD20-binding protein present.

In certain embodiments, internalization rates of a CD20-binding protein of the invention compared to a CD20 antibody known in the art may be determined using assays performed at comparable extracellular CD20 receptor occupancies, instead of being determined using assays performed at comparable concentrations of the administered CD20 binding molecules (i.e. a CD20-binding protein of the invention and a CD20 antibody). The percent CD20 receptor occupancy ($RO_{CD20}$) may be determined using models and formulae, such as, e.g., $$RO_{CD20} = \frac{K_D + A_{tot} + CD20_{tot} - \sqrt{(-K_D - A_{tot} - CD20_{tot})^2 - 4 \cdot A_{tot} \cdot CD20_{tot}}}{2 \cdot CD20_{tot}}$$

where RO is the receptor occupancy of the extracellular CD20 in the internalization assay, $K_D$ is the dissociation constant of the CD20 binding molecule of interest to the extracellular CD20 receptor, $A_{tot}$ is the total number of CD20 binding molecules in the assay, and $CD20_{tot}$ is the total number of cell surface CD20 molecules in the assay, (see e.g. Muller P, Brennan F. *Clin Pharmacol Ther* 85: 247-58 (2009)).

For example, based on the internalization assay described in the Examples below using Non-Hodgkin's lymphoma cell lines which express approximately $3.5 \times 10^5$ to $5 \times 10^5$ cell-surface accessible, extracellular CD20 molecules per cell that are plated at approximately one million cells per dish and administering the exemplary CD20-binding protein αCD20scFv1::SLT-1A (SEQ ID NO:52) with a $K_D$ of 82.5 nM, this exemplary CD20-binding protein of the invention would be predicted to represent the following receptor occupancy percentages at the following concentrations: 6% of the available cell surface CD20 at 5 nM of CD20-binding protein, 38% of the available cell surface CD20 at 50 nM, and 86% of the available cell surface CD20 at 500 nM of CD20-binding protein.

As used in the specification and the claims herein, the phrase "an appropriate physiological temperature for the cell" refers to temperatures known in the art and/or identifiable by the skilled worker which fall within a range suitable for healthy growth, propagation, and/or function of that particular cell or cell type; corresponding to the core temperature of the species from which the cell is derived; or corresponding to a healthy, living organism comprising the cell. For example, temperatures around 37° C. are appropriate for many mammalian cells depending on the species.

For purposes of the present invention, the phrase "internalization of a protein complex comprising the CD20-binding protein bound to CD20" means the internalization of the CD20-binding protein is CD20-mediated in that it begins with a CD20-binding protein and a CD20 forming a complex at an extracellular position and ends with both the CD20-binding protein and the CD20 molecule entering the cell prior to dissociation of the CD20-binding protein from the CD20 molecule to which it has bound.

For purposes of the present invention, the phrase "CD20 natively present on the surface of a cell" means a cell expresses the CD20 molecule using its own protein synthesis machinery and localizes the CD20 molecule to a cellular surface using its own intracellular routing machinery such that the CD20 molecule is physically coupled to said cell and at least a part of the CD20 molecule is accessible from an extracellular space, i.e. on the surface of a cell.

In certain embodiments, the CD20-binding protein is capable of inducing rapid cellular internalization in the cell type selected from the following group: malignant B-cell, B-cell leukemia cell, B-cell lymphoma cell, B-cell myeloma cell, acute myeloid leukemia (AML) cell, acute non-lymphocytic leukemia cell, B-cell chronic lymphocytic leukemia (B-cell CLL) cell, B-cell lymphoma cell, B-cell non-Hodgkin's lymphoma (B-cell NHL) cell, B-cell precursor acute lymphoblastic leukemia (BCP-ALL or B-ALL) cell, B-cell prolymphocytic leukemia (B-PLL) cell, Burkitt's lymphoma (BL) cell, chronic lymphocytic leukemia (CLL) cell, chronic myeloid leukemia (CML) cell, diffuse large B-cell lymphoma (DLBCL or DLBL) cell, follicular lymphoma (FL) cell, hairy cell leukemia (HCL) cell, Hodgkin's lymphoma (HL or HD) cell, immunoblastic large cell lymphoma cell, mantle cell lymphoma (MCL) cell, melanoma cell, multiple myeloma (MM) cell, neoplastic plasma cell, nodular lymphocyte predominant Hodgkin's lymphoma (NLPHL) cell, non-Hodgkin's lymphoma (NHL) cell, plasmablastic lymphoma cell, plasma cell myeloma cell, precursor B-lymphoblastic lymphoma (B-LBL) cell, small lymphocytic lymphoma (SLL) cell, malignant T-cell, T-cell leukemia cell, T-cell lymphoma (TCL) cell, T-cell large granular lymphocyte leukemia (T-LGLL) cell, T-cell prolymphocytic leukemia (T-PLL), Waldenström's macroglobulinemias (WM) cell, healthy B-cell lineage cell, and healthy T-cell.

B. Cell Kill Via Targeted Shiga Toxin Cytotoxicity

Because members of the Shiga toxin family are adapted to killing eukaryotic cells, CD20-binding proteins designed using Shiga toxin effector regions can show potent cell-kill activity. The A Subunits of members of the Shiga toxin family comprise enzymatic domains capable of killing a eukaryotic cell once in the cell's cytosol. Certain embodiments of the CD20-binding proteins of the invention take advantage of this cytotoxic mechanism.

In certain embodiments of the CD20-binding proteins of the invention, upon contacting a cell expressing CD20 such that at least a part of CD20 is accessible from the extracellular space, the CD20-binding protein is capable of causing death of the cell. CD20 positive "cell kill" may be accomplished using a CD20-binding protein of the invention under varied conditions of target cells, such as an ex vivo manipulated target cell, a target cell cultured in vitro, a target cell within a tissue sample cultured in vitro, or a target cell in vivo.

The expression CD20 need not be native in order for targeted cell killing by a CD20-binding protein of the invention. Expression of CD20 could be artificial such as, for example, by forced or induced expression after infection with a viral expression vector, see e.g. adenoviral, adeno-associated viral, and retroviral systems. For example, CD20 expression may be induced by exposing a cell or population of cells to ionizing radiation (Wattenberg M et al., *Br J Cancer* 110: 1472-80 (2014)). CD20 expressing lymphomatoid granulomatosis cells may be the result of viral infection and/or immunosuppressive drug therapies (Katzenstein A et al., *Am J Surg Pathol* 34: e35-48 (2010)).

C. Selective Cytotoxicity Between CD20 Expressing Cells and Non-CD20 Expressing Cells By targeting the delivery of enzymatically active Shiga toxin regions or cytotoxic agents the interiors of CD20 expressing cells, potent cell-kill activity can be restricted to preferentially killing CD20 positive cell types, such as, e.g., neoplastic or malignant plasma cells. The cytotoxic CD20-binding proteins of the invention are useful for the elimination of populations of specific CD20 expressing cell types. For example, the cytotoxic CD20-binding proteins of the invention are useful for the treatment of certain cancers, tumors, and/or growth abnormalities by eliminating CD20+ cells that express elevated levels of CD20 protein at one or more cellular surfaces.

According to the present invention, selective cytotoxicity may be quantified in terms of the ratio (a/b) of (a) cytotoxicity towards a population of CD20+ cells to (b) cytotoxicity towards a population of CD20− cells. In certain embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of CD20+ cells or CD20+ cell populations compared to CD20− cells or CD20− cell populations. For example, administration of certain embodiments of the CD20-binding protein to two different populations of cell types with respect to the presence of an extracellular CD20 target biomolecule, the CD20-binding protein is capable of causing cell death to the CD20 target biomolecule positive cells at a $CD_{50}$ at least three times or less than the $CD_{50}$ to CD20 target biomolecule negative cells.

In certain embodiments, administration of the CD20-binding protein of the invention to a mixture of cell types results in the CD20-binding protein selectively killing CD20 expressing cells displaying an extracellular CD20 target compared to cell types lacking extracellular CD20 targets. Because members of the Shiga toxin family are adapted for killing eukaryotic cells, CD20-binding proteins designed using Shiga toxin effector regions can show potent cytotoxic activity. By targeting the delivery of enzymatically active Shiga toxin regions to CD20 positive cells using high-affinity CD20 binding regions, such as, e.g., immunoglobulin-type binding regions, this potent cell kill activity can be restricted to preferentially killing only CD20 positive cells and/or to CD20-overexpressing cells.

Certain CD20 positive cell types may be killed in the presence of other cells, including other CD20 positive cells, based on different levels of extracellular CD20 target expression among the target cells and non-target cells. For example, cells which overexpress CD20 may be killed among healthy cells, whether CD20 positive or not.

In certain embodiments, the CD20-binding protein of the invention is capable of selectively or preferentially causing the death of a specific cell type within a mixture of two or more different cell types. This enables targeting cytotoxic activity to specific cell types with a high preferentially, such as with at least a 3-fold cytotoxic effect, over "bystander" cell types that do not express any significant amount of the appropriate extracellular CD20 target(s), such as, e.g., CD20 negative cells. This enables the targeted cell-killing of specific cell types expressing CD20 on cellular surfaces with a high preferentially, such as with at least a 3-fold cytotoxic effect, over "bystander" cell types that do not express significant amounts of the appropriate CD20 target(s) or are not exposing significant amounts of the appropriate CD20 target at a cellular surface.

Alternatively, use of the CD20-binding proteins of the invention enables targeting cytotoxic activity to specific cell types with a high preferentially, such as with at least a 3-fold cytotoxic effect, over "bystander" cell types that are CD20+ but express CD20 at lower cell surface amounts or densities than target cells. Thus, preferential killing of one CD20+ cell type may be accomplished in mixtures of multiple CD20+ where some CD20+ cell types are bystander cells, such as mixtures of CD20+ cell types with varying CD20 expression levels, optionally in the presence of CD20 negative cells as well.

In certain further embodiments, administration of the CD20-binding protein of the invention to two populations of cell types which differ in the presence and/or polypeptide sequence of a extracellular CD20 target, the CD20-binding protein is capable of causing cell death as defined by the half-maximal cytotoxic concentration ($CD_{50}$) to a population of CD20+ target cells, e.g., at a dose at least three times lower than the $CD_{50}$ dose of the same CD20-binding protein to a CD20– cell population.

In certain embodiments, the cytotoxic activity toward populations of cell types physically coupled with an extracellular CD20 target is at least 3-fold higher than the cytotoxic activity toward populations of cell types not physically coupled with significant amounts of extracellular CD20 target(s) of at least one of the CD20 binding regions of the cytotoxic CD20-binding protein. According to the present invention, selective cytotoxicity may be quantified in terms of the ratio (a/b) of (a) cytotoxicity towards a population of cells physically coupled with a significant amount of an extracellular CD20 target of at least one of the CD20 binding regions of the cytotoxic CD20-binding protein to (b) cytotoxicity towards a population of cells of a cell type not physically coupled with a significant amount of an extracellular CD20 target of at least one of the CD20 binding regions of the cytotoxic CD20-binding protein. In certain embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of cells or cell types expressing an extracellular CD20 target or physically coupled with an extracellular CD20 target of at least one of the CD20 binding regions of the cytotoxic CD20-binding protein compared to populations of cells or cell types which do not express an extracellular CD20 target or are not physically coupled with significant amounts of an extracellular CD20 target of at least one of the CD20 binding regions of the cytotoxic CD20-binding protein. For example, administration of certain embodiments of the CD20-binding protein to two different populations of cell types with respect to the presence of an extracellular CD20 target biomolecule, the CD20-binding protein is capable of causing cell death to the cell-types physically coupled with an extracellular CD20 target biomolecule of one or more of its CD20 binding regions at a $CD_{50}$ at least three times or less than the $CD_{50}$ to cell types which are not physically coupled with an extracellular CD20 target of its CD20 binding region.

In certain embodiments of the cytotoxic CD20-binding proteins of the invention, administration of the cytotoxic CD20-binding protein to two different populations of cell types, the cytotoxic CD20-binding protein is capable of causing cell death as defined by the half-maximal cytotoxic concentration ($CD_{50}$) on a first cell population, whose members express CD20 at a cellular surface, at a dose at least three-times lower than the $CD_{50}$ dose of the same cytotoxic CD20-binding protein to a second population of cells whose members do not express CD20, do not express a significant amount of CD20, or are not exposing a significant amount of an extracellular CD20 target of at least one of the CD20 binding regions of the cytotoxic CD20-binding protein In certain embodiments, the cytotoxic activity of a CD20-binding protein of the invention toward populations of cell types expressing CD20 at a cellular surface is at least 3-fold higher than the cytotoxic activity toward populations of cell types not physically coupled with any extracellular CD20 target bound specifically by that CD20-binding protein of the invention.

According to the present invention, selective cytotoxicity may be quantified in terms of the ratio (a/b) of (a) cytotoxicity towards a population of cells expressing an extracellular CD20 target of the CD binding region of the embodiment to (b) cytotoxicity towards a population of cells of a cell type not physically coupled with any extracellular CD20 target of the CD20 binding region of the embodiment. In certain embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of cells or cell types expressing CD20 compared to populations of cells or cell types which do not express CD20.

Levels of extracellular CD20 target biomolecules on the surface of cells may be determined using various methods known to the skilled worker, such as, e.g., FACS methods. As used herein, a significant amount of an extracellular CD20 expressed at a cellular surface is greater than 10,000, 20,000, 30,000, 40,000, or 50,000 mean fluorescence intensity (MFI) by FACS analysis depending on the cell type.

A cell which "overexpresses" a target biomolecule includes a cell which has significantly higher levels of the target biomolecule physically coupled at its cell surface compared to a healthy cell of the same tissue type. Overexpression may be caused by a variety of circumstances, such as, e.g., gene amplification, increased transcription, increased translation, reduced CD20 shedding, and/or reduced removal of the CD20 target biomolecule. The skilled worker may determine overexpression of a particular target biomolecule using methods known in the art.

This preferential cell-killing function allows a targeted cell to be killed by certain CD20-binding proteins of the invention under varied conditions and in the presence of non-targeted bystander cells, such as ex vivo manipulated mixtures of cell types, in vitro cultured tissues with mixtures of cell types, or in vivo in the presence of multiple cell types (e.g. in situ or in its native location within a multicellular organism).

D. Delivery of Additional Exogenous Material into the Interior of a Target Cell

In addition to direct cell killing, proteins of the invention optionally may be used for delivery of additional exogenous materials into the interiors of target cells. The delivery of additional exogenous materials may be used, e.g., for cytotoxic, cytostatic, information gathering, and/or diagnostic functions. Non-toxic variants of the CD20-binding proteins of the invention, or optionally toxic variants, may be used to deliver additional exogenous materials to and/or label the interiors of cells physically coupled with an extracellular CD20 target of the CD20-binding protein. Various types of cells and/or cell populations which express CD20 to at least one cellular surface may be targeted by the CD20-binding proteins for receiving exogenous materials. The functional components of the present invention are modular, in that various Shiga toxin effector regions and additional exogenous materials may be linked to various binding regions to provide diverse applications, such as non-invasive in vivo imaging of tumor cells.

Because the CD20-binding proteins, whether toxic or nontoxic, and catalytically inactive forms thereof, are capable of entering cells physically coupled with an extracellular CD20 target recognized by its binding region, certain embodiments of the CD20-binding proteins of the invention may be used to deliver additional exogenous materials into the interior of targeted cell types. In one sense, the entire CD20-binding protein is an exogenous material which will enter the cell; thus, the "additional" exogenous materials are heterologous materials linked to but other than the core CD20-binding protein itself.

"Additional exogenous material" as used herein refers to one or more molecules, often not generally present within a native target cell, where the CD20-binding proteins of the present invention can be used to specifically transport such material to the interior of a cell. Non-limiting examples of additional exogenous materials are cytotoxic agents, peptides, polypeptides, proteins, polynucleotides, detection promoting agents, and small molecule chemotherapeutic agents.

In certain embodiments of the CD20-binding proteins of the present invention for delivery of additional exogenous material, the additional exogenous material is a cytotoxic agent, such as, e.g., a small molecule chemotherapeutic agent, cytotoxic antibiotic, alkylating agent, antimetabolite, topoisomerase inhibitor, and/or tubulin inhibitor. Non-limiting examples of cytotoxic agents include aziridines, cisplatins, tetrazines, procarbazine, hexamethylmelamine, vinca alkaloids, taxanes, camptothecins, etoposide, doxorubicin, mitoxantrone, teniposide, novobiocin, aclarubicin, anthracyclines, actinomycin, bleomycin, plicamycin, mitomycin, daunorubicin, epirubicin, idarubicin, dolastatins, maytansines, docetaxel, adriamycin, calicheamicin, auristatins, pyrrolobenzodiazepine, carboplatin, 5-fluorouracil (5-FU), capecitabine, mitomycin C, paclitaxel, 1,3-Bis(2-chloroethyl)-1-nitrosourea (BCNU), rifampicin, cisplatin, methotrexate, and gemcitabine.

In certain embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA). In certain embodiments, the additional exogenous material is an antigen, such as antigens derived from bacterial proteins, viral proteins, proteins mutated in cancer, proteins aberrantly expressed in cancer, or T-cell complementary determining regions. For example, exogenous materials include antigens, such as those characteristic of antigen-presenting cells infected by bacteria, and T-cell complementary determining regions capable of functioning as exogenous antigens.

Because the CD20-binding proteins are capable of inducing cellular internalization of CD20 after binding to an extracellular part of CD20, certain embodiments of the CD20-binding proteins of the invention may be used to deliver additional exogenous materials into the interior of CD20 expressing cells. In one sense, the entire CD20-binding protein is an exogenous material which will enter the cell; thus, the "additional" exogenous materials are materials linked to but other than the core CD20-binding protein itself.

"Additional exogenous material" as used herein refers to one or more molecules, often not generally present within a native target cell, where the CD20-binding proteins of the present invention can be used to specifically transport such material to the interior of a cell. In general, additional exogenous material is selected from peptides, polypeptides, proteins, and polynucleotides. One example of an additional exogenous material that is a peptide is an influenza virus antigen, such as the influenza Matrix 58-66 peptide (SEQ ID NO:44). One exemplary embodiment of a CD20-binding protein that may deliver that antigen into a target cell that expresses CD20 is provided in SEQ ID NO:54.

Additional exogenous material may include an interior polypeptide sequence within the core CD20-binding protein structure, such as the influenza Matrix 58-66 peptide (SEQ ID NO:44). Similarly, additional exogenous material may include a terminally-located polypeptide sequence linked to a terminal of the CD20-binding structure. Certain embodiments of the CD20-binding proteins of the invention that may deliver that antigen, as an additional exogenous material, into a target cell that expresses CD20 at a cell surface is the CD20-binding protein that comprises or consists essentially of the polypeptide shown in any one of SEQ ID NOs: 46-112.

Additional examples of exogenous materials that may be linked to the CD20-binding proteins of the invention include antigens such as those derived from bacterial proteins, such as those characteristic of antigen-presenting cells infected by bacteria. Further examples of additional exogenous materials are proteins mutated in cancer or proteins that are aberrantly expressed in cancer. Further examples of additional exogenous materials include T-cell complementary determining regions capable of functioning as exogenous antigens.

Further examples of exogenous materials that may be linked to the CD20-binding proteins of the invention include proteins other than antigens, such as enzymes. Further types of exogenous material are polynucleotides. Among the polynucleotides that can be transported are those formulated to have regulatory function, such as small interfering RNA (siRNA) and microRNA (miRNA).

Additional examples of exogenous materials include antigens such as those derived from bacterial proteins, such as those characteristic of antigen-presenting cells that are infected with bacteria. Further examples of exogenous antigens are ones that are derived from a protein mutated in cancer or proteins that are aberrantly expressed in cancer. T-cell complementary determining regions (CDR) can also act as exogenous antigen for the purposes of the present invention. Additional examples of exogenous materials include polypeptides and proteins larger than an antigenic peptide, such as enzymes. Exogenous materials comprising polypeptides or proteins may optionally comprise one or more antigens whether known or unknown to the skilled worker. A further type of exogenous material is nucleic acids. Among the nucleic acids that can be transported are those formulated to have regulatory function, such as small interfering RNA (siRNA) and microRNA (miRNA).

E. Information Gathering for Diagnostic Functions

Certain CD20-binding proteins of the invention have uses in the in vitro and/or in vivo detection of specific cells, cell types, and/or cell populations. In certain embodiments, the CD20-binding proteins described herein are used for both diagnosis and treatment, or for diagnosis alone. When the same CD20-binding protein is used for both diagnosis and treatment, a cytotoxic CD20-binding protein variant which incorporates a detection promoting agent for diagnosis may be rendered non-toxic by catalytic inactivation of a Shiga toxin effector region via one or more amino acid substitutions, including exemplary substitutions described herein. Catalytically inactive forms of the cytotoxic CD20-binding proteins of the invention that are conjugated to detection promoting agents optionally may be used for diagnostic functions, such as for companion diagnostics used in conjunction with a therapeutic regimen comprising the same or a related binding region.

The ability to conjugate detection promoting agents known in the art to various CD20-binding proteins of the invention provides useful compositions for the detection of cancer, tumor, and immune cells. These diagnostic embodiments of the CD20-binding proteins of the invention may be used for information gathering via various imaging techniques and assays known in the art. For example, diagnostic embodiments of the CD20-binding proteins of the invention may be used for information gathering via imaging of intracellular organelles (e.g. endocytotic, Golgi, endoplasmic reticulum, and cytosolic compartments) of individual cancer cells, or immune cells in a patient or biopsy sample.

Various types of information may be gathered using the diagnostic embodiments of the CD20-binding proteins of the invention whether for diagnostic uses or other uses. This information may be useful, for example, in diagnosing neoplastic cell types, determining therapeutic susceptibilities of a patient's disease, assaying the progression of anti-neoplastic therapies over time, assaying the progression of immunomodulatory therapies over time, assaying the progression of antimicrobial therapies over time, evaluating the presence of unwanted cell types in transplantation materials, and/or evaluating the presence of residual tumor cells after surgical excision of a tumor mass.

For example, subpopulations of patients might be ascertained using information gathered using the diagnostic variants of the CD20-binding proteins of the invention, and then individual patients could be categorized into subpopulations based on their unique characteristic(s) revealed using those diagnostic embodiments. For example, the effectiveness of specific pharmaceuticals or therapies might be one type of criterion used to define a patient subpopulation. For example, a non-toxic diagnostic variant of a particular cytotoxic CD20-binding protein of the invention may be used to differentiate which patients are in a class or subpopulation of patients predicted to respond positively to a cytotoxic variant of the same cytotoxic CD20-binding protein of the invention. Accordingly, associated methods for patient identification, patient stratification and diagnosis using cytotoxic CD20-binding proteins and their non-toxic variants are considered to be within the scope of the present invention.

The effectiveness and potency of immunotoxins and ligand-toxin fusions as cytotoxic molecules is influenced by the densities of their target antigen(s) density on a target cell surface (see e.g. Decket T et al., *Blood* 103: 2718-26 (2004); Du X et al., *Blood* 111: 338-43 (2008); Baskar S et al., *mAbs* 4: 349-61 (2012)), epitope location (Press O et al., *J Immunol* 141: 4410-7 (1988); Godal A et al., *In J Cancer* 52: 631-5 (1992): Yazdi P et al., *Cancer Res* 55: 3763-71 (1995)), rate of internalization of the surface bound cytotoxic molecule (see e.g. Du X et al., *Cancer Res* 68: 6300-5 (2008)), and the intracellular itinerary (Tortorella L et al., *PLoS One* 7: e47320 (2012)).

The cell surface representation and/or density of an extracellular CD20 target biomolecule may influence the applications for which certain CD20-binding proteins of the invention may be most suitably used. Differences in cell surface representation and/or density of CD20 between cells may alter the internalization and/or cytotoxicity of a given CD20-binding protein of the invention both quantitatively and qualitatively. The cell surface representation and/or density of CD20 can vary among CD20 target positive cells or even on the same cell at different points in the cell cycle or cell differentiation. The total cell surface representation of CD20 on a particular cell or population of cells may be determined using methods known to the skilled worker, such as a FACS flow cytometry method.

An example of a FACS based assay for determining cell surface representation of an extracellular CD20 antigen for a particular cell type is as follows. An anti-CD20 antibody is labeled with a fluorophore, such as, e.g. a fluorescein derivative like fluorescein isothiocyanate (FITC), an Alexa Fluor® Dye like Alexa488, or some other fluorescent tag. A population of cells of the cell type of interest are grown and harvested at a density of $1\times10^6$ cells per milliliter (mL) and treated with 0.1 to 1.0 milligrams (mg) per mL (mg/mL) of labeled anti-CD20 antibody for 30 minutes on ice. Then the cold, treated cells are washed twice to remove unbound antibody. Alternatively, an unlabeled anti-CD20 antibody is used and is detected by a secondary antibody, such as, e.g., an anti-mouse IgG conjugated with a fluorophore, such as, e.g., Alexa488 or FITC. Direct immunofluorescence is used to quantify the amount of extracellular CD20 such as by using a FACS device.

For example, CD20 is usually expressed at high levels on B-cells compared with most cell surface targets, often more than 250,000 molecules per cell, allowing dense accumulation of the CD20 binding molecules on the plasma membrane of B-cells (Glennie M et al., *Mol Immunol* 44: 3823-37 (2007)).

IV. Variations in the Polypeptide Sequence of the CD20-Binding Protein which Maintain Overall Structure and Function The skilled worker will recognize that variations may be made to the CD20-binding proteins of the invention (and polynucleotides encoding them) without diminishing their biological activities, e.g. by maintaining the overall structure and function of the CD20-binding protein. For example, some modifications may facilitate expression, purification, pharmacokinetic properties, and/or immunogenicity. Such modifications are well known to the skilled worker and include, for example, a methionine added at the amino terminus to provide an initiation site, additional amino acids placed on either terminus to create conveniently located restriction sites or termination codons, and biochemical affinity tags fused to either terminus to provide for convenient detection and/or purification. Also contemplated herein is the inclusion of additional amino acid residues at the amino and/or carboxy termini, such as sequences for epitope tags or other moieties. The additional amino acid residues may be used for various purposes including, e.g., to facilitate cloning, expression, post-translational modification, synthesis, purification, detection, and/or administration. Non-limiting examples of epitope tags and moieties are: chitin binding protein domains, enteropeptidase cleavage sites, Factor Xa cleavage sites, FlAsH tags, FLAG tags, green fluorescent proteins (GFP), glutathione-S-transferase moieties, HA tags, maltose binding protein domains, myc tags, polyhistidine tags, ReAsH tags, strep-tags, strep-tag II, TEV protease sites, thioredoxin domains, thrombin cleavage site, and V5 epitope tags.

In certain of the above embodiments, the CD20-binding protein of the invention is a variant in which there are one or more conservative amino acid substitutions introduced into the polypeptide region(s). As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids (see, for example, Table B below). An example of a conservative substitution with a residue normally not found in endogenous, mammalian peptides and proteins is the conservative substitution of an arginine or lysine residue with, for example, ornithine, canavanine, aminoethylcysteine, or another basic amino acid. For further information concerning phenotypically silent substitutions in peptides and proteins see, e.g., Bowie J et al., Science 247: 1306-10 (1990).

In the conservative substitution scheme in Table B below, exemplary conservative substitutions of amino acids are grouped by physicochemical properties—I: neutral, hydrophilic; II: acids and amides: III: basic; IV: hydrophobic; V: aromatic, bulky amino acids, VI hydrophilic uncharged, VII aliphatic uncharged. VIII non-polar uncharged, IX cycloalkenyl-associated, X hydrophobic, XI polar, XII small, XIII turn-permitting, and XIV flexible. For example, conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

TABLE B

| Examples of Conservative Amino Acid Substitutions | | | | | | | | | | | | | |
|---|---|---|---|---|---|---|---|---|---|---|---|---|---|
| I | II | III | IV | V | VI | VII | VIII | IX | X | XI | XII | XIII | XIV |
| A | D | H | C | F | N | A | C | F | A | C | A | A | D |
| G | E | K | I | W | Q | G | M | H | C | D | C | C | E |
| P | Q | R | L | Y | S | I | P | W | F | E | D | D | G |
| S | N | | M | | T | L | | Y | G | H | G | E | K |
| T | | | V | | | V | | | H | K | N | G | P |
| | | | | | | | | | I | N | P | H | Q |
| | | | | | | | | | L | Q | S | K | R |
| | | | | | | | | | M | R | T | N | S |
| | | | | | | | | | R | S | V | Q | T |
| | | | | | | | | | T | T | | R | |
| | | | | | | | | | V | | | S | |
| | | | | | | | | | W | | | P | |
| | | | | | | | | | Y | | | T | |

In certain embodiments, a CD20-binding protein of the invention may comprise functional fragments or variants of a polypeptide region of the invention that have, at most, 20, 15, 10, 9, 8, 7, 6, 5, 4, 3, 2, or 1 amino acid substitution(s) compared to a polypeptide sequence recited herein, as long as the polypeptide region retains measurable biological activity alone or as a component of a CD20-binding protein. Variants of CD20-binding proteins are within the scope of the invention as a result of changing a polypeptide of the CD20-binding protein by altering one or more amino acids or deleting or inserting one or more amino acids, such as within the immunoglobulin-type binding region or the Shiga toxin effector region, in order to achieve desired properties, such as changed cytotoxicity, changed cytostatic effects, changed immunogenicity, and/or changed serum half-life. A polypeptide of a CD20-binding protein of the invention may further be with or without a signal sequence.

In certain embodiments, a CD20-binding protein of the invention shares at least 85%, 90%, 95%, 96%, 97%, 98%, 99% or more amino acid sequence identity to any one of the amino acid sequences of a CD20-binding protein recited herein, as long as it retains measurable biological activity, such as cytotoxicity, CD20 binding, enzymatic catalysis, or subcellular routing. The immunoglobulin-type binding region may differ from the amino acid sequences of a CD20-binding protein recited herein, as long as it retains binding functionality to an extracellular part of CD20. Binding functionality will most likely be retained if the amino acid sequences of the ABRs are identical. For example, a CD20-binding protein that consists essentially of 85% amino acid identity to the polypeptide shown in any one of SEQ ID NOs: 46-112 in which for the purposes of determining the degree of amino acid identity, the amino acid residues that form the ABR are disregarded is within the claim scope. Binding functionality can be determined by the skilled worker using standard techniques.

In certain embodiments, the Shiga toxin effector region may be altered to change its enzymatic activity and/or cytotoxicity so long as the Shiga toxin effector region retains one or more other Shiga toxin effector functions. This change may or may not result in a change in the cytotoxicity of a CD20-binding protein of which the altered Shiga toxin effector region is a component. Possible alterations include mutations to the Shiga toxin effector region selected from the group consisting of: a truncation, deletion, inversion, insertion, rearrangement, and substitution.

The cytotoxicity of the A Subunits of members of the Shiga toxin family may be altered, reduced, or eliminated by mutation or truncation. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Slt-I A1 in a cell-free ribosome inactivation assay (LaPointe, *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe, *J Biol Chem* 280: 23310-18 (2005)). A truncation analysis demonstrated that a fragment of StxA from residues 75 to 268 still retains significant enzymatic activity in vitro (Haddad, *J Bacteriol* 175: 4970-8 (1993)). A truncated fragment of Slt-I A1 containing residues 1-239 displayed significant enzymatic activity in vitro and cytotoxicity by de novo expression in the cytosol (LaPointe, *J Biol Chem* 280: 23310-18 (2005)). Expression of a Slt-I A1 fragment truncated to residues 1-239 in the endoplasmic reticulum was not cytotoxic because it could not retrotranslocate into the cytosol (LaPointe, *J Biol Chem* 280: 23310-18 (2005)).

The most critical residues for enzymatic activity and/or cytotoxicity in the Shiga toxin A Subunits have been mapped to the following residue-positions: asparagine-75, tyrosine-77, glutamate-167, arginine-170, and arginine-176 among others (Di, *Toxicon* 57: 535-39 (2011)). In particular, a double-mutant construct of Stx2A containing glutamate-E167-to-lysine and arginine-176-to-lysine mutations was completely inactivated; whereas, many single mutations in Stx1 and Stx2 showed a 10-fold reduction in cytotoxicity. Further, truncation of Stx1A to 1-239 or 1-240 reduced its cytotoxicity, and similarly, truncation of Stx2A to a conserved hydrophobic residue reduced its cytotoxicity.

The most critical residues for binding eukaryotic ribosomes and/or eukaryotic ribosome inhibition in the Shiga toxin A Subunit have been mapped to the following residue-positions arginine-172, arginine-176, arginine-179, arginine-188, tyrosine-189, valine-191, and leucine-233 among others (McCluskey A et al., *PLoS One* 7: e31191 (2012).

Shiga-like toxin 1 A Subunit truncations are catalytically active, capable of enzymatically inactivating ribosomes in vitro, and cytotoxic when expressed within a cell (LaPointe, *J Biol Chem* 280: 23310-18 (2005)). The smallest Shiga toxin A Subunit fragment exhibiting full enzymatic activity is a polypeptide composed of residues 1-239 of Slt1A (LaPointe, *J Biol Chem* 280: 23310-18 (2005)). Although the smallest fragment of the Shiga toxin A Subunit reported to retain substantial catalytic activity was residues 75-247 of StxA (Al-Jaufy, *Infect Immun* 62: 956-60 (1994)), a StxA truncation expressed de novo within a eukaryotic cell requires only up to residue 240 to reach the cytosol and exert catalytic inactivation of ribosomes (LaPointe, *J Biol Chem* 280: 23310-18 (2005)).

In certain embodiments derived from SLT-1A (SEQ ID NO:1), StxA (SEQ ID NO:2), or SLT-2A (SEQ ID NO:3), these changes include substitution of the asparagine at position 75, tyrosine at position 77, tyrosine at position 114, aspartate at position 167, arginine at position 170, arginine at position 176, and/or substitution of the tryptophan at position 203. Examples of such substitutions will be known to the skilled worker based on the prior art, such as asparagine at position 75 to alanine, tyrosine at position 77 to serine, substitution of the tyrosine at position 114 to alanine, substitution of the aspartate at position 167 to glutamate, substitution of the arginine at position 170 to alanine, substitution of the arginine at position 176 to lysine, and/or substitution of the tryptophan at position 203 to alanine.

CD20-binding proteins of the invention may optionally be conjugated to one or more additional agents which may include therapeutic and/or diagnostic agents known in the art, including such agents as described herein.

V. Production, Manufacture, and Purification of a CD20-Binding Protein

The CD20-binding proteins of the invention may be produced using biochemical engineering techniques well known to those of skill in the art. For example, CD20-binding proteins of the invention may be manufactured by standard synthetic methods, by use of recombinant expression systems, or by any other suitable method. The CD20-binding proteins of the invention may be produced as fusion proteins, chemically coupled conjugates, and/or combinations thereof, such as, e.g., a fusion protein component covalently linked to one or more components. Thus, the CD20-binding proteins may be synthesized in a number of ways, including, e.g. methods comprising: (1) synthesizing a polypeptide or polypeptide component of a CD20-binding protein using standard solid-phase or liquid-phase methodology, either stepwise or by fragment assembly, and isolating and purifying the final peptide compound product; (2) expressing a polynucleotide that encodes a polypeptide or polypeptide component of a CD20-binding protein in a host cell and recovering the expression product from the host cell or host cell culture; or (3) cell-free in vitro expression of a polynucleotide encoding a polypeptide or polypeptide component of a CD20-binding protein, and recovering the expression product; or by any combination of the methods of (1), (2) or (3) to obtain fragments of the peptide component, subsequently joining (e.g. ligating) the fragments to obtain the peptide component, and recovering the peptide component.

CD20-binding proteins of the invention may be prepared by linking the polypeptide components either directly or indirectly. The CD20 binding region and the Shiga toxin effector region may be linked by any method presently known in the art for such purposes, so long as the linking means does not substantially impede a desired functionality of either polypeptide component.

It may be preferable to synthesize a polypeptide or polypeptide component of a CD20-binding protein of the invention by means of solid-phase or liquid-phase peptide synthesis. CD20-binding proteins of the invention may suitably be manufactured by standard synthetic methods. Thus, peptides may be synthesized by, e.g. methods comprising synthesizing the peptide by standard solid-phase or liquid-phase methodology, either stepwise or by fragment assembly, and isolating and purifying the final peptide product. In this context, reference may be made to WO 1998/11125 or, inter alia, Fields, G et al., *Principles and Practice qf Solid-Phase Peptide Synthesis* (Synthetic Peptides, Gregory A. Grant, ed., Oxford University Press. U.K., 2nd ed., 2002) and the synthesis examples therein.

CD20-binding proteins of the invention may be prepared (produced and purified) using recombinant techniques well known in the art. In general, methods for preparing polypeptides by culturing host cells transformed or transfected with a vector comprising the encoding polynucleotide and recovering the polypeptide from cell culture are described in, e.g. Sambrook J et al., *Molecular Cloning: A Laboratory Manual* (Cold Spring Harbor Laboratory Press, NY, U.S., 1989); Dieffenbach C et al., *PCR Primer: A Laboratoy Manual* (Cold Spring Harbor Laboratory Press, N.Y., U.S., 1995). Any suitable host cell may be used to produce a CD20-binding protein of the invention. Host cells may be cells stably or transiently transfected, transformed, transduced or infected with one or more expression vectors which drive expression of a polypeptide of the invention. In addition, a CD20-binding protein of the invention may be produced by modifying the polynucleotide encoding the CD20-binding protein that result in altering one or more amino acids or deleting or inserting one or more amino acids in order to achieve desired properties, such as changed cytotoxicity, changed cytostatic effects, changed immunogenicity, and/or changed serum half-life.

There are a wide variety of expression systems which may be chosen to produce a protein of the invention. For example, host organisms for expression of proteins of the invention include prokaryotes, such as *E. coli* and *B. subtilis*, eukaryotic cells, such as yeast and filamentous fungi (like *S. cerevisiae, P. pastoris, A. awamori*, and *K. lactis*), algae (like *C. reinhardtii*), insect cell lines, mammalian cells (like CHO cells), plant cell lines, and eukaryotic organisms such as transgenic plants (like *A. thaliana* and *N. benthamiana*).

Accordingly, the present invention also provides methods for producing a CD20-binding protein of the invention according to above recited methods and using (i) a polynucleotide encoding part or all of a protein of the invention or a polypeptide component thereof, (ii) an expression vector comprising at least one polynucleotide of the invention capable of encoding part or all of a protein of the invention or a polypeptide component thereof when introduced into a suitable host cell or cell-free expression system, and/or (iii) a host cell comprising a polynucleotide or expression vector of the invention.

When a polypeptide or protein is expressed using recombinant techniques in a host cell or cell-free system, it is advantageous to separate (or purify) the desired polypeptide or protein away from other components, such as host cell factors, in order to obtain preparations that are of high purity or are substantially homogeneous. Purification can be accomplished by methods well known in the art, such as centrifugation techniques, extraction techniques, chromatographic and fractionation techniques (e.g. size separation by gel filtration, charge separation by ion-exchange column, hydrophobic interaction chromatography, reverse phase chromatography, chromatography on silica or cation-exchange resins such as DEAE and the like, chromatofocusing, and Protein A Sepharose chromatography to remove contaminants), and precipitation techniques (e.g. ethanol precipitation or ammonium sulfate precipitation). Any number of biochemical purification techniques may be used to increase the purity of a CD20-binding protein of the invention. In certain embodiments, the CD20-binding proteins of the invention may optionally be purified in homo-multimeric forms (i.e. a protein complex of two or more identical CD20-binding proteins) or in hetero-multimeric forms (i.e. a protein complex of two or more non-identical CD20-binding proteins).

In the Examples below are descriptions of non-limiting examples of methods for producing a CD20-binding protein of the invention, as well as specific but non-limiting aspects of CD20-binding protein production for the disclosed, exemplary, CD20-binding proteins.

VI. Pharmaceutical Compositions Comprising a CD20-Binding Protein

The present invention provides CD20-binding proteins for use, alone or in combination with one or more additional therapeutic agents, in a pharmaceutical composition, for treatment or prophylaxis of conditions, diseases, disorders, or symptoms described in further detail below (e.g. cancers, malignant tumors, non-malignant tumors, and immune disorders). The present invention further provides pharmaceutical compositions comprising a CD20-binding protein of the invention, or a pharmaceutically acceptable salt or solvate thereof, according to the invention, together with at least one pharmaceutically acceptable carrier, excipient, or vehicle. In certain embodiments, the pharmaceutical composition of the invention may comprise homo-multimeric and/or hetero-multimeric forms of the CD20-binding proteins of the invention. The pharmaceutical compositions will be useful in methods of treating, ameliorating, or preventing a disease, condition, disorder, or symptom described in further detail below. Each such disease, condition, disorder, or symptom is envisioned to be a separate embodiment with respect to uses of a pharmaceutical composition according to the invention. The invention further provides pharmaceutical compositions for use in at least one method of treatment according to the invention, as described in more detail below.

As used herein, the terms "patient" and "subject" are used interchangeably to refer to any organism, commonly vertebrates such as humans and animals, which presents symptoms, signs, and/or indications of at least one disease, disorder, or condition. These terms include mammals such as the non-limiting examples of primates, livestock animals (e.g. cattle, horses, pigs, sheep, goats, etc.), companion animals (e.g. cats, dogs, etc.) and laboratory animals (e.g. mice, rabbits, rats, etc.).

As used herein, "treat," "treating," or "treatment" and grammatical variants thereof refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease, disorder, or condition. With regard to tumors and/or cancers, treatment includes reductions in overall tumor burden and/or individual tumor size.

As used herein, the terms "prevent," "preventing," "prevention" and grammatical variants thereof refer to an approach for preventing the development of, or altering the pathology of, a condition, disease, or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount" or "therapeutically effective amount" is an amount or dose of a composition (e.g. a therapeutic composition or agent) that produces at least one desired therapeutic effect in a subject, such as preventing or treating a target condition or beneficially alleviating a symptom associated with the condition. The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly (see e.g. *Remington: The Science and Practice of Pharmacy* (Gennaro A, ed., Mack Publishing Co., Easton, Pa., U.S., 19th ed., 1995)).

Diagnostic compositions comprise a CD20-binding protein of the invention and one or more detection promoting agents. The phrase "diagnostically sufficient amount" refers to an amount that provides adequate detection and accurate measurement for information gathering purposes by the particular assay or diagnostic technique utilized. Generally, the diagnostically sufficient amount for whole organism in vivo diagnostic use will be a non-cumulative dose of between 0.1 mg to 100 mg of the detection promoting agent linked CD20-binding protein per kilogram of subject per subject (mg/kg). Typically, the amount of CD20-binding protein used in these information gathering methods will be as low as possible provided that it is still a diagnostically sufficient amount. For example, for in vivo detection in an organism, the amount of CD20-binding protein administered to a subject will be as low as feasibly possible.

Diagnostic compositions comprise a CD20-binding protein of the invention and one or more detection promoting agents. Various detection promoting agents are known in the art, such as isotopes, dyes, colorimetric agents, contrast enhancing agents, fluorescent agents, bioluminescent agents, and magnetic agents. These agents may be incorporated into the CD20-binding protein at any position. The incorporation of the agent may be via an amino acid residue(s) of the CD20-binding protein or via some type of linkage known in the art, including via linkers and/or chelators. The incorporation of the agent is in such a way to enable the detection of the presence of the diagnostic composition in a screen, assay, diagnostic procedure, and/or imaging technique.

When producing or manufacturing a diagnostic composition of the invention, a protein of the invention may be directly or indirectly linked to one or more detection promoting agents. There are numerous detection promoting agents known to the skilled worker which can be operably linked to the CD20-binding proteins of the invention for information gathering methods, such as for diagnostic and/or prognostic applications to diseases, disorders, or conditions of an organism (see e.g. Cai W et al., *J Nucl Med* 48: 304-10 (2007); Nayak T. Brechbiel M, *Bioconjug Chem* 20: 825-41 (2009); Paudyal P et al., *Oncol Rep* 22: 115-9 (2009): Qiao J et al., *PLoS ONE* 6: e18103 (2011); Sano K et al., *Breast Cancer Res* 14: R61 (2012)). For example, detection promoting agents include image enhancing contrast agents, such as fluorescent dyes (e.g. Alexa680, indocyanine green, and Cy5.5), isotopes and radionuclides, such as $^{11}$C, $^{13}$N, $^{15}$O, $^{18}$F, $^{32}$P, $^{51}$Mn, $^{52m}$Mn, $^{52}$Fe, $^{55}$Co, $^{62}$Cu, $^{64}$Cu, $^{67}$Cu, $^{67}$Ga, $^{68}$Ga, $^{72}$As, $^{73}$Se, $^{75}$Br, $^{76}$Br, $^{82m}$Rb, $^{83}$Sr, $^{86}$Y, $^{90}$Y, $^{89}$Zr, $^{94m}$Tc, $^{94}$Tc, $^{99m}$Tc, $^{110}$In, $^{111}$In, $^{120}$I, $^{123}$I, $^{124}$I, $^{125}$I, $^{131}$I, $^{154}$Gd, $^{155}$Gd, $^{156}$Gd, $^{157}$Gd, $^{158}$Gd, $^{177}$Lu, $^{186}$Re, $^{188}$Re, and $^{223}$R; paramagnetic ions, such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III), metals, such as lanthanum (III), gold (III), lead (II), and bismuth (III); ultrasound-contrast enhancing agents, such as liposomes; radiopaque agents, such as barium, gallium, and thallium compounds. Detection promoting agents may be incorporated directly or indirectly by using an intermediary functional group, such as chelators like 2-benzyl DTPA, PAMAM, NOTA, DOTA, TETA, analogs thereof, and functional equivalents of any of the foregoing (see Leyton J et al., *Clin Cancer Res* 14: 7488-96 (2008)).

When producing or manufacturing a diagnostic composition of the invention, a protein of the invention may be directly or indirectly linked to one or more detection promoting agents. There are numerous standard techniques known to the skilled worker for incorporating, affixing, and/or conjugating various detection promoting agents to proteins, especially to immunoglobulins and immunoglobulin-derived domains (Wu A, *Methods* 65: 139-47 (2014)). Similarly, there are numerous imaging approaches known to the skilled worker, such as non-invasive in vivo imaging techniques commonly used in the medical arena, for example: computed tomography imaging (CT scanning), optical imaging (including direct, fluorescent, and bioluminescent imaging), magnetic resonance imaging (MRI), positron emission tomography (PET), single-photon emission computed tomography (SPECT), ultrasound, and x-ray computed tomography imaging (see Kaur S et al., *Cancer Lett* 315: 97-111 (2012), for review).

VII. Production or Manufacture of a Pharmaceutical Composition Comprising a CD20-Binding Protein Pharmaceutically acceptable salts or solvates of any of the CD20-binding proteins of the invention are likewise within the scope of the present invention.

The term "solvate" in the context of the present invention refers to a complex of defined stoichiometry formed between a solute (in casu, a polypeptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

CD20-binding proteins of the present invention, or salts thereof, may be formulated as pharmaceutical compositions prepared for storage or administration, which typically comprise a therapeutically effective amount of a compound of the invention, or a salt thereof, in a pharmaceutically acceptable carrier. The term "pharmaceutically acceptable carrier" includes any of the standard pharmaceutical carriers. Pharmaceutically acceptable carriers for therapeutic use are well known in the pharmaceutical art, and are described, for example, in *Remington's Pharmaceutical Sciences* (Mack Publishing Co. (A. Gennaro, ed., 1985)). As used herein, "pharmaceutically acceptable carrier" includes any and all physiologically acceptable, i.e. compatible, solvents, dispersion media, coatings, antimicrobial agents, isotonic, and absorption delaying agents, and the like. Pharmaceutically acceptable carriers or diluents include those used in formulations suitable for oral, rectal, nasal or parenteral (including subcutaneous, intramuscular, intravenous, intradermal, and transdermal) administration. Exemplary pharmaceutically acceptable carriers include sterile aqueous solutions or dispersions and sterile powders for the extemporaneous preparation of sterile injectable solutions or dispersions. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants. In certain embodiments, the carrier is suitable for intravenous, intramuscular, subcutaneous, parenteral, spinal or epidermal administration (e.g. by injection or infusion). Depending on selected route of administration, the CD20-binding protein or other pharmaceutical component may be coated in a material intended to protect the compound from the action of low pH and other natural inactivating conditions to which the active CD20-binding protein may encounter when administered to a patient by a particular route of administration.

The formulations of the pharmaceutical compositions of the invention may conveniently be presented in unit dosage form and may be prepared by any of the methods well known in the art of pharmacy. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration. Subcutaneous or transdermal modes of administration may be particularly suitable for therapeutic CD20-binding proteins described herein.

The pharmaceutical compositions of the invention may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

In another aspect, the present invention provides pharmaceutical compositions comprising one or a combination of different CD20-binding proteins of the invention, or an ester, salt or amide of any of the foregoing, and at least one pharmaceutically acceptable carrier.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g. glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g. sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a CD20-binding protein of the invention in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a CD20-binding protein of the invention is designed to be administered by, e.g. intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

As described elsewhere herein, a protein of the present invention or composition thereof (e.g. pharmaceutical or diagnostic composition) may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see e.g. *Sustained and Controlled Release Drug Delivery Systems* (J. Robinson, ed., Marcel Dekker, Inc., NY, U.S., 1978)).

In certain embodiments, the composition of the present invention (e.g. pharmaceutical or diagnostic composition) may be formulated to ensure a desired distribution in vivo. For example, the blood-brain barrier excludes many large and/or hydrophilic compounds. To target a therapeutic compound or composition of the invention to a particular in vivo location, it can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 catenin and the like.

Pharmaceutical compositions include parenteral formulations designed to be used as implants or particulate systems. Examples of implants are depot formulations composed of polymeric or hydrophobic components such as emulsions, ion exchange resins, and soluble salt solutions. Examples of particulate systems are microspheres, microparticles, nanocapsules, nanospheres, and nanoparticles (see e.g. Honda M et al., *Int J Nanomedicine* 8: 495-503 (2013); Sharma A et al., *Biomed Res Int* 2013: 960821 (2013); Ramishetti S, Huang L, *Ther Deliv* 3: 1429-45 (2012)). Controlled release formulations may be prepared using polymers sensitive to ions, such as, e.g. liposomes, polaxamer 407, and hydroxyapatite.

VIII. Polynucleotides, Expression Vectors, and Host Cells

Beyond the CD20-binding proteins of the present invention, the polynucleotides which encode such CD20-binding proteins, or functional portions thereof, are within the scope of the present invention. The term "polynucleotide" is equivalent to the term "nucleic acids" both of which include polymers of deoxyribonucleic acids (DNAs), polymers of ribonucleic acids (RNAs), analogs of these DNAs or RNAs generated using nucleotide analogs, and derivatives, fragments and homologs thereof. The polynucleotide of the invention may be single-, double-, or triple-stranded. Disclosed polynucleotides are specifically disclosed to include all polynucleotides capable of encoding an exemplary CD20-binding protein, for example, taking into account the wobble known to be tolerated in the third position of RNA codons, yet encoding for the same amino acid as a different RNA codon (see Stothard P, *Biotechniques* 28: 1102-4 (2000)).

In one aspect, the invention provides polynucleotides which encode a CD20-binding protein of the invention, or a fragment or derivative thereof. The polynucleotides may include, e.g., nucleic acid sequence encoding a polypeptide at least 50%, 55%, 60%, 65%, 70%, 75%, 80%, 85%, 90%, 95%, 99% or more, identical to a polypeptide comprising one of the amino acid sequences of the CD20-binding protein. The invention also includes polynucleotides comprising nucleotide sequences that hybridize under stringent conditions to a polynucleotide which encodes a CD20-binding protein of the invention, or a fragment or derivative thereof, or the antisense or complement of any such sequence.

Derivatives or analogs of the polynucleotides (or CD20-binding proteins) of the invention include, inter alia, polynucleotide (or polypeptide) molecules having regions that are substantially homologous to the polynucleotides or CD20-binding proteins of the invention, e.g. by at least about 45%, 50%, 70%, 80%, 95%, 98%, or even 99% identity (with a preferred identity of 80-99%) over a polynucleotide or polypeptide sequence of the same size or when compared to an aligned sequence in which the alignment is done by a computer homology program known in the art. An exemplary program is the GAP program (Wisconsin Sequence Analysis Package, Version 8 for UNIX, Genetics Computer Group. University Research Park, Madison, Wis., U.S.) using the default settings, which uses the algorithm of Smith T, Waterman M, *Adv. Appl. Math.* 2: 482-9 (1981). Also included are polynucleotides capable of hybridizing to the complement of a sequence encoding the proteins of the invention under stringent conditions (see e.g. Ausubel F, et al., *Current Protocols in Molecular Biology* (John Wiley & Sons, New York, N.Y., U.S., 1993)), and below. Stringent conditions are known to those skilled in the art and may be found in *Current Protocols in Molecular Biology* (John Wiley & Sons, NY, U.S., Ch. Sec. 6.3.1-6.3.6 (1989).

The present invention further provides expression vectors that comprise the polynucleotides within the scope of the invention. The polynucleotides capable of encoding the CD20-binding proteins of the invention may be inserted into known vectors, including bacterial plasmids, viral vectors and phage vectors, using material and methods well known in the art to produce expression vectors. Such expression vectors will include the polynucleotides necessary to support production of contemplated CD20-binding proteins within any host cell of choice or cell-free expression systems (e.g. pTxb1 and pIVEX2.3 described in the Examples below). The specific polynucleotides comprising expression vectors for use with specific types of host cells or cell-free expression systems are well known to one of ordinary skill in the art, can be determined using routine experimentation, or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in the context of the present invention, an expression vector encoding a CD20-binding protein comprising a single polypeptide chain (e.g. an scFv linked to a Shiga toxin effector region) includes at least an expression unit for the single polypeptide chain, whereas a CD20-binding protein comprising, e.g. two or more polypeptide chains (e.g. one chain comprising a $V_L$ domain and a second chain comprising a $V_H$ domain linked to a toxin effector region) includes at least two expression units, one for each of the two polypeptide chains of the CD20-binding protein. For expression of multi-chain CD20-binding proteins, an expression unit for each polypeptide chain may also be separately contained on different expression vectors (e.g. expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Creation and isolation of host cell lines comprising a polynucleotide of the invention or capable of producing a CD20-binding protein of the invention can be accomplished using standard techniques known in the art.

CD20-binding proteins within the scope of the present invention may be variants or derivatives of the CD20-binding proteins described herein that are produced by modifying the polynucleotide encoding a CD20-binding protein by altering one or more amino acids or deleting or inserting one or more amino acids that may render it more suitable to achieve desired properties, such as more optimal expression by a host cell.

IX. Delivery Devices and Kits

In certain embodiments, the invention relates to a device comprising one or more compositions of matter of the invention, such as a pharmaceutical composition, for delivery to a subject. Thus, a delivery device comprising one or more compounds of the invention may be used to administer to a patient a composition of matter of the invention by various delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

Also within the scope of the invention are kits comprising at least one composition of matter of the invention, and optionally, packaging and instructions for use. Kits may be useful for drug administration and/or diagnostic information gathering. A kit of the invention may optionally comprise at least one additional reagent (e.g., standards, markers and the like). Kits typically include a label indicating the intended use of the contents of the kit. The kit may further comprise reagents and other tools for detecting a cell type (e.g. tumor cell) in a sample or in a subject, or for diagnosing whether a patient belongs to a group that responds to a therapeutic strategy which makes use of a compound, composition or related method of the invention as described herein.

X. Methods for Using a CD20-Binding Protein or a Pharmaceutical Composition Thereof Generally, it is an object of the invention to provide pharmacologically active agents, as well as compositions comprising the same, that can be used in the prevention and/or treatment of diseases, disorders, and conditions, such as cancers, tumors, growth abnormalities, immune disorders, or further pathological conditions mentioned herein. Accordingly, the present invention provides methods of using the CD20-binding proteins of the present invention and compositions thereof (e.g. pharmaceutical and diagnostic compositions) for the killing of CD20 cells, delivering of additional exogenous materials into CD20 expressing cells, labeling of the interiors of CD20 expressing cells, and for treating diseases, disorders, and conditions as described herein.

In particular, it is an object of the invention to provide such pharmacologically active agents, compositions, and/or methods that have certain advantages compared to the agents, compositions, and/or methods that are currently known in the art. Accordingly, the present invention provides methods of using CD20-binding proteins characterized by specified polypeptide sequences and pharmaceutical compositions thereof. For example, any of the polypeptide sequences in SEQ ID NOs: 1-112, can be specifically utilized as a component of the CD20-binding protein used in the following methods.

The present invention provides methods of inducing cellular internalization of a CD20-binding protein into one or more cell(s) expressing CD20 at a cellular surface, the methods comprising the step of contacting the cell(s) with a CD20-binding protein of the present invention or a composition thereof (e.g. a pharmaceutical or diagnostic composition of the invention) either in vitro or in viva, such as within a patient or subject. In addition, the present invention provides methods of rapidly internalizing the CD20-binding protein into the interior of a cell, by contacting the cell with a CD20-binding protein of the invention either in vivo or in vitro, such as within a patient. In certain further embodiments of these methods of inducing cellular internalization or rapidly internalizing the CD20-binding protein, the cellular internalization of the CD20-binding protein occurs within five hours at 37 degrees Celsius or another appropriate physiological temperature. For certain further embodiments of these methods, the cellular internalization of the CD20-binding protein occurs within one hour at 37 degrees Celsius or another appropriate physiological temperature.

In addition, the present invention provides a method of inducing cellular internalization of a CD20-binding protein into a CD20 positive cell(s) expressing CD20 at a cellular surface, the method comprising the step of contacting the cell(s) with a CD20-binding protein of the present invention or a pharmaceutical or diagnostic composition thereof. In certain embodiments, the step of contacting the cell(s) occurs in vitro. In certain other embodiments, the step of contacting the cell(s) occurs in viva, such as within a patient. In certain further embodiments of the inducing cellular internalization method, the cellular internalization of the CD20-binding protein occurs within five hours at 37 degrees Celsius or another appropriate physiological temperature. For certain further embodiments of the inducing cellular internalization method, the cellular internalization of the CD20-binding protein occurs within one hour at 37 degrees Celsius or another appropriate physiological temperature. For certain further embodiments of the inducing cellular internalization method, the administration of a plurality of the CD20-binding protein to a plurality of said CD20 expressing cells at a concentration equivalent to 50% cell surface CD20 occupancy, cellular internalization occurs for the majority of the CD20-binding protein is internalized into one or more of said CD20 expressing cells within one hour at 37 degrees Celsius or another appropriate physiological temperature.

Similarly, the present invention provides a method of internalizing a cell surface localized CD20 bound by a CD20-binding protein in a patient, the method comprising the step of administering to the patient a CD20-binding protein of the present invention or a composition thereof (e.g. a pharmaceutical or diagnostic composition of the invention) either in vitro or in vivo, such as within a patient. In certain further embodiments of the internalizing method, the cellular internalization of said cell surface localized CD20 bound by a CD20-binding protein occurs within five hours at 37 degrees Celsius or another appropriate physiological temperature for the cell. In certain further embodiments of the internalizing method, the cellular internalization of said cell surface localized CD20 bound by a CD20-binding protein occurs within one hour at 37 degrees Celsius or another appropriate physiological temperature for the cell.

In addition, the present invention provides a method of inducing cellular internalization of a CD20-binding protein into a CD20 positive cell(s) expressing CD20 at a cellular surface, the method comprising the step of contacting the cell(s) with a CD20-binding protein of the present invention or a pharmaceutical or diagnostic composition thereof. In certain embodiments, the step of contacting the cell(s) occurs in vitro. In certain other embodiments, the step of contacting the cell(s) occurs in vivo. In certain further embodiments of the inducing cellular internalization method, the cellular internalization of the CD20-binding protein occurs within five hours at 37 degrees Celsius or another appropriate physiological temperature for the cell. For certain further embodiments of the inducing cellular internalization method, the cellular internalization of the CD20-binding protein occurs within one hour at 37 degrees Celsius or another appropriate physiological temperature for the cell. For certain further embodiments of the inducing cellular internalization method, the administration of a plurality of the CD20-binding protein to a plurality of said CD20 expressing cells at a concentration equivalent to 50% cell surface CD20 occupancy, cellular internalization occurs for the majority of the CD20-binding protein is internalized into one or more of said CD20 expressing cells within one hour at 37 degrees Celsius or another appropriate physiological temperature for the cell.

Similarly, the present invention provides a method of internalizing a cell surface localized CD20 bound by a CD20-binding protein in a patient, the method comprising the step of administering to the patient a CD20-binding protein of the present invention or a composition thereof (e.g. a pharmaceutical or diagnostic composition of the invention). In certain further embodiments of the internalizing method, the cellular internalization of said cell surface localized CD20 bound by a CD20-binding protein occurs within five hours at 37 degrees Celsius or another appropriate physiological temperature for the cell. In certain further embodiments of the internalizing method, the cellular internalization of said cell surface localized CD20 bound by a CD20-binding protein occurs within one hour at 37 degrees Celsius or another appropriate physiological temperature for the cell.

Similarly, the present invention provides methods of internalizing into a CD20+ cell(s) a cell surface localized CD20 bound by a CD20-binding protein, the methods comprising the step of contacting the cell surface localized CD20 with a CD20-binding protein of the present invention or a composition thereof (e.g. a pharmaceutical or diagnostic composition of the invention) either in vitro or in vivo, such as within a patient. In certain further embodiments, the method of internalizing a cell surface localized CD20 bound by a CD20-binding protein occurs in a patient, the method comprising the step of administering to the patient a CD20-binding protein, or a pharmaceutical or diagnostic composition of the present invention. In certain further embodiments of the internalizing method, the cellular internalization of said cell surface localized CD20 bound by a CD20-binding protein occurs within five hours at 37 degrees Celsius or another appropriate physiological temperature for the cell. In certain further embodiments of the internalizing method, the cellular internalization of said cell surface localized CD20 bound by a CD20-binding protein occurs within one hour at 37 degrees Celsius or another appropriate physiological temperature for the cell.

The present invention provides methods of killing a cell(s) expressing CD20 at a cellular surface, the method comprising the step of contacting a CD20 expressing cell(s), either in vitro or in vivo, with a CD20-binding protein or a pharmaceutical composition of the present invention. In certain further embodiments, the method is for killing a CD20 positive cell(s) and the method comprises the step of contacting a CD20 positive cell(s) with a CD20-binding protein or a pharmaceutical composition of the present invention. In certain embodiments, the step of contacting the cell(s) occurs in vivo, such as within a subject or patient.

In certain embodiments, a CD20-binding protein or pharmaceutical composition of the present invention can be used to kill one or more CD20+ cells in a mixture of different cell types including CD20+ cells and CD20− cells, such as mixtures comprising cancer cells, healthy cells, hematological cells, immune cells, infected cells, and/or tumor cells. In certain embodiments, a CD20-binding protein or pharmaceutical composition of the present invention can be used to kill CD20+ malignant cells, such as cancer or tumor cells, in a mixture of different cell types. In certain embodiments, a CD20-binding protein or pharmaceutical composition of the present invention can be used to kill specific CD20+ cell types in a mixture of different cell types, such as pre-administration tissue material for therapeutic purposes. In certain embodiments, a CD20-binding protein or pharmaceutical composition of the present invention can be used to kill specific CD20+ cell types in a mixture of cell types, such as pre-administration tissue material for therapeutic purposes.

The CD20-binding proteins and pharmaceutical compositions of the invention have varied applications, including, e.g., uses in depleting unwanted cell types from tissues in vitro, ex vivo, and/or in vivo. It is within the scope of the present invention to utilize the CD20-binding protein of the invention or pharmaceutical composition thereof for the purposes of ex vivo depletion of CD20+ cells from isolated cell populations removed from a patient.

In certain embodiments, a CD20-binding protein or pharmaceutical composition of the present invention, alone or in combination with other compounds or pharmaceutical compositions can show potent cell-kill activity when administered to a population of cells, in vitro, ex vivo, and/or in vivo in a subject such as in a patient in need of treatment. By targeting the delivery of enzymatically active Shiga toxin regions using high-affinity binding regions to CD20+ cell types, this potent cell-kill activity can be restricted to specifically and selectively kill certain cell types within an organism, such as certain cancer cells, neoplastic cells, malignant cells, non-malignant tumor cells, and/or immune cells.

The present invention provides a method of killing a CD20+ cell in a patient in need thereof, the method comprising the step of administering to the patient at least one CD20-binding protein of the present invention or a pharmaceutical composition thereof.

CD20 is expressed by numerous mature B-cell neoplasms, such as in NHL and CLL (van Meerten T et al., *Clin Cancer Res* 12: 4027-35 (2006)). In addition, CD20 is expressed by mature T-cell and NK-cell neoplasms. CD20 is expressed by malignant T-cells such as in T-cell lymphomas (TCLs), including mycosis fungoides (MF), natural killer cell lymphoma (NK-cell lymphoma), peripheral T-cell lymphomas (PTCLs), and cutaneous T-cell lymphomas (Buckner C et al., *Ann Clin Lab Sci* 37: 263-7 (2007); Rahemtullah A et al., *Am J Surg Pathol* 32: 1593-607 (2008); Balmer N et al., *Am J Dermatopathol* 31: 187-92 (2009); Martin B et al., *J Cutan Pathol* 38: 663-9 (2011); Jiang Q et al., *Diagn Pathol* 7: 133 (2012); Hagen J et al., *Am J Dermatopathol* 35: 833-41 (2013); Harms K et al., *J Cutan Pathol* 41: 494-503 (2014)). CD20 is expressed by malignant T-cells in T-cell large granular lymphocyte leukemia (T-LGLL) (Miyazaki K et al., *Intern Med* 48: 1443-7 (2009)).

Certain embodiments of the CD20-binding protein or pharmaceutical compositions thereof can be used to kill a CD20+ cancer and/or tumor cell(s) in a patient, such as, e.g. B-cell or T-cell cancers. The terms "cancer cell" or "cancerous cell" refers to various neoplastic cells which grow and divide in an abnormally accelerated fashion and will be clear to the skilled person. Generally, cancers and/or tumors can be defined as diseases, disorders, or conditions that are amenable to treatment and/or prevention. The cancers and tumors (either malignant or non-malignant) which are comprised of cancer cells and/or tumor cells which may benefit from methods and compositions of the invention will be clear to the skilled person. Neoplastic cells are often associated with one or more of the following: unregulated growth, lack of differentiation, local tissue invasion, angiogenesis, and metastasis.

The term "tumor cell" includes both malignant and non-malignant cells (e.g. non-cancerous, benign tumor cells, non-cancerous "cancer" stem cells, tumor stem cells, pre-malignant cancer-initiating cells, tumor-initiating cells, or tumorigenic cells all of which can give rise to daughter cells which become malignant tumor and/or cancer cells but are unable to metastasize on their own (see e.g. Martinez-Climent J et al., *Haematologica* 95: 293-302 (2010))). For example, the following non-limiting examples of conditions involving cells with limited malignant potential may be diagnosed and/or treated using CD20-binding proteins of the invention: monoclonal B-cell lymphocytosis (MBL), localized follicular lymphoma (localized FL), gastric extranodal marginal zone (MALT) lymphomas, and intrafollicular neoplasia (Limpens J et al., *Oncogene* 6: 2271-6 (1991); Liu H et al., *Lancet* 357: 39-40 (2001); Richard P et al., *J Clin Pathol* 59: 995-6 (2006); Roulland S et al., *J Exp Med* 203: 2425-31 (2006); Marti G et al., *Br J Haematol* 139:701-8 (2007); Agel N et al., *Histopathology* 52: 256-60 (2008); Rawstron A et al., *N Engl J Med* 359: 575-83 (2008)). Similarly, cancer initiating cells and/or cancer stem cells may be detected and/or treated using CD20-binding proteins of the invention, such as, e.g., acute myeloid leukemia (AML) stem cells, B-cell non-Hodgkin's lymphoma (B-cell NHL) initiating cells, chronic myeloid leukemia (CML) stem cells, Hodgkin's lymphoma (HL or HD) stem-like cells, and mantle cell lymphoma (MCL) initiating cells (see e.g. Hope K et al., *Nat Immunol* 5: 738-43 (2004); Wang J, Dick J, *Trends Cell Biol* 15: 494-501 (2005); Ishikawa F et al., *Nat Biotechnol* 25: 1315-21 (2007); Jones R et al., *Blood* 113: 5920-6 (2009); Chen Z et al., *Stem Cell Res* 5: 212-225 (2010); Chomel J et al., *Blood* 118: 3657-60 (2011); Druker B, *J Clin Invest* 121: 396-409 (2011); Gerber J et al., *Blood* 119: 3571-7 (2012)).

Certain embodiments of the CD20-binding protein or pharmaceutical compositions thereof can be used to kill a CD20+ immune cell (whether healthy or malignant) in a patient. Certain embodiments of the CD20-binding protein or pharmaceutical compositions can be used to kill a healthy CD20+ immune cell(s) in a patient. CD20 is expressed by normal, B-cell lineage cells within certain cell developmental stages (van Meerten T et al., *Clin Cancer Res* 12: 4027-35 (2006)). CD20 is expressed by a subset of normal T-cells (Martin B et al., *J Cutan Pathol* 38: 663-9 (2011)).

If the CD20-binding proteins of the present invention comprise or are conjugated to an additional exogenous material, as described above, those CD20-binding proteins can be utilized in a method of delivering that exogenous material into a CD20 expressing cell or CD20+ target cell. The present invention provides methods for delivering exogenous materials to the inside of a CD20 expressing cell(s) or CD20+ cell(s), the methods comprising contacting the cell(s) with a CD20-binding protein of the present invention or a composition thereof (e.g. a pharmaceutical or diagnostic composition of the invention) either in vitro or in vivo, such as within a patient. Additionally, the present invention provides a method for delivering exogenous material to the inside of a CD20 expressing cell(s) comprising contacting the cell(s), either in vitro or in vivo, with a CD20-binding protein, pharmaceutical composition, and/or diagnostic composition of the present invention. The present invention further provides a method for delivering exogenous material to the inside of a CD20 expressing cell(s) in a patient, the method comprising the step of administering to the patient a CD20-binding protein of the present invention (with or without cytotoxic activity), wherein the CD20 expressing cell(s) is physically coupled with an extracellular CD20 target biomolecule of the CD20-binding protein.

In certain embodiments of the methods for delivering exogenous materials, the additional exogenous material is selected from the group consisting of cytotoxic agents, peptides, polypeptides, proteins, polynucleotides, and/or small molecule chemotherapeutic agents. In certain embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA). In certain embodiments, the additional exogenous material is a peptide and the peptide is an antigen. In certain embodiments, the additional exogenous material is an antigen derived from a bacterial protein. In certain other embodiments, the antigen is derived from a protein mutated in cancer. Further embodiments are ones in which the antigen is derived from a protein aberrantly expressed in cancer. Still further embodiments are ones in which the antigen is derived from a T-cell complementary determining region.

Additionally, the present invention provides a method of treating a disease, disorder, or condition in a patient comprising the step of administering to a patient in need thereof a therapeutically effective amount of at least one of the CD20-binding proteins of the present invention or a pharmaceutical composition thereof. Contemplated diseases, disorders, and conditions that can be treated using this method include cancers, hematological disorders, malignant tumors, non-malignant tumors immune disorders, and growth abnormalities. Administration of a "therapeutically effective dosage" of a compound of the invention may result in a decrease in severity of disease symptoms, an increase in frequency and duration of disease symptom-free periods, or a prevention of impairment or disability due to the disease affliction.

The therapeutically effective amount of a compound of the present invention will depend on the route of administration, the type of mammal being treated, and the physical characteristics of the specific patient under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

An acceptable route of administration may refer to any administration pathway known in the art, including but not limited to aerosol, enteral, nasal, ophthalmic, oral, parenteral, rectal, vaginal, or transdermal (e.g. topical administration of a cream, gel or ointment, or by means of a transdermal patch). "Parenteral administration" is typically associated with injection at or in communication with the intended site of action, including intratumoral injection, infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

For administration of a pharmaceutical composition of the invention, the dosage range will generally be from about 0.0001 to 100 mg/kg, and more, usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular patient.

Pharmaceutical compositions of the invention will typically be administered to the same patient on multiple occasions. Intervals between single dosages can be, for example, 2-5 days, weekly, monthly, every two or three months, every six months, or yearly. Intervals between administrations can also be irregular, based on regulating blood levels or other markers in the subject or patient. Dosage regimens for a compound of the invention include intravenous administration of 1 mg/kg body weight or 3 mg/kg body weight with the compound administered every two to four weeks for six dosages, then every three months at 3 mg/kg body weight or 1 mg/kg body weight.

A pharmaceutical composition of the present invention may be administered via one or more routes of administration, using one or more of a variety of methods known in the art. As will be appreciated by the skilled worker, the route and/or mode of administration will vary depending upon the desired results. Routes of administration for CD20-binding proteins or pharmaceutical compositions of the invention include, e.g. intravenous, intramuscular, intradermal, intraperitoneal, subcutaneous, spinal, or other parenteral routes of administration, for example by injection or infusion at or in communication with the intended site of action (e.g. intratumoral injection). In other embodiments, a CD20-binding protein or pharmaceutical composition of the invention may be administered by a non-parenteral route, such as a topical, epidermal or mucosal route of administration, for example, intranasally, orally, vaginally, rectally, sublingually, or topically.

Therapeutic CD20-binding proteins or pharmaceutical compositions of the invention may be administered with one or more of a variety of medical devices known in the art. For example, in one embodiment, a pharmaceutical composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery: and osmotic drug delivery systems. These and other such implants, delivery systems, and modules are known to those skilled in the art.

A CD20-binding protein or pharmaceutical composition of the present invention may be administered alone or in combination with one or more other therapeutic or diagnostic agents. A combination therapy may include a CD20-binding protein of the invention or pharmaceutical composition thereof combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which might complement or otherwise be beneficial in a therapeutic or prophylactic treatment regimen.

Treatment of a patient with a CD20-binding protein or pharmaceutical composition of the invention preferably leads to cell death of targeted cells and/or the inhibition of growth of targeted cells. As such, CD20-binding proteins of the invention, and pharmaceutical compositions comprising them, will be useful in methods for treating a variety of pathological disorders in which killing or depleting target cells may be beneficial, such as, inter alia, cancers, tumors, immune disorders, or growth abnormalities involving cells which express CD20, including neoplasia, overactive B-cells, and/or overactive T-cells.

The CD20-binding proteins and pharmaceutical compositions of the invention are useful for killing malignant cells which express elevated levels of CD20 at a cellular surface. The CD20-binding proteins and pharmaceutical compositions of the invention are particularly useful for killing neoplastic cells which express elevated levels of CD20 at a cellular surface.

The present invention provides methods of killing cell(s) comprising the step of contacting a cell(s) with a cytotoxic CD20-binding protein of the invention or a pharmaceutical composition comprising a CD20-binding protein of the invention. In certain embodiments, the step of contacting the cell(s) occurs in vitro. In certain other embodiments, the step of contacting the cell(s) occurs in vivo. The present invention further provides methods of treating diseases, disorders, and/or conditions in patients comprising the step of administering to a patient in need thereof a therapeutically effective amount of a CD20-binding protein or a pharmaceutical composition of the invention. In certain embodiments, the disease, disorder, or condition to be treated using a method of the invention is selected from: a cancer, tumor (malignant and non-malignant), growth abnormality, or immune disorder. In a further aspect, the above in vivo method to provide methods may be combined with an ex vivo method of depleting a CD20+ cell type(s) in a tissue intended for transplantation into a recipient, including for both autologous and heterologous transplants.

The CD20-binding proteins and pharmaceutical compositions of the present invention may be utilized in a method of treating a condition, disease, or disorder in a patient, the method comprising administering to a patient, in need thereof, a therapeutically effective amount of the CD20-binding protein or a pharmaceutical composition of the present invention. In certain embodiments of these treating methods of the present invention, the disease, disorder, or condition to be treated using a method of the present invention involves the cancer cell, tumor cell, and/or immune cell which express CD20 at a cellular surface. In certain embodiments of these treating methods of the present invention, the disease, disorder, or condition to be treated using a method of the present invention involves a CD20 positive cancer cell, tumor cell, and/or immune cell. In certain embodiments of these treating methods of the present invention, the disease to be treated is selected from the group consisting of: hematologic cancer, leukemia, lymphoma, melanoma, and myeloma. In certain embodiments of the methods of the present invention, the condition, disease, or disorder being treated is related to hematologic diseases, rheumatic diseases, hematologic cancers, leukemias, lymphomas, melanomas, myelomas, acute myeloid leukemias (acute myelogenous leukemia or AML), acute non-lymphocytic leukemias, B-cell chronic lymphocytic leukemias (B-cell CLL), B-cell lymphomas, B-cell non-Hodgkin's lymphomas (B-cell NHL), B-cell precursor acute lymphoblastic leukemias (BCP-ALL or B-ALL), B-cell prolymphocytic leukemias (B-PLL), Burkitt's lymphomas (BL), chronic lymphocytic leukemias (CLL), chronic myeloid leukemias (CML), diffuse large B-cell lymphomas (DLBCL or DLBL), follicular lymphomas (FL), hairy cell leukemias (HCL), Hodgkin's lymphomas (HL or HD), immunoblastic large cell lymphomas, mantle cell lymphomas (MCL), multiple myelomas (MM), nodular lymphocyte predominant Hodgkin's lymphomas (NLPHL), non-Hodgkin's lymphomas (NHL), plasmablastic lymphomas, plasma cell neoplasmas, plasma cell myelomas, precursor B-lymphoblastic lymphomas (B-LBL), small lymphocytic lymphomas (SLL), T-cell large granular lymphocyte leukemias (T-LGLL), T-cell lymphomas (TCL), T-cell prolymphocytic leukemias (T-PLL), Waldenström's macroglobulinemias (WM), amyloidosis, ankylosing spondylitis, asthma, Crohn's disease, diabetes, graft rejection, graft-versus-host disease, Graves' disease, Graves' ophthalmopathy, Hashimoto's thyroiditis, hemolytic uremic syndrome, HIV-related diseases, lupus erythematosus, multiple sclerosis, neuromyclitis optica spectrum disorders, N-methyl D-aspartate (NMDA) receptor encephalitis, opsoclonus myoclonus syndrome (OMS), paroxysmal nocturnal hemoglobinuria, polyarteritis nodosa, polyarthritis, psoriasis, psoriatic arthritis, rheumatoid arthritis, scleritis, scleroderma, septic shock, Sjorgren's syndrome, ulcerative colitis, and vasculitis.

In certain embodiments, a CD20-binding protein or pharmaceutical composition of the present invention is used to treat a B-cell-, plasma cell-, T-cell- or antibody-mediated disease or disorder, such as for example hematologic diseases, rheumatic diseases, hematologic cancers, leukemias, lymphomas, melanomas, myelomas, acute myeloid leukemias (acute myelogenous leukemia or AML), acute non-lymphocytic leukemias, B-cell chronic lymphocytic leukemias (B-cell CLL), B-cell lymphomas, B-cell non-Hodgkin's lymphomas (B-cell NHL), B-cell precursor acute lymphoblastic leukemias (BCP-ALL or B-ALL), B-cell prolymphocytic leukemias (B-PLL), Burkitt's lymphomas (BL), chronic lymphocytic leukemias (CLL), chronic myeloid leukemias (CML), diffuse large B-cell lymphomas (DLBCL or DLBL), follicular lymphomas (FL), hairy cell leukemias (HCL), Hodgkin's lymphomas (HL or HD), immunoblastic large cell lymphomas, mantle cell lymphomas (MCL), multiple myelomas (MM), nodular lymphocyte predominant Hodgkin's lymphomas (NLPHL), non-Hodgkin's lymphomas (NHL), plasmablastic lymphomas, plasma cell neoplasmas, plasma cell myelomas, precursor B-lymphoblastic lymphomas (B-LBL), small lymphocytic lymphomas (SLL), T-cell large granular lymphocyte leukemias (T-LGLL), T-cell lymphomas (TCL), T-cell prolymphocytic leukemias (T-PLL), Waldenström's macroglobulinemias (WM), amyloidosis, ankylosing spondylitis, asthma, Crohn's disease, diabetes, graft rejection, graft-versus-host disease, Graves' disease, Graves' ophthalmopathy, Hashimoto's thyroiditis, hemolytic uremic syndrome, HIV-related diseases, lupus erythematosus, multiple sclerosis, neuromyelitis optica spectrum disorders, N-methyl D-aspartate (NMDA) receptor encephalitis, opsoclonus myoclonus syndrome (OMS), paroxysmal nocturnal hemoglobinuria, polyarteritis nodosa, polyarthritis, psoriasis, psoriatic arthritis, rheumatoid arthritis, scleritis, scleroderma, septic shock, Sjorgren's syndrome, ulcerative colitis, and vasculitis.

In certain embodiments, a CD20-binding protein or pharmaceutical composition of the present invention is used to treat a B-cell and/or T-cell mediated disease or disorder, such as for example certain hematologic cancers and rheumatic diseases including leukemias, lymphomas, myelomas, amyloidosis, ankylosing spondylitis, asthma, Crohn's disease, diabetes, graft rejection, graft-versus-host disease, Graves' disease, Graves' ophthalmopathy, Hashimoto's thyroiditis, hemolytic uremic syndrome, HIV-related diseases, lupus erythematosus, multiple sclerosis, neuromyelitis optica spectrum disorders, N-methyl D-aspartate (NMDA) receptor encephalitis, opsoclonus myoclonus syndrome (OMS), paroxysmal nocturnal hemoglobinuria, polyarteritis nodosa, polyarthritis, psoriasis, psoriatic arthritis, rheumatoid arthritis, scleritis, scleroderma, septic shock, Sjorgren's syndrome, ulcerative colitis, and vasculitis. In addition, the CD20-binding proteins or pharmaceutical compositions of the present invention may be used to treat cancers which involve CD20 expression but are not derived from a B-cell lineage, such as certain melanomas, T-cell leukemias, and T-cell lymphomas.

The CD20-binding proteins and pharmaceutical compositions of the present invention are commonly anti-neoplastic agents, meaning they are capable of treating and/or preventing the development, maturation, or spread of CD20+ neoplastic or malignant cells by inhibiting the growth, by inhibiting proliferation, and/or by causing the death of malignant and/or neoplastic cells.

In certain embodiments, the present invention provides methods for treating malignancies or neoplasms in a mammalian subject, such as a human, the method comprising the step of administering to a subject in need thereof a therapeutically effective amount of a CD20-binding protein or pharmaceutical composition of the invention.

Additionally, the CD20-binding proteins of the invention may be utilized in a method for treating cancer, wherein the tumor or cancer cell expresses on its surface a CD20 antigen, which method comprises administering the protein of the present invention to a patient in need of such treatment. Some cancers shown to have expression of CD20 include, but are not limited to: B-cell lymphomas (including both non-Hodgkin's and Hodgkin's), hairy cell leukemia, B-cell chronic lymphocytic leukemia, multiple myeloma, T-cell leukemia, T-cell lymphomas, and melanoma cancer stem cells.

The CD20-binding proteins and pharmaceutical compositions of the present invention may be utilized in a method of treating cancer comprising administering to a patient, in need thereof, a therapeutically effective amount of the CD20-binding protein or a pharmaceutical composition of the present invention. In certain embodiments of the methods of the present invention, the cancer being treated is selected from the group consisting of: hematologic cancer, leukemia, lymphoma, melanoma, and myeloma. Non-limiting examples of subtypes of hematologic cancers (e.g. leukemias, lymphomas, and myelomas) that may be treated with the CD20-binding proteins and pharmaceutical compositions of the invention include acute myeloid leukemias (acute myelogenous leukemia or AML), acute non-lymphocytic leukemias. B-cell lymphomas, B-cell non-Hodgkin's lymphomas (B-cell NHL), B-cell acute lymphoblastic leukemias (B-ALL or BCP-ALL). B-cell prolymphocytic leukemias (B-PLL), B-lymphoblastic lymphomas (B-LBL), Burkitt's lymphomas (BL), atypical Burkitt's lymphomas (atypical BL), chronic lymphocytic leukemias (CLL), chronic myeloid leukemias (CML), cutaneous B-cell lymphomas (CBCL), diffuse large B-cell lymphomas (DLBCL or DLBL), follicular lymphomas (FL), hairy cell leukemias (HCL), heavy chain diseases, Hodgkin's lymphomas (HL or HD), immunoblastic large cell lymphomas, lymphomatoid granulomatosis (LG or LYG), lymphoplasmacytic lymphomas, mantle cell lymphomas (MCL), marginal zone lymphomas (MZL), multiple myelomas (MM), nodular lymphocyte predominant Hodgkin's lymphomas (NLPHL), non-Hodgkin's lymphomas (NHL), plasmablastic lymphomas (PBL), plasmablastic lymphomas associated with multicentric Castleman disease, plasma cell neoplasmas, plasma cell myelomas, primary effusion lymphomas (PEL), small lymphocytic lymphomas (SLL), T-cell large granular lymphocyte leukemias (T-LGLL), T-cell lymphomas (TCL), peripheral T-cell lymphomas (PTCL), T-cell prolymphocytic leukemias (T-PLL), mycosis fungiodes (MF), and Waldenström's macroglobulinemias (WM).

In certain cancers, depletion and/or inhibition of B-cells generally may improve disease outcomes, such as, e.g. by depleting cancer escape promoting regulatory B-cells (see e.g. Olkhanud P et al., *Cancer Res* 69: 5996-6004 (2009); Olkhanud P et al., *Cancer Res* 71: 3505-15 (2011)).

The CD20-binding proteins and pharmaceutical compositions of the present invention may be utilized in a method of treating an immune disorder comprising administering to a patient, in need thereof, a therapeutically effective amount of the CD20-binding protein or a pharmaceutical composition of the present invention. Non-limiting examples of immune disorder that may be treated are rheumatic diseases related to inflammation. In certain embodiments of the methods of the present invention, the immune disorder is related to an inflammation associated with a disease selected from the group consisting of: amyloidosis, ankylosing spondylitis, asthma, Crohn's disease, diabetes, graft rejection, graft-versus-host disease, Graves' disease, Graves' ophthalmopathy, Hashimoto's thyroiditis, heavy chain disease, hemolytic uremic syndrome, HIV-related diseases, lupus erythematosus, multiple sclerosis, neuromyelitis optica spectrum disorders, N-methyl D-aspartate (NMDA) receptor encephalitis, opsoclonus myoclonus syndrome (OMS), paroxysmal nocturnal hemoglobinuria, polyarteritis nodosa, polyarthritis, psoriasis, psoriatic arthritis, rheumatoid arthritis, scleritis, scleroderma, septic shock, Sjorgren's syndrome, ulcerative colitis, and vasculitis (see e.g. Fenalti G et al., *Diabetes* 57: 1293-301 (2008); Rizzi M et al., *PLoS One* 5: e10838 (2010); Hampe C. *Autoimmunity* 45: 320-31 (2012); Hampe C, *Scientifica* (Cairo) pii: 215308 (2012); Hargreaves C et al., *J Immunol* 190: 5373-81 (2013)).

It is within the scope of the present invention to utilize the protein of the present invention or pharmaceutical composition thereof for the purposes of purging patient cell populations (e.g. bone marrow) of malignant, neoplastic, or otherwise unwanted T-cells and/or B-cells and then reinfusing the T-cell and/or B-cells depleted material into the patient (see e.g. van Heeckeren W et al., *Br J Haematol* 132: 42-55 (2006); Alpdogan O, van den Brink M, *Semin Oncol* 39: 629-42 (2012)).

It is within the scope of the present invention to provide a prophylaxis or treatment for diseases or conditions mediated by B-cells and/or T-cells by administering the CD20-binding protein of the invention, or a pharmaceutical composition thereof, to a patient in need thereof for the purpose of killing B-cells and/or T-cells in the patient. This usage is compatible with preparing or conditioning a patient for bone marrow transplantation, stem cell transplantation, tissue transplantation, or organ transplantation, regardless of the source of the transplanted material, e.g. human or non-human sources.

It is within the scope of the present invention to utilize the CD20-binding protein of the invention or pharmaceutical composition thereof for the purposes of er vivo depletion of B-cells and/or T-cells from isolated cell populations removed from a patient. In one non-limiting example, the CD20-binding protein of the invention may be used in a method for prophylaxis of organ and/or tissue transplant rejection wherein the donor organ or tissue is perfused prior to transplant with a cytotoxic CD20-binding protein of the invention or a pharmaceutical composition thereof in order to purge the organ of unwanted donor B-cells and/or T-cells (see e.g. Alpdogan O, van den Brink M. *Semin Oncol* 39: 629-42 (2012)).

It is also within the scope of the present invention to utilize the CD20-binding protein of the invention or pharmaceutical composition thereof for the purposes of depleting B-cells and/or T-cells from a donor cell population as a prophylaxis against graft-versus-host disease, and induction of tolerance, in a patient to undergo a bone marrow and or stem cell transplant (see e.g. van Heeckeren W et al., *Br J Haematol* 132: 42-55 (2006); Alpdogan O, van den Brink M, *Semin Oncol* 39: 629-42 (2012)).

Among certain embodiments of the present invention is using the CD20-binding protein as a component of a medicament for the treatment or prevention of a cancer, tumor, other growth abnormality, or immune disorder involving a CD20 expressing cell or CD20+ cell. For example, immune disorders presenting on the skin of a patient may be treated with such a medicament in efforts to reduce inflammation. In another example, skin tumors (e.g. melanomas) may be treated with such a medicament in efforts to reduce tumor size or eliminate the tumor completely.

Among certain embodiment of the present invention is a method of using a CD20-binding protein, pharmaceutical composition, and/or diagnostic composition of the invention to detect the presence of a CD20 expressing cell and/or CD20+ cell type for the purpose of information gathering regarding diseases, conditions and/or disorders characterized by CD20 cell surface expression, characterized by changes in the amount of cell surface accessible CD20, and/or associated with changes in CD20 cell surface expression. The method comprises contacting a cell with a diagnostically sufficient amount of a CD20-binding protein to detect the CD20-binding protein by an assay or diagnostic technique. The term "diagnostically sufficient amount" refers to an amount that provides adequate detection and accurate measurement for information gathering purposes by the particular assay or diagnostic technique utilized. Generally, the diagnostically sufficient amount for a whole organism in vivo diagnostic use will be a non-cumulative dose between 0.1 mg to 100 mg of the detection promoting agent linked CD20-binding protein per kg of subject per subject. Typically, the amount of CD20-binding protein used in these information gathering methods will be as low as possible provided that it is still a diagnostically sufficient amount. For example, for in vivo detection in an organism, the amount of CD20-binding protein administered to a subject will be as low as possible.

The cell-type specific targeting of CD20-binding proteins of the invention combined with detection promoting agents provides a way to detect and image CD20 expressing cells physically coupled with an extracellular CD20 target biomolecule of a binding region of the CD20-binding protein. Imaging of cells using the CD20-binding proteins of the invention may be performed in vitro or in vivo by any suitable technique known in the art. Diagnostic information may be collected using various methods known in the art, including whole body imaging of an organism or using ex vivo samples taken from an organism. The term "sample" used herein refers to any number of things, but not limited to, fluids such as blood, urine, serum, lymph, saliva, anal secretions, vaginal secretions, and semen, and tissues obtained by biopsy procedures. For example, various detection promoting agents may be utilized for non-invasive in vivo tumor imaging by techniques such as magnetic resonance imaging (MRI), optical methods (such as direct, fluorescent, and bioluminescent imaging), positron emission tomography (PET), single-photon emission computed tomography (SPECT), ultrasound, x-ray computed tomography, and combinations of the aforementioned (see, Kaur S et al., *Cancer Lett* 315: 97-111 (2012), for review).

Among certain embodiments of the present invention is a method of using a CD20-binding protein of the present invention comprising a detection promoting agent for the collection of information useful in the diagnosis, prognosis, or characterization of a disease, disorder, or condition. Among certain embodiments of the present invention is a method of detecting a cell using a CD20-binding protein and/or diagnostic composition of the present invention comprising the steps of contacting a cell with the CD20-binding protein and/or diagnostic composition of the present invention and detecting the presence of the CD20-binding protein and/or diagnostic composition. In certain embodiments, the step of contacting the cell(s) occurs in vitro and/or ex vivo. In certain embodiments, the step of contacting the cell(s) occurs in vivo. In certain embodiments, the step of detecting the cell(s) occurs in vitro and/or ex vivo. In certain embodiments, the step of detecting the cell(s) occurs in vivo.

The method of using a CD20-binding protein, pharmaceutical composition, or diagnostic composition of the invention to detect the presence of a CD20 expressing cell or CD20+ cell for the purpose of information gathering may be performed on cells in vivo within a patient, including on cells in situ, e.g. at a disease locus, on cells in vitro, and/or in an ex vivo setting on cells and tissues removed from an organism, e.g. a biopsy material. The detection of CD20 expressing and/or CD20+ cells, cell types, and cell populations may be used in the diagnosis and imaging of cells that express elevated levels of CD20, such as, e.g., tumor and cancer cells. The CD20-binding proteins and diagnostic compositions of the invention may be employed to image or visualize a site of possible accumulation of CD20 expressing and/or CD20+ cells in an organism. These methods may be used to identify sites of tumor development or residual tumor cells after a therapeutic intervention.

Diagnostic compositions of the invention may be used to characterize a disease, disorder, or condition as potentially treatable by a related pharmaceutical composition of the invention. Certain compositions of matter of the invention may be used to determine whether a patient belongs to a group that responds to a therapeutic strategy which makes use of a compound, composition or related method of the invention as described herein or is well suited for using a delivery device of the invention.

Diagnostic compositions of the invention may be used after a disease, e.g. cancer, is detected in order to better characterize it, such as to monitor distant metastases, heterogeneity, and stage of cancer progression. The phenotypic assessment of disease disorder or infection can help prognosis and prediction during therapeutic decision making. In disease reoccurrence, certain methods of the invention may be used to discriminate local versus systemic problems.

Diagnostic compositions of the invention may be used to assess responses to therapeutic(s) regardless of the type of therapeutic, e.g. small molecule drug or biological drug, or cell-based therapy. For example, certain embodiments of the diagnostics of the invention may be used to measure changes in tumor size, changes in CD20+ cell populations including number and distribution, or monitoring a different marker than the antigen targeted by a therapy already being administered to a patient (see Smith-Jones P et al., *Nat. Biotechnol* 22: 701-6 (2004): Evans M et al., *Proc. Natl. Acad. Sci. U.S.A.* 108: 9578-82 (2011))

Certain embodiments of the method used to detect the presence of a CD20 expressing cell type may be used to gather information regarding diseases, disorders, and conditions, such as, for example cancers, tumors and immune disorders related to hematologic disease, rheumatic disease, hematologic cancer, leukemia, lymphoma, melanoma, myeloma, amyloidosis, ankylosing spondylitis, asthma, Crohn's disease, diabetes, graft rejection, graft-versus-host disease, Graves' disease, Graves' ophthalmopathy, Hashimoto's thyroiditis, hemolytic uremic syndrome, HIV-related diseases, lupus erythematosus, multiple sclerosis, neuromyelitis optica spectrum disorders, N-methyl D-aspartate (NMDA) receptor encephalitis, opsoclonus myoclonus syndrome (OMS), paroxysmal nocturnal hemoglobinuria, polyarteritis nodosa, polyarthritis, psoriasis, psoriatic arthritis, rheumatoid arthritis, scleritis, scleroderma, septic shock, Sjorgren's syndrome, ulcerative colitis, and vasculitis. Non-limiting examples of types of hematologic cancers (e.g. leukemias, lymphomas, and myelomas) that CD20-binding proteins and diagnostic compositions of the invention may be used to gather information about include acute myeloid leukemias (acute myelogenous leukemia or AML), acute non-lymphocytic leukemias, B-cell chronic lymphocytic leukemias (B-cell CLL), B-cell lymphomas, B-cell non-Hodgkin's lymphomas (B-cell NHL), B-cell precursor acute lymphoblastic leukemias (BCP-ALL or B-ALL), B-cell pro-lymphocytic leukemias (B-PLL). Burkitt's lymphomas (BL), chronic lymphocytic leukemias (CLL), chronic myeloid leukemias (CML), diffuse large B-cell lymphomas (DLBCL or DLBL), follicular lymphomas (FL), hairy cell leukemias (HCL), Hodgkin's lymphomas (HL or HD), immunoblastic large cell lymphomas, mantle cell lymphomas (MCL), multiple myelomas (MM), nodular lymphocyte predominant Hodgkin's lymphomas (NLPHL), non-Hodgkin's lymphomas (NHL), plasmablastic lymphomas, plasma cell neoplasmas, plasma cell myelomas, precursor B-lymphoblastic lymphomas (B-LBL), small lymphocytic lymphomas (SLL), T-cell large granular lymphocyte leukemias (T-LGLL), T-cell lymphomas (TCL), T-cell prolymphocytic leukemias (T-PLL), and Waldenström's macroglobulinemias (WM).

Among certain embodiment of the present invention is a method of using a CD20-binding protein or diagnostic composition of the invention to label or detect the interiors of specific cells, such as, e.g., certain CD20+ neoplastic cells, immune cell types, and other CD20+ cell types (see e.g., Koyama Y et al., *Clin Cancer Res* 13: 2936-45 (2007); Ogawa M et al., *Cancer Res* 69: 1268-72 (2009); Yang L et al., *Small* 5: 235-43 (2009)). Based on the ability of the CD20-binding proteins of the invention to enter specific cell types and route within cells via retrograde intracellular transport, the interior compartments of specific cell types are labeled for detection. This can be performed on cells in vivo within a patient, including on cells in situ, e.g. at a disease locus, on cells in vitro, and/or in an ex vivo setting on cells and tissues removed from an organism, e.g. a biopsy material.

Diagnostic compositions of the invention may be used to characterize a disease, disorder, or condition as potentially treatable by a related pharmaceutical composition of the invention. Certain compositions of matter of the invention may be used to determine whether a patient belongs to a group that responds to a therapeutic strategy which makes use of a compound, composition or related method of the invention as described herein or is well suited for using a delivery device of the invention.

Diagnostic compositions of the invention may be used after a disease, e.g. cancer, is detected in order to better characterize it, such as to monitor distant metastases, heterogeneity, and stage of cancer progression. The phenotypic assessment of disease disorder or infection can help prognostic and prediction during therapeutic decision making. In disease reoccurrence, certain methods of the invention may be used to determine if local or systemic problem.

Diagnostic compositions of the invention may be used to assess responses to therapeutic(s) regardless of the type of therapeutic, e.g. small molecule drug, biological drug, or cell-based therapy. For example, certain embodiments of the diagnostics of the invention may be used to measure changes in tumor size, changes in CD20+ cell populations including number and distribution, or monitoring a different marker than the antigen targeted by a therapy already being administered to a patient (see Smith-Jones P et al., *Nat Biotechnol* 22: 701-6 (2004); Evans M et al., *Proc Natl Acad Sci USA* 108: 9578-82 (2011)).

In certain embodiments, the proteins of the invention and/or compositions thereof are used for both diagnosis and treatment, or for diagnosis alone.

Certain embodiments of the invention are below, numbered 1-40 and referring to Table C for biological sequences (see also WO 2014164680 A1): (1) A CD20-binding protein for the internalization of the CD20 antigen in a cell, wherein the protein comprises a binding region specific for CD20 and a toxin effector region derived from Shiga-like toxin 1 (SLT-1), wherein the protein induces rapid internalization of CD20 present on the surface of the cell. (2) The CD20-binding protein of embodiment 1, wherein the protein induces internalization of CD20 in a B-cell lineage cell in less than about one hour. (3) The CD20-binding protein of claim 1, wherein the toxin effector region comprises amino acids 75 to 251 of NO:1 (see Table C). (4) The CD20-binding protein of embodiment 1, wherein the toxin effector region comprises amino acids 1 to 251 of NO:1. (5) The CD20-binding protein of embodiment 1, wherein the toxin effector region comprises amino acids 1 to 261 of NO:1. (6) The CD20-binding protein of embodiment 1, wherein the protein is cytotoxic.

(7) The CD20-binding protein of embodiment 1, wherein the CD20 binding region is selected from the group consisting of an Fab fragment, an F(ab')2 fragment, an Fd fragment, an Fv fragment a dAb fragment, a scFv, a diabody, a CDR3 peptide, a constrained FR3-CDR3-FR4 peptide, a nanobody, a bivalent nanobody, small modular immunopharmaceuticals (SMIPs), a shark variable IgNAR domain, a minibody, and any fragment or chemically or genetically manipulated counterparts that retain CD20 binding function. (8) The CD20-binding protein of embodiment 1, wherein the binding region is a scFv.

(9) The CD20-binding protein of embodiment 8, wherein the binding region comprises (A) (i) a heavy chain variable (VH) domain comprising HCDR1, HCDR2, HCDR3 amino acid sequences as shown in NO:6, NO:7, and NO:8, respectively, and (ii) a light chain variable (VL) domain comprising LCDR1, LCDR2, and LCDR3 amino acid sequences as shown in NO:9, NO: 10, and NO: 11, respectively; or (B) (i) a heavy chain variable (VH) domain comprising HCDR1, HCDR2, and HCDR3 amino acid sequences as shown in NO:21, NO:22, and NO:23, respectively, and (ii) a light chain variable (VL) domain comprising LCDR1, LCDR2, and LCDR3 amino acid sequences as shown in NO:24, NO: 10, and NO: 11, respectively.

(10) The CD20-binding protein of embodiment 8, wherein the CD20 binding region comprises amino acids 2 to 245 of NO:4. (11) The CD20-binding protein of embodiment 1, wherein the CD20 binding region comprises amino acids 2 to 245 of NO: 4 and the toxin effector region comprises amino acids 75 to 251 of NO: 1. (12) The CD20-binding protein of embodiment 1, which comprises NO:4. (13) A CD20-binding protein for killing a cell which expresses CD20 on its surface wherein the binding region comprises a heavy chain variable (VH) domain comprising HCDR1, HCDR2, and HCDR3 amino acid sequences as shown in NO:6, NO:7, and NO:8, respectively, and a light chain variable (VL) domain comprising LCDR1, LCDR2, and LCDR3 amino acid sequences as shown in NO:9, NO: 10, and NO: 11, respectively, whereby administration, the protein is capable of killing a cell which expresses CD20 on its surface.

(14) The CD20 binding-protein of embodiment 13, wherein the CD20 binding region comprises amino acids 2 to 245 of NO:4. (15) The CD20 binding-protein of embodiment 13, wherein the CD20 binding region comprises amino acids 2 to 245 of NO: 4 and the toxin effector region comprises amino acids 75 to 251 of NO: 1. (16) The CD20 binding-protein of embodiment 13 which comprises NO:4.

(17) A CD20 binding-protein for the delivery of exogenous material into the cell that expresses CD20 on its surface, wherein the protein comprises a binding region specific for CD20, a toxin effector region wherein said toxin effector region is derived from Shiga-like toxin 1 (SLT-1), and the exogenous material, whereby administration, the protein is capable of delivering the exogenous material into a cell which expresses CD20 on its surface.

(18) The CD20-binding protein of embodiment 17, wherein the binding region comprises (A) (i) a heavy chain variable (VH) domain comprising HCDR1, HCDR2, HCDR3 amino acid sequences as shown in NO:6, NO:7, and NO:8, respectively, and (ii) a light chain variable (VL) domain comprising LCDR1, LCDR2, and LCDR3 amino acid sequences as shown in NO:9. NO: 10, and NO: 11, respectively; or (B) (i) a heavy chain variable (VH) domain comprising HCDR1, HCDR2, and HCDR3 amino acid sequences as shown in NO:21, NO:22, and NO:23, respectively, and (ii) a light chain variable (VL) domain comprising LCDR1, LCDR2, and LCDR3 amino acid sequences as shown in NO:23, NO: 10, and NO: 11, respectively.

(19) The CD20-binding protein of embodiment 18, wherein the exogenous material is selected from the group consisting of a peptide, a protein, and a nucleic acid. (20) The CD20 binding-protein of embodiment 19, wherein the exogenous material is a peptide and the peptide is an antigen. (21) The CD20 binding-protein of embodiment 20, wherein the antigen is encoded between the binding region and the toxin effector region of the protein. (22) The CD20 binding-protein of embodiment 19 wherein the antigen is derived from a viral protein. (23) The CD20 binding-protein of embodiment 21 wherein the antigen is NO:2. (24) The CD20 binding-protein of embodiment 21 comprising NO:5. (25) The CD20 binding-protein of embodiment 20, wherein the antigen is derived from a bacterial protein. (26) The CD20 binding-protein of embodiment 20, wherein the antigen is derived from a protein mutated in cancer. (27) The CD20 binding-protein of embodiment 20, wherein the antigen is derived from a protein aberrantly expressed in cancer. (28) The CD20 binding-protein of embodiment 20, wherein the antigen is derived from a T-cell CDR region.

(29) The CD20 binding-protein of embodiment 19, wherein the exogenous material is a protein. (30) The CD20 binding-protein of embodiment 29, wherein the protein is an enzyme. (31) The CD20 binding-protein of embodiment 19 wherein the exogenous material is a nucleic acid. (31) The CD20 binding-protein of embodiment 30 wherein the nucleic acid is a siRNA. (32) A polynucleotide that encodes the CD20 binding-protein of embodiment 1. (33) An expression vector that comprises the polynucleotide of embodiment 32. (34) A host cell comprising the expression vector of embodiment 33.

(35) A method of rapidly internalizing the CD20 antigen into the cell of a patient, the method comprising the step of administering to the patient a protein of any one of embodiments 1-12. (36) A method of killing a cell in a patient expressing the CD20 antigen on its surface, the method comprising the step of administering to a patient a protein of any of embodiments 1-16. (37) A method of delivering exogenous material into a cell of a patient that expresses CD20 on its surface, the method comprising the step of administering to the patient a protein of any one of embodiments 17-31. (39) A method of treating cancer in a patient, wherein the cancer expresses on the tumor or cancer cell surface a CD20 antigen, the method comprising the step of administering to the patient a protein of any one of embodiments 1-31. (40) The method of embodiment 39 wherein the cancer is lymphoma.

TABLE C

Sequences referred to in embodiments 1-40

| Number | Text Description | Sequence |
| --- | --- | --- |
| NO: 1 | SLT-1 A subunit polypeptide | KEFTLDFSTAKTYVDSLNVIRSAIGTPLQTISSGGTSLLMIDSGSGDN<br>LFAVDVRGIDPEEGFNNLRLIVERNNLYVTGFVNRTNNVFYRFASH<br>VTFPGTTAVTLSGDSSYTTLQRVAGISRTGMQINRHSLTTSYLDLMS<br>HSGTSLTQSVARAMLRFVTVTAEALRFRQIQRGFRTTLDDLSGRSY<br>VMTAEDVDLTLNWGRLSSVLPDYHGQDSVRVGRISFGSINAILGSV<br>ALILNCHHHARVARMASDEFPSMCPADGRVRGITHNKILWDSSTLG<br>AILMRRTISS |
| NO: 2 | SLT-1 A subunit polynucleotide (consensus) | aargarttyacnytngaynywsnacngcnaaracntaygtngaywsnytnaaygtnathmgnwsng<br>cnathggnacnccnytncaracnathwsnwsnggnggnacnwsnytnytnatgathgaywsnggn<br>wsnggngayaayytnttygcngtngaygtnmgnggnathgayccngargarggnmgnttyaayaa<br>yytnmgnytnathgtngarmgnaayaayytntaygtnacnggnttygtnaaymgnacnaayaaygt<br>nttytaymgntygcngayttywsncaygtnacttyccnggnacnacngcngtnacnytnwsnggn<br>gaywsnwsntayacnacnytncarmgngtngcnggnathwsnmgnacnggnatgcarathaay<br>mgncaywsnytnacnacnwsntayytngayytnatgwsncaywsnggnacnwsnytnacncar<br>wsngtngcnmgngcnatgytmmgnttygtnacngtnacngcngargcnytnmgnttymgncarat<br>hcarmgnggnttymgnacnacnytngaygayytnwsnggnmgnwntaygtnatgacngcngar<br>gaygtngayytnacnytnaaytggggnmgnytnwsnwsngtnytnccngaytaycayggncarga<br>ywsngtnmgngtnggnmgnathwsnttyggnwsnathaaygcnathytnggnwsngtngnytna<br>thytnaaytgycaycaycaygcnwsnmgngtngcnmgnatggcnwsngaygarttyccnwsnat<br>gtgyccngcngayggnmgngtnmgnggnathacncayaayaarathytntgggaywsnwsnacn<br>ytnggngcnathytnatgmgnmgnacnathwsnwsn |
| NO: 3 | Influenza Matrix 58-66 | GILGFVFTL |
| NO: 4 | MT-3724 polypeptide | QVQLQQPGAELVKPGASVKMSCKTSGYTFTSYNVHWVKQTPGQG<br>LEWIGAIYPGNGDTSFNQKFKGKATLTADKSSSTVYMQLSSLTSED<br>SAVYYCARSNYYGSSYVWFFDVWGAGTTVTVSSGSTSGSGKPGS<br>GEGSQIVLSQSPTILSASPGEKVTMTCRASSSVSYMDWYQQKPGSS<br>PKPWIYATSNLASGVPARFSGSGSGTSYSLTISRVEAEDAATYYCQQ<br>WISNPPTFGAGTKLELKEFPKPSTPPGSSGGAPKEFTLDFSTAKTYV<br>DSLNVIRSAIGTPLQTISSGGTSLLMIDSGSGDNLFAVDVRGIDPEEG<br>RFNNLRLIVERNNLYVTGFVNRTNNVFYRFADFSHVTFPGTTAVTLS<br>GDSSYTTLQRVAGTSRTGMQINRHSLTTSYLDLMSHSGTSLTQSVA<br>RAMLRFVTVTAEALRFRQIQRGFRTTLDDLSGRSYVMTAEDVDLT<br>LNWGRLSSVLPDYHGQDSVRVGRISFGSINAILGSVALILNCHHHA<br>SRVAR |
| NO: 5 | MT-3724 polynucleotide consensus | cargtncarytnarcarccnggngcngarytngtnaarccnggngcnwsngtnaaratgwsntgyaa<br>racnwsnggntayacnttyacnwsntayaaygtncaytgggtnaarcaracnccnggncarggnytn<br>gartggathggngcnathtayccnggnaayggngayacnwsnttyaaycaraarttyaarggnaargc<br>nacnynacngcngayaarwsnwsnwsnacngtntayatgcarytnwsnwsnytnacnwsngarg<br>aywsngcngtntaytaytgygcnmgnwsnaaytaytayggnwsnwsntaygtntggttyttygayg<br>tntggggngcnggnacnacngtnacngtnwsnwsnggnwsnacnwsnggnwsnggnaarccng<br>gnwsnggngarggnwsncarathgtnytnwsncarwsnccnacnathytnwsngcnwsnccngg<br>ngaraargtnacnatgacntgymgngcnwsnwsnwsngtnwsntayatggaytggtaycarcaraa<br>rccnggnwsnwsnccnaarccntggathtaygcnacnwsnaayytngcnwsnggngtnccngcn<br>mgnttywsnggnwsnggnwsnggnacnwsntaywsnytnacnathwsnmgngtngargcnga<br>rgaygcngcnacntaytaytgycarcartggathwsnaayccnccnacnttyggngcnggnacnaary<br>tngarytnaargarttyccnaarccnwsnacnccnccnggnwsnwsnggnggngcnccnaargartt<br>yacnytngayttywsnacngcnaaracntaygtngaywsnytnaaygtnathmgnwsngcnathg<br>gnacnccnytncaracnathwsnwsnggnggnacnwsnytnytnatgathgaywsnggnwsngg<br>ngayaayytnttygcngtngaygtnmgnggnathgayccngargarggnmgnttyaayaayytnm<br>gnytnathgtngarmgnaayaayytntaygtnacnggnttygtnaaymgnacnaayaaygtnttytay<br>mgnttygcngayttywsncaygtnacnttyccnggnacnacngcngtnacnytnwsnggngayws<br>nwsntayacnacnytncarmgngtngcnggnathwsnmgnacnggnatgcarathaaymgncay<br>wsnytnacnacnwsntayytngayytnatgwsncaywsnggnacnwsnytnacncarwsngtng<br>cnmgngcnatgytnmgnttygtnacngtnacngcngargcnytnmgnttyrmgncarathcarmgn<br>ggnttymgnacnacnytngaygayytnwsnggnmgnwsntaygtnatgacngcngargaygtng<br>ayytnacnytnaaytggggnmgnytnwsnwsngtnytnccngaytaycayggncargaywsngtn<br>mgngtnggnmgnathwsnttyggnwsnathaaygcnathytnggnwsngtngcnytnathytnaa<br>ytgycaycaycaygcnwsnmgngtngcnmgn |
| NO: 6 | Heavy chain CDR1 | GYTFTSYNYH |
| NO: 7 | Heavy chain CDR2 | AIYPGNGDTSFNQKFKG |
| NO: 8 | Heavy chain CDR | SNYYGSSYVWFFDY |
| NO: 9 | Light chain CDR1 | RASSSVSYMD |

TABLE C-continued

Sequences referred to in embodiments 1-40

| Number | Text Description | Sequence |
| --- | --- | --- |
| NO: 10 | Light chain CDR2 | ATSNLAS |
| NO: 11 | Light chain CDR3 | QQWISNPPT |
| NO: 12 | B9E9-SLTA polypeptide | QVQLVQSGA TABLE C-continued Sequences referred to in embodiments 1-40

| Number | Text Description | Sequence |
|---|---|---|
| | | ngtngcnmgngcnatgytnmgnttygtnacngtnacngcngargcnytnmgnttymgncarathc armgnggnttymgnacnacnytngaygayytnwsnggnmgnwsntaygtnatgacngcngarga ygtngayytnacnytnaaytggggnmgnytnwsnwsngtnytnccngaytaycayggncargay wsngtnmgngtnggnmgnathwsnttyggnwsnathaaygcnathytnggnwsngtngcnytna thytnaaytgycaycaycaygcnwsnmgngtngctnmgn |
| no: 16 | MT-3727 polypeptide | QVQLQQPGAELVKPGASVKMSCKTSGYTFTSYNVHWVKQTPGQG LEWIGAIYPGNGDTSFNWKFKGKATLTADKSSSTVYMQLSSLTSED SAVYYCARSNYYGSSYVWFFDVWGAGTTVTVSSGSTSGSGKPGS GEGSQIVLSQSPTILSASPGEKVTMTCRASSSVSYMDWYQQKPGSS PKPWIYATSNLASGVPARFSGSGSGTSYSLTISRVEAEDAATYYCQQ WISNPPTFGAGTKLELKEFPKTSTPPGSSGGAPGILGFVFTLKEFTLD FSTAKTYVDSLNVIRSAIGTPLQTISSGGTSLLMIDSGSGDNLFAVDV RGIDPEEGRFNNLRLIVERNNLYVTGFVNRTNNVFYRFADFSHVTF PGTTAVTLSGDSSYTTLQRVAGISRTGMQINRHSLTTSYLDLMSHS GTSLTQSVARAMLRFVTVTAEALRFRQIQRGFRTTLDDLSGRSYV MTAEDVDLTLNWGRLSSVLPDYHGQDSVRVGRISFGSINAILGSVA LILNCHHHASRVAR |
| NO: 17 | MT-3727 polynucleotide consensus | cargtncarytncarcarccnggngcngarytngtnaarccnggngcnwsngtnaaratgwsntgyaa racnwsnggntayacnttyacnwsntayaaygtncaytgggtnaarcaracnccnggncarggnytn gartggathggngcnathtayccnggnaayggngayacnwsnttyaaycaraarttyaarggnaargc nacnytnacngcngayaarwsnwsnwsnacngtntayatgcarytnwsnwsnytnacnwsngarg aywsngcngtntaytaytgygcnmgnwsnaaytaytayggnwsnwsntaygtntggttyttygayg tntggggncnggnacnacngtnacngtnwsnwsnggnwsnacnwsnggnwsnggnaarccng gnwsnggngarggnwsncarathgtnytnwsncarwsnccnacnathytnwsngcnwsnccngg ngaraargtnacnatgacntgymgncnwsnwsnwsngtnwsntayatggaytggtaycarcaraa rccnggnwsnwsnccnaarccntggathtaygcnacnwsnaayytngcnwsnggngtnccngcn mgnttywsnggnwsnggnwsnggnacnwsntaywsnytnacnathwsnmgngtngargcnga rgaygcngcnacntaytaytgycarcartggathwsnaayccnccnacattyggngcnggnacnaary tngarytnaargarttyccnaarccnwsnacnccnccnggnwsnwsnggnggngcnccnggnathy tnggnttygtnttyacnytnaargarttyacnytngayttywsnacngcnaaracntaygtngaywsnyt naaygtnathmgnwsngcnathggnacnccnytncaracnathwsnwsnggnggnacnwsnytn ytnatgathgaywsngnwsnggngayaayytnttygcngtngaygtnmgnggnathgayccnga rgarggnmgnttyaayaayytnmgnytnathgtngarmgnaayaayytntaygtnacnggnttygtn aaymgnacnaayaaygtnttytaymgnttygcngayttywsncaygtnacnttyccnggnacnacn gcngtnacnytnwsnggngaywsnwsntayacnacnytncarmgngtngcnggnathwsnmgn acnggnatgcarathaaymgncaywsnytnacnacnwsntayytngayytnatgwsncaywsngg nacnwsnytnacncarwsngtngcnmgngcnatgytnmgnttygtnacngcngargcny tnmgnttymgncarathcarmgnggnttymgnacnacnytngaygayytnwsnggnmgnwsnt aygtnatgacngcngargaygtngayytnacnytnaaytggggnmgnytnwsnwsngtnytnccn gaytaycayggncargaywsngtnmgngtnggnmgnathwsnttyggnwsnathaaygcnathy tnggnwsngtngcnytnathytnaaytgycaycaycaygcnwsnmgngtngcnmgn |
| NO: 18 | 218 Linker | GSTSGSGKPGSGEGS |
| NO: 19 | Strep leader sequence | MWSHPQFEK |
| NO: 20 | Murine IgG3 (mhinge) | EFPKPSTPPGSSGGAP |
| NO: 21 | Heavy chain CDR1 | GYTFTSYNMH |
| NO: 22 | Heavy chain CDR2 | AIYPGNGDTSYNQKFKG |
| NO: 23 | Heavy chain CDR3 | AQLRPNYWYFDV |
| NO: 24 | Light chain CDR1 | RASSSVSYMH |

Certain embodiments of the invention are below, numbered 41-87 (see also WO 2014164680 A1). (41) For certain embodiments of the CD20-binding proteins of the present invention, the CD20-binding protein comprises (a) a CD20 binding region comprising an immunoglobulin-type binding region and capable of specifically binding an extracellular part of CD20 and (b) a Shiga toxin effector region comprising a polypeptide derived from the amino acid sequence of the A Subunit of at least one member of the Shiga toxin family; whereby administration of the CD20-binding protein to a cell expressing CD20 on a cellular surface, the CD20-binding protein is capable of inducing r complementary determining region 3 fragment, constrained FR3-CDR3-FR4 polypeptide, single-domain antibody fragment, single-chain variable fragment, antibody variable fragment, antigen-binding fragment, Fd fragment, fibronectin-derived 10$^{th}$ fibronectin type III domain, tenacsin type III domain, ankyrin repeat motif domain, low-density-lipoprotein-receptor-derived A-domain, lipocalin, Kunitz domain, Protein-A-derived Z domain, gamma-B crystalline-derived domain, ubiquitin-derived domain, Sac7d-derived polypeptide, Fyn-derived SH2 domain, engineered antibody mimic, and any genetically manipulated counterparts of any of the foregoing that retain CD20 binding functionality.

(43) For certain embodiments, the CD20-binding proteins are capable of inducing rapid cellular internalization of a CD20 natively present on the surface of a cell. (44) In certain further embodiments, the CD20-binding proteins are capable of inducing, in less than about one hour, cellular internalization of a CD20 natively present on the surface of a cell. (45) In certain further embodiments, the CD20-binding proteins are capable of inducing, in less than about one hour, cellular internalization of a CD20 natively present on the surface of a member of a B-cell lineage.

(46) For certain embodiments, administration of the CD20-binding protein to a cell which expresses CD20 on a cellular surface, the CD20-binding proteins are capable of causing the death of the cell. (47) In certain other embodiments, the CD20-binding proteins comprise Shiga toxin effector regions that lack catalytic activity and are not capable of causing the death of a cell.

(48) For certain embodiments, administration of the CD20-binding protein to a first populations of cells whose members express CD20, and a second population of cells whose members do not express CD20, the cytotoxic effect of the CD20-binding protein to members of the first population of cells relative to members of the second population of cells is at least 3-fold greater.

(49) For certain embodiments, the CD20-binding proteins comprise the Shiga toxin effector region comprising or consisting essentially of amino acids 75 to 251 of SEQ ID NO:1, SEQ ID NO:2, or SEQ ID NO:3. (50) Further embodiments are CD20-binding proteins in which the Shiga toxin effector region comprises or consists essentially of amino acids 1 to 241 of SEQ ID NO:1, SEQ ID NO:2, or SEQ ID NO:3; amino acids 1 to 251 of SEQ ID NO:1, SEQ ID NO:2, or SEQ ID NO:3; and/or amino acids 1 to 261 of SEQ ID NO:1, SEQ ID NO:2, or SEQ ID NO:3.

(51) For certain embodiments, the CD20-binding protein comprises or consists essentially of amino acids of SEQ ID NO:52, SEQ ID NO:46, SEQ ID NO:60, or SEQ ID NO:54.

(52) In certain embodiments, the CD20-binding proteins comprise the CD20 binding region comprising: (a) a heavy chain variable domain comprising HCDR1, HCDR2, and HCDR3 amino acid sequences as shown in SEQ ID NO:11, SEQ ID NO:12, and SEQ ID NO:13, respectively, and a light chain variable domain comprising LCDR1, LCDR2, and LCDR3 amino acid sequences as shown in SEQ ID NO: 14, SEQ ID NO:15, and SEQ ID NO:16, respectively; or (b) a heavy chain variable domain comprising HCDR1, HCDR2, and HCDR3 amino acid sequences as shown in SEQ ID NO:5, SEQ ID NO:6, and SEQ ID NO:7, respectively, and a light chain variable domain comprising LCDR1, LCDR2, and LCDR3 amino acid sequences as shown in SEQ ID NO:24, SEQ ID NO:15, and SEQ ID NO:16, respectively; or (c) a heavy chain variable (VH) domain comprising HCDR1, HCDR2, and HCDR3 amino acid sequences as shown in SEQ ID NO:5, SEQ ID NO:6, and SEQ ID NO:19, respectively, and a light chain variable (VL) domain comprising LCDR1, LCDR2, and LCDR3 amino acid sequences as shown in SEQ ID NO:20, SEQ ID NO:15, and SEQ ID NO:22, respectively. (53) Further embodiments are CD20-binding proteins comprising the immunoglobulin-type binding region comprising or consisting essentially of amino acids 2-245 of SEQ ID NO:52. (54) Further embodiments are CD20-binding proteins comprising the immunoglobulin-type binding region comprising or consisting essentially of amino acids 2-245 of SEQ ID NO:52 and the Shiga toxin effector region comprising or consisting essentially of amino acids 75-251 of SEQ ID NO:1. (55) Further embodiments are CD20-binding proteins comprising or consisting essentially of SEQ ID NO:52 or SEQ ID NO:54.

(56) In certain embodiments, the CD20-binding proteins comprise Shiga toxin effector regions which comprise a mutation relative to a naturally occurring A Subunit of a member of the Shiga toxin family which changes the enzymatic activity of the Shiga toxin effector region, the mutation selected from at least one amino acid residue deletion or substitution.

(57) Certain embodiments of the CD20-binding proteins can also be utilized for the delivery of additional exogenous material into a cell that expresses CD20 on a cellular surface. (58) These embodiments comprise a CD20 binding region comprising (a) an immunoglobulin-type polypeptide capable of specifically binding an extracellular part of a CD20 molecule, (b) a Shiga toxin effector region comprising a polypeptide derived from the amino acid sequence of at least one member of the Shiga toxin family, and (c) an additional exogenous material; whereby administration of the CD20-binding protein to a cell expressing CD20 on a cellular surface, the CD20-binding protein is capable of inducing rapid cellular internalization of a protein complex comprising the CD20-binding protein bound to CD20 and capable of delivering the additional exogenous material into the interior of the cell. (59) In certain further embodiments, the CD20-binding proteins comprise the CD20 binding region comprising: (a) a heavy chain variable domain comprising HCDR1, HCDR2, and HCDR3 amino acid sequences as shown in SEQ ID NO: 11, SEQ ID NO:12, and SEQ ID NO:13, respectively, and a light chain variable domain comprising LCDR1, LCDR2, and LCDR3 amino acid sequences as shown in SEQ ID NO:14, SEQ ID NO:15, and SEQ ID NO:16, respectively; or (b) a heavy chain variable domain comprising HCDR1, HCDR2, and HCDR3 amino acid sequences as shown in SEQ ID NO:5, SEQ ID NO:6, and SEQ ID NO:7, respectively, and a light chain variable domain comprising LCDR1, LCDR2, and LCDR3 amino acid sequences as shown in SEQ ID NO:24, SEQ ID NO:15, and SEQ ID NO:16, respectively; or (c) a heavy chain variable (VH) domain comprising HCDR1, HCDR2, and HCDR3 amino acid sequences as shown in SEQ ID NO:5, SEQ ID NO:6, and SEQ ID NO:19, respectively, and a light chain variable (VL) domain comprising LCDR1, LCDR2, and LCDR3 amino acid sequences as shown in SEQ ID NO:20, SEQ ID NO:15, and SEQ ID NO:22, respectively.

(60) In certain embodiments, the additional exogenous material is selected from the group consisting of peptides, polypeptides, proteins, and polynucleotides. (61) In certain embodiments, the additional exogenous material comprises a protein or polypeptide comprising an enzyme. (62) In certain other embodiments, the additional exogenous material is a nucleic acid, such as, e.g. a ribonucleic acid that functions as a small inhibiting RNA (siRNA) or microRNA (miRNA).

(63) In certain embodiments, the additional exogenous material is a peptide and the peptide is an antigen. (64) In certain embodiments, the additional exogenous material is an antigen derived from a bacterial protein. (65) In certain other embodiments, the antigen is derived from a protein mutated in cancer. (66) Further embodiments are ones in which the antigen is derived from a protein aberrantly expressed in cancer. (67) Still further embodiments are ones in which the antigen is derived from a T-cell complementary determining region.

(68) For certain embodiments, the antigen is included within the CD20-binding protein as part of a polypeptide fusion in which the peptide antigen is located between the binding region and the toxin effector region of a single-chain protein. (69) In certain embodiments, the additional exogenous material is an antigen derived from a viral protein. (70) In certain embodiments, the antigen comprises or consists essentially of SEQ ID NO:44, the influenza Matrix 58-66 antigen. (71) In certain further embodiments, the CD20-binding protein comprises or consists essentially of SEQ ID NO:54.

(72) The invention also includes pharmaceutical compositions comprising a CD20-binding protein of the present invention and at least one pharmaceutically acceptable excipient or carrier; and the use of such a cytotoxic protein or a composition comprising it in methods of the invention as further described herein.

(73) The present invention also provides polynucleotides that encode the CD20-binding proteins of the invention, expression vectors that comprise the polynucleotides of the invention, as well as host cells comprising the expression vectors of the invention.

(74) Additionally, the present invention provides a method of rapidly inducing cellular internalization of a CD20-binding protein of the present invention into a CD20 expressing cell(s), the method comprising the step of contacting the cell(s) with a CD20-binding protein of the present invention or a pharmaceutical composition thereof. (75) Similarly, the present invention provides a method of internalizing a cell surface localized CD20 bound by a CD20-binding protein in a patient, the method comprising the step of administering to the patient a CD20-binding protein or pharmaceutical composition of the present invention.

(76) Additionally, the present invention provides a method of killing a CD20 expressing cell(s) comprising contacting the cell(s), either in vitro or in vivo, with a CD20-binding protein or pharmaceutical composition of the present invention.

(77) Additionally, the present invention provides a method for delivering exogenous material to the inside of a cell(s) comprising contacting the cell(s), either in vitro or in vivo, with a CD20-binding protein or pharmaceutical composition of the present invention.

(78) The present invention further provides a method for delivering exogenous material to the inside of a cell(s) in a patient, wherein the cell expresses CD20 on its surface, the method comprising the step of administering to the patient a CD20-binding protein of the present invention.

(79) Additionally, the present invention provides methods of killing cells comprising the step of contacting the cell with a CD20-binding protein of the invention or a pharmaceutical composition of the invention. (80) In certain embodiments of the cell killing method, the step of contacting the cell(s) occurs in vitro. (81) In certain other embodiments, the step of contacting the cell(s) occurs in vivo.

(82) Also, the present invention provides a method of treating a disease, disorder, or condition in patients comprising the step of administering to a patient in need thereof a therapeutically effective amount of a CD20-binding protein of the invention or a pharmaceutical composition of the invention. (83) In certain embodiments of the treating method, the disease, disorder, or condition to be treated using this method of the invention involves a cell(s) or cell type(s) which express CD20 on a cellular surface, such as, e.g., a cancer cell, a tumor cell, or an immune cell. (84) A further embodiment is a method of treating a disease involving a cancer or tumor cell associated with the disease selected from the group consisting of: bone cancer, leukemia, lymphoma, melanoma, or myeloma. (85) In certain embodiments of this method, the disorder is an immune disorder associated with a disease selected from the group consisting of: amyloidosis, ankylosing spondylitis, asthma, Crohn's disease, diabetes, graft rejection, graft-vs.-host disease, Hashimoto's thyroiditis, hemolytic uremic syndrome, HIV-related diseases, lupus erythematosus, multiple sclerosis, polyarteritis nodosa, polyarthritis, psoriasis, psoriatic arthritis, rheumatoid arthritis, scleroderma, septic shock, Sjorgren's syndrome, ulcerative colitis, and vasculitis.

(86) Among certain embodiments of the present invention is the use of a CD20-binding protein of the invention in the manufacture of a medicament for the treatment or prevention of a cancer or immune disorder. (87) Among certain embodiments of the present invention is a cytotoxic protein or a pharmaceutical composition comprising said protein for use in the treatment or prevention of a cancer, tumor, or immune disorder.

The present invention is further illustrated by the following non-limiting examples of CD20-binding proteins comprising Shiga toxin effector regions derived from A Subunits of members of the Shiga toxin family and CD20 binding regions comprising immunoglobulin-type polypeptides capable of binding extracellular parts of CD20.

EXAMPLES

The following examples demonstrate certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

The following examples demonstrate the ability of exemplary CD20-binding proteins to selectively kill cells which express CD20 on their cell surfaces. The exemplary CD20-binding proteins bound to extracellular antigens on CD20 expressed by targeted cell types and entered the targeted cells. Exemplary CD20-binding proteins showed peak cellular internalization within one hour of being administered to different human Burkitt's lymphoma cell lines at 37° C. and at CD20-binding protein concentrations well below cell-surface saturation levels (e.g. at 38% of full CD20 occupancy). The internalized CD20-binding proteins routed their Shiga toxin effector region to the cytosol to inactivate ribosomes and subsequently caused the apoptotic death of the targeted cells. Thus, the exemplary CD20-binding proteins were capable of internalizing within CD20 expressing cell types by virtue of their Shiga toxin effector regions inducing rapid cellular internalization after the CD20-binding proteins formed a complex with cell surface CD20.

Exemplary CD20-binding proteins tested in the Examples below include αCD20scFv1::SLT-1A version 1 (SEQ ID NO:52), αCD20scFv1::SLT-1A version 2 (SEQ ID NO:54), αCD20scFv2::SLT-1A (SEQ ID NO:46), and αCD20scFv3::SLT-1A (SEQ ID NO:60).

Example 1

Construction, Production, and Purification of Exemplary CD20-Binding Proteins First, a CD20 binding region and a Shiga toxin effector region were designed or selected. In the examples below, the Shiga toxin effector region was derived from the A subunit of Shiga-like Toxin 1 (SLT-1A). A polynucleotide was obtained containing a fragment of SLT-1A cloned into the pECHE9A plasmid and encoding amino acids 1-251 of SLT-1A (Cheung M et al., *Mol Cancer* 9: 28 (2010)).

The CD20 binding region was designed as a recombinant scFv derived from the 1H4 CD20 monoclonal antibody (Haisma H et al., *Blood* 92: 184-90 (1999)). The two immunoglobulin variable regions ($V_L$ and $V_H$) were separated by a linker (SEQ ID NO:41).

Second, the CD20 binding region and Shiga toxin effector region were combined to form a single-chain, recombinant polypeptide. In this example, a polynucleotide encoding the recombinant scFv derived from 1H4 CD20 monoclonal antibody was cloned in frame with a "murine hinge" polynucleotide derived from polynucleotides encoding a murine IgG3 molecule (SEQ ID NO:43) and in frame with a polynucleotide encoding SLT-1A (residues 1-251 of SEQ ID NO:1). The full-length sequence begins with Strep-tag® (SEQ ID NO:45) encoding polynucleotide sequence cloned in frame to facilitate detection and purification. The polynucleotide sequence of this example was codon optimized for efficient expression in *E. coli* using services from DNA 2.0, Inc. (Menlo Park, Calif., U.S.) to produce the expression vector which encoded αCD20scFv1::SLT-1A version 1.

A different CD20-binding protein comprising an influenza antigen was constructed and produced in a similar manner. DNA 2.0, Inc. (Menlo Park, Calif., U.S.) synthesized the multiple polynucleotides, including the antigen sequence (SEQ ID NO:44) and the required polynucleotide components were joined in frame using vector pJ201 to create the open reading frame coding for the following single-chain polypeptide (from amino-terminus to carboxy-terminus) Strep-tag® (SEQ ID NO:45), the 1H4-derived recombinant scFv (described above), the murine IgG3 molecule (SEQ ID NO:43), the linker (SEQ ID NO:44), and the SLT-1A-derived sequence (residues 1-251 of SEQ ID NO:1). This recombinant polynucleotide was cloned into pTXB1 for polypeptide production purposes. Again, codon optimization for efficient expression in *E. coli* was performed by DNA 2.0, Inc. (Menlo Park, Calif., U.S.) to produce the expression vector which encoded αCD20scFv1::SLT-1A version 2.

Third, both versions 1 and 2 of the αCD20scFv1::SLT-1A recombinant CD20-binding proteins were produced by using standard techniques for both bacterial and cell-free, protein translation systems. Protein purification was accomplished using standard techniques known in the art, including capto-L and chitin affinity chromatography.

In certain purifications, exemplary CD20-binding proteins were produced in bacteria and purified with the IMPACT™ (Intein Mediated Purification with an Affinity Chitin-binding Tag) system (New England Biolabs, Ipswich, Mass., U.S.). Chitin affinity purification was performed according to the manufacturer's instructions except in certain purifications, a protein L column chromatography step was performed and then the intein was cleaved. Then uncleaved material was removed using chromatography through a chitin resin in flow-through mode.

Example 2

Determining the Dissociation Constant ($K_D$) of Exemplary CD20-Binding Proteins The cell binding characteristics of both versions 1 and 2 of the αCD20scFv1::SLT-1A CD20-binding proteins were determined by a fluorescence-based flow cytometry assay. Each sample contained $0.5\times10^6$ of either CD20 expressing cells (Raji (CD20+)) or non-expressing cells (BC1 (CD20−)) and was incubated with 100 μL of various dilutions of the CD20-binding proteins in phosphate buffered saline Hyclone 1×PBS (Fisher Scientific, Waltham, Mass., U.S.) with 1% bovine serum albumin (BSA) (Calbiochem. San Diego, Calif., U.S.), hereinafter referred to as "1×PBS+1% BSA" for 1 hour at 4 degrees Celsius (° C.). The highest concentration of CD20-binding protein was selected to lead to saturation of the reaction. The cells were washed twice with 1×PBS+1% BSA. The cells were incubated for 1 hour at 4° C. with 100 μL of 1×PBS+1% BSA containing 0.3 μg of anti-Strep Tag® mAb-FITC (#A01736-100, Genscript, Piscataway, N.J., U.S.). The cells were washed twice with 1×PBS+1% BSA, suspended in 200 μL of 1×PBS, and subjected to flow cytometry. The baseline corrected mean fluorescence intensity (MFI) data for all the samples was obtained by subtracting the MFI of the FITC alone sample (negative control) from each experimental sample. Graphs were plotted of MFI versus "concentration of protein" using Prism software (GraphPad Software, San Diego, Calif., U.S.). Using the Prism software function of one-site binding [$Y=B_{max}*X/(K_D+X)$] under the heading binding-saturation, the $B_{max}$ and $K_D$ were calculated using baseline corrected data. Abs values were corrected for background by subtracting the Abs values measured for wells containing only PBS. $B_{max}$ is the maximum specific binding reported in MFI. $K_D$ is the equilibrium binding constant, reported in nanomolar (nM).

Over multiple experiments, the $K_D$ of αCD20scFv1::SLT-1A version 1 for Raji (CD20+) cells was determined to be about 80-100 nM. In one experiment, the $B_{max}$ for the αCD20scFv1::SLT-1A version 1 CD20-binding protein binding to CD20+ cells was measured to be about 140,000 MFI with a $K_D$ of about 83 nM (Table 1), whereas there was no meaningful binding to CD20− cells observed in this assay. In one experiment, the $B_{max}$ for αCD20scFv1::SLT-1A version 2 binding to CD20+ cells was measured to be about 110,000 MFI with a $K_D$ of about 101 nM (Table 1), whereas there was no meaningful binding to CD20− cells observed in this assay.

TABLE 1

Binding Characteristics: Representative values for $B_{max}$ and $K_D$ for exemplary CD20-binding proteins

| CD20-Binding Protein | target bio-molecule | Target Positive Cells $B_{max}$ (MFI) | Target Positive Cells $K_D$ (nM) | Target Negative Cells $B_{max}$ (MFI) | Target Negative Cells $K_D$ (nM) |
|---|---|---|---|---|---|
| αCD20scFv1::SLT-1A version 1 | CD20 | 139,000 | 82.5 | 15,800 | 1,050 |
| αCD20scFv1::SLT-1A version 2 | CD20 | 112,000 | 101.0 | 8,300 | 280 |

Example 3

Determining the Half Maximal Inhibitory Concentration ($IC_{50}$) of Exemplary CD20-Binding Proteins The ribosome inactivation capabilities of both versions 1 and 2 of the αCD20scFv1::SLT-1A CD20-binding proteins were determined using a cell-free, in vitro protein translation assay using the TNT® Quick Coupled Transcription/Translation kit (L1170 Promega Madison, Wis., U.S.). The kit includes Luciferase T7 Control DNA (L4821 Promega Madison, Wis., U.S.) and TNT® Quick Master Mix. The ribosome activity reaction was prepared according to the manufacturer's instructions.

A series of 10-fold dilutions of the αCD20scFv1::SLT-1A version to be tested was prepared in appropriate buffer and a series of identical TNT reaction mixture components were created for each dilution. Each sample in the dilution series of the αCD20scFv1::SLT-1A proteins was combined with each of the TNT reaction mixtures along with the Luciferase T7 Control DNA. The test samples were incubated for 1.5 hours at 30° C. After the incubation, Luciferase Assay Reagent (E1483 Promega, Madison, Wis., U.S.) was added to all test samples and the amount of luciferase protein translation was measured by luminescence according to the manufacturer's instructions. The level of translational inhibition was determined by non-linear regression analysis of log-transformed concentrations of total protein versus relative luminescence units. Using statistical software (GraphPad Prism, San Diego. Calif., U.S.), the half maximal inhibitory concentration ($IC_{50}$) value was calculated for each sample using the Prism software function of log(inhibitor) vs. response (three parameters) [Y=Bottom+((Top−Bottom)/(1+10^(X−Log IC50)))] under the heading dose-response-inhibition. The $IC_{50}$ for experimental proteins and SLT-1A-only control protein were calculated. The percent of SLT-1A-only control protein was calculated by [(IC50 of SLT-1A control protein/IC50 of experimental protein)×100].

The inhibitory effect of both versions of αCD20scFv1::SLT-1A on cell-free protein synthesis was strong. Multiple experiments determined that the $IC_{50}$ of both versions of αCD20scFv1::SLT-1A was around 50 picomolar (pM). In one experiment, the $IC_{50}$ of αCD20scFv1::SLT-1A version 1 on protein synthesis was about 38 pM or within 19% of the SLT-1A-only positive control (Table 2). Similarly, the $IC_{50}$ of αCD20scFv1::SLT-1A version 2 on protein synthesis in this cell-free assay was about 58 pM or within 18% of the SLT-1A-only positive control (Table 2).

TABLE 2

Ribosome Inactivation: Representative half-maximal inhibitory concentrations ($IC_{50}$) for exemplary CD20-binding proteins

| CD20-Binding Protein | $IC_{50}$ (pM) | $IC_{50}$ of SLT-1A-only positive control (pM) | Percentage of $IC_{50}$ of SLT-1A control |
|---|---|---|---|
| αCD20scFv1::SLT-1A version 1 | 38.3 | 31.2 | 81% |
| αCD20scFv1::SLT-1A version 2 | 58.3 | 47.8 | 82% |

Example 4

Determining Cellular Internalization by Immunofluorescence Assay

Immunofluorescence studies were performed in order to analyze the binding and internalization profiles of CD20-binding proteins αCD20scFv1::SLT-1A version 1 and αCD20scFv2::SLT-1A in CD20+ cell lines (Daudi, Raji, and Ramos) as compared to CD20− cell lines (BC-1, Jurkat (J45.01), and U266). For example, 50 nM of the respective CD 20-binding proteins were incubated with $0.8 \times 10^6$ Raji cells for 1 hour at 37° C. to allow for binding and internalization of the CD20-binding protein. The cells were then washed with 1=PBS, fixed and permeabilized with BD cytofix/cytoperm (BD Biosciences, San Jose, Calif., U.S.), and then washed twice with 1×BD Perm/Wash™ Buffer (BD Biosciences, San Jose. Calif., U.S.). The cells were incubated with Alexa Fluor®-555 labeled mouse anti-SLT-1A antibody (BEI Resources, Manassas, Va., U.S.) in IX BD Perm/Wash™ Buffer for 45 minutes at room temperature. Cells were then washed and fixed with BD cytofix (BD Biosciences, San Jose, Calif., U.S.) for 10 minutes at 4'C. The cells were then washed with 1×PBS and resuspended in 1×PBS, and then the cells were allowed to adhere onto poly-L-lysine coated glass slides (VWR, Radnor, Pa., U.S.). Slides were coverslipped with 4',6-diamidino-2-phenylindole (DAPI)-containing Vectashield (Fisher Scientific, Waltham, Mass., U.S.) and viewed by Zeiss Fluorescence Microscope (Zeiss, Thornwood, N.Y., U.S.).

Immunofluorescence studies showed that αCD20scFv1::SLT-1A version 1 and αCD20scFv2::SLT-1A bound to cell surfaces and entered into cells expressing CD20 at a cellular surface within one hour at 37° C.

The rate of CD20+ cell internalization was studied for the cytotoxic protein αCD20scFv1::SLT-1A version 1 using CD20+ Raji and Daudi cells at 37° C. The maximal cellular internalization of αCD20scFv1::SLT-1A version 1 inside CD20+ Raji and Daudi cells was observed around 1 hour after administration of αCD20scFv1::SLT-1A version 1 at concentrations ranging from 50 to 500 nM. After two hours, the intensity of immunofluorescence staining was reduced compared to the immunofluorescence staining observed at the one hour time point regardless of concentration of αCD20scFv1::SLT-1A version 1 within the range of 50 to 500 nM. Within one hour, αCD20scFv1::SLT-1A version 1 exhibited cellular internalization into about 80% of CD20+ Raji cells within a population of CD20+ Raji cells. In these internalization studies contacting Raji and Daudi cells with 50 to 500 nM of αCD20scFv1::SLT-1A version 1, the cell surface CD20 occupancy was estimated to be between 38% (50 nM of αCD20scFv1::SLT-I A version 1) and 86% (500 nM of αCD20scFv1::SLT-1A version 1).

Example 5

CD20+ Cell Kill Assay: Determining the Cytotoxic Selectivity and Half-Maximal Cytotoxic Concentrations ($CD_{50}$) of CD20-Binding Proteins The cytotoxicity profiles of both versions of αCD20scFv1::SLT-1A were determined by a CD20+ cell kill assay. This assay determines the capacity of a CD20-binding protein to kill cells expressing CD20 at a cellular surface as compared to cells that do not express the target biomolecule CD20. Cells were plated (2×10 per well) in 20 L cell culture medium in 384 well plates. The αCD20scFv1::SLT-1A protein to be tested was diluted either 5-fold or 10-fold in a 1×PBS, and 5 µL of the dilutions or buffer control were added to the cells. Control wells containing only cell culture media were used for baseline correction. The cell samples were incubated for 3 days at 37° C. and in an atmosphere of 5% carbon dioxide ($CO_2$) with the CD20-binding protein to be tested or only PBS buffer. The total cell survival or percent viability was determined using a luminescent readout using the CellTiter-Glo® Luminescent Cell Viability Assay (G7573 Promega Madison, Wis., U.S.) according to the manufacturer's instructions. The "percent viability" of experimental wells was calculated using the following equation: (Test RLU−Average Media RLU)/(Average Cells RLU−Average Media RLU)*100. Log polypeptide concentration versus Percent Viability was plotted using Prism software (GraphPad Prism, San Diego, Calif., U.S.) and log (inhibitor) vs. normalized response (variable slope) analysis was used to determine the half-maximal cytotoxic concentration ($CD_{50}$) value for the exemplary CD20-binding proteins. In addition, cell samples from lymphoma patients were analyzed using this cell kill assay to determine the cytotoxicity profile of αCD20scFv1::SLT-1A version 1.

Over multiple experiments, both versions of αCD20scFv1::SLT-1A demonstrated CD20-specific cell kill with 10 to 1000-fold specificity compared to cell kill of CD20 negative cell lines (Table 3). The CD20-specific cell kill profile of both versions of αCD20scFv1::SLT-1A also contrasted to the ability of the component SLT-1A (amino acids 1-251) to kill cells which lacked CD20-specificity (Table 3). The $CD_{50}$ values of both versions of the αCD20scFv1::SLT-1A protein were measured to be about 3-70 nM for CD20+ cells, depending on the cell line, as compared to over 600-2,000 for CD20− cell lines (Table 3). The $CD_{50}$ of the αCD20scFv1::SLT-1A version 1 CD20-binding protein was over 100 to 400 fold greater (less cytotoxic) for cells which did not express CD20 at a cellular surface as compared to cells expressing CD20 at a cellular surface. The $CD_{50}$ of both αCD20scFv1::SLT-1A versions toward human lymphoma cells from patient samples was about 7-40 nM (Table 3).

TABLE 3

Selective Cytotoxicity: Representative half-maximal cytotoxic concentrations ($CD_{50}$) for exemplary CD20-binding proteins

| | | $CD_{50}$ (nM) | | |
| --- | --- | --- | --- | --- |
| | CD20 status | αCD20scFv1::SLT-1A version 1 | αCD20scFv1::SLT-1A version 2 | SLT-1A only negative control |
| Cell Line | | | | |
| Daudi | positive | 5.6 | 67.0 | 650 |
| Raji | positive | 2.8 | 4.5 | 1,100 |
| ST486 | positive | 3.7 | 7.0 | 940 |
| Ramos | positive | 27.0 | 33.0 | 470 |
| BC-1 | negative | 2,000 | 2,100.0 | 160 |
| Jurkat | negative | 1,400 | 600.0 | 120 |
| U226 | negative | 2,500 | not determined | 960 |
| Patient Samples | | | | |
| follicular lymphoma, rituximab refractory | positive | 7.1 | 39.0 | 690,000 |
| Burkitt's lymphoma transformed by Epstein-Barr Virus | positive | 9.0 | 12.0 | 960 |

Example 6

Comparative CD20+ Cell Kill: Determining the Relative Cytotoxicities of CD20-Binding Proteins to CD20+ Cells Three potentially cytotoxic CD20-binding proteins were tested using the CD20+ cell kill assay using Raji cells (CD20+) as described above in Example 5. A set of representative results is reported in Table 4. Over multiple experiments, αCD20scFv1::SLT-1A version 1 exhibited a 50 to 100-fold greater cell kill function as compared to the CD20-binding protein αCD20scFv2::SLT-1A (SEQ ID NO:46) (Table 4).

TABLE 4

Representative Half-Maximal Cytotoxic Concentrations ($CD_{50}$) for Exemplary CD20-Binding Proteins to CD20+ Raji Cells

| CD20-Binding Protein | $CD_{50}$ (nM) |
|---|---|
| SLT-1A only negative control | 429 |
| αCD20scFv1::SLT-1A version 1 | 2 |
| αCD20scFv2::SLT-1A | 103 |

Example 7

Determining the Targeted Cytotoxicity for CD20-Binding Proteins Using in Vivo Xenograft Studies Two xenograft model systems based on an immunocompromised mouse strains were used to study the ability of exemplary CD20-binding proteins to kill CD20+ tumor cells in vivo and in a tumor environment over time and for various dosages. These xenograft model systems rely on well-characterized mouse strains that lack graft versus host responses, among other immune system deficiencies. First, an intravenous tumor model was studied using SCID (severe combined immune deficiency) mice to create disseminated tumors throughout the mice in order to test the in vivo effects of exemplary CD20-binding proteins on human tumor cells. Second, a subcutaneous tumor model was studied using BALBc/nude mice to create subcutaneous tumors on the mice, again in order to test the in vivo effects of exemplary CD20-binding proteins on human tumor cells.

For the first xenograft system, thirty-two C.B.-17 SCID mice (in four groups of eight animals) were challenged with $1 \times 10^7$ Raji-luc human lymphoma derived cells (Molecular Imaging, Ann Arbor, Mich., U.S.) in 200 μL PBS. On days 5-9 and 12-16 following tumor challenge, the following groups received the following through intravenous administration: Group 1: PBS; Group 2: αCD20scFv1::SLT-1A version 2 at a dose of 2 mg/kg; Group 3: αCD20scFv1::SLT-1A version 1 at a dose of 2 mg/kg; and Group 4: αCD20scFv1::SLT-1A version 1 at a dose of 4 mg/kg (days 5-9 only). Bioluminescence, in $1 \times 10^6$ photons/second units (p/s), was measured on days 5, 10, 15, and 20 using a Caliper IVIS 50 optical imaging system (Perkin Elmer, Waltham, Mass., U.S.). FIG. 2 shows how both versions of αCD20scFv1::SLT-1A, and αCD20scFv1::SLT-1A version 1 at both dosage levels, resulted in statistically significant less total bioluminescence compared to the PBS control. The decrease in total bioluminescence was reflective of statistically significant reductions in disseminated tumor burdens after treatment with a CD20-binding protein of the invention. FIG. 3 indicates a statistically significant increase in survival with administration of either version of αCD20scFv1::SLT-1A. The mean survival age was increased by five days with all treatments compared to the PBS negative control.

For the second xenograft model, twenty-eight BALBc/nude (in four groups of six or seven animals) were challenged subcutaneously with $2.5 \times 10^6$ Raji human lymphoma cells (Washington Biotechnology, Simpsonville, Md., U.S.). Tumor volume was determined using standard methods known in the art utilizing calipers. Day 0 was set at the time when the mean tumor volume for each mouse reached approximately 160 mm³ (one mouse from each group had a tumor greater than 260 mm³ so it was excluded). On days 0-4 and 7-11 the groups received intravenous administration of the following by group: Group 1: PBS; Group 2: αCD20scFv1::SLT-1A version 2 at a dose of 2 mg/kg; Group 3: αCD20scFv1::SLT-1A version 1 at a dose of 2 mg/kg; Group 4: αCD20scFv1::SLT-1A version 1 at a dose of 4 mg/kg. Tumor volume was measured and graphed as a function of day of study. FIG. 4 demonstrates how treatment with αCD20scFv1::SLT-1A version 1 (at both dosage levels) resulted in significantly reduced tumor volume compared to the PBS control through to Day 24. This is also reflected in the tumor free mouse number through Day 54, reported in Table 5.

TABLE 5

Elimination of Tumors by Exemplary CD20-Binding Proteins in a Subcutaneous-Tumor Mouse Model

| Group | Tumor Free Mice/Total Mice |
|---|---|
| PBS negative control | 0/7 |
| αCD20scFv1::SLT-1A version 2, 2 mg/kg | 6/7 |
| αCD20scFv1::SLT-1A version 1, 2 mg/kg | 5/6 |
| αCD20scFv1::SLT-1A version 1, 4 mg/kg | 6/7 |

Example 8

Determining In Vivo Effects of a CD20-Binding Protein in Non-Human Primates

The exemplary CD20-binding protein αCD20scFv1::SLT-1A version 1 was administered to non-human primates in order to test for in vivo effects. In vivo depletion of peripheral blood B lymphocytes in cynomolgus primates was observed after parenteral administration of different doses of αCD20scFv1::SLT-1A version 1.

In one experiment, ten cynomolgus primates were intravenously injected with PBS or αCD20scFv1::SLT-1A version 1 at different doses (50, 150, and 450 micrograms drug/kilogram body weight (mcg/kg)) on alternative days for 2 weeks. Then, peripheral blood samples collected prior to dosing on days 3 and 8 were analyzed for the percentage of B lymphocytes which expressed CD20 (FIGS. 5 and 6). In cynomolgus monkeys, two distinct B-cell subsets have been described by flow-cytometry: (1) CD21 negative, CD40 positive cells which express high levels of CD20, and CD21 positive and (2) CD40 positive cells which express lower levels of CD20 (Vugmeyster Y et al., *Cytometry* 52: 101-9 (2003)). Dose-dependent B-cell depletion as compared to baseline levels from blood samples collected prior to treatment was observed on day 3 (4, 14 and 45% decrease in animals dosed at 50, 150 and 450 mcg/kg) and day 8 (32, 52 and 75% decrease in animals dosed at 50, 150 and 450 mcg/kg) (Table 6). This experiment showed that αCD20scFv1::SLT-1A version 1 was capable of killing CD20 positive, primate B-cells in vivo.

TABLE 6

CD20-Binding Protein Dose Dependent B-Cell Depletion in Non-Human Primates

| | Percent Decrease in CD40+, CD20+ cells | | | Percent Decrease in CD21+, CD40+, CD20+ cells | | |
|---|---|---|---|---|---|---|
| Day | 50 mcg/kg | 150 mcg/kg | 450 mcg/kg | 50 mcg/kg | 150 mcg/kg | 450 mcg/kg |
| 3 | 38 | 57 | 69 | 4 | 14 | 45 |
| 8 | 65 | 81 | 86 | 32 | 52 | 75 |

Example 9

A CD20-Binding Protein Derived from the A Subunit of Shiga-Like Toxin-1 and the CD20 Binding Region of the Antibody Ofatumumab In this example, the Shiga toxin effector region is derived from the A subunit of Shiga-like Toxin 1 (SLT-1A). An immunoglobulin-type binding region αCD20 is derived from the monoclonal antibody ofatumumab (Gupta I, Jewell R, *Ann N Y Acad Sci* 1263: 43-56 (2012)) which comprises an immunoglobulin-type binding region capable of binding human CD20.

Construction, Production, and Purification of the CD20-Binding Protein SLT-1A::αCD20

The immunoglobulin-type binding region αCD20 and Shiga toxin effector region are linked together to form a protein. For example, a fusion protein is produced by expressing a polynucleotide encoding the CD20-binding protein SLT-1A::αCD20. Expression of the SLT-1A::αCD20 CD20-binding protein is accomplished using either bacterial and/or cell-free, protein translation systems as described in the previous examples.

Determining the In Vitro Characteristics of the CD20-Binding Protein SLT-1A::αCD20

The binding characteristics of the CD20-binding protein of this example for CD20+ cells and CD20– cells is determined by a fluorescence-based, flow-cytometry assay as described above in the previous examples. The $B_{max}$ for SLT-1A::αCD20 binding to CD20+ cells is measured to be approximately 50,000-200,000 MFI with a KO within the range of 0.01-100 nM, whereas there is no significant binding to CD20– cells in this assay.

The ribosome inactivation capabilities of the SLT-1A::αCD20 CD20-binding protein is determined in a cell-free, in vitro protein translation as described above in the previous examples. The inhibitory effect of the CD20-binding protein of this example on cell-free protein synthesis is significant. The $IC_{50}$ of SLT-1A::αCD20 on protein synthesis in this cell-free assay is approximately 0.1-100 pM.

Determining the Cytotoxicity of the CD20-Binding Protein SLT-1A::αCD20 Using a Cell-Kill Assay The cytotoxicity characteristics of SLT-1A::αCD20 are determined by the general cell-kill assay as described above in the previous examples using CD20+ cells. In addition, the selective cytotoxicity characteristics of SLT-1A::αCD20 are determined by the same general cell-kill assay using CD20– cells as a comparison to the CD20+ cells. The $CD_{50}$ of the CD20-binding protein of this example is approximately 0.01-100 nM for CD20+ cells depending on the cell line. The $CD_{50}$ of the CD20-binding protein is approximately 10-10,000 fold greater (less cytotoxic) for cells not expressing CD20 at a cellular surface as compared to cells which do express CD20 at a cellular surface.

Determining the In Vivo Effects of the CD20-Binding Protein SLT-1A::αCD20 Using Animal Models Animal models are used to determine the in vivo effects of the CD20-binding protein SLT-1A::αCD20 on neoplastic cells. Various mice strains are used to test the effect of the CD20-binding protein after intravenous administration on xenograft tumors in mice resulting from the injection into those mice of human neoplastic cells which express CD20 on their cell surfaces. Non-human primates may be used to test the effect of SLT-1A::αCD20 on peripheral blood B-cells as described above in Example 8.

After successful B-cell depletion, SLT-1A::αCD20 is tested for relief of an autoimmune disease in an animal model. For example, animal models for psoriasis include CD 18 hypomorphic mice (Bullard D et al., *Proc Nat Acad Sci U.S.A.* 93: 2116-21 (1996) and transgenic rats expressing HLA-B27 (see e.g. Keith J et al., *Arthritis Res Ther* 7: R769-76 (2005)). Animal models of specific autoimmune diseases are used to test for anti-inflammatory effects of the CD20-binding protein after intravenous administration of various dosages of SLT-1A::αCD20.

Example 10

CD20-Binding Proteins Based on Various CD20 Binding Domains

In this example, the Shiga toxin effector region is derived from the A subunit of Shiga-like Toxin 1 (SLT-1A SEQ ID NO:1), Shiga toxin (StxA SEQ ID NO:2), and/or Shiga-like Toxin 2 (SLT-2A SEQ ID NO:3). An immunoglobulin-type binding region is derived from the CD20 binding region from any molecule chosen from Table 7 and which binds an extracellular part of CD20. The exemplary cytotoxic CD20-binding proteins of this example are created and tested as described in the previous examples using CD20+ cells expressing CD20 at a cellular surface.

TABLE 7

Exemplary CD20 Binding Domains
Source of CD20 Binding Domain

| | |
|---|---|
| monoclonal antibody 1F5 and derivatives such, as, e.g., humanized variants and immunoglobulin-derived binding domains like scFvs | See e.g. Press O et at, *Blood* 69: 584-91 (1987) |

TABLE 7-continued

Exemplary CD20 Binding Domains
Source of CD20 Binding Domain

| | |
|---|---|
| monoclonal antibody 1H4 and derivatives such as, e.g., humanized variants and immunoglobulin-derived binding domains like scFvs | See e.g. Haisma H et al., *Blood* 92: 184-90 (1998) |
| monoclonal antibody 1K1791 and derivatives such as, e.g., humanized variants and immunoglobulin-derived binding domains like scFvs | See e.g. Nishida M et al., *Intl J Oncol* 32: 1263-74 (2008) |
| monoclonal antibody 2B8, Leu16, Leuδ, and derivatives such as, e.g., humanized variants and immunoglobulin-derived binding domains like scFvs | See e.g. Reff M et al., *Blood* 83: 435-45 (1994); Maloney D et al., *Blood* 84: 2457-66 (1994); WO 2005016969: PCT/EP2004/009033 |
| monoclonal antibody 2F2 and derivatives such as, e.g., humanized variants and immunoglobulin-derived binding domains like scFvs | See e.g. Teeling J et al., *Blood* 104: 1793-800 (2004) |
| monoclonal antibody 2H7 and derivatives such, as, e.g., humanized variants and immunoglobulin-derived binding domains like scFvs | See e.g. Liu A et al., *Proc Natl Acad Sci* 84: 3439-43 (1987); Polyak M et al., *Blood* 99: 3256-62 (2002): Nickerson-Nutter C et al., *Rheumatology* 50: 1033-44 (2011) |
| monoclonal antibody 7D8 and derivatives such as, e.g., humanized variants and immunoglobulin-derived binding domains like scFvs | See e.g. Teeling J et al., *Blood* 104: 1793-800 (2004) |
| monoclonal antibody 8E4 and derivatives such as, e.g., humanized variants and immunoglobulin-derived binding domains like scFvs | Wu L et al., *Cancer Lett* 292: 208-14 (2010) |
| monoclonal antibody 11B8 and derivatives such as, e.g., humanized variants and immunoglobulin-derived binding domains like scFvs | See e.g. Boross P et al., *Haematologica* 96: 1822-30 (2011) |
| monoclonal antibody AME-133v, LY2469298, and derivatives such as, e.g., humanized variants and immunoglobulin-derived binding domains like scFvs | See e.g. Robak T, Robak E, *BioDrugs* 25: 13-25 (2011) |
| antibodies recognizing the phosphor-CD20 antigen B1, B-ly1 and derivatives such as, e.g., humanized variants and immunoglobulin-derived binding domains like scFvs | See e.g. Tedder T et al., *Eur J Immunol* 16: 881-7 (1986); Cardarelli P et al., *Cancer Immunol Immunother* 51: 15-24 (2002); U.S. Pat. No. 5,843,398 |
| monoclonal antibody B9E9 and derivatives such as, e.g., humanized variants and immunoglobulin-derived binding domains like scFvs | See e.g. Schultz J et al., *Cancer Res* 60: 6663-9 (2000) |
| BM-ca and derivatives such, as, e.g., humanized variants and immunoglobulin-derived binding domains like scFvs | See e.g. Kobayashi H et al., *Cancer Med* 2: 130-43 (2013) |
| monoclonal antibody C2B8 and derivatives such as, e.g., humanized variants and immunoglobulin-derived binding domains like scFvs | See e.g. Reff M et al., *Blood* 83: 435-45 (1994) |
| monoclonal antibody CKI and derivatives such as, e.g., humanized variants and immunoglobulin-derived binding domains like scFvs | See e.g. Hooijberg E et al., *Cancer Res* 55: 840-6 (1995); Hooijberg E et al., *Hybridoma* 15: 23-31 (1996) |
| GA101, RO5072759, and derivatives such as, e.g., humanized variants and immunoglobulin-derived binding domains like scFvs | See e.g. Mössner E et al., *Blood* 115: 4393-402 (2010); Alduaij W et al., *Blood* 117: 4519-29 (2011); Robak T, Robak E, *BioDrugs* 25: 13-25 (2011); Salles G et al., *Blood* 119: 5126-32 (2012) |
| ibritumomab and derivatives such as, e.g., humanized variants and immunoglobulin-derived binding domains like scFvs | See e.g. Wiseman G et al., *Clin Cancer Res* 5: 3281s-3286s (1999); Cang S et al., *J Hematol Oncol* 5: 64 (2012) |
| obinutuzumab and derivatives such as, e.g., humanized variants and immunoglobulin-derived binding domains like scFvs | See e.g. Mössner E et al., *Blood* 115: 4393-402 (2010); Robak T, Robak E, *BioDrugs* 25: 13-25 (2011); Salles G et al., *Blood* 119: 5126-32 (2012); Golay J et al., *Blood* 122: 3482-91 (2013) |

TABLE 7-continued

Exemplary CD20 Binding Domains
Source of CD20 Binding Domain

| | |
|---|---|
| ocaratuzumab and derivatives such as, e.g., humanized variants and immunoglobulin-derived binding domains like scFvs | Cang S et al., *J Hematol Oncol* 5: 64 (2012) |
| ocrelizumab, PRO70769, and derivatives such as, e.g., humanized variants and immunoglobulin-derived binding domains like scFvs | See e.g. Morschhauser F et al., *Ann Oncol* 21: 1870-6 (2010); Cang S et al., *J Hematol Oncol* 5: 64 (2012) |
| ofatumumab and derivatives such as, e.g., immunoglobulin-derived binding domains like scFvs | See e.g. Hagenbeek A et al., *Blood* 111: 5486-95 (2008); Cang S et al., *J Hematol Oncol* 5: 64 (2012) |
| monoclonal antibodies OUBM1-OUBM8 | See e.g. Uchiyama S et al., *Cancer Sci* 101: 201-9 (2010) |
| monoclonal antibody PRO131921 and derivatives such as, e.g., humanized variants and immunoglobulin-derived binding domains like scFvs | See e.g. Robak T, Robak E, *BioDrugs* 25: 13-25 (2011); Cang S et al., *J Hematol Oncol* 5: 64 (2012) |
| rituximab and derivatives such as, e.g., humanized variants and immunoglobulin-derived binding domains like scFvs | See e.g. Reff M et al., *Blood* 83: 435-45 (1994); Anderson D et al., *Biochem Soc Trans* 25: 705-8 (1997); Golay J et al., *Blood* 122: 3482-91 (2013); Kinder M et al., *J Biol Chem* 288: 3084-54 (2013); Zhang H et al., *Cell Physiol Biochem* 32: 645-54 (2013); Ahmadzadeh V et al., *Protein Expr Purif* 102: 45-41 (2014) |
| antibody TGLA and derivatives such as, e.g., humanized variants and immunoglobulin-derived binding domains like scFvs | See e.g. Lv M et al., *Cancer Lett* 294: 66-73 (2010) |
| tositumomab and derivatives such as, e.g., humanized variants and immunoglobulin-derived binding domains like scFvs | See e.g. Cheson B, *Curr Opin Investig Drugs* 3: 165-70 (2002) |
| TRU-015 and derivatives such as, e.g., humanized variants, scFv variants, and CDRs | See e.g Burge D et al., *Clin Ther* 30: 1806-16 (2008); Robak T, Robak E, *BioDrugs* 25: 13-25 (2011)) |
| ublituximab and derivatives such as, e.g., humanized variants and immunoglobulin-derived binding domains like scFvs | See e.g. Abdelwahed R et al., *Invest Ophthalmol Vis Sci* 54: 3657-65 (2013); Garff-Tavernier M et al., *Leukemia* 28: 230-3 (2014) |
| veltuzumab, IMMU-106, hA20, and derivatives such as, e.g., humanized variants and immunoglobulin-derived binding domains like scFvs | See e.g. Morschhauser F et al., *J Clin Oncol* 27: 3346-53 (2009); Cang S et al., *J Hematol Oncol* 5: 64 (2012); Ellbrecht C et al., *JAMA Dermatol* jamadermatol.2014.1939 (2014) |
| CD20 binding scFv(s) and derivatives such as, e.g., HL23, scFv-1, scFv-3, scFv-5, and scFv-8 | See e.g. Geng S et al., *Cell Mol Immunol* 3: 439-43 (2006): Olafesn T et al., *Protein Eng Des Sel* 23: 243-9 (2010); Fang H et al., *Sci China Life Sci* 54: 255-62 (2011) |
| various CD20 binding antibodies, antigen, binding portions thereof, and derivatives such as, e.g., humanized variants and immunoglobulin-derived binding domains like scFvs | Lim S et al., *Haematologica* 95: 135-43 (2010); U.S. Pat. No. 4,861,579; U.S. Pat No. 5,500,362; U.S. Pat. No. 5,595,721; U.S. Pat. No. 5,677,180; U.S. Pat. No. 5,721,108; U.S. Pat. No. 5,736,337; U.S. Pat. No. 5,776,456; U.S. Pat. No. 5,843,398; U.S. Pat. No. 5,849,898; U.S. Pat. No. 6,015,542; U.S. Pat. No. 6,090,365; U.S. Pat. No. 6,120,767; U.S. Pat. No. 6,171,586; U.S. Pat. No. 6,194,551; U.S. Pat. No. 6,224,866; U.S. Pat. No. 6,242,195; U.S. Pat. No. 6,287,537; U.S. Pat. No. 6,306,393; U.S. Pat. No. 6,368,596; U.S. Pat. No. 6,399,062; U.S. Pat. No. 6,410,393; U.S. Pat. No. 6,455,043; U.S. Pat. No. 6,528,624; U.S. Pat. No. 6,538,124; U.S. Pat. No. 6,565,827; U.S. Pat. No. 6,652,852; U.S. Pat. No. 6,682,734; U.S. Pat. No. 7,879,984; U.S. Pat. No. 8,101,179; U.S. Pat. No. 8,153,125; U.S. Pat. No. 8,337,844; US 2001/0018041; US 2002/0004587; US 2002/0006404; US 2002/0009427; US 2002/0009444; US 2002/0012665; US 2002/0041847; US 2002/0058029; US 2002/0128488; US |

TABLE 7-continued

Exemplary CD20 Binding Domains
Source of CD20 Binding Domain

| | |
|---|---|
| | 2002/0136719; US 2002/0197255; US 2002/0197256; US 2003/0021781; US 2003/0026801; US 2003/0068664; US 2003/0082172; US 2003/0095963; US 2003/0103971; US 2003/0133930; US 2003/0147885; US 2003/0157108; US 2003/0180292; US 2003/0185796: US 2003/0219433; US 2003/0219838; WO95/03770; WO98/58964; WO99/22764; WO00/09160; WO00/27428; WO00/27433; WO00/42072; WO00/44788; WO00/67795; WO00/67796; WO00/76542; WO01/03734; WO01/10460; WO01/10461; WO01/10462; WO01/13945; WO01/72333; WO01/80884; WO01/97858; WO02/060955; WO02/079255; WO02/096948; WO02/102312; WO03/002607; WO03/061694; WO2004/032828; WO 2014076292; PCT/US2004/014326; EP20040751628; EP20040764037; PCT/US2006/020408; PCT/US2007/080925; PCT/US2008/007464; PCT/US2008/071709; EP20100013084 |
| fibronectin domain based alternative to antibodies such as, e.g., FN3$_{(CD20)}$ monoclonal antibodies which bind to various mammalian CD20 antigens | See e.g. Natarajan A et al., *Clin Cancer Res* 19: 6820-9 (2013) US 2011/0091483; US 12/0941,583; PCT/US2010/055826; EP20140151932; PCT/GB2012/052532; US 13/048,135; EP20140151932; PCT/GB2012/052532; US 13/048,135; PCT/US2006/046034 |
| nucleic acids which can be used to generate anti-CD20 antibodies, antigen binding fragments, and derivatives thereof | U.S. Pat. No. 8,097,713; US 12/0965956 |

While certain embodiments of the invention have been described by way of illustration, it will be apparent that the invention may be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety. The international patent application publications WO 2014164680 A1 and WO 2014164693 A2, the international patent applications PCT/US2014/023198 and PCT/US2014/023231, and the U.S. provisional patent application Ser. Nos. 61/777,130, 61/951,110, and 61/951,121 are each incorporated herein by reference in their entirety. The complete disclosures of all electronically available biological sequence information from GenBank (National Center for Biotechnology Information, U.S.) for amino acid and nucleotide sequences cited herein are each incorporated herein by reference in their entirety.

The invention is claimed as follows:

1. A CD20-binding protein comprising:
   a) a CD20 binding region capable of specifically binding an extracellular part of CD20, wherein the CD20 binding region comprises the polypeptide represented by amino acids 2 to 245 of any one of SEQ ID NOs: 46-63, 90-98, 103-105, 108-110, and 112, and
   b) a Shiga toxin A Subunit effector region polypeptide comprising an amino acid sequence that is at least 95% identical to an amino acid sequence selected from:
      i) amino acids 75 to 251 of SEQ ID NO: 1 or SEQ ID NO: 2;
      ii) amino acids 1 to 251 of SEQ ID NO: 1 or SEQ ID NO: 2; and
      iii) amino acids 1 to 261 of SEQ ID NO: 1 or SEQ ID NO: 2;
   wherein the CD20 binding region is linked via one or more peptide linker(s) to the Shiga toxin A Subunit effector region polypeptide;
   wherein, when the CD20-binding protein is administered to CD20 positive cells at a concentration equivalent to 50% cell-surface CD20 occupancy, the CD20-binding protein internalizes into one or more of the CD20 positive cells within five hours at 37 degrees Celsius.

2. The CD20-binding protein of claim 1, wherein, when the CD20-binding protein is administered to CD20 positive cells at a concentration equivalent to 50% cell-surface CD20 occupancy, the CD20-binding protein internalizes into one or more of the CD20 positive cells within one hour at 37 degrees Celsius.

3. The CD20-binding protein of claim 1, wherein the CD20 positive cell is a descendant or member of a B-cell lineage.

4. The CD20-binding protein of claim 1, wherein the CD20 positive cell is:
   malignant B-cell, B-cell leukemia cell, B-cell lymphoma cell, B-cell myeloma cell, acute myeloid leukemia cell, acute non-lymphocytic leukemia cell, B-cell chronic lymphocytic leukemia cell, B-cell lymphoma cell, B-cell non-Hodgkin's lymphoma cell, B-cell precursor acute lymphoblastic leukemia cell, B-cell prolymphocytic leukemia cell, Burkitt's lymphoma cell, chronic lymphocytic leukemia cell, chronic myeloid leukemia cell, diffuse large B-cell lymphoma cell, follicular lymphoma cell, hairy cell leukemia cell, Hodgkin's lymphoma cell, immunoblastic large cell lymphoma cell, mantle cell lymphoma cell, melanoma cell, multiple myeloma cell, neoplastic plasma cell, nodular lymphocyte predominant Hodgkin's lymphoma cell, non-Hodgkin's lymphoma cell, plasmablastic lymphoma cell, plasma cell myeloma cell, precursor B-lymphoblastic lymphoma cell, small lymphocytic lymphoma cell, malignant T-cell, T-cell leukemia cell, T-cell lymphoma cell, T-cell large granular lymphocyte leukemia cell, T-cell prolymphocytic leukemia cell, healthy B-cell lineage cell, or healthy T-cell.

5. The CD20-binding protein of claim 1, wherein, when the CD20-binding protein is administered to one or more CD20 positive cells at a physiological temperature, the CD20-binding protein is capable of one or more of the following behaviors in said one or more CD20 positive cells:
   (i) internalizing inside said one or more CD20 positive cells within one hour,
   (ii) subcellular routing at least one Shiga toxin A Subunit effector region polypeptide to the cytosol of said one or more CD20 positive cells,
   (iii) disrupting the ribosome function of said one or more CD20 positive cells, and
   (iv) killing of said one or more CD20 positive cells.

6. The CD20-binding protein of claim 5, wherein the CD20-binding protein exhibits a cytotoxic effect that is at least 3-fold greater to a first population cells whose members are CD20 positive relative to a second population of cells whose members do not express CD20 at a cellular surface.

7. The CD20-binding protein of claim 1, wherein the Shiga toxin A Subunit effector region polypeptide comprises a polypeptide comprising the amino acid sequence selected from:
   a) amino acids 75 to 251 of SEQ ID NO: 1 or SEQ ID NO: 2;
   b) amino acids 1 to 251 of SEQ ID NO: 1 or SEQ ID NO: 2; and
   c) amino acids 1 to 261 of SEQ ID NO: 1 or SEQ ID NO: 2.

8. A CD20-binding protein comprising:
   a) a CD20 binding region capable of specifically binding an extracellular part of CD20,
     and comprising the polypeptide represented by amino acids 2 to 245 of any one of SEQ ID NOs: 46-112, and
   b) a Shiga toxin A Subunit effector region polypeptide, wherein the polypeptide is represented by amino acids 75 to 251 of SEQ ID NO:1
   wherein the CD20 binding region is linked via one or more peptide linker(s) to the Shiga toxin A Subunit effector region polypeptide; and
   wherein, when the CD20-binding protein is administered to CD20 positive cells at a concentration equivalent to 50% cell-surface CD20 occupancy, the CD20-binding protein internalizes into one or more of the CD20 positive cells within five hours at 37 degrees Celsius.

9. The CD20-binding protein of claim 8, which comprises the polypeptide shown in any one of SEQ ID NOs: 47-51 and 53-63.

10. The CD20-binding protein of claim 1, further comprising an additional exogenous peptide.

11. A pharmaceutical composition comprising
   the CD20-binding protein of claim 1; and
   at least one pharmaceutically acceptable excipient or carrier.

12. A diagnostic composition comprising
   the CD20-binding protein of claim 1; and
   a detection promoting agent.

13. A kit comprising:
   (i) the CD20-binding protein of claim 1;
   (ii) the pharmaceutical composition according to claim 11; or
   (iii) the diagnostic composition according to claim 12; and
   an additional reagent and/or pharmaceutical delivery device.

14. The CD20-binding protein of claim 1 or 8, wherein the amino acid residue corresponding to position 75 of SEQ ID NO: 1 or 2 is asparagine, the amino acid residue corresponding to position 77 of SEQ ID NO: 1 or 2 is tyrosine, the amino acid residue corresponding to position 167 of SEQ ID NO: 1 or 2 is glutamate, the amino acid residue corresponding to position 170 of SEQ ID NO: 1 or 2 is arginine, and the amino acid residue corresponding to position 176 of SEQ ID NO: 1 or 2 is arginine.

15. The CD20-binding protein of claim 1 or 8, wherein at least one of the one or more peptide linker(s) comprises an IgG3 linker.

16. The pharmaceutical composition of claim 11, wherein the amino acid residue corresponding to position 75 of SEQ ID NO: 1 or 2 is asparagine, the amino acid residue corresponding to position 77 of SEQ ID NO: 1 or 2 is tyrosine, the amino acid residue corresponding to position 167 of SEQ ID NO: 1 or 2 is glutamate, the amino acid residue corresponding to position 170 of SEQ ID NO: 1 or 2 is arginine, and the amino acid residue corresponding to position 176 of SEQ ID NO: 1 or 2 is arginine.

17. The diagnostic composition of claim 12, wherein the amino acid residue corresponding to position 75 of SEQ ID NO: 1 or 2 is asparagine, the amino acid residue corresponding to position 77 of SEQ ID NO: 1 or 2 is tyrosine, the amino acid residue corresponding to position 167 of SEQ ID NO: 1 or 2 is glutamate, the amino acid residue corresponding to position 170 of SEQ ID NO: 1 or 2 is arginine, and the amino acid residue corresponding to position 176 of SEQ ID NO: 1 or 2 is arginine.

18. A method of delivering an exogenous peptide to a cell, the method comprising administering the exogenous peptide of claim 10 to a CD20-expressing cell, wherein the CD20-binding protein delivers the additional exogenous material into the interior of the cell within five hours at 37 degrees Celsius.

* * * * *

SEQUENCE LISTING

```
<160> NUMBER OF SEQ ID NOS: 159

<210> SEQ ID NO 1
<211> LENGTH: 293
<212> TYPE: PRT
<213> ORGANISM: Escherichia coli
<220> FEATURE:
<223> OTHER INFORMATION: Shiga-like toxin 1 Subunit A (SLT-1A)

<400> SEQUENCE: 1

Lys Glu Phe Thr Leu Asp Phe Ser Thr Ala Lys Thr T

```
Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
        290

<210> SEQ ID NO 2
<211> LENGTH: 293
<212> TYPE: PRT
<213> ORGANISM: Shigella dysenteriae
<220> FEATURE:
<223> OTHER INFORMATION: Shiga toxin Subunit A (StxA)

<400> SEQUENCE: 2

Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
                 20                  25                  30

Ser Gly Gly Thr Ser Leu Leu Met Ile Asp Ser Gly Thr Gly Asp Asn
             35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110
```

```
Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290

<210> SEQ ID NO 3
<211> LENGTH: 297
<212> TYPE: PRT
<213> ORGANISM: Escherichia coli
<220> FEATURE:
<223> OTHER INFORMATION: Shiga-like toxin 2 Subunit A (SLT-2A)

<400> SEQUENCE: 3

Asp Glu Phe Thr Val Asp Phe Ser Ser Gln Lys Ser Tyr Val Asp Ser
1               5                   10                  15

Leu Asn Ser Ile Arg Ser Ala Ile Ser Thr Pro Leu Gly Asn Ile Ser
            20                  25                  30

Gln Gly Gly Val Ser Val Ser Val Ile Asn His Val Leu Gly Gly Asn
        35                  40                  45

Tyr Ile Ser Leu Asn Val Arg Gly Leu Asp Pro Tyr Ser Glu Arg Phe
    50                  55                  60

Asn His Leu Arg Leu Ile Met Glu Arg Asn Asn Leu Tyr Val Ala Gly
65                  70                  75                  80

Phe Ile Asn Thr Glu Thr Asn Ile Phe Tyr Arg Phe Ser Asp Phe Ser
                85                  90                  95

His Ile Ser Val Pro Asp Val Ile Thr Val Ser Met Thr Thr Asp Ser
            100                 105                 110

Ser Tyr Ser Ser Leu Gln Arg Ile Ala Asp Leu Glu Arg Thr Gly Met
        115                 120                 125

Gln Ile Gly Arg His Ser Leu Val Gly Ser Tyr Leu Asp Leu Met Glu
    130                 135                 140

Phe Arg Gly Arg Ser Met Thr Arg Ala Ser Ser Arg Ala Met Leu Arg
145                 150                 155                 160

Phe Val Thr Val Ile Ala Glu Ala Leu Arg Phe Arg Gln Ile Gln Arg
                165                 170                 175
```

```
Gly Phe Arg Pro Ala Leu Ser Glu Ala Ser Pro Leu Tyr Thr Met Thr
            180                 185                 190

Ala Gln Asp Val Asp Leu Thr Leu Asn Trp Gly Arg Ile Ser Asn Val
            195                 200                 205

Leu Pro Glu Tyr Arg Gly Glu Gly Val Arg Ile Gly Arg Ile Ser
    210                 215                 220

Phe Asn Ser Leu Ser Ala Ile Leu Gly Ser Val Ala Val Ile Leu Asn
225                 230                 235                 240

Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
            260                 265                 270

Asn Val Leu Trp Glu Ala Asn Thr Ile Ala Ala Leu Leu Asn Arg Lys
            275                 280                 285

Pro Gln Asp Leu Thr Glu Pro Asn Gln
            290                 295

<210> SEQ ID NO 4
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Shiga toxin effector region SLT-1A

<400> SEQUENCE: 4

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220
```

```
Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR1

<400> SEQUENCE: 5

Gly Tyr Thr Phe Thr Ser Tyr Asn Met His
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR2

<400> SEQUENCE: 6

Ala Ile Tyr Pro Gly Asn Gly Asp Thr Ser Tyr Asn Gln Lys Phe Lys
1               5                   10                  15

Gly

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR3

<400> SEQUENCE: 7

Ala Gln Leu Arg Pro Asn Tyr Trp Tyr Phe Asp Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR1

<400> SEQUENCE: 8

Arg Ala Ser Ser Ser Val Ser Tyr Met His
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: light chain CDR2

<400> SEQUENCE: 9

Ala Thr Ser Asn Leu Ala Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3

<400> SEQUENCE: 10

Gln Gln Trp Ile Ser Asn Pro Pro Thr
1               5

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR1

<400> SEQUENCE: 11

Gly Tyr Thr Phe Thr Ser Tyr Asn Val His
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR2

<400> SEQUENCE: 12

Ala Ile Tyr Pro Gly Asn Gly Asp Thr Ser Phe Asn Gln Lys Phe Lys
1               5                   10                  15

Gly

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR3

<400> SEQUENCE: 13

Ser Asn Tyr Tyr Gly Ser Ser Tyr Val Trp Phe Phe Asp Val
1               5                   10

<210> SEQ ID NO 14
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR1

<400> SEQUENCE: 14

Arg Ala Ser Ser Ser Val Ser Tyr Met Asp
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR2

<400> SEQUENCE: 15

Ala Thr Ser Asn Leu Ala Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3

<400> SEQUENCE: 16

Gln Gln Trp Ile Ser Asn Pro Pro Thr
1               5

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR1

<400> SEQUENCE: 17

Gly Tyr Thr Phe Thr Ser Tyr Asn Met His
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR2

<400> SEQUENCE: 18

Ala Ile Tyr Pro Gly Asn Gly Asp Thr Ser Tyr Asn Gln Lys Phe Lys
1               5                   10                  15

Gly
```

```
<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR3

<400> SEQUENCE: 19

Ser Thr Tyr Tyr Gly Gly Asp Trp Tyr Phe Asn Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR1

<400> SEQUENCE: 20

Arg Ala Ser Ser Ser Val Ser Tyr Ile His
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR2

<400> SEQUENCE: 21

Ala Thr Ser Asn Leu Ala Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3

<400> SEQUENCE: 22

Gln Gln Trp Thr Ser Asn Pro Pro Thr
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR1

<400> SEQUENCE: 23

Gly Phe Thr Phe Asn Asp Tyr Ala Met His
1               5                   10
```

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR2

<400> SEQUENCE: 24

Thr Ile Ser Trp Asn Ser Gly Ser Ile Gly Tyr Ala Asp Ser Val Lys
1               5                   10                  15
Gly

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR3

<400> SEQUENCE: 25

Asp Ile Gln Tyr Gly Asn Tyr Tyr Gly Met Asp Val
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR1

<400> SEQUENCE: 26

Arg Ala Ser Gln Ser Val Ser Ser Tyr Leu Ala
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR2

<400> SEQUENCE: 27

Asp Ala Ser Asn Arg Ala Thr
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3

<400> SEQUENCE: 28

Gln Gln Arg Ser Asn Trp Pro Ile Thr
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR1

<400> SEQUENCE: 29

Gly Tyr Thr Phe Thr Ser Tyr Asn Met His
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR2

<400> SEQUENCE: 30

Ala Ile Tyr Pro Gly Asn Gly Asp Thr Ser Tyr Asn Gln Lys Phe Lys
1               5                   10                  15

Gly

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR3

<400> SEQUENCE: 31

Val Val Tyr Tyr Ser Asn Ser Tyr Trp Tyr Phe Asp Val
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR1

<400> SEQUENCE: 32

Arg Ala Ser Ser Ser Val Ser Tyr Met His
1               5                   10

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR2

```
<400> SEQUENCE: 33

Ala Pro Ser Asn Leu Ala Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3

<400> SEQUENCE: 34

Gln Gln Trp Ser Phe Asn Pro Pro Thr
1               5

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR1

<400> SEQUENCE: 35

Gly Tyr Ala Phe Ser Tyr Ser Trp Ile Asn
1               5                   10

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR2

<400> SEQUENCE: 36

Arg Ile Phe Pro Gly Asp Gly Asp Thr Asp Tyr Asn Gly Lys Phe Lys
1               5                   10                  15

Gly

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain CDR3

<400> SEQUENCE: 37

Asn Val Phe Asp Gly Tyr Trp Leu Val Tyr
1               5                   10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
```

-continued

```
      peptide
<220> FEATURE:
<223> OTHER INFORMATION: light chain CDR1

<400> SEQUENCE: 38

Arg Ser Ser Lys Ser Leu Leu His Ser Asn Gly Ile Thr Tyr Leu Tyr
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR2

<400> SEQUENCE: 39

Gln Met Ser Asn Leu Val Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain CDR3

<400> SEQUENCE: 40

Ala Gln Asn Leu Glu Leu Pro Tyr Thr
1               5

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: exemplary linker 1

<400> SEQUENCE: 41

Gly Ser Thr Ser Gly Ser Gly Lys Pro Gly Ser Gly Glu Gly Ser
1               5                   10                  15

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: exemplary linker 2 (G4S)5

<400> SEQUENCE: 42

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 43
<211> LENGTH: 16
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: exemplary linker 3

<400> SEQUENCE: 43

Glu Phe Pro Lys Pro Ser Thr Pro Pro Gly Ser Ser Gly Gly Ala Pro
1               5                   10                  15

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker extension

<400> SEQUENCE: 44

Gly Ile Leu Gly Phe Val Phe Thr Leu
1               5

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Strep-tag

<400> SEQUENCE: 45

Trp Ser His Pro Gln Phe Glu Lys
1               5

<210> SEQ ID NO 46
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv1 linked to SLT-1A variant 1

<400> SEQUENCE: 46

Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
                20                  25                  30

Tyr Asn Met His Trp Val Lys Gln Thr Pro Gly Gln Gly Leu Glu Trp
            35                  40                  45

Ile Gly Ala Ile Tyr Pro Gly Asn Gly Asp Thr Ser Tyr Asn Gln Lys
        50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ala Gln Leu Arg Pro Asn Tyr Trp Tyr Phe Asp Val Trp
            100                 105                 110
```

Gly Ala Gly Thr Thr Val Thr Val Ser Ser Gly Gly Gly Ser Gly
            115                 120                 125

Gly Gly Gly Ser Gly Gly Gly Ser Gly Gly Gly Ser Gly Gly
130                 135                 140

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
                165                 170                 175

Ser Tyr Met His Trp Tyr Gln Gln Lys Pro Gly Ser Ser Pro Lys Pro
            180                 185                 190

Trp Ile Tyr Ala Thr Ser Asn Leu Ala Ser Gly Val Pro Ala Arg Phe
        195                 200                 205

Ser Gly Ser Gly Ser Gly Thr Ser Tyr Ser Leu Thr Ile Ser Arg Val
    210                 215                 220

Glu Ala Glu Asp Ala Ala Thr Tyr Tyr Cys Gln Gln Trp Ile Ser Asn
225                 230                 235                 240

Pro Pro Thr Phe Gly Ala Gly Thr Lys Leu Glu Leu Lys Gly Gly Gly
                245                 250                 255

Gly Ser Gly Gly Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
        275                 280                 285

Gln Thr Ile Ser Ser Gly Gly Thr Ser Leu Leu Met Ile Asp Ser Gly
    290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
            340                 345                 350

Ala Asp Phe Ser His Val Thr Phe Pro Gly Thr Thr Ala Val Thr Leu
        355                 360                 365

Ser Gly Asp Ser Ser Tyr Thr Thr Leu Gln Arg Val Ala Gly Ile Ser
    370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                405                 410                 415

Ala Met Leu Arg Phe Val Thr Val Thr Ala Glu Ala Leu Arg Phe Arg
            420                 425                 430

Gln Ile Gln Arg Gly Phe Arg Thr Thr Leu Asp Asp Leu Ser Gly Arg
        435                 440                 445

Ser Tyr Val Met Thr Ala Glu Asp Val Asp Leu Thr Leu Asn Trp Gly
    450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Cys His His His Ala Ser Arg Val Ala Arg
            500                 505                 510

<210> SEQ ID NO 47
<211> LENGTH: 511
<212> TYPE: PRT

<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: alphaCD20-scFv1 linked to SLT-1A variant 2

<400> SEQUENCE: 47

Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Gln Gly Leu Glu Trp
        35                  40                  45

Ile Gly Ala Ile Tyr Pro Gly Asn Gly Asp Thr Ser Tyr Asn Gln Lys
50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ala Gln Leu Arg Pro Asn Tyr Trp Tyr Phe Asp Val Trp
            100                 105                 110

Gly Ala Gly Thr Thr Val Thr Val Ser Ser Gly Gly Gly Ser Gly Gly
        115                 120                 125

Gly Gly Ser Gly Gly Gly Ser Gly Gly Gly Ser Gly Gly
130                 135                 140

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
                165                 170                 175

Ser Tyr Met His Trp Tyr Gln Gln Lys Pro Gly Ser Ser Pro Lys Pro
            180                 185                 190

Trp Ile Tyr Ala Thr Ser Asn Leu Ala Ser Gly Val Pro Ala Arg Phe
        195                 200                 205

Ser Gly Ser Gly Ser Gly Thr Ser Tyr Ser Leu Thr Ile Ser Arg Val
210                 215                 220

Glu Ala Glu Asp Ala Ala Thr Tyr Tyr Cys Gln Gln Trp Ile Ser Asn
225                 230                 235                 240

Pro Pro Thr Phe Gly Ala Gly Thr Lys Leu Glu Leu Lys Gly Gly Gly
                245                 250                 255

Gly Ser Gly Gly Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
        275                 280                 285

Gln Thr Ile Ser Ser Gly Gly Thr Ser Leu Leu Met Ile Asp Ser Gly
290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
            340                 345                 350

Ala Asp Phe Ser His Val Thr Phe Pro Gly Thr Thr Ala Val Thr Leu
        355                 360                 365

Ser Gly Asp Ser Ser Tyr Thr Thr Leu Gln Arg Val Ala Gly Ile Ser

```
              370                 375                 380
Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                405                 410                 415

Ala Met Leu Arg Phe Val Thr Val Thr Ala Glu Ala Leu Arg Phe Arg
                420                 425                 430

Gln Ile Gln Arg Gly Phe Arg Thr Thr Leu Asp Asp Leu Ser Gly Arg
                435                 440                 445

Ser Tyr Val Met Thr Ala Glu Asp Val Asp Leu Thr Leu Asn Trp Gly
                450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Ser His His His Ala Ser Arg Val Ala Arg
                500                 505                 510
```

<210> SEQ ID NO 48
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv1 linked to SLT-1A variant 3

<400> SEQUENCE: 48

```
Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
                20                  25                  30

Tyr Asn Met His Trp Val Lys Gln Thr Pro Gly Gln Gly Leu Glu Trp
            35                  40                  45

Ile Gly Ala Ile Tyr Pro Gly Asn Gly Asp Thr Ser Tyr Asn Gln Lys
50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ala Gln Leu Arg Pro Asn Tyr Trp Tyr Phe Asp Val Trp
                100                 105                 110

Gly Ala Gly Thr Thr Val Thr Val Ser Ser Gly Ser Thr Ser Gly Ser
            115                 120                 125

Gly Lys Pro Gly Ser Gly Glu Gly Ser Asp Ile Val Leu Ser Gln Ser
        130                 135                 140

Pro Ala Ile Leu Ser Ala Ser Pro Gly Glu Lys Val Thr Met Thr Cys
145                 150                 155                 160

Arg Ala Ser Ser Ser Val Ser Tyr Met His Trp Tyr Gln Gln Lys Pro
                165                 170                 175

Gly Ser Ser Pro Lys Pro Trp Ile Tyr Ala Thr Ser Asn Leu Ala Ser
                180                 185                 190

Gly Val Pro Ala Arg Phe Ser Gly Ser Gly Ser Gly Thr Ser Tyr Ser
            195                 200                 205

Leu Thr Ile Ser Arg Val Glu Ala Glu Asp Ala Ala Thr Tyr Tyr Cys
```

```
            210                 215                 220
Gln Gln Trp Ile Ser Asn Pro Pro Thr Phe Gly Ala Gly Thr Lys Leu
225                 230                 235                 240

Glu Leu Lys Glu Phe Pro Lys Pro Ser Thr Pro Pro Gly Ser Ser Gly
                245                 250                 255

Gly Ala Pro Lys Glu Phe Thr Leu Asp Phe Ser Thr Ala Lys Thr Tyr
                260                 265                 270

Val Asp Ser Leu Asn Val Ile Arg Ser Ala Ile Gly Thr Pro Leu Gln
            275                 280                 285

Thr Ile Ser Ser Gly Gly Thr Ser Leu Leu Met Ile Asp Ser Gly Ser
290                 295                 300

Gly Asp Asn Leu Phe Ala Val Asp Val Arg Gly Ile Asp Pro Glu Glu
305                 310                 315                 320

Gly Arg Phe Asn Asn Leu Arg Leu Ile Val Glu Arg Asn Asn Leu Tyr
                325                 330                 335

Val Thr Gly Phe Val Asn Arg Thr Asn Asn Val Phe Tyr Arg Phe Ala
                340                 345                 350

Asp Phe Ser His Val Thr Phe Pro Gly Thr Thr Ala Val Thr Leu Ser
            355                 360                 365

Gly Asp Ser Ser Tyr Thr Thr Leu Gln Arg Val Ala Gly Ile Ser Arg
370                 375                 380

Thr Gly Met Gln Ile Asn Arg His Ser Leu Thr Thr Ser Tyr Leu Asp
385                 390                 395                 400

Leu Met Ser His Ser Gly Thr Ser Leu Thr Gln Ser Val Ala Arg Ala
                405                 410                 415

Met Leu Arg Phe Val Thr Val Thr Ala Glu Ala Leu Arg Phe Arg Gln
                420                 425                 430

Ile Gln Arg Gly Phe Arg Thr Thr Leu Asp Asp Leu Ser Gly Arg Ser
            435                 440                 445

Tyr Val Met Thr Ala Glu Asp Val Asp Leu Thr Leu Asn Trp Gly Arg
450                 455                 460

Leu Ser Ser Val Leu Pro Asp Tyr His Gly Gln Asp Ser Val Arg Val
465                 470                 475                 480

Gly Arg Ile Ser Phe Gly Ser Ile Asn Ala Ile Leu Gly Ser Val Ala
                485                 490                 495

Leu Ile Leu Asn Cys His His His Ala Ser Arg Val Ala Arg
            500                 505                 510

<210> SEQ ID NO 49
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv1 linked to SLT-1A variant 4

<400> SEQUENCE: 49

Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
                20                  25                  30

Tyr Asn Met His Trp Val Lys Gln Thr Pro Gly Gln Gly Leu Glu Trp
            35                  40                  45

Ile Gly Ala Ile Tyr Pro Gly Asn Gly Asp Thr Ser Tyr Asn Gln Lys
```

```
            50                  55                  60
Phe Lys Gly Lys Ala Thr Leu Thr Ala Asp Lys Ser Ser Ser Thr Ala
 65                  70                  75                  80

Tyr Met Gln Leu Ser Ser Leu Thr Ser Glu Asp Ser Ala Val Tyr Tyr
                     85                  90                  95

Cys Ala Arg Ala Gln Leu Arg Pro Asn Tyr Trp Tyr Phe Asp Val Trp
                100                 105                 110

Gly Ala Gly Thr Thr Val Thr Val Ser Ser Gly Ser Thr Ser Gly Ser
                115                 120                 125

Gly Lys Pro Gly Ser Gly Glu Gly Ser Asp Ile Val Leu Ser Gln Ser
                130                 135                 140

Pro Ala Ile Leu Ser Ala Ser Pro Gly Glu Lys Val Thr Met Thr Cys
145                 150                 155                 160

Arg Ala Ser Ser Ser Val Ser Tyr Met His Trp Tyr Gln Gln Lys Pro
                165                 170                 175

Gly Ser Ser Pro Lys Pro Trp Ile Tyr Ala Thr Ser Asn Leu Ala Ser
                180                 185                 190

Gly Val Pro Ala Arg Phe Ser Gly Ser Gly Ser Gly Thr Ser Tyr Ser
                195                 200                 205

Leu Thr Ile Ser Arg Val Glu Ala Glu Asp Ala Ala Thr Tyr Tyr Cys
                210                 215                 220

Gln Gln Trp Ile Ser Asn Pro Pro Thr Phe Gly Ala Gly Thr Lys Leu
225                 230                 235                 240

Glu Leu Lys Glu Phe Pro Lys Pro Ser Thr Pro Pro Gly Ser Ser Gly
                245                 250                 255

Gly Ala Pro Lys Glu Phe Thr Leu Asp Phe Ser Thr Ala Lys Thr Tyr
                260                 265                 270

Val Asp Ser Leu Asn Val Ile Arg Ser Ala Ile Gly Thr Pro Leu Gln
                275                 280                 285

Thr Ile Ser Ser Gly Gly Thr Ser Leu Leu Met Ile Asp Ser Gly Ser
                290                 295                 300

Gly Asp Asn Leu Phe Ala Val Asp Val Arg Gly Ile Asp Pro Glu Glu
305                 310                 315                 320

Gly Arg Phe Asn Asn Leu Arg Leu Ile Val Glu Arg Asn Asn Leu Tyr
                325                 330                 335

Val Thr Gly Phe Val Asn Arg Thr Asn Asn Val Phe Tyr Arg Phe Ala
                340                 345                 350

Asp Phe Ser His Val Thr Phe Pro Gly Thr Thr Ala Val Thr Leu Ser
                355                 360                 365

Gly Asp Ser Ser Tyr Thr Thr Leu Gln Arg Val Ala Gly Ile Ser Arg
                370                 375                 380

Thr Gly Met Gln Ile Asn Arg His Ser Leu Thr Thr Ser Tyr Leu Asp
385                 390                 395                 400

Leu Met Ser His Ser Gly Thr Ser Leu Thr Gln Ser Val Ala Arg Ala
                405                 410                 415

Met Leu Arg Phe Val Thr Val Thr Ala Glu Ala Leu Arg Phe Arg Gln
                420                 425                 430

Ile Gln Arg Gly Phe Arg Thr Thr Leu Asp Asp Leu Ser Gly Arg Ser
                435                 440                 445

Tyr Val Met Thr Ala Glu Asp Val Asp Leu Thr Leu Asn Trp Gly Arg
                450                 455                 460

Leu Ser Ser Val Leu Pro Asp Tyr His Gly Gln Asp Ser Val Arg Val
465                 470                 475                 480
```

-continued

```
Gly Arg Ile Ser Phe Gly Ser Ile Asn Ala Ile Leu Gly Ser Val Ala
                485                 490                 495

Leu Ile Leu Asn Ser His His His Ala Ser Arg Val Ala Arg
            500                 505                 510

<210> SEQ ID NO 50
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv1 linked to SLT-1A variant 5

<400> SEQUENCE: 50

Met Gln

```
Asp Val Arg Gly Ile Asp Pro Glu Glu Gly Arg Phe Asn Asn Leu Arg
                325                 330                 335

Leu Ile Val Glu Arg Asn Asn Leu Tyr Val Thr Gly Phe Val Asn Arg
                340                 345                 350

Thr Asn Asn Val Phe Tyr Arg Phe Ala Asp Phe Ser His Val Thr Phe
            355                 360                 365

Pro Gly Thr Thr Ala Val Thr Leu Ser Gly Asp Ser Ser Tyr Thr Thr
        370                 375                 380

Leu Gln Arg Val Ala Gly Ile Ser Arg Thr Gly Met Gln Ile Asn Arg
385                 390                 395                 400

His Ser Leu Thr Thr Ser Tyr Leu Asp Leu Met Ser His Ser Gly Thr
                405                 410                 415

Ser Leu Thr Gln Ser Val Ala Arg Ala Met Leu Arg Phe Val Thr Val
                420                 425                 430

Thr Ala Glu Ala Leu Arg Phe Arg Gln Ile Gln Arg Gly Phe Arg Thr
            435                 440                 445

Thr Leu Asp Asp Leu Ser Gly Arg Ser Tyr Val Met Thr Ala Glu Asp
        450                 455                 460

Val Asp Leu Thr Leu Asn Trp Gly Arg Leu Ser Ser Val Leu Pro Asp
465                 470                 475                 480

Tyr His Gly Gln Asp Ser Val Arg Val Gly Arg Ile Ser Phe Gly Ser
                485                 490                 495

Ile Asn Ala Ile Leu Gly Ser Val Ala Leu Ile Leu Asn Ser His His
            500                 505                 510

His Ala Ser Arg Val Ala Arg
            515

<210> SEQ ID NO 51
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv1 linked to StxA variant 1

<400> SEQUENCE: 51

Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Gln Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ala Gln Leu Arg Pro Asn Tyr Trp Tyr Phe Asp Val Trp
            100                 105                 110

Gly Ala Gly Thr Thr Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140
```

-continued

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
            165                 170                 175

Ser Tyr Met His Trp Tyr Gln Gln Lys Pro Gly Ser Ser Pro Lys Pro
        180                 185                 190

Trp Ile Tyr Ala Thr Ser Asn Leu Ala Ser Gly Val Pro Ala Arg Phe
    195                 200                 205

Ser Gly Ser Gly Ser Gly Thr Ser Tyr Ser Leu Thr Ile Ser Arg Val
210                 215                 220

Glu Ala Glu Asp Ala Ala Thr Tyr Tyr Cys Gln Gln Trp Ile Ser Asn
225                 230                 235                 240

Pro Pro Thr Phe Gly Ala Gly Thr Lys Leu Glu Leu Lys Gly Gly Gly
            245                 250                 255

Gly Ser Gly Gly Lys Glu Phe Thr Leu Asp Phe Ser Thr Ala Lys Thr
        260                 265                 270

Tyr Val Asp Ser Leu Asn Val Ile Arg Ser Ala Ile Gly Thr Pro Leu
    275                 280                 285

Gln Thr Ile Ser Ser Gly Gly Thr Ser Leu Leu Met Ile Asp Ser Gly
290                 295                 300

Thr Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
            325                 330                 335

Tyr Val Thr Gly Phe Val Asn Arg Thr Asn Asn Val Phe Tyr Arg Phe
        340                 345                 350

Ala Asp Phe Ser His Val Thr Phe Pro Gly Thr Thr Ala Val Thr Leu
    355                 360                 365

Ser Gly Asp Ser Ser Tyr Thr Thr Leu Gln Arg Val Ala Gly Ile Ser
370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
            405                 410                 415

Ala Met Leu Arg Phe Val Thr Val Thr Ala Glu Ala Leu Arg Phe Arg
        420                 425                 430

Gln Ile Gln Arg Gly Phe Arg Thr Thr Leu Asp Asp Leu Ser Gly Arg
    435                 440                 445

Ser Tyr Val Met Thr Ala Glu Asp Val Asp Leu Thr Leu Asn Trp Gly
450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
            485                 490                 495

Ala Leu Ile Leu Asn Cys His His Ala Ser Arg Val Ala Arg
        500                 505                 510

<210> SEQ ID NO 52
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: alphaCD20-scFv2 linked to SLT-1A variant 1

<400> SEQUENCE: 52

```
Met Gln Val Gln Leu Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
            35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
            115                 120                 125

Gly Ser Gly Lys Pro Gly Ser Gly Glu Gly Ser Gln Ile Val Leu Ser
130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
    210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255

Ser Gly Gly Ala Pro Lys Glu Phe Thr Leu Asp Phe Ser Thr Ala Lys
            260                 265                 270

Thr Tyr Val Asp Ser Leu Asn Val Ile Arg Ser Ala Ile Gly Thr Pro
        275                 280                 285

Leu Gln Thr Ile Ser Ser Gly Gly Thr Ser Leu Leu Met Ile Asp Ser
    290                 295                 300

Gly Ser Gly Asp Asn Leu Phe Ala Val Asp Val Arg Gly Ile Asp Pro
305                 310                 315                 320

Glu Glu Gly Arg Phe Asn Asn Leu Arg Leu Ile Val Glu Arg Asn Asn
                325                 330                 335

Leu Tyr Val Thr Gly Phe Val Asn Arg Thr Asn Asn Val Phe Tyr Arg
            340                 345                 350

Phe Ala Asp Phe Ser His Val Thr Phe Pro Gly Thr Thr Ala Val Thr
        355                 360                 365

Leu Ser Gly Asp Ser Ser Tyr Thr Thr Leu Gln Arg Val Ala Gly Ile
    370                 375                 380

Ser Arg Thr Gly Met Gln Ile Asn Arg His Ser Leu Thr Thr Ser Tyr
385                 390                 395                 400
```

-continued

```
Leu Asp Leu Met Ser His Ser Gly Thr Ser Leu Thr Gln Ser Val Ala
            405                 410                 415

Arg Ala Met Leu Arg Phe Val Thr Val Thr Ala Glu Ala Leu Arg Phe
        420                 425                 430

Arg Gln Ile Gln Arg Gly Phe Arg Thr Thr Leu Asp Asp Leu Ser Gly
        435                 440                 445

Arg Ser Tyr Val Met Thr Ala Glu Asp Val Asp Leu Thr Leu Asn Trp
    450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Cys His His His Ala Ser Arg Val Ala Arg
                500                 505                 510

<210> SEQ ID NO 53
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A variant 2

<400> SEQUENCE: 53

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
        115                 120                 125

Gly Ser Gly Lys Pro Gly Ser Gly Glu Gly Ser Gln Ile Val Leu Ser
    130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
    210                 215                 220

Tyr Cys Gln Gln Trp Ile Ser Asn Pro Pro Thr Phe Gly Ala Gly Thr
225                 230                 235                 240
```

-continued

Lys Leu Glu Leu Lys Glu Phe Pro Lys Pro Ser Thr Pro Pro Gly Ser
                245                 250                 255

Ser Gly Gly Ala Pro Lys Glu Phe Thr Leu Asp Phe Ser Thr Ala Lys
            260                 265                 270

Thr Tyr Val Asp Ser Leu Asn Val Ile Arg Ser Ala Ile Gly Thr Pro
        275                 280                 285

Leu Gln Thr Ile Ser Ser Gly Thr Ser Leu Leu Met Ile Asp Ser
    290                 295                 300

Gly Ser Gly Asp Asn Leu Phe Ala Val Asp Val Arg Gly Ile Asp Pro
305                 310                 315                 320

Glu Glu Gly Arg Phe Asn Asn Leu Arg Leu Ile Val Glu Arg Asn Asn
                325                 330                 335

Leu Tyr Val Thr Gly Phe Val Asn Arg Thr Asn Asn Val Phe Tyr Arg
            340                 345                 350

Phe Ala Asp Phe Ser His Val Thr Phe Pro Gly Thr Thr Ala Val Thr
        355                 360                 365

Leu Ser Gly Asp Ser Ser Tyr Thr Thr Leu Gln Arg Val Ala Gly Ile
    370                 375                 380

Ser Arg Thr Gly Met Gln Ile Asn Arg His Ser Leu Thr Thr Ser Tyr
385                 390                 395                 400

Leu Asp Leu Met Ser His Ser Gly Thr Ser Leu Thr Gln Ser Val Ala
                405                 410                 415

Arg Ala Met Leu Arg Phe Val Thr Val Thr Ala Glu Ala Leu Arg Phe
            420                 425                 430

Arg Gln Ile Gln Arg Gly Phe Arg Thr Thr Leu Asp Asp Leu Ser Gly
        435                 440                 445

Arg Ser Tyr Val Met Thr Ala Glu Asp Val Asp Leu Thr Leu Asn Trp
    450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Ser His His His Ala Ser Arg Val Ala Arg
            500                 505                 510

<210> SEQ ID NO 54
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A variant 3

<400> SEQUENCE: 54

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

```
Tyr Met Gln Leu Ser Ser Leu Thr Ser Glu Asp Ser Ala Val Tyr Tyr
             85                  90                  95
Cys Ala Arg Ser Asn Tyr Tyr Gly Ser Ser Tyr Val Trp Phe Phe Asp
            100                 105                 110
Val Trp Gly Ala Gly Thr Thr Val Thr Val Ser Ser Gly Ser Thr Ser
        115                 120                 125
Gly Ser Gly Lys Pro Gly Ser Gly Glu Gly Ser Gln Ile Val Leu Ser
130                 135                 140
Gln Ser Pro Thr Ile Leu Ser Ala Ser Pro Gly Glu Lys Val Thr Met
145                 150                 155                 160
Thr Cys Arg Ala Ser Ser Ser Val Ser Tyr Met Asp Trp Tyr Gln Gln
            165                 170                 175
Lys Pro Gly Ser Ser Pro Lys Pro Trp Ile Tyr Ala Thr Ser Asn Leu
            180                 185                 190
Ala Ser Gly Val Pro Ala Arg Phe Ser Gly Ser Gly Ser Gly Thr Ser
            195                 200                 205
Tyr Ser Leu Thr Ile Ser Arg Val Glu Ala Glu Asp Ala Ala Thr Tyr
            210                 215                 220
Tyr Cys Gln Gln Trp Ile Ser Asn Pro Pro Thr Phe Gly Ala Gly Thr
225                 230                 235                 240
Lys Leu Glu Leu Lys Glu Phe Pro Lys Pro Ser Thr Pro Pro Gly Ser
            245                 250                 255
Ser Gly Gly Ala Pro Gly Ile Leu Gly Phe Val Phe Thr Leu Lys Glu
            260                 265                 270
Phe Thr Leu Asp Phe Ser Thr Ala Lys Thr Tyr Val Asp Ser Leu Asn
            275                 280                 285
Val Ile Arg Ser Ala Ile Gly Thr Pro Leu Gln Thr Ile Ser Ser Gly
            290                 295                 300
Gly Thr Ser Leu Leu Met Ile Asp Ser Gly Ser Gly Asp Asn Leu Phe
305                 310                 315                 320
Ala Val Asp Val Arg Gly Ile Asp Pro Glu Glu Gly Arg Phe Asn Asn
            325                 330                 335
Leu Arg Leu Ile Val Glu Arg Asn Asn Leu Tyr Val Thr Gly Phe Val
            340                 345                 350
Asn Arg Thr Asn Asn Val Phe Tyr Arg Phe Ala Asp Phe Ser His Val
            355                 360                 365
Thr Phe Pro Gly Thr Thr Ala Val Thr Leu Ser Gly Asp Ser Ser Tyr
            370                 375                 380
Thr Thr Leu Gln Arg Val Ala Gly Ile Ser Arg Thr Gly Met Gln Ile
385                 390                 395                 400
Asn Arg His Ser Leu Thr Thr Ser Tyr Leu Asp Leu Met Ser His Ser
            405                 410                 415
Gly Thr Ser Leu Thr Gln Ser Val Ala Arg Ala Met Leu Arg Phe Val
            420                 425                 430
Thr Val Thr Ala Glu Ala Leu Arg Phe Arg Gln Ile Gln Arg Gly Phe
            435                 440                 445
Arg Thr Thr Leu Asp Asp Leu Ser Gly Arg Ser Tyr Val Met Thr Ala
450                 455                 460
Glu Asp Val Asp Leu Thr Leu Asn Trp Gly Arg Leu Ser Ser Val Leu
465                 470                 475                 480
Pro Asp Tyr His Gly Gln Asp Ser Val Arg Val Gly Arg Ile Ser Phe
            485                 490                 495
Gly Ser Ile Asn Ala Ile Leu Gly Ser Val Ala Leu Ile Leu Asn Cys
```

```
                 500                 505                 510
His His His Ala Ser Arg Val Ala Arg
        515                 520

<210> SEQ ID NO 55
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A variant 4

<400> SEQUENCE: 55

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
        115                 120                 125

Gly Ser Gly Lys Pro Gly Ser Gly Glu Gly Ser Gln Ile Val Leu Ser
130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255

Ser Gly Gly Ala Pro Gly Ile Leu Gly Phe Val Phe Thr Leu Lys Glu
            260                 265                 270

Phe Thr Leu Asp Phe Ser Thr Ala Lys Thr Tyr Val Asp Ser Leu Asn
        275                 280                 285

Val Ile Arg Ser Ala Ile Gly Thr Pro Leu Gln Thr Ile Ser Ser Gly
290                 295                 300

Gly Thr Ser Leu Leu Met Ile Asp Ser Gly Ser Gly Asp Asn Leu Phe
305                 310                 315                 320

Ala Val Asp Val Arg Gly Ile Asp Pro Glu Glu Gly Arg Phe Asn Asn
```

```
                325                 330                 335
Leu Arg Leu Ile Val Glu Arg Asn Asn Leu Tyr Val Thr Gly Phe Val
            340                 345                 350

Asn Arg Thr Asn Asn Val Phe Tyr Arg Phe Ala Asp Phe Ser His Val
            355                 360                 365

Thr Phe Pro Gly Thr Thr Ala Val Thr Leu Ser Gly Asp Ser Ser Tyr
370                 375                 380

Thr Thr Leu Gln Arg Val Ala Gly Ile Ser Arg Thr Gly Met Gln Ile
385                 390                 395                 400

Asn Arg His Ser Leu Thr Thr Ser Tyr Leu Asp Leu Met Ser His Ser
            405                 410                 415

Gly Thr Ser Leu Thr Gln Ser Val Ala Arg Ala Met Leu Arg Phe Val
            420                 425                 430

Thr Val Thr Ala Glu Ala Leu Arg Phe Arg Gln Ile Gln Arg Gly Phe
            435                 440                 445

Arg Thr Thr Leu Asp Asp Leu Ser Gly Arg Ser Tyr Val Met Thr Ala
450                 455                 460

Glu Asp Val Asp Leu Thr Leu Asn Trp Gly Arg Leu Ser Ser Val Leu
465                 470                 475                 480

Pro Asp Tyr His Gly Gln Asp Ser Val Arg Val Gly Arg Ile Ser Phe
                485                 490                 495

Gly Ser Ile Asn Ala Ile Leu Gly Ser Val Ala Leu Ile Leu Asn Ser
            500                 505                 510

His His His Ala Ser Arg Val Ala Arg
            515                 520

<210> SEQ ID NO 56
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A variant 5

<400> SEQUENCE: 56

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Gly Gly Gly
        115                 120                 125

Ser Gly Gly Gly Gly Ser Gly Gly Gly Ser Gly Gly Gly Gly Ser
    130                 135                 140

Gly Gly Gly Gly Ser Gln Ile Val Leu Ser Gln Ser Pro Thr Ile Leu
```

```
            145                 150                 155                 160
        Ser Ala Ser Pro Gly Glu Lys Val Thr Met Thr Cys Arg Ala Ser Ser
                        165                 170                 175

Ser Val Ser Tyr Met Asp Trp Tyr Gln Gln Lys Pro Gly Ser Ser Pro
                        180                 185                 190

Lys Pro Trp Ile Tyr Ala Thr Ser Asn Leu Ala Ser Gly Val Pro Ala
                        195                 200                 205

Arg Phe Ser Gly Ser Gly Ser Gly Thr Ser Tyr Ser Leu Thr Ile Ser
                        210                 215                 220

Arg Val Glu Ala Glu Asp Ala Ala Thr Tyr Tyr Cys Gln Gln Trp Ile
        225                 230                 235                 240

Ser Asn Pro Pro Thr Phe Gly Ala Gly Thr Lys Leu Glu Leu Lys Glu
                        245                 250                 255

Phe Pro Lys Pro Ser Thr Pro Pro Gly Ser Ser Gly Ala Pro Lys
                        260                 265                 270

Glu Phe Thr Leu Asp Phe Ser Thr Ala Lys Thr Tyr Val Asp Ser Leu
                        275                 280                 285

Asn Val Ile Arg Ser Ala Ile Gly Thr Pro Leu Gln Thr Ile Ser Ser
                290                 295                 300

Gly Gly Thr Ser Leu Leu Met Ile Asp Ser Gly Ser Gly Asp Asn Leu
        305                 310                 315                 320

Phe Ala Val Asp Val Arg Gly Ile Asp Pro Glu Glu Gly Arg Phe Asn
                        325                 330                 335

Asn Leu Arg Leu Ile Val Glu Arg Asn Asn Leu Tyr Val Thr Gly Phe
                        340                 345                 350

Val Asn Arg Thr Asn Asn Val Phe Tyr Arg Phe Ala Asp Phe Ser His
                        355                 360                 365

Val Thr Phe Pro Gly Thr Thr Ala Val Thr Leu Ser Gly Asp Ser Ser
                        370                 375                 380

Tyr Thr Thr Leu Gln Arg Val Ala Gly Ile Ser Arg Thr Gly Met Gln
        385                 390                 395                 400

Ile Asn Arg His Ser Leu Thr Thr Ser Tyr Leu Asp Leu Met Ser His
                        405                 410                 415

Ser Gly Thr Ser Leu Thr Gln Ser Val Ala Arg Ala Met Leu Arg Phe
                        420                 425                 430

Val Thr Val Thr Ala Glu Ala Leu Arg Phe Arg Gln Ile Gln Arg Gly
                        435                 440                 445

Phe Arg Thr Thr Leu Asp Asp Leu Ser Gly Arg Ser Tyr Val Met Thr
        450                 455                 460

Ala Glu Asp Val Asp Leu Thr Leu Asn Trp Gly Arg Leu Ser Ser Val
        465                 470                 475                 480

Leu Pro Asp Tyr His Gly Gln Asp Ser Val Arg Val Gly Arg Ile Ser
                        485                 490                 495

Phe Gly Ser Ile Asn Ala Ile Leu Gly Ser Val Ala Leu Ile Leu Asn
                        500                 505                 510

Cys His His His Ala Ser Arg Val Ala Arg
                        515                 520

<210> SEQ ID NO 57
<211> LENGTH: 522
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: alphaCD20-scFv2 linked to SLT-1A variant 6

<400> SEQUENCE: 57

| | | | | | | | | | | | | | | | |
|---|---|---|---|---|---|---|---|---|---|---|---|---|---|---|---|
| Met | Gln | Val | Gln | Leu | Gln | Gln | Pro | Gly | Ala | Glu | Leu | Val | Lys | Pro | Gly |
| 1 | | | | 5 | | | | | 10 | | | | | 15 | |
| Ala | Ser | Val | Lys | Met | Ser | Cys | Lys | Thr | Ser | Gly | Tyr | Thr | Phe | Thr | Ser |
| | | | 20 | | | | | 25 | | | | | 30 | | |
| Tyr | Asn | Val | His | Trp | Val | Lys | Gln | Thr | Pro | Gly | Gln | Gly | Leu | Glu | Trp |
| | | | 35 | | | | | 40 | | | | | 45 | | |
| Ile | Gly | Ala | Ile | Tyr | Pro | Gly | Asn | Gly | Asp | Thr | Ser | Phe | Asn | Gln | Lys |
| | | 50 | | | | | 55 | | | | | 60 | | | |
| Phe | Lys | Gly | Lys | Ala | Thr | Leu | Thr | Ala | Asp | Lys | Ser | Ser | Ser | Thr | Val |
| 65 | | | | | 70 | | | | | 75 | | | | | 80 |
| Tyr | Met | Gln | Leu | Ser | Ser | Leu | Thr | Ser | Glu | Asp | Ser | Ala | Val | Tyr | Tyr |
| | | | | 85 | | | | | 90 | | | | | 95 | |
| Cys | Ala | Arg | Ser | Asn | Tyr | Tyr | Gly | Ser | Ser | Tyr | Val | Trp | Phe | Phe | Asp |
| | | | 100 | | | | | 105 | | | | | 110 | | |
| Val | Trp | Gly | Ala | Gly | Thr | Thr | Val | Thr | Val | Ser | Ser | Gly | Gly | Gly | Gly |
| | | | 115 | | | | | 120 | | | | | 125 | | |
| Ser | Gly | Gly | Gly | Gly | Ser | Gly | Gly | Gly | Ser | Gly | Gly | Gly | Gly | Gly | Ser |
| | 130 | | | | | 135 | | | | | 140 | | | | |
| Gly | Gly | Gly | Gly | Ser | Gln | Ile | Val | Leu | Ser | Gln | Ser | Pro | Thr | Ile | Leu |
| 145 | | | | | 150 | | | | | 155 | | | | | 160 |
| Ser | Ala | Ser | Pro | Gly | Glu | Lys | Val | Thr | Met | Thr | Cys | Arg | Ala | Ser | Ser |
| | | | | 165 | | | | | 170 | | | | | 175 | |
| Ser | Val | Ser | Tyr | Met | Asp | Trp | Tyr | Gln | Gln | Lys | Pro | Gly | Ser | Ser | Pro |
| | | | 180 | | | | | 185 | | | | | 190 | | |
| Lys | Pro | Trp | Ile | Tyr | Ala | Thr | Ser | Asn | Leu | Ala | Ser | Gly | Val | Pro | Ala |
| | | | 195 | | | | | 200 | | | | | 205 | | |
| Arg | Phe | Ser | Gly | Ser | Gly | Ser | Gly | Thr | Ser | Tyr | Ser | Leu | Thr | Ile | Ser |
| | | | 210 | | | | | 215 | | | | | 220 | | |
| Arg | Val | Glu | Ala | Glu | Asp | Ala | Ala | Thr | Tyr | Tyr | Cys | Gln | Gln | Trp | Ile |
| 225 | | | | | 230 | | | | | 235 | | | | | 240 |
| Ser | Asn | Pro | Pro | Thr | Phe | Gly | Ala | Gly | Thr | Lys | Leu | Glu | Leu | Lys | Glu |
| | | | | 245 | | | | | 250 | | | | | 255 | |
| Phe | Pro | Lys | Pro | Ser | Thr | Pro | Pro | Gly | Ser | Ser | Gly | Gly | Ala | Pro | Lys |
| | | | 260 | | | | | 265 | | | | | 270 | | |
| Glu | Phe | Thr | Leu | Asp | Phe | Ser | Thr | Ala | Lys | Thr | Tyr | Val | Asp | Ser | Leu |
| | | | | 275 | | | | | 280 | | | | | 285 | |
| Asn | Val | Ile | Arg | Ser | Ala | Ile | Gly | Thr | Pro | Leu | Gln | Thr | Ile | Ser | Ser |
| | | | 290 | | | | | 295 | | | | | 300 | | |
| Gly | Gly | Thr | Ser | Leu | Leu | Met | Ile | Asp | Ser | Gly | Ser | Gly | Asp | Asn | Leu |
| 305 | | | | | 310 | | | | | 315 | | | | | 320 |
| Phe | Ala | Val | Asp | Val | Arg | Gly | Ile | Asp | Pro | Glu | Glu | Gly | Arg | Phe | Asn |
| | | | | 325 | | | | | 330 | | | | | 335 | |
| Asn | Leu | Arg | Leu | Ile | Val | Glu | Arg | Asn | Asn | Leu | Tyr | Val | Thr | Gly | Phe |
| | | | 340 | | | | | 345 | | | | | 350 | | |
| Val | Asn | Arg | Thr | Asn | Asn | Val | Phe | Tyr | Arg | Phe | Ala | Asp | Phe | Ser | His |
| | | | 355 | | | | | 360 | | | | | 365 | | |
| Val | Thr | Phe | Pro | Gly | Thr | Thr | Ala | Val | Thr | Leu | Ser | Gly | Asp | Ser | Ser |
| | | | 370 | | | | | 375 | | | | | 380 | | |
| Tyr | Thr | Thr | Leu | Gln | Arg | Val | Ala | Gly | Ile | Ser | Arg | Thr | Gly | Met | Gln |
| 385 | | | | | 390 | | | | | 395 | | | | | 400 |

```
Ile Asn Arg His Ser Leu Thr Thr Ser Tyr Leu Asp Leu Met Ser His
            405                 410                 415

Ser Gly Thr Ser Leu Thr Gln Ser Val Ala Arg Ala Met Leu Arg Phe
        420                 425                 430

Val Thr Val Thr Ala Glu Ala Leu Arg Phe Arg Gln Ile Gln Arg Gly
            435                 440                 445

Phe Arg Thr Thr Leu Asp Asp Leu Ser Gly Arg Ser Tyr Val Met Thr
450                 455                 460

Ala Glu Asp Val Asp Leu Thr Leu Asn Trp Gly Arg Leu Ser Ser Val
465                 470                 475                 480

Leu Pro Asp Tyr His Gly Gln Asp Ser Val Arg Val Gly Arg Ile Ser
                485                 490                 495

Phe Gly Ser Ile Asn Ala Ile Leu Gly Ser Val Ala Leu Ile Leu Asn
            500                 505                 510

Ser His His His Ala Ser Arg Val Ala Arg
            515                 520

<210> SEQ ID NO 58
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to StxA variant 1

<400> SEQUENCE: 58

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
        115                 120                 125

Gly Ser Gly Lys Pro Gly Ser Gly Glu Gly Ser Gln Ile Val Leu Ser
    130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
    210                 215                 220
```

```
Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
            245                 250                 255

Ser Gly Gly Ala Pro Lys Glu Phe Thr Leu Asp Phe Ser Thr Ala Lys
        260                 265                 270

Thr Tyr Val Asp Ser Leu Asn Val Ile Arg Ser Ala Ile Gly Thr Pro
    275                 280                 285

Leu Gln Thr Ile Ser Ser Gly Thr Ser Leu Leu Met Ile Asp Ser
290                 295                 300

Gly Thr Gly Asp Asn Leu Phe Ala Val Asp Val Arg Gly Ile Asp Pro
305                 310                 315                 320

Glu Glu Gly Arg Phe Asn Asn Leu Arg Leu Ile Val Glu Arg Asn Asn
                325                 330                 335

Leu Tyr Val Thr Gly Phe Val Asn Arg Thr Asn Asn Val Phe Tyr Arg
            340                 345                 350

Phe Ala Asp Phe Ser His Val Thr Phe Pro Gly Thr Thr Ala Val Thr
        355                 360                 365

Leu Ser Gly Asp Ser Ser Tyr Thr Thr Leu Gln Arg Val Ala Gly Ile
    370                 375                 380

Ser Arg Thr Gly Met Gln Ile Asn Arg His Ser Leu Thr Thr Ser Tyr
385                 390                 395                 400

Leu Asp Leu Met Ser His Ser Gly Thr Ser Leu Thr Gln Ser Val Ala
                405                 410                 415

Arg Ala Met Leu Arg Phe Val Thr Val Thr Ala Glu Ala Leu Arg Phe
            420                 425                 430

Arg Gln Ile Gln Arg Gly Phe Arg Thr Thr Leu Asp Asp Leu Ser Gly
        435                 440                 445

Arg Ser Tyr Val Met Thr Ala Glu Asp Val Asp Leu Thr Leu Asn Trp
    450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Cys His His His Ala Ser Arg Val Ala Arg
            500                 505                 510

<210> SEQ ID NO 59
<211> LENGTH: 521
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to StxA variant 2

<400> SEQUENCE: 59

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60
```

```
Phe Lys Gly Lys Ala Thr Leu Thr Ala Asp Lys Ser Ser Ser Thr Val
 65                  70                  75                  80

Tyr Met Gln Leu Ser Ser Leu Thr Ser Glu Asp Ser Ala Val Tyr Tyr
                 85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
        115                 120                 125

Gly Ser Gly Lys Pro Gly Ser Gly Glu Gly Ser Gln Ile Val Leu Ser
130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255

Ser Gly Gly Ala Pro Gly Ile Leu Gly Phe Val Phe Thr Leu Lys Glu
            260                 265                 270

Phe Thr Leu Asp Phe Ser Thr Ala Lys Thr Tyr Val Asp Ser Leu Asn
        275                 280                 285

Val Ile Arg Ser Ala Ile Gly Thr Pro Leu Gln Thr Ile Ser Ser Gly
290                 295                 300

Gly Thr Ser Leu Leu Met Ile Asp Ser Gly Thr Gly Asp Asn Leu Phe
305                 310                 315                 320

Ala Val Asp Val Arg Gly Ile Asp Pro Glu Gly Arg Phe Asn Asn
                325                 330                 335

Leu Arg Leu Ile Val Glu Arg Asn Asn Leu Tyr Val Thr Gly Phe Val
            340                 345                 350

Asn Arg Thr Asn Asn Val Phe Tyr Arg Phe Ala Asp Phe Ser His Val
        355                 360                 365

Thr Phe Pro Gly Thr Thr Ala Val Thr Leu Ser Gly Asp Ser Ser Tyr
370                 375                 380

Thr Thr Leu Gln Arg Val Ala Gly Ile Ser Arg Thr Gly Met Gln Ile
385                 390                 395                 400

Asn Arg His Ser Leu Thr Thr Ser Tyr Leu Asp Leu Met Ser His Ser
                405                 410                 415

Gly Thr Ser Leu Thr Gln Ser Val Ala Arg Ala Met Leu Arg Phe Val
            420                 425                 430

Thr Val Thr Ala Glu Ala Leu Arg Phe Arg Gln Ile Gln Arg Gly Phe
        435                 440                 445

Arg Thr Thr Leu Asp Asp Leu Ser Gly Arg Ser Tyr Val Met Thr Ala
450                 455                 460

Glu Asp Val Asp Leu Thr Leu Asn Trp Gly Arg Leu Ser Ser Val Leu
465                 470                 475                 480
```

```
Pro Asp Tyr His Gly Gln Asp Ser Val Arg Val Gly Arg Ile Ser Phe
            485                 490                 495

Gly Ser Ile Asn Ala Ile Leu Gly Ser Val Ala Leu Ile Leu Asn Cys
        500                 505                 510

His His His Ala Ser Arg Val Ala Arg
        515                 520

<210> SEQ ID NO 60
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv3 linked to SLT-1A variant 1

<400> SEQUENCE: 60

Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Arg Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ser Thr Tyr Tyr Gly Gly Asp Trp Tyr Phe Asn Val Trp
            100                 105                 110

Gly Ala Gly Thr Thr Val Thr Val Ser Ala Gly Ser Thr Ser Gly Ser
        115                 120                 125

Gly Lys Pro Gly Ser Gly Glu Gly Ser Thr Lys Gly Gln Ile Val Leu
    130                 135                 140

Ser Gln Ser Pro Ala Ile Leu Ser Ala Ser Pro Gly Glu Lys Val Thr
145                 150                 155                 160

Met Thr Cys Arg Ala Ser Ser Ser Val Ser Tyr Ile His Trp Phe Gln
                165                 170                 175

Gln Lys Pro Gly Ser Ser Pro Lys Pro Trp Ile Tyr Ala Thr Ser Asn
            180                 185                 190

Leu Ala Ser Gly Val Pro Val Arg Phe Ser Gly Ser Gly Ser Gly Thr
        195                 200                 205

Ser Tyr Ser Leu Thr Ile Ser Arg Val Glu Ala Glu Asp Ala Ala Thr
    210                 215                 220

Tyr Tyr Cys Gln Gln Trp Thr Ser Asn Pro Pro Thr Phe Gly Gly Gly
225                 230                 235                 240

Thr Lys Leu Glu Ile Lys Glu Phe Pro Lys Pro Ser Thr Pro Pro Gly
                245                 250                 255

Ser Ser Gly Gly Ala Pro Lys Glu Phe Thr Leu Asp Phe Ser Thr Ala
            260                 265                 270

Lys Thr Tyr Val Asp Ser Leu Asn Val Ile Arg Ser Ala Ile Gly Thr
        275                 280                 285

Pro Leu Gln Thr Ile Ser Ser Gly Gly Thr Ser Leu Leu Met Ile Asp
    290                 295                 300
```

Ser Gly Ser Gly Asp Asn Leu Phe Ala Val Asp Val Arg Gly Ile Asp
305                 310                 315                 320

Pro Glu Glu Gly Arg Phe Asn Asn Leu Arg Leu Ile Val Glu Arg Asn
                325                 330                 335

Asn Leu Tyr Val Thr Gly Phe Val Asn Arg Thr Asn Asn Val Phe Tyr
            340                 345                 350

Arg Phe Ala Asp Phe Ser His Val Thr Phe Pro Gly Thr Thr Ala Val
            355                 360                 365

Thr Leu Ser Gly Asp Ser Ser Tyr Thr Thr Leu Gln Arg Val Ala Gly
        370                 375                 380

Ile Ser Arg Thr Gly Met Gln Ile Asn Arg His Ser Leu Thr Thr Ser
385                 390                 395                 400

Tyr Leu Asp Leu Met Ser His Ser Gly Thr Ser Leu Thr Gln Ser Val
                405                 410                 415

Ala Arg Ala Met Leu Arg Phe Val Thr Val Thr Ala Glu Ala Leu Arg
            420                 425                 430

Phe Arg Gln Ile Gln Arg Gly Phe Arg Thr Thr Leu Asp Asp Leu Ser
        435                 440                 445

Gly Arg Ser Tyr Val Met Thr Ala Glu Asp Val Asp Leu Thr Leu Asn
450                 455                 460

Trp Gly Arg Leu Ser Ser Val Leu Pro Asp Tyr His Gly Gln Asp Ser
465                 470                 475                 480

Val Arg Val Gly Arg Ile Ser Phe Gly Ser Ile Asn Ala Ile Leu Gly
                485                 490                 495

Ser Val Ala Leu Ile Leu Asn Cys His His His Ala Ser Arg Val Ala
            500                 505                 510

Arg

<210> SEQ ID NO 61
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv3 linked to SLT-1A variant 2

<400> SEQUENCE: 61

Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Arg Gly Leu Glu Trp
        35                  40                  45

Ile Gly Ala Ile Tyr Pro Gly Asn Gly Asp Thr Ser Tyr Asn Gln Lys
50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ser Thr Tyr Tyr Gly Gly Asp Trp Tyr Phe Asn Val Trp
            100                 105                 110

Gly Ala Gly Thr Thr Val Thr Val Ser Ala Gly Ser Thr Ser Gly Ser
        115                 120                 125

Gly Lys Pro Gly Ser Gly Glu Gly Ser Thr Lys Gly Gln Ile Val Leu

```
                130                 135                 140
Ser Gln Ser Pro Ala Ile Leu Ser Ala Ser Pro Gly Glu Lys Val Thr
145                 150                 155                 160

Met Thr Cys Arg Ala Ser Ser Val Ser Tyr Ile His Trp Phe Gln
                165                 170                 175

Gln Lys Pro Gly Ser Ser Pro Lys Pro Trp Ile Tyr Ala Thr Ser Asn
                180                 185                 190

Leu Ala Ser Gly Val Pro Val Arg Phe Ser Gly Ser Gly Ser Gly Thr
                195                 200                 205

Ser Tyr Ser Leu Thr Ile Ser Arg Val Glu Ala Glu Asp Ala Ala Thr
            210                 215                 220

Tyr Tyr Cys Gln Gln Trp Thr Ser Asn Pro Thr Phe Gly Gly Gly
225                 230                 235                 240

Thr Lys Leu Glu Ile Lys Glu Phe Pro Lys Pro Ser Thr Pro Pro Gly
                245                 250                 255

Ser Ser Gly Gly Ala Pro Lys Glu Phe Thr Leu Asp Phe Ser Thr Ala
                260                 265                 270

Lys Thr Tyr Val Asp Ser Leu Asn Val Ile Arg Ser Ala Ile Gly Thr
                275                 280                 285

Pro Leu Gln Thr Ile Ser Ser Gly Gly Thr Ser Leu Leu Met Ile Asp
                290                 295                 300

Ser Gly Ser Gly Asp Asn Leu Phe Ala Val Asp Val Arg Gly Ile Asp
305                 310                 315                 320

Pro Glu Glu Gly Arg Phe Asn Asn Leu Arg Leu Ile Val Glu Arg Asn
                325                 330                 335

Asn Leu Tyr Val Thr Gly Phe Val Asn Arg Thr Asn Asn Val Phe Tyr
                340                 345                 350

Arg Phe Ala Asp Phe Ser His Val Thr Phe Pro Gly Thr Thr Ala Val
                355                 360                 365

Thr Leu Ser Gly Asp Ser Ser Tyr Thr Thr Leu Gln Arg Val Ala Gly
            370                 375                 380

Ile Ser Arg Thr Gly Met Gln Ile Asn Arg His Ser Leu Thr Thr Ser
385                 390                 395                 400

Tyr Leu Asp Leu Met Ser His Ser Gly Thr Ser Leu Thr Gln Ser Val
                405                 410                 415

Ala Arg Ala Met Leu Arg Phe Val Thr Val Thr Ala Glu Ala Leu Arg
                420                 425                 430

Phe Arg Gln Ile Gln Arg Gly Phe Arg Thr Thr Leu Asp Asp Leu Ser
                435                 440                 445

Gly Arg Ser Tyr Val Met Thr Ala Glu Asp Val Asp Leu Thr Leu Asn
                450                 455                 460

Trp Gly Arg Leu Ser Ser Val Leu Pro Asp Tyr His Gly Gln Asp Ser
465                 470                 475                 480

Val Arg Val Gly Arg Ile Ser Phe Gly Ser Ile Asn Ala Ile Leu Gly
                485                 490                 495

Ser Val Ala Leu Ile Leu Asn Ser His His Ala Ser Arg Val Ala
                500                 505                 510

Arg

<210> SEQ ID NO 62
<211> LENGTH: 522
<212> TYPE: PRT
<213> ORGANISM: Artificial Sequence
<220> FEATURE:
```

<220> FEATURE:
<223> OTHER INFORMATION: Description of Artificial Sequence: Synthetic polypeptide
<220> FEATURE:
<223> OTHER Tyr Thr Thr Leu Gln Arg Val Ala Gly Ile Ser Arg Thr Gly Met Gln
385                 390                 395                 400

Ile Asn Arg His Ser Leu Thr Ser Tyr Leu Asp Leu Met Ser His
            405                 410                 415

Ser Gly Thr Ser Leu Thr Gln Ser Val Ala Arg Ala Met Leu Arg Phe
            420                 425                 430

Val Thr Val Thr Ala Glu Ala Leu Arg Phe Arg Gln Ile Gln Arg Gly
            435                 440                 445

Phe Arg Thr Thr Leu Asp Asp Leu Ser Gly Arg Ser Tyr Val Met Thr
    450                 455                 460

Ala Glu Asp Val Asp Leu Thr Leu Asn Trp Gly Arg Leu Ser Ser Val
465                 470                 475                 480

Leu Pro Asp Tyr His Gly Gln Asp Ser Val Arg Val Gly Arg Ile Ser
            485                 490                 495

Phe Gly Ser Ile Asn Ala Ile Leu Gly Ser Val Ala Leu Ile Leu Asn
            500                 505                 510

Ser His His His Ala Ser Arg Val Ala Arg
            515                 520

<210> SEQ ID NO 63
<211> LENGTH: 523
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv3 linked to StxA variant 1

<400> SEQUENCE: 63

Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Arg Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ser Thr Tyr Tyr Gly Gly Asp Trp Tyr Phe Asn Val Trp
            100                 105                 110

Gly Ala Gly Thr Thr Val Thr Val Ser Ala Gly Gly Gly Ser Gly
        115                 120                 125

Gly Gly Gly Ser Gly Gly Gly Ser Gly Gly Gly Ser Gly Gly
        130                 135                 140

Gly Gly Ser Thr Lys Gly Gln Ile Val Leu Ser Gln Ser Pro Ala Ile
145                 150                 155                 160

Leu Ser Ala Ser Pro Gly Glu Lys Val Thr Met Thr Cys Arg Ala Ser
            165                 170                 175

Ser Ser Val Ser Tyr Ile His Trp Phe Gln Gln Lys Pro Gly Ser Ser
            180                 185                 190

Pro Lys Pro Trp Ile Tyr Ala Thr Ser Asn Leu Ala Ser Gly Val Pro
        195                 200                 205

-continued

```
Val Arg Phe Ser Gly Ser Gly Ser Gly Thr Ser Tyr Ser Leu Thr Ile
        210                 215                 220

Ser Arg Val Glu Ala Glu Asp Ala Ala Thr Tyr Tyr Cys Gln Gln Trp
225                 230                 235                 240

Thr Ser Asn Pro Pro Thr Phe Gly Gly Gly Thr Lys Leu Glu Ile Lys
                245                 250                 255

Glu Phe Pro Lys Pro Ser Thr Pro Pro Gly Ser Ser Gly Gly Ala Pro
            260                 265                 270

Lys Glu Phe Thr Leu Asp Phe Ser Thr Ala Lys Thr Tyr Val Asp Ser
        275                 280                 285

Leu Asn Val Ile Arg Ser Ala Ile Gly Thr Pro Leu Gln Thr Ile Ser
290                 295                 300

Ser Gly Gly Thr Ser Leu Leu Met Ile Asp Ser Gly Thr Gly Asp Asn
305                 310                 315                 320

Leu Phe Ala Val Asp Val Arg Gly Ile Asp Pro Glu Glu Gly Arg Phe
                325                 330                 335

Asn Asn Leu Arg Leu Ile Val Glu Arg Asn Asn Leu Tyr Val Thr Gly
            340                 345                 350

Phe Val Asn Arg Thr Asn Asn Val Phe Tyr Arg Phe Ala Asp Phe Ser
        355                 360                 365

His Val Thr Phe Pro Gly Thr Thr Ala Val Thr Leu Ser Gly Asp Ser
370                 375                 380

Ser Tyr Thr Thr Leu Gln Arg Val Ala Gly Ile Ser Arg Thr Gly Met
385                 390                 395                 400

Gln Ile Asn Arg His Ser Leu Thr Thr Ser Tyr Leu Asp Leu Met Ser
                405                 410                 415

His Ser Gly Thr Ser Leu Thr Gln Ser Val Ala Arg Ala Met Leu Arg
            420                 425                 430

Phe Val Thr Val Thr Ala Glu Ala Leu Arg Phe Arg Gln Ile Gln Arg
        435                 440                 445

Gly Phe Arg Thr Thr Leu Asp Asp Leu Ser Gly Arg Ser Tyr Val Met
450                 455                 460

Thr Ala Glu Asp Val Asp Leu Thr Leu Asn Trp Gly Arg Leu Ser Ser
465                 470                 475                 480

Val Leu Pro Asp Tyr His Gly Gln Asp Ser Val Arg Val Gly Arg Ile
                485                 490                 495

Ser Phe Gly Ser Ile Asn Ala Ile Leu Gly Ser Val Ala Leu Ile Leu
            500                 505                 510

Asn Ser His His His Ala Ser Arg Val Ala Arg
        515                 520
```

<210> SEQ ID NO 64
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv4 linked to SLT-1A variant 1

<400> SEQUENCE: 64

```
Met Glu Val Gln Leu Val Glu Ser Gly Gly Gly Leu Val Gln Pro Gly
1               5                   10                  15

Arg Ser Leu Arg Leu Ser Cys Ala Ala Ser Gly Phe Thr Phe Asn Asp
            20                  25                  30
```

```
Tyr Ala Met His Trp Val Arg Gln Ala Pro Gly Lys Gly Leu Glu Trp
             35                  40                  45
Val Ser Thr Ile Ser Trp Asn Ser Gly Ser Ile Gly Tyr Ala Asp Ser
 50                  55                  60
Val Lys Gly Arg Phe Thr Ile Ser Arg Asp Asn Ala Lys Lys Ser Leu
 65                  70                  75                  80
Tyr Leu Gln Met Asn Ser Leu Arg Ala Glu Asp Thr Ala Leu Tyr Tyr
                 85                  90                  95
Cys Ala Lys Asp Ile Gln Tyr Gly Asn Tyr Tyr Gly Met Asp Val
                100                 105                 110
Trp Gly Gln Gly Thr Thr Val Thr Val Ser Ser Gly Ser Thr Ser Gly
                115                 120                 125
Ser Gly Lys Pro Gly Ser Gly Glu Gly Ser Glu Ile Val Leu Thr Gln
        130                 135                 140
Ser Pro Ala Thr Leu Ser Leu Ser Pro Gly Glu Arg Ala Thr Leu Ser
145                 150                 155                 160
Cys Arg Ala Ser Gln Ser Val Ser Ser Tyr Leu Ala Trp Tyr Gln Gln
                165                 170                 175
Lys Pro Gly Gln Ala Pro Arg Leu Leu Ile Tyr Asp Ala Ser Asn Arg
            180                 185                 190
Ala Thr Gly Ile Pro Ala Arg Phe Ser Gly Ser Gly Ser Gly Thr Asp
            195                 200                 205
Phe Thr Leu Thr Ile Ser Ser Leu Glu Pro Glu Asp Phe Ala Val Tyr
        210                 215                 220
Tyr Cys Gln Gln Arg Ser Asn Trp Pro Ile Thr Phe Gly Gln Gly Thr
225                 230                 235                 240
Arg Leu Glu Ile Lys Glu Phe Pro Lys Pro Ser Thr Pro Pro Gly Ser
                245                 250                 255
Ser Gly Gly Ala Pro Lys Glu Phe Thr Leu Asp Phe Ser Thr Ala Lys
            260                 265                 270
Thr Tyr Val Asp Ser Leu Asn Val Ile Arg Ser Ala Ile Gly Thr Pro
            275                 280                 285
Leu Gln Thr Ile Ser Ser Gly Gly Thr Ser Leu Leu Met Ile Asp Ser
        290                 295                 300
Gly Ser Gly Asp Asn Leu Phe Ala Val Asp Val Arg Gly Ile Asp Pro
305                 310                 315                 320
Glu Glu Gly Arg Phe Asn Asn Leu Arg Leu Ile Val Glu Arg Asn Asn
                325                 330                 335
Leu Tyr Val Thr Gly Phe Val Asn Arg Thr Asn Asn Val Phe Tyr Arg
            340                 345                 350
Phe Ala Asp Phe Ser His Val Thr Phe Pro Gly Thr Thr Ala Val Thr
            355                 360                 365
Leu Ser Gly Asp Ser Ser Tyr Thr Thr Leu Gln Arg Val Ala Gly Ile
        370                 375                 380
Ser Arg Thr Gly Met Gln Ile Asn Arg His Ser Leu Thr Thr Ser Tyr
385                 390                 395                 400
Leu Asp Leu Met Ser His Ser Gly Thr Ser Leu Thr Gln Ser Val Ala
                405                 410                 415
Arg Ala Met Leu Arg Phe Val Thr Val Thr Ala Glu Ala Leu Arg Phe
            420                 425                 430
Arg Gln Ile Gln Arg Gly Phe Arg Thr Thr Leu Asp Asp Leu Ser Gly
            435                 440                 445
Arg Ser Tyr Val Met Thr Ala Glu Asp Val Asp Leu Thr Leu Asn Trp
```

```
            450                 455                 460
Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Cys His His His Ala Ser Arg Val Ala Arg
                500                 505                 510

<210> SEQ ID NO 65
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv4 linked to SLT-1A variant 2

<400> SEQUENCE: 65

Met Glu Val Gln Leu Val Glu Ser Gly Gly Gly Leu Val Gln Pro Gly
1               5                   10                  15

Arg Ser Leu Arg Leu Ser Cys Ala Ala Ser Gly Phe Thr Phe Asn Asp
            20                  25                  30

Tyr Ala Met His Trp Val Arg Gln Ala Pro Gly Lys Gly Leu Glu Trp
        35                  40                  45

Val Ser Thr Ile Ser Trp Asn Ser Gly Ser Ile Gly Tyr Ala Asp Ser
50                  55                  60

Val Lys Gly Arg Phe Thr Ile Ser Arg Asp Asn Ala Lys Lys Ser Leu
65                  70                  75                  80

Tyr Leu Gln Met Asn Ser Leu Arg Ala Glu Asp Thr Ala Leu Tyr Tyr
                85                  90                  95

Cys Ala Lys Asp Ile Gln Tyr Gly Asn Tyr Tyr Tyr Gly Met Asp Val
            100                 105                 110

Trp Gly Gln Gly Thr Thr Val Thr Val Ser Ser Gly Ser Thr Ser Gly
        115                 120                 125

Ser Gly Lys Pro Gly Ser Gly Glu Gly Ser Glu Ile Val Leu Thr Gln
    130                 135                 140

Ser Pro Ala Thr Leu Ser Leu Ser Pro Gly Glu Arg Ala Thr Leu Ser
145                 150                 155                 160

Cys Arg Ala Ser Gln Ser Val Ser Ser Tyr Leu Ala Trp Tyr Gln Gln
                165                 170                 175

Lys Pro Gly Gln Ala Pro Arg Leu Leu Ile Tyr Asp Ala Ser Asn Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220

Tyr Cys Gln Gln Arg Ser Asn Trp Pro Ile Thr Phe Gly Gln Gly Thr
225                 230                 235                 240

Arg Leu Glu Ile Lys Glu Phe Pro Lys Pro Ser Thr Pro Pro Gly Ser
                245                 250                 255

Ser Gly Gly Ala Pro Lys Glu Phe Thr Leu Asp Phe Ser Thr Ala Lys
            260                 265                 270

Thr Tyr Val Asp Ser Leu Asn Val Ile Arg Ser Ala Ile Gly Thr Pro
        275                 280                 285

Leu Gln Thr Ile Ser Ser Gly Gly Thr Ser Leu Leu Met Ile Asp Ser
```

```
                290                 295                 300
Gly Ser Gly Asp Asn Leu Phe Ala Val Asp Val Arg Gly Ile Asp Pro
305                 310                 315

```
            130                 135                 140
Gly Gly Gly Ser Glu Ile Val Leu Thr Gln Ser Pro Ala Thr Leu Ser
145                 150                 155                 160

Leu Ser Pro Gly Glu Arg Ala Thr Leu Ser Cys Arg Ala Ser Gln Ser
                165                 170                 175

Val Ser Ser Tyr Leu Ala Trp Tyr Gln Gln Lys Pro Gly Gln Ala Pro
            180                 185                 190

Arg Leu Leu Ile Tyr Asp Ala Ser Asn Arg Ala Thr Gly Ile Pro Ala
        195                 200                 205

Arg Phe Ser Gly Ser Gly Ser Gly Thr Asp Phe Thr Leu Thr Ile Ser
    210                 215                 220

Ser Leu Glu Pro Glu Asp Phe Ala Val Tyr Tyr Cys Gln Gln Arg Ser
225                 230                 235                 240

Asn Trp Pro Ile Thr Phe Gly Gln Gly Thr Arg Leu Glu Ile Lys Glu
                245                 250                 255

Phe Pro Lys Pro Ser Thr Pro Pro Gly Ser Ser Gly Gly Ala Pro Lys
            260                 265                 270

Glu Phe Thr Leu Asp Phe Ser Thr Ala Lys Thr Tyr Val Asp Ser Leu
        275                 280                 285

Asn Val Ile Arg Ser Ala Ile Gly Thr Pro Leu Gln Thr Ile Ser Ser
    290                 295                 300

Gly Gly Thr Ser Leu Leu Met Ile Asp Ser Gly Ser Gly Asp Asn Leu
305                 310                 315                 320

Phe Ala Val Asp Val Arg Gly Ile Asp Pro Glu Glu Gly Arg Phe Asn
                325                 330                 335

Asn Leu Arg Leu Ile Val Glu Arg Asn Asn Leu Tyr Val Thr Gly Phe
            340                 345                 350

Val Asn Arg Thr Asn Asn Val Phe Tyr Arg Phe Ala Asp Phe Ser His
        355                 360                 365

Val Thr Phe Pro Gly Thr Thr Ala Val Thr Leu Ser Gly Asp Ser Ser
    370                 375                 380

Tyr Thr Thr Leu Gln Arg Val Ala Gly Ile Ser Arg Thr Gly Met Gln
385                 390                 395                 400

Ile Asn Arg His Ser Leu Thr Thr Ser Tyr Leu Asp Leu Met Ser His
                405                 410                 415

Ser Gly Thr Ser Leu Thr Gln Ser Val Ala Arg Ala Met Leu Arg Phe
            420                 425                 430

Val Thr Val Thr Ala Glu Ala Leu Arg Phe Arg Gln Ile Gln Arg Gly
        435                 440                 445

Phe Arg Thr Thr Leu Asp Asp Leu Ser Gly Arg Ser Tyr Val Met Thr
    450                 455                 460

Ala Glu Asp Val Asp Leu Thr Leu Asn Trp Gly Arg Leu Ser Ser Val
465                 470                 475                 480

Leu Pro Asp Tyr His Gly Gln Asp Ser Val Arg Val Gly Arg Ile Ser
                485                 490                 495

Phe Gly Ser Ile Asn Ala Ile Leu Gly Ser Val Ala Leu Ile Leu Asn
            500                 505                 510

Ser His His His Ala Ser Arg Val Ala Arg
        515                 520

<210> SEQ ID NO 67
<211> LENGTH: 521
<212> TYPE: PRT
<213> ORGANISM: Artificial Sequence
```

<220> FEATURE:
<223> OTHER INFORMATION: Description of Artificial Sequence: Synthetic
      polypeptide
<220> FEATURE:
<223> OTHER INFORMATION: alphaCD20-scFv4 linked to StxA variant 1

<400> SEQUENCE: 67

```
Met Glu Val Gln Leu Val Glu Ser Gly Gly Gly Leu Val Gln Pro Gly
1               5                   10                  15

Arg Ser Leu Arg Leu Ser Cys Ala Ala Ser Gly Phe Thr Phe Asn Asp
            20                  25                  30

Tyr Ala Met His Trp Val Arg Gln Ala Pro Gly Lys Gly Leu Glu Trp
        35                  40                  45

Val Ser Thr Ile Ser Trp Asn Ser Gly Ser Ile Gly Tyr Ala Asp Ser
    50                  55                  60

Val Lys Gly Arg Phe Thr Ile Ser Arg Asp Asn Ala Lys Lys Ser Leu
65                  70                  75                  80

Tyr Leu Gln Met Asn Ser Leu Arg Ala Glu Asp Thr Ala Leu Tyr Tyr
                85                  90                  95

Cys Ala Lys Asp Ile Gln Tyr Gly Asn Tyr Tyr Gly Met Asp Val
            100                 105                 110

Trp Gly Gln Gly Thr Thr Val Thr Val Ser Ser Gly Ser Thr Ser Gly
            115                 120                 125

Ser Gly Lys Pro Gly Ser Gly Glu Gly Ser Glu Ile Val Leu Thr Gln
130                 135                 140

Ser Pro Ala Thr Leu Ser Leu Ser Pro Gly Glu Arg Ala Thr Leu Ser
145                 150                 155                 160

Cys Arg Ala Ser Gln Ser Val Ser Ser Tyr Leu Ala Trp Tyr Gln Gln
                165                 170                 175

Lys Pro Gly Gln Ala Pro Arg Leu Leu Ile Tyr Asp Ala Ser Asn Arg
            180                 185                 190

Ala Thr Gly Ile Pro Ala Arg Phe Ser Gly Ser Gly Ser Gly Thr Asp
        195                 200                 205

Phe Thr Leu Thr Ile Ser Ser Leu Glu Pro Glu Asp Phe Ala Val Tyr
    210                 215                 220

Tyr Cys Gln Gln Arg Ser Asn Trp Pro Ile Thr Phe Gly Gln Gly Thr
225                 230                 235                 240

Arg Leu Glu Ile Lys Glu Phe Pro Lys Pro Ser Thr Pro Pro Gly Ser
                245                 250                 255

Ser Gly Gly Ala Pro Gly Ile Leu Gly Phe Val Phe Thr Leu Lys Glu
            260                 265                 270

Phe Thr Leu Asp Phe Ser Thr Ala Lys Thr Tyr Val Asp Ser Leu Asn
        275                 280                 285

Val Ile Arg Ser Ala Ile Gly Thr Pro Leu Gln Thr Ile Ser Ser Gly
    290                 295                 300

Gly Thr Ser Leu Leu Met Ile Asp Ser Gly Thr Gly Asp Asn Leu Phe
305                 310                 315                 320

Ala Val Asp Val Arg Gly Ile Asp Pro Glu Glu Gly Arg Phe Asn Asn
                325                 330                 335

Leu Arg Leu Ile Val Glu Arg Asn Asn Leu Tyr Val Thr Gly Phe Val
            340                 345                 350

Asn Arg Thr Asn Asn Val Phe Tyr Arg Phe Ala Asp Phe Ser His Val
        355                 360                 365

Thr Phe Pro Gly Thr Thr Ala Val Thr Leu Ser Gly Asp Ser Ser Tyr
    370                 375                 380
```

```
Thr Thr Leu Gln Arg Val Ala Gly Ile Ser Arg Thr Gly Met Gln Ile
385                 390                 395                 400

Asn Arg His Ser Leu Thr Thr Ser Tyr Leu Asp Leu Met Ser His Ser
            405                 410                 415

Gly Thr Ser Leu Thr Gln Ser Val Ala Arg Ala Met Leu Arg Phe Val
        420                 425                 430

Thr Val Thr Ala Glu Ala Leu Arg Phe Arg Gln Ile Gln Arg Gly Phe
    435                 440                 445

Arg Thr Thr Leu Asp Asp Leu Ser Gly Arg Ser Tyr Val Met Thr Ala
    450                 455                 460

Glu Asp Val Asp Leu Thr Leu Asn Trp Gly Arg Leu Ser Ser Val Leu
465                 470                 475                 480

Pro Asp Tyr His Gly Gln Asp Ser Val Arg Val Gly Arg Ile Ser Phe
                485                 490                 495

Gly Ser Ile Asn Ala Ile Leu Gly Ser Val Ala Leu Ile Leu Asn Ser
            500                 505                 510

His His His Ala Ser Arg Val Ala Arg
            515                 520

<210> SEQ ID NO 68
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv5 linked to SLT-1A variant 1

<400> SEQUENCE: 68

Met Glu Ile Val Leu Thr Gln Ser Pro Ala Thr Leu Ser Leu Ser Pro
1               5                   10                  15

Gly Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Asn Trp Pro
                85                  90                  95

Ile Thr Phe Gly Gln Gly Thr Arg Leu Glu Ile Lys Gly Ser Thr Ser
            100                 105                 110

Gly Ser Gly Lys Pro Gly Ser Gly Glu Gly Ser Glu Val Gln Leu Val
        115                 120                 125

Glu Ser Gly Gly Gly Leu Val Gln Pro Gly Arg Ser Leu Arg Leu Ser
130                 135                 140

Cys Ala Ala Ser Gly Phe Thr Phe Asn Asp Tyr Ala Met His Trp Val
145                 150                 155                 160

Arg Gln Ala Pro Gly Lys Gly Leu Glu Trp Val Ser Thr Ile Ser Trp
                165                 170                 175

Asn Ser Gly Ser Ile Gly Tyr Ala Asp Ser Val Lys Gly Arg Phe Thr
            180                 185                 190

Ile Ser Arg Asp Asn Ala Lys Lys Ser Leu Tyr Leu Gln Met Asn Ser
        195                 200                 205
```

```
Leu Arg Ala Glu Asp Thr Ala Leu Tyr Tyr Cys Ala Lys Asp Ile Gln
            210                 215                 220

Tyr Gly Asn Tyr Tyr Tyr Gly Met Asp Val Trp Gly Gln Gly Thr Thr
225                 230                 235                 240

Val Thr Val Ser Ser Glu Phe Pro Lys Pro Ser Thr Pro Pro Gly Ser
            245                 250                 255

Ser Gly Gly Ala Pro Lys Glu Phe Thr Leu Asp Phe Ser Thr Ala Lys
            260                 265                 270

Thr Tyr Val Asp Ser Leu Asn Val Ile Arg Ser Ala Ile Gly Thr Pro
            275                 280                 285

Leu Gln Thr Ile Ser Ser Gly Thr Ser Leu Leu Met Ile Asp Ser
290                 295                 300

Gly Ser Gly Asp Asn Leu Phe Ala Val Asp Val Arg Gly Ile Asp Pro
305                 310                 315                 320

Glu Glu Gly Arg Phe Asn Asn Leu Arg Leu Ile Val Glu Arg Asn Asn
            325                 330                 335

Leu Tyr Val Thr Gly Phe Val Asn Arg Thr Asn Asn Val Phe Tyr Arg
            340                 345                 350

Phe Ala Asp Phe Ser His Val Thr Phe Pro Gly Thr Thr Ala Val Thr
            355                 360                 365

Leu Ser Gly Asp Ser Ser Tyr Thr Thr Leu Gln Arg Val Ala Gly Ile
370                 375                 380

Ser Arg Thr Gly Met Gln Ile Asn Arg His Ser Leu Thr Thr Ser Tyr
385                 390                 395                 400

Leu Asp Leu Met Ser His Ser Gly Thr Ser Leu Thr Gln Ser Val Ala
            405                 410                 415

Arg Ala Met Leu Arg Phe Val Thr Val Thr Ala Glu Ala Leu Arg Phe
            420                 425                 430

Arg Gln Ile Gln Arg Gly Phe Arg Thr Thr Leu Asp Asp Leu Ser Gly
            435                 440                 445

Arg Ser Tyr Val Met Thr Ala Glu Asp Val Asp Leu Thr Leu Asn Trp
            450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
            485                 490                 495

Val Ala Leu Ile Leu Asn Cys His His His Ala Ser Arg Val Ala Arg
            500                 505                 510
```

<210> SEQ ID NO 69
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv5 linked to SLT-1A variant 2

<400> SEQUENCE: 69

```
Met Glu Ile Val Leu Thr Gln Ser Pro Ala Thr Leu Ser Leu Ser Pro
1               5                   10                  15

Gly Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
            35                  40                  45
```

```
Ile Tyr Asp Ala Ser Asn Arg Ala Thr Gly Ile Pro Ala Arg Phe Ser
     50                  55                  60
Gly Ser Gly Ser Gly Thr Asp Phe Thr Leu Thr Ile Ser Ser Leu Glu
 65                  70                  75                  80
Pro Glu Asp Phe Ala Val Tyr Tyr Cys Gln Gln Arg Ser Asn Trp Pro
                 85                  90                  95
Ile Thr Phe Gly Gln Gly Thr Arg Leu Glu Ile Lys Gly Ser Thr Ser
            100                 105                 110
Gly Ser Gly Lys Pro Gly Ser Gly Glu Gly Ser Glu Val Gln Leu Val
        115                 120                 125
Glu Ser Gly Gly Gly Leu Val Gln Pro Gly Arg Ser Leu Arg Leu Ser
130                 135                 140
Cys Ala Ala Ser Gly Phe Thr Phe Asn Asp Tyr Ala Met His Trp Val
145                 150                 155                 160
Arg Gln Ala Pro Gly Lys Gly Leu Glu Trp Val Ser Thr Ile Ser Trp
                165                 170                 175
Asn Ser Gly Ser Ile Gly Tyr Ala Asp Ser Val Lys Gly Arg Phe Thr
            180                 185                 190
Ile Ser Arg Asp Asn Ala Lys Lys Ser Leu Tyr Leu Gln Met Asn Ser
        195                 200                 205
Leu Arg Ala Glu Asp Thr Ala Leu Tyr Tyr Cys Ala Lys Asp Ile Gln
210                 215                 220
Tyr Gly Asn Tyr Tyr Tyr Gly Met Asp Val Trp Gly Gln Gly Thr Thr
225                 230                 235                 240
Val Thr Val Ser Ser Glu Phe Pro Lys Pro Ser Thr Pro Pro Gly Ser
                245                 250                 255
Ser Gly Gly Ala Pro Lys Glu Phe Thr Leu Asp Phe Ser Thr Ala Lys
            260                 265                 270
Thr Tyr Val Asp Ser Leu Asn Val Ile Arg Ser Ala Ile Gly Thr Pro
        275                 280                 285
Leu Gln Thr Ile Ser Ser Gly Thr Ser Leu Leu Met Ile Asp Ser
290                 295                 300
Gly Ser Gly Asp Asn Leu Phe Ala Val Asp Val Arg Gly Ile Asp Pro
305                 310                 315                 320
Glu Glu Gly Arg Phe Asn Asn Leu Arg Leu Ile Val Glu Arg Asn Asn
                325                 330                 335
Leu Tyr Val Thr Gly Phe Val Asn Arg Thr Asn Asn Val Phe Tyr Arg
            340                 345                 350
Phe Ala Asp Phe Ser His Val Thr Phe Pro Gly Thr Thr Ala Val Thr
        355                 360                 365
Leu Ser Gly Asp Ser Ser Tyr Thr Thr Leu Gln Arg Val Ala Gly Ile
370                 375                 380
Ser Arg Thr Gly Met Gln Ile Asn Arg His Ser Leu Thr Thr Ser Tyr
385                 390                 395                 400
Leu Asp Leu Met Ser His Ser Gly Thr Ser Leu Thr Gln Ser Val Ala
                405                 410                 415
Arg Ala Met Leu Arg Phe Val Thr Val Thr Ala Glu Ala Leu Arg Phe
            420                 425                 430
Arg Gln Ile Gln Arg Gly Phe Arg Thr Thr Leu Asp Asp Leu Ser Gly
        435                 440                 445
Arg Ser Tyr Val Met Thr Ala Glu Asp Val Asp Leu Thr Leu Asn Trp
450                 455                 460
```

```
Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Ser His His His Ala Ser Arg Val Ala Arg
                500                 505                 510

<210> SEQ ID NO 70
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv5 linked to SLT-1A variant 3

<400> SEQUENCE: 70

Met Glu Ile Val Leu Thr Gln Ser Pro Ala Thr Leu Ser Leu Ser Pro
1               5                   10                  15

Gly Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Asn Arg Ala Thr Gly Ile Pro Ala Arg Phe Ser
50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Asn Trp Pro
                85                  90                  95

Ile Thr Phe Gly Gln Gly Thr Arg Leu Glu Ile Lys Gly Ser Thr Ser
            100                 105                 110

Gly Ser Gly Lys Pro Gly Ser Gly Glu Gly Ser Glu Val Gln Leu Val
        115                 120                 125

Glu Ser Gly Gly Gly Leu Val Gln Pro Gly Arg Ser Leu Arg Leu Ser
130                 135                 140

Cys Ala Ala Ser Gly Phe Thr Phe Asn Asp Tyr Ala Met His Trp Val
145                 150                 155                 160

Arg Gln Ala Pro Gly Lys Gly Leu Glu Trp Val Ser Thr Ile Ser Trp
                165                 170                 175

Asn Ser Gly Ser Ile Gly Tyr Ala Asp Ser Val Lys Gly Arg Phe Thr
            180                 185                 190

Ile Ser Arg Asp Asn Ala Lys Lys Ser Leu Tyr Leu Gln Met Asn Ser
        195                 200                 205

Leu Arg Ala Glu Asp Thr Ala Leu Tyr Tyr Cys Ala Lys Asp Ile Gln
210                 215                 220

Tyr Gly Asn Tyr Tyr Gly Met Asp Val Trp Gly Gln Gly Thr Thr
225                 230                 235                 240

Val Thr Val Ser Ser Glu Phe Pro Lys Pro Ser Thr Pro Pro Gly Ser
                245                 250                 255

Ser Gly Gly Ala Pro Lys Glu Phe Thr Leu Asp Phe Ser Thr Ala Lys
            260                 265                 270

Thr Tyr Val Asp Ser Leu Asn Val Ile Arg Ser Ala Ile Gly Thr Pro
        275                 280                 285

Leu Gln Thr Ile Ser Ser Gly Gly Thr Ser Leu Leu Met Ile Asp Ser
    290                 295                 300
```

```
Gly Ser Gly Asp Asn Leu Phe Ala Val Asp Val Arg Gly Ile Asp Pro
305                 310                 315                 320

Glu Glu Gly Arg Phe Asn Asn Leu Arg Leu Ile Val Glu Arg Asn Asn
                325                 330                 335

Leu Tyr Val Thr Gly Phe Val Asn Arg Thr Asn Asn Val Phe Tyr Arg
            340                 345                 350

Phe Ala Asp Phe Ser His Val Thr Phe Pro Gly Thr Thr Ala Val Thr
        355                 360                 365

Leu Ser Gly Asp Ser Ser Tyr Thr Thr Leu Gln Arg Val Ala Gly Ile
    370                 375                 380

Ser Arg Thr Gly Met Gln Ile Asn Arg His Ser Leu Thr Thr Ser Tyr
385                 390                 395                 400

Leu Asp Leu Met Ser His Ser Gly Thr Ser Leu Thr Gln Ser Val Ala
                405                 410                 415

Arg Ala Met Leu Arg Phe Val Thr Val Thr Ala Glu Ala Leu Arg Phe
            420                 425                 430

Arg Gln Ile Gln Arg Gly Phe Arg Thr Thr Leu Asp Asp Leu Ser Gly
        435                 440                 445

Arg Ser Tyr Val Met Thr Ala Glu Asp Val Asp Leu Thr Leu Asn Trp
    450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Ser His His His Ala Ser Arg Val Ala Arg
            500                 505                 510
```

<210> SEQ ID NO 71
<211> LENGTH: 531
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv5 linked to StxA variant 1

<400> SEQUENCE: 71

```
Met Glu Ile Val Leu Thr Gln Ser Pro Ala Thr Leu Ser Leu Ser Pro
1               5                   10                  15

Gly Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys Gln Gln Arg Ser Asn Trp Pro
                85                  90                  95

Ile Thr Phe Gly Gln Gly Thr Arg Leu Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Gly Gly Gly Gly Ser Glu Val Gln Leu Val Glu Ser Gly Gly Gly Leu
    130                 135                 140
```

Val Gln Pro Gly Arg Ser Leu Arg Leu Ser Cys Ala Ala Ser Gly Phe
145                 150                 155                 160

Thr Phe Asn Asp Tyr Ala Met His Trp Val Arg Gln Ala Pro Gly Lys
            165                 170                 175

Gly Leu Glu Trp Val Ser Thr Ile Ser Trp Asn Ser Gly Ser Ile Gly
            180                 185                 190

Tyr Ala Asp Ser Val Lys Gly Arg Phe Thr Ile Ser Arg Asp Asn Ala
            195                 200                 205

Lys Lys Ser Leu Tyr Leu Gln Met Asn Ser Leu Arg Ala Glu Asp Thr
210                 215                 220

Ala Leu Tyr Tyr Cys Ala Lys Asp Ile Gln Tyr Gly Asn Tyr Tyr Tyr
225                 230                 235                 240

Gly Met Asp Val Trp Gly Gln Gly Thr Thr Val Thr Val Ser Ser Glu
            245                 250                 255

Phe Pro Lys Pro Ser Thr Pro Pro Gly Ser Ser Gly Gly Ala Pro Gly
            260                 265                 270

Ile Leu Gly Phe Val Phe Thr Leu Lys Glu Phe Thr Leu Asp Phe Ser
            275                 280                 285

Thr Ala Lys Thr Tyr Val Asp Ser Leu Asn Val Ile Arg Ser Ala Ile
290                 295                 300

Gly Thr Pro Leu Gln Thr Ile Ser Ser Gly Gly Thr Ser Leu Leu Met
305                 310                 315                 320

Ile Asp Ser Gly Thr Gly Asp Asn Leu Phe Ala Val Asp Val Arg Gly
            325                 330                 335

Ile Asp Pro Glu Glu Gly Arg Phe Asn Asn Leu Arg Leu Ile Val Glu
            340                 345                 350

Arg Asn Asn Leu Tyr Val Thr Gly Phe Val Asn Arg Thr Asn Asn Val
            355                 360                 365

Phe Tyr Arg Phe Ala Asp Phe Ser His Val Thr Phe Pro Gly Thr Thr
            370                 375                 380

Ala Val Thr Leu Ser Gly Asp Ser Ser Tyr Thr Thr Leu Gln Arg Val
385                 390                 395                 400

Ala Gly Ile Ser Arg Thr Gly Met Gln Ile Asn Arg His Ser Leu Thr
            405                 410                 415

Thr Ser Tyr Leu Asp Leu Met Ser His Ser Gly Thr Ser Leu Thr Gln
            420                 425                 430

Ser Val Ala Arg Ala Met Leu Arg Phe Val Thr Val Thr Ala Glu Ala
            435                 440                 445

Leu Arg Phe Arg Gln Ile Gln Arg Gly Phe Arg Thr Thr Leu Asp Asp
450                 455                 460

Leu Ser Gly Arg Ser Tyr Val Met Thr Ala Glu Asp Val Asp Leu Thr
465                 470                 475                 480

Leu Asn Trp Gly Arg Leu Ser Ser Val Leu Pro Asp Tyr His Gly Gln
            485                 490                 495

Asp Ser Val Arg Val Gly Arg Ile Ser Phe Gly Ser Ile Asn Ala Ile
            500                 505                 510

Leu Gly Ser Val Ala Leu Ile Leu Asn Ser His His His Ala Ser Arg
            515                 520                 525

Val Ala Arg
    530

<210> SEQ ID NO 72
<211> LENGTH: 511
<212> TYPE: PRT

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: alphaCD20-scFv6 linked to SLT-1A variant 1

<400> SEQUENCE: 72

```
Met Gln Ile Val Leu Ser Gln Ser Pro Ala Ile Leu Ser Ala Ser Pro
1               5                   10                  15

Gly Glu Lys Val Thr Met Thr Cys Arg Ala Ser Ser Val Ser Tyr
            20                  25                  30

Met His Trp Tyr Gln Gln Lys Pro Gly Ser Ser Pro Lys Pro Trp Ile
        35                  40                  45

Tyr Ala Pro Ser Asn Leu Ala Ser Gly Val Pro Ala Arg Phe Ser Gly
    50                  55                  60

Ser Gly Ser Gly Thr Ser Tyr Ser Leu Thr Ile Ser Arg Val Glu Ala
65                  70                  75                  80

Glu Asp Ala Ala Thr Tyr Tyr Cys Gln Gln Trp Ser Phe Asn Pro Pro
                85                  90                  95

Thr Phe Gly Ala Gly Thr Lys Leu Glu Leu Lys Ser Gly Ser Thr Ser
            100                 105                 110

Gly Ser Gly Lys Pro Gly Ser Gly Glu Gly Ser Gln Ala Tyr Leu Gln
        115                 120                 125

Gln Ser Gly Ala Glu Leu Val Arg Pro Gly Ala Ser Val Lys Met Ser
    130                 135                 140

Cys Lys Ala Ser Gly Tyr Thr Phe Thr Ser Tyr Asn Met His Trp Val
145                 150                 155                 160

Lys Gln Thr Pro Arg Gln Gly Leu Glu Trp Ile Gly Ala Ile Tyr Pro
                165                 170                 175

Gly Asn Gly Asp Thr Ser Tyr Asn Gln Lys Phe Lys Gly Lys Ala Thr
            180                 185                 190

Leu Thr Val Asp Lys Ser Ser Thr Ala Tyr Met Gln Leu Ser Ser
        195                 200                 205

Leu Thr Ser Glu Asp Ser Ala Val Tyr Phe Cys Ala Arg Val Val Tyr
    210                 215                 220

Tyr Ser Asn Ser Tyr Trp Tyr Phe Asp Val Trp Gly Thr Gly Thr Thr
225                 230                 235                 240

Val Thr Val Ser Glu Phe Pro Lys Pro Ser Thr Pro Pro Gly Ser Ser
                245                 250                 255

Gly Gly Ala Pro Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
        275                 280                 285

Gln Thr Ile Ser Ser Gly Gly Thr Ser Leu Leu Met Ile Asp Ser Gly
    290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
            340                 345                 350

Ala Asp Phe Ser His Val Thr Phe Pro Gly Thr Thr Ala Val Thr Leu
        355                 360                 365

Ser Gly Asp Ser Ser Tyr Thr Thr Leu Gln Arg Val Ala Gly Ile Ser
```

-continued

```
            370                 375                 380
Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                405                 410                 415

Ala Met Leu Arg Phe Val Thr Val Thr Ala Glu Ala Leu Arg Phe Arg
                420                 425                 430

Gln Ile Gln Arg Gly Phe Arg Thr Thr Leu Asp Asp Leu Ser Gly Arg
                435                 440                 445

Ser Tyr Val Met Thr Ala Glu Asp Val Asp Leu Thr Leu Asn Trp Gly
                450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Cys His His His Ala Ser Arg Val Ala Arg
                500                 505                 510

<210> SEQ ID NO 73
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv6 linked to SLT-1A variant 2

<400> SEQUENCE: 73

Met Gln Ile Val Leu Ser Gln Ser Pro Ala Ile Leu Ser Ala Ser Pro
1               5                   10                  15

Gly Glu Lys Val Thr Met Thr Cys Arg Ala Ser Ser Ser Val Ser Tyr
                20                  25                  30

Met His Trp Tyr Gln Gln Lys Pro Gly Ser Ser Pro Lys Pro Trp Ile
                35                  40                  45

Tyr Ala Pro Ser Asn Leu Ala Ser Gly Val Pro Ala Arg Phe Ser Gly
50                  55                  60

Ser Gly Ser Gly Thr Ser Tyr Ser Leu Thr Ile Ser Arg Val Glu Ala
65                  70                  75                  80

Glu Asp Ala Ala Thr Tyr Tyr Cys Gln Gln Trp Ser Phe Asn Pro Pro
                85                  90                  95

Thr Phe Gly Ala Gly Thr Lys Leu Glu Leu Lys Ser Gly Ser Thr Ser
                100                 105                 110

Gly Ser Gly Lys Pro Gly Ser Gly Glu Gly Ser Gln Ala Tyr Leu Gln
                115                 120                 125

Gln Ser Gly Ala Glu Leu Val Arg Pro Gly Ala Ser Val Lys Met Ser
                130                 135                 140

Cys Lys Ala Ser Gly Tyr Thr Phe Thr Ser Tyr Asn Met His Trp Val
145                 150                 155                 160

Lys Gln Thr Pro Arg Gln Gly Leu Glu Trp Ile Gly Ala Ile Tyr Pro
                165                 170                 175

Gly Asn Gly Asp Thr Ser Tyr Asn Gln Lys Phe Lys Gly Lys Ala Thr
                180                 185                 190

Leu Thr Val Asp Lys Ser Ser Ser Thr Ala Tyr Met Gln Leu Ser Ser
                195                 200                 205

Leu Thr Ser Glu Asp Ser Ala Val Tyr Phe Cys Ala Arg Val Val Tyr
```

```
            210                 215                 220
Tyr Ser Asn Ser Tyr Trp Tyr Phe Asp Val Trp Gly Thr Gly Thr Thr
225                 230                 235                 240

Val Thr Val Ser Glu Phe Pro Lys Pro Ser Thr Pro Pro Gly Ser Ser
                245                 250                 255

Gly Gly Ala Pro Lys Glu Phe Thr Leu Asp Phe Ser Thr Ala Lys Thr
                260                 265                 270

Tyr Val Asp Ser Leu Asn Val Ile Arg Ser Ala Ile Gly Thr Pro Leu
            275                 280                 285

Gln Thr Ile Ser Ser Gly Gly Thr Ser Leu Leu Met Ile Asp Ser Gly
        290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
                340                 345                 350

Ala Asp Phe Ser His Val Thr Phe Pro Gly Thr Thr Ala Val Thr Leu
            355                 360                 365

Ser Gly Asp Ser Ser Tyr Thr Thr Leu Gln Arg Val Ala Gly Ile Ser
        370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                405                 410                 415

Ala Met Leu Arg Phe Val Thr Val Thr Ala Glu Ala Leu Arg Phe Arg
                420                 425                 430

Gln Ile Gln Arg Gly Phe Arg Thr Thr Leu Asp Asp Leu Ser Gly Arg
            435                 440                 445

Ser Tyr Val Met Thr Ala Glu Asp Val Asp Leu Thr Leu Asn Trp Gly
        450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Ser His His Ala Ser Arg Val Ala Arg
            500                 505                 510

<210> SEQ ID NO 74
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv6 linked to SLT-1A variant 3

<400> SEQUENCE: 74

Met Gln Ile Val Leu Ser Gln Ser Pro Ala Ile Leu Ser Ala Ser Pro
1               5                   10                  15

Gly Glu Lys Val Thr Met Thr Cys Arg Ala Ser Ser Ser Val Ser Tyr
                20                  25                  30

Met His Trp Tyr Gln Gln Lys Pro Gly Ser Ser Pro Lys Pro Trp Ile
            35                  40                  45

Tyr Ala Pro Ser Asn Leu Ala Ser Gly Val Pro Ala Arg Phe Ser Gly
```

```
                50              55              60
Ser Gly Ser Gly Thr Ser Tyr Ser Leu Thr Ile Ser Arg Val Glu Ala
 65              70              75              80

Glu Asp Ala Ala Thr Tyr Tyr Cys Gln Gln Trp Ser Phe Asn Pro Pro
                85              90              95

Thr Phe Gly Ala Gly Thr Lys Leu Glu Leu Lys Ser Gly Gly Gly Gly
            100             105             110

Ser Gly Gly Gly Gly Ser Gly Gly Gly Ser Gly Gly Gly Gly Ser
            115             120             125

Gly Gly Gly Gly Ser Gln Ala Tyr Leu Gln Gln Ser Gly Ala Glu Leu
            130             135             140

Val Arg Pro Gly Ala Ser Val Lys Met Ser Cys Lys Ala Ser Gly Tyr
145             150             155             160

Thr Phe Thr Ser Tyr Asn Met His Trp Val Lys Gln Thr Pro Arg Gln
                165             170             175

Gly Leu Glu Trp Ile Gly Ala Ile Tyr Pro Gly Asn Gly Asp Thr Ser
            180             185             190

Tyr Asn Gln Lys Phe Lys Gly Lys Ala Thr Leu Thr Val Asp Lys Ser
            195             200             205

Ser Ser Thr Ala Tyr Met Gln Leu Ser Ser Leu Thr Ser Glu Asp Ser
210             215             220

Ala Val Tyr Phe Cys Ala Arg Val Val Tyr Tyr Ser Asn Ser Tyr Trp
225             230             235             240

Tyr Phe Asp Val Trp Gly Thr Gly Thr Thr Val Thr Val Ser Glu Phe
            245             250             255

Pro Lys Pro Ser Thr Pro Pro Gly Ser Ser Gly Gly Ile Leu Gly Phe
            260             265             270

Val Phe Thr Leu Gly Ala Pro Lys Glu Phe Thr Leu Asp Phe Ser Thr
            275             280             285

Ala Lys Thr Tyr Val Asp Ser Leu Asn Val Ile Arg Ser Ala Ile Gly
            290             295             300

Thr Pro Leu Gln Thr Ile Ser Ser Gly Gly Thr Ser Leu Leu Met Ile
305             310             315             320

Asp Ser Gly Ser Gly Asp Asn Leu Phe Ala Val Asp Val Arg Gly Ile
            325             330             335

Asp Pro Glu Glu Gly Arg Phe Asn Asn Leu Arg Leu Ile Val Glu Arg
            340             345             350

Asn Asn Leu Tyr Val Thr Gly Phe Val Asn Arg Thr Asn Asn Val Phe
            355             360             365

Tyr Arg Phe Ala Asp Phe Ser His Val Thr Phe Pro Gly Thr Thr Ala
            370             375             380

Val Thr Leu Ser Gly Asp Ser Ser Tyr Thr Thr Leu Gln Arg Val Ala
385             390             395             400

Gly Ile Ser Arg Thr Gly Met Gln Ile Asn Arg His Ser Leu Thr Thr
            405             410             415

Ser Tyr Leu Asp Leu Met Ser His Ser Gly Thr Ser Leu Thr Gln Ser
            420             425             430

Val Ala Arg Ala Met Leu Arg Phe Val Thr Val Thr Ala Glu Ala Leu
            435             440             445

Arg Phe Arg Gln Ile Gln Arg Gly Phe Arg Thr Thr Leu Asp Asp Leu
450             455             460

Ser Gly Arg Ser Tyr Val Met Thr Ala Glu Asp Val Asp Leu Thr Leu
465             470             475             480
```

-continued

```
Asn Trp Gly Arg Leu Ser Ser Val Leu Pro Asp Tyr His Gly Gln Asp
                485                 490                 495

Ser Val Arg Val Gly Arg Ile Ser Phe Gly Ser Ile Asn Ala Ile Leu
            500                 505                 510

Gly Ser Val Ala Leu Ile Leu Asn Ser His His His Ala Ser Arg Val
        515                 520                 525

Ala Arg
    530

<210> SEQ ID NO 75
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv6 linked to StxA variant 1

<400> SEQUENCE: 75

Met Gln Ile Val Leu Ser Gln Ser Pro Ala Ile Leu Ser Ala Ser Pro
1               5                   10                  15

Gly Glu Lys Val Thr Met Thr Cys Arg Ala Ser Ser Val Ser Tyr
            20                  25                  30

Met His Trp Tyr Gln Gln Lys Pro Gly Ser Ser Pro Lys Pro Trp Ile
        35                  40                  45

Tyr Ala Pro Ser Asn Leu Ala Ser Gly Val Pro Ala Arg Phe Ser Gly
    50                  55                  60

Ser Gly Ser Gly Thr Ser Tyr Ser Leu Thr Ile Ser Arg Val Glu Ala
65                  70                  75                  80

Glu Asp Ala Ala Thr Tyr Tyr Cys Gln Gln Trp Ser Phe Asn Pro Pro
                85                  90                  95

Thr Phe Gly Ala Gly Thr Lys Leu Glu Leu Lys Ser Gly Ser Thr Ser
            100                 105                 110

Gly Ser Gly Lys Pro Gly Ser Gly Glu Gly Ser Gln Ala Tyr Leu Gln
        115                 120                 125

Gln Ser Gly Ala Glu Leu Val Arg Pro Gly Ala Ser Val Lys Met Ser
    130                 135                 140

Cys Lys Ala Ser Gly Tyr Thr Phe Thr Ser Tyr Asn Met His Trp Val
145                 150                 155                 160

Lys Gln Thr Pro Arg Gln Gly Leu Glu Trp Ile Gly Ala Ile Tyr Pro
                165                 170                 175

Gly Asn Gly Asp Thr Ser Tyr Asn Gln Lys Phe Lys Gly Lys Ala Thr
            180                 185                 190

Leu Thr Val Asp Lys Ser Ser Ser Thr Ala Tyr Met Gln Leu Ser Ser
        195                 200                 205

Leu Thr Ser Glu Asp Ser Ala Val Tyr Phe Cys Ala Arg Val Val Tyr
    210                 215                 220

Tyr Ser Asn Ser Tyr Trp Tyr Phe Asp Val Trp Gly Thr Gly Thr Thr
225                 230                 235                 240

Val Thr Val Ser Glu Phe Pro Lys Pro Ser Thr Pro Pro Gly Ser Ser
                245                 250                 255

Gly Gly Ala Pro Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
        275                 280                 285
```

```
Gln Thr Ile Ser Ser Gly Gly Thr Ser Leu Met Ile Asp Ser Gly
    290                 295                 300

Thr Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
                340                 345                 350

Ala Asp Phe Ser His Val Thr Phe Pro Gly Thr Thr Ala Val Thr Leu
            355                 360                 365

Ser Gly Asp Ser Ser Tyr Thr Thr Leu Gln Arg Val Ala Gly Ile Ser
    370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                405                 410                 415

Ala Met Leu Arg Phe Val Thr Val Thr Ala Glu Ala Leu Arg Phe Arg
                420                 425                 430

Gln Ile Gln Arg Gly Phe Arg Thr Thr Leu Asp Asp Leu Ser Gly Arg
            435                 440                 445

Ser Tyr Val Met Thr Ala Glu Asp Val Asp Leu Thr Leu Asn Trp Gly
    450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Ser His His His Ala Ser Arg Val Ala Arg
            500                 505                 510

<210> SEQ ID NO 76
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv7 linked to SLT-1A variant 1

<400> SEQUENCE: 76

Met Gln Ala Tyr Leu Gln Gln Ser Gly Ala Glu Leu Val Arg Pro Gly
1               5                   10                  15

Ala Ser Val Lys Met Ser Cys Lys Ala Ser Gly Tyr Thr Phe Thr Ser
                20                  25                  30

Tyr Asn Met His Trp Val Lys Gln Thr Pro Arg Gln Gly Leu Glu Trp
            35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Phe
                85                  90                  95

Cys Ala Arg Val Val Tyr Tyr Ser Asn Ser Tyr Trp Tyr Phe Asp Val
                100                 105                 110

Trp Gly Thr Gly Thr Thr Val Thr Val Ser Gly Ser Thr Ser Gly Ser
            115                 120                 125
```

Gly Lys Pro Gly Ser Gly Glu Gly Ser Gln Ile Val Leu Ser Gln Ser
            130                 135                 140

Pro Ala Ile Leu Ser Ala Ser Pro Gly Glu Lys Val Thr Met Thr Cys
145                 150                 155                 160

Arg Ala Ser Ser Ser Val Ser Tyr Met His Trp Tyr Gln Gln Lys Pro
                165                 170                 175

Gly Ser Ser Pro Lys Pro Trp Ile Tyr Ala Pro Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
    210                 215                 220

Gln Gln Trp Ser Phe Asn Pro Pro Thr Phe Gly Ala Gly Thr Lys Leu
225                 230                 235                 240

Glu Leu Lys Ser Glu Phe Pro Lys Pro Ser Thr Pro Pro Gly Ser Ser
                245                 250                 255

Gly Gly Ala Pro Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
        275                 280                 285

Gln Thr Ile Ser Ser Gly Gly Thr Ser Leu Leu Met Ile Asp Ser Gly
    290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
            340                 345                 350

Ala Asp Phe Ser His Val Thr Phe Pro Gly Thr Thr Ala Val Thr Leu
        355                 360                 365

Ser Gly Asp Ser Ser Tyr Thr Thr Leu Gln Arg Val Ala Gly Ile Ser
    370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                405                 410                 415

Ala Met Leu Arg Phe Val Thr Val Thr Ala Glu Ala Leu Arg Phe Arg
            420                 425                 430

Gln Ile Gln Arg Gly Phe Arg Thr Thr Leu Asp Asp Leu Ser Gly Arg
        435                 440                 445

Ser Tyr Val Met Thr Ala Glu Asp Val Asp Leu Thr Leu Asn Trp Gly
    450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Cys His His Ala Ser Arg Val Ala Arg
            500                 505                 510

<210> SEQ ID NO 77
<211> LENGTH: 511
<212> TYPE: PRT
<213> ORGANISM: Artificial Sequence
<220> FEATURE:

<220> FEATURE:
<223> OTHER INFORMATION: Description of Artificial Sequence: Synthetic
polypeptide
<220> FEATURE:
<223> OTHER INFORMATION: alphaCD20-scFv7 linked to SLT-1A variant 2

<400> SEQUENCE: 77

```
Met Gln Ala Tyr Leu Gln Gln Ser Gly Ala Glu Leu Val Arg Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Arg Gln Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Phe
                85                  90                  95

Cys Ala Arg Val Val Tyr Tyr Ser Asn Ser Tyr Trp Tyr Phe Asp Val
            100                 105                 110

Trp Gly Thr Gly Thr Thr Val Thr Val Ser Gly Ser Thr Ser Gly Ser
        115                 120                 125

Gly Lys Pro Gly Ser Gly Glu Gly Ser Gln Ile Val Leu Ser Gln Ser
    130                 135                 140

Pro Ala Ile Leu Ser Ala Ser Pro Gly Glu Lys Val Thr Met Thr Cys
145                 150                 155                 160

Arg Ala Ser Ser Ser Val Ser Tyr Met His Trp Tyr Gln Gln Lys Pro
                165                 170                 175

Gly Ser Ser Pro Lys Pro Trp Ile Tyr Ala Pro Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
    210                 215                 220

Gln Gln Trp Ser Phe Asn Pro Pro Thr Phe Gly Ala Gly Thr Lys Leu
225                 230                 235                 240

Glu Leu Lys Ser Glu Phe Pro Lys Pro Ser Thr Pro Pro Gly Ser Ser
                245                 250                 255

Gly Gly Ala Pro Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
        275                 280                 285

Gln Thr Ile Ser Ser Gly Gly Thr Ser Leu Leu Met Ile Asp Ser Gly
    290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
            340                 345                 350

Ala Asp Phe Ser His Val Thr Phe Pro Gly Thr Thr Ala Val Thr Leu
        355                 360                 365

Ser Gly Asp Ser Ser Tyr Thr Thr Leu Gln Arg Val Ala Gly Ile Ser
    370                 375                 380
```

```
Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
            405                 410                 415

Ala Met Leu Arg Phe Val Thr Val Thr Ala Glu Ala Leu Arg Phe Arg
        420                 425                 430

Gln Ile Gln Arg Gly Phe Arg Thr Thr Leu Asp Asp Leu Ser Gly Arg
            435                 440                 445

Ser Tyr Val Met Thr Ala Glu Asp Val Asp Leu Thr Leu Asn Trp Gly
    450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
            485                 490                 495

Ala Leu Ile Leu Asn Ser His His His Ala Ser Arg Val Ala Arg
        500                 505                 510
```

<210> SEQ ID NO 78
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv7 linked to SLT-1A variant 3

<400> SEQUENCE: 78

```
Met Gln Ala Tyr Leu Gln Gln Ser Gly Ala Glu Leu Val Arg Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Arg Gln Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Phe
                85                  90                  95

Cys Ala Arg Val Val Tyr Tyr Ser Asn Ser Tyr Trp Tyr Phe Asp Val
            100                 105                 110

Trp Gly Thr Gly Thr Thr Val Thr Val Ser Gly Ser Thr Ser Gly Ser
        115                 120                 125

Gly Lys Pro Gly Ser Gly Glu Gly Ser Gln Ile Val Leu Ser Gln Ser
    130                 135                 140

Pro Ala Ile Leu Ser Ala Ser Pro Gly Glu Lys Val Thr Met Thr Cys
145                 150                 155                 160

Arg Ala Ser Ser Ser Val Ser Tyr Met His Trp Tyr Gln Gln Lys Pro
                165                 170                 175

Gly Ser Ser Pro Lys Pro Trp Ile Tyr Ala Pro Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
    210                 215                 220
```

```
Gln Gln Trp Ser Phe Asn Pro Pro Thr Phe Gly Ala Gly Thr Lys Leu
225                 230                 235                 240

Glu Leu Lys Ser Glu Phe Pro Lys Pro Ser Thr Pro Pro Gly Ser Ser
            245                 250                 255

Gly Gly Ala Pro Gly Ile Leu Gly Phe Val Phe Thr Leu Lys Glu Phe
        260                 265                 270

Thr Leu Asp Phe Ser Thr Ala Lys Thr Tyr Val Asp Ser Leu Asn Val
        275                 280                 285

Ile Arg Ser Ala Ile Gly Thr Pro Leu Gln Thr Ile Ser Ser Gly Gly
        290                 295                 300

Thr Ser Leu Leu Met Ile Asp Ser Gly Ser Gly Asp Asn Leu Phe Ala
305                 310                 315                 320

Val Asp Val Arg Gly Ile Asp Pro Glu Glu Gly Arg Phe Asn Asn Leu
            325                 330                 335

Arg Leu Ile Val Glu Arg Asn Asn Leu Tyr Val Thr Gly Phe Val Asn
            340                 345                 350

Arg Thr Asn Asn Val Phe Tyr Arg Phe Ala Asp Phe Ser His Val Thr
            355                 360                 365

Phe Pro Gly Thr Thr Ala Val Thr Leu Ser Gly Asp Ser Ser Tyr Thr
        370                 375                 380

Thr Leu Gln Arg Val Ala Gly Ile Ser Arg Thr Gly Met Gln Ile Asn
385                 390                 395                 400

Arg His Ser Leu Thr Thr Ser Tyr Leu Asp Leu Met Ser His Ser Gly
            405                 410                 415

Thr Ser Leu Thr Gln Ser Val Ala Arg Ala Met Leu Arg Phe Val Thr
            420                 425                 430

Val Thr Ala Glu Ala Leu Arg Phe Arg Gln Ile Gln Arg Gly Phe Arg
            435                 440                 445

Thr Thr Leu Asp Asp Leu Ser Gly Arg Ser Tyr Val Met Thr Ala Glu
        450                 455                 460

Asp Val Asp Leu Thr Leu Asn Trp Gly Arg Leu Ser Ser Val Leu Pro
465                 470                 475                 480

Asp Tyr His Gly Gln Asp Ser Val Arg Val Gly Arg Ile Ser Phe Gly
            485                 490                 495

Ser Ile Asn Ala Ile Leu Gly Ser Val Ala Leu Ile Leu Asn Ser His
            500                 505                 510

His His Ala Ser Arg Val Ala Arg
            515                 520
```

<210> SEQ ID NO 79
<211> LENGTH: 522
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: alphaCD20-scFv7 linked to StxA variant 1

<400> SEQUENCE: 79

```
Met Gln Ala Tyr Leu Gln Gln Ser Gly Ala Glu Leu Val Arg Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Arg Gln Gly Leu Glu Trp
        35                  40                  45
```

-continued

```
Ile Gly Ala Ile Tyr Pro Gly Asn Gly Asp Thr Ser Tyr Asn Gln Lys
 50                  55                  60

Phe Lys Gly Lys Ala Thr Leu Thr Val Asp Lys Ser Ser Ser Thr Ala
 65                  70                  75                  80

Tyr Met Gln Leu Ser Ser Leu Thr Ser Glu Asp Ser Ala Val Tyr Phe
                 85                  90                  95

Cys Ala Arg Val Val Tyr Tyr Ser Asn Ser Tyr Trp Tyr Phe Asp Val
            100                 105                 110

Trp Gly Thr Gly Thr Thr Val Thr Val Ser Gly Gly Gly Gly Ser Gly
        115                 120                 125

Gly Gly Gly Ser Gly Gly Gly Gly Ser Gly Gly Gly Gly Ser Gly Gly
130                 135                 140

Gly Gly Ser Ser Gln Ile Val Leu Ser Gln Ser Pro Ala Ile Leu Ser
145                 150                 155                 160

Ala Ser Pro Gly Glu Lys Val Thr Met Thr Cys Arg Ala Ser Ser Ser
                165                 170                 175

Val Ser Tyr Met His Trp Tyr Gln Gln Lys Pro Gly Ser Ser Pro Lys
            180                 185                 190

Pro Trp Ile Tyr Ala Pro Ser Asn Leu Ala Ser Gly Val Pro Ala Arg
        195                 200                 205

Phe Ser Gly Ser Gly Ser Gly Thr Ser Tyr Ser Leu Thr Ile Ser Arg
    210                 215                 220

Val Glu Ala Glu Asp Ala Ala Thr Tyr Tyr Cys Gln Gln Trp Ser Phe
225                 230                 235                 240

Asn Pro Pro Thr Phe Gly Ala Gly Thr Lys Leu Glu Leu Lys Ser Glu
                245                 250                 255

Phe Pro Lys Pro Ser Thr Pro Pro Gly Ser Ser Gly Gly Ala Pro Lys
            260                 265                 270

Glu Phe Thr Leu Asp Phe Ser Thr Ala Lys Thr Tyr Val Asp Ser Leu
        275                 280                 285

Asn Val Ile Arg Ser Ala Ile Gly Thr Pro Leu Gln Thr Ile Ser Ser
    290                 295                 300

Gly Gly Thr Ser Leu Leu Met Ile Asp Ser Gly Thr Gly Asp Asn Leu
305                 310                 315                 320

Phe Ala Val Asp Val Arg Gly Ile Asp Pro Glu Glu Gly Arg Phe Asn
                325                 330                 335

Asn Leu Arg Leu Ile Val Glu Arg Asn Asn Leu Tyr Val Thr Gly Phe
            340                 345                 350

Val Asn Arg Thr Asn Asn Val Phe Tyr Arg Phe Ala Asp Phe Ser His
        355                 360                 365

Val Thr Phe Pro Gly Thr Thr Ala Val Thr Leu Ser Gly Asp Ser Ser
    370                 375                 380

Tyr Thr Thr Leu Gln Arg Val Ala Gly Ile Ser Arg Thr Gly Met Gln
385                 390                 395                 400

Ile Asn Arg His Ser Leu Thr Thr Ser Tyr Leu Asp Leu Met Ser His
                405                 410                 415

Ser Gly Thr Ser Leu Thr Gln Ser Val Ala Arg Ala Met Leu Arg Phe
            420                 425                 430

Val Thr Val Thr Ala Glu Ala Leu Arg Phe Arg Gln Ile Gln Arg Gly
        435                 440                 445

Phe Arg Thr Thr Leu Asp Asp Leu Ser Gly Arg Ser Tyr Val Met Thr
    450                 455                 460

Ala Glu Asp Val Asp Leu Thr Leu Asn Trp Gly Arg Leu Ser Ser Val
```

```
            465                 470                 475                 480
Leu Pro Asp Tyr His Gly Gln Asp Ser Val Arg Val Gly Arg Ile Ser
                485                 490                 495

Phe Gly Ser Ile Asn Ala Ile Leu Gly Ser Val Ala Leu Ile Leu Asn
            500                 505                 510

Ser His His His Ala Ser Arg Val Ala Arg
        515                 520

<210> SEQ ID NO 80
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv8 linked to SLT-1A variant 1

<400> SEQUENCE: 80

Met Gln Val Gln Leu Val Gln Ser Gly Ala Glu Val Lys Lys Pro Gly
1               5                   10                  15

Ser Ser Val Lys Val Ser Cys Lys Ala Ser Gly Tyr Ala Phe Ser Tyr
            20                  25                  30

Ser Trp Ile Asn Trp Val Arg Gln Ala Pro Gly Gln Gly Leu Glu Trp
        35                  40                  45

Met Gly Arg Ile Phe Pro Gly Asp Gly Asp Thr Asp Tyr Asn Gly Lys
    50                  55                  60

Phe Lys Gly Arg Val Thr Ile Thr Ala Asp Lys Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Asn Val Phe Asp Gly Tyr Trp Leu Val Tyr Trp Gly Gln
            100                 105                 110

Gly Thr Leu Val Thr Val Ser Ser Gly Ser Thr Ser Gly Ser Gly Lys
        115                 120                 125

Pro Gly Ser Gly Glu Gly Ser Asp Ile Val Met Thr Gln Thr Pro Leu
    130                 135                 140

Ser Leu Pro Val Thr Pro Gly Glu Pro Ala Ser Ile Ser Cys Arg Ser
145                 150                 155                 160

Ser Lys Ser Leu Leu His Ser Asn Gly Ile Thr Tyr Leu Tyr Trp Tyr
                165                 170                 175

Leu Gln Lys Pro Gly Gln Ser Pro Gln Leu Leu Ile Tyr Gln Met Ser
            180                 185                 190

Asn Leu Val Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Ala Gln Asn Leu Glu Leu Pro Tyr Thr Phe Gly Gly
225                 230                 235                 240

Gly Thr Lys Val Glu Ile Lys Glu Phe Pro Lys Pro Ser Thr Pro Pro
                245                 250                 255

Gly Ser Ser Gly Gly Ala Pro Lys Glu Phe Thr Leu Asp Phe Ser Thr
            260                 265                 270

Ala Lys Thr Tyr Val Asp Ser Leu Asn Val Ile Arg Ser Ala Ile Gly
        275                 280                 285

Thr Pro Leu Gln Thr Ile Ser Ser Gly Gly Thr Ser Leu Leu Met Ile
```

```
                290                 295                 300
Asp Ser Gly Ser Gly Asp Asn Leu Phe Ala Val Asp Val Arg Gly Ile
305                 310                 315                 320

Asp Pro Glu Glu Gly Arg Phe Asn Asn Leu Arg Leu Ile Val Glu Arg
                325                 330                 335

Asn Asn Leu Tyr Val Thr Gly Phe Val Asn Arg Thr Asn Asn Val Phe
                340                 345                 350

Tyr Arg Phe Ala Asp Phe Ser His Val Thr Phe Pro Gly Thr Thr Ala
                355                 360                 365

Val Thr Leu Ser Gly Asp Ser Ser Tyr Thr Thr Leu Gln Arg Val Ala
                370                 375                 380

Gly Ile Ser Arg Thr Gly Met Gln Ile Asn Arg His Ser Leu Thr Thr
385                 390                 395                 400

Ser Tyr Leu Asp Leu Met Ser His Ser Gly Thr Ser Leu Thr Gln Ser
                405                 410                 415

Val Ala Arg Ala Met Leu Arg Phe Val Thr Val Thr Ala Glu Ala Leu
                420                 425                 430

Arg Phe Arg Gln Ile Gln Arg Gly Phe Arg Thr Thr Leu Asp Asp Leu
                435                 440                 445

Ser Gly Arg Ser Tyr Val Met Thr Ala Glu Asp Val Asp Leu Thr Leu
                450                 455                 460

Asn Trp Gly Arg Leu Ser Ser Val Leu Pro Asp Tyr His Gly Gln Asp
465                 470                 475                 480

Ser Val Arg Val Gly Arg Ile Ser Phe Gly Ser Ile Asn Ala Ile Leu
                485                 490                 495

Gly Ser Val Ala Leu Ile Leu Asn Cys His His His Ala Ser Arg Val
                500                 505                 510

Ala Arg

<210> SEQ ID NO 81
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv8 linked to SLT-1A variant 2

<400> SEQUENCE: 81

Met Gln Val Gln Leu Val Gln Ser Gly Ala Glu Val Lys Lys Pro Gly
1               5                   10                  15

Ser Ser Val Lys Val Ser Cys Lys Ala Ser Gly Tyr Ala Phe Ser Tyr
                20                  25                  30

Ser Trp Ile Asn Trp Val Arg Gln Ala Pro Gly Gln Gly Leu Glu Trp
            35                  40                  45

Met Gly Arg Ile Phe Pro Gly Asp Gly Asp Thr Asp Tyr Asn Gly Lys
        50                  55                  60

Phe Lys Gly Arg Val Thr Ile Thr Ala Asp Lys Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Asn Val Phe Asp Gly Tyr Trp Leu Val Tyr Trp Gly Gln
                100                 105                 110

Gly Thr Leu Val Thr Val Ser Ser Gly Ser Thr Gly Ser Gly Lys
            115                 120                 125
```

Pro Gly Ser Gly Glu Gly Ser Asp Ile Val Met Thr Gln Thr Pro Leu
        130                 135                 140

Ser Leu Pro Val Thr Pro Gly Glu Pro Ala Ser Ile Ser Cys Arg Ser
145                 150                 155                 160

Ser Lys Ser Leu Leu His Ser Asn Gly Ile Thr Tyr Leu Tyr Trp Tyr
                165                 170                 175

Leu Gln Lys Pro Gly Gln Ser Pro Gln Leu Leu Ile Tyr Gln Met Ser
            180                 185                 190

Asn Leu Val Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
210                 215                 220

Val Tyr Tyr Cys Ala Gln Asn Leu Glu Leu Pro Tyr Thr Phe Gly Gly
225                 230                 235                 240

Gly Thr Lys Val Glu Ile Lys Glu Phe Pro Lys Pro Ser Thr Pro Pro
                245                 250                 255

Gly Ser Ser Gly Gly Ala Pro Lys Glu Phe Thr Leu Asp Phe Ser Thr
            260                 265                 270

Ala Lys Thr Tyr Val Asp Ser Leu Asn Val Ile Arg Ser Ala Ile Gly
        275                 280                 285

Thr Pro Leu Gln Thr Ile Ser Ser Gly Gly Thr Ser Leu Leu Met Ile
290                 295                 300

Asp Ser Gly Ser Gly Asp Asn Leu Phe Ala Val Asp Val Arg Gly Ile
305                 310                 315                 320

Asp Pro Glu Glu Gly Arg Phe Asn Asn Leu Arg Leu Ile Val Glu Arg
                325                 330                 335

Asn Asn Leu Tyr Val Thr Gly Phe Val Asn Arg Thr Asn Asn Val Phe
            340                 345                 350

Tyr Arg Phe Ala Asp Phe Ser His Val Thr Phe Pro Gly Thr Thr Ala
        355                 360                 365

Val Thr Leu Ser Gly Asp Ser Ser Tyr Thr Thr Leu Gln Arg Val Ala
370                 375                 380

Gly Ile Ser Arg Thr Gly Met Gln Ile Asn Arg His Ser Leu Thr Thr
385                 390                 395                 400

Ser Tyr Leu Asp Leu Met Ser His Ser Gly Thr Ser Leu Thr Gln Ser
                405                 410                 415

Val Ala Arg Ala Met Leu Arg Phe Val Thr Val Thr Ala Glu Ala Leu
            420                 425                 430

Arg Phe Arg Gln Ile Gln Arg Gly Phe Arg Thr Thr Leu Asp Asp Leu
        435                 440                 445

Ser Gly Arg Ser Tyr Val Met Thr Ala Glu Asp Val Asp Leu Thr Leu
450                 455                 460

Asn Trp Gly Arg Leu Ser Ser Val Leu Pro Asp Tyr His Gly Gln Asp
465                 470                 475                 480

Ser Val Arg Val Gly Arg Ile Ser Phe Gly Ser Ile Asn Ala Ile Leu
                485                 490                 495

Gly Ser Val Ala Leu Ile Leu Asn Ser His His Ala Ser Arg Val
            500                 505                 510

Ala Arg

<210> SEQ ID NO 82
<211> LENGTH: 514
<212> TYPE: PRT

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv9 linked to SLT-1A variant 1

<400> SEQUENCE: 82

```
Met Asp Ile Val Met Thr Gln Thr Pro Leu Ser Leu Pro Val Thr Pro
1               5                   10                  15
Gly Glu Pro Ala Ser Ile Ser Cys Arg Ser Ser Lys Ser Leu Leu His
            20                  25                  30
Ser Asn Gly Ile Thr Tyr Leu Tyr Trp Tyr Leu Gln Lys Pro Gly Gln
        35                  40                  45
Ser Pro Gln Leu Leu Ile Tyr Gln Met Ser Asn Leu Val Ser Gly Val
    50                  55                  60
Pro Asp Arg Phe Ser Gly Ser Gly Thr Asp Phe Thr Leu Lys
65                  70                  75                  80
Ile Ser Arg Val Glu Ala Glu Asp Val Gly Val Tyr Tyr Cys Ala Gln
                85                  90                  95
Asn Leu Glu Leu Pro Tyr Thr Phe Gly Gly Gly Thr Lys Val Glu Ile
            100                 105                 110
Lys Gly Ser Thr Ser Gly Ser Gly Lys Pro Gly Ser Gly Glu Gly Ser
        115                 120                 125
Gln Val Gln Leu Val Gln Ser Gly Ala Glu Val Lys Lys Pro Gly Ser
    130                 135                 140
Ser Val Lys Val Ser Cys Lys Ala Ser Gly Tyr Ala Phe Ser Tyr Ser
145                 150                 155                 160
Trp Ile Asn Trp Val Arg Gln Ala Pro Gly Gln Gly Leu Glu Trp Met
                165                 170                 175
Gly Arg Ile Phe Pro Gly Asp Gly Asp Thr Asp Tyr Asn Gly Lys Phe
            180                 185                 190
Lys Gly Arg Val Thr Ile Thr Ala Asp Lys Ser Thr Ser Thr Ala Tyr
        195                 200                 205
Met Glu Leu Ser Ser Leu Arg Ser Glu Asp Thr Ala Val Tyr Tyr Cys
    210                 215                 220
Ala Arg Asn Val Phe Asp Gly Tyr Trp Leu Val Tyr Trp Gly Gln Gly
225                 230                 235                 240
Thr Leu Val Thr Val Ser Ser Glu Phe Pro Lys Pro Ser Thr Pro Pro
                245                 250                 255
Gly Ser Ser Gly Gly Ala Pro Lys Glu Phe Thr Leu Asp Phe Ser Thr
            260                 265                 270
Ala Lys Thr Tyr Val Asp Ser Leu Asn Val Ile Arg Ser Ala Ile Gly
        275                 280                 285
Thr Pro Leu Gln Thr Ile Ser Ser Gly Gly Thr Ser Leu Leu Met Ile
    290                 295                 300
Asp Ser Gly Ser Gly Asp Asn Leu Phe Ala Val Asp Val Arg Gly Ile
305                 310                 315                 320
Asp Pro Glu Glu Gly Arg Phe Asn Asn Leu Arg Leu Ile Val Glu Arg
                325                 330                 335
Asn Asn Leu Tyr Val Thr Gly Phe Val Asn Arg Thr Asn Asn Val Phe
            340                 345                 350
Tyr Arg Phe Ala Asp Phe Ser His Val Thr Phe Pro Gly Thr Thr Ala
        355                 360                 365
Val Thr Leu Ser Gly Asp Ser Ser Tyr Thr Thr Leu Gln Arg Val Ala
```

```
                    370                 375                 380
Gly Ile Ser Arg Thr Gly Met Gln Ile Asn Arg His Ser Leu Thr Thr
385                 390                 395                 400

Ser Tyr Leu Asp Leu Met Ser His Ser Gly Thr Ser Leu Thr Gln Ser
                405                 410                 415

Val Ala Arg Ala Met Leu Arg Phe Val Thr Val Thr Ala Glu Ala Leu
            420                 425                 430

Arg Phe Arg Gln Ile Gln Arg Gly Phe Arg Thr Thr Leu Asp Asp Leu
        435                 440                 445

Ser Gly Arg Ser Tyr Val Met Thr Ala Glu Asp Val Asp Leu Thr Leu
    450                 455                 460

Asn Trp Gly Arg Leu Ser Ser Val Leu Pro Asp Tyr His Gly Gln Asp
465                 470                 475                 480

Ser Val Arg Val Gly Arg Ile Ser Phe Gly Ser Ile Asn Ala Ile Leu
                485                 490                 495

Gly Ser Val Ala Leu Ile Leu Asn Cys His His His Ala Ser Arg Val
            500                 505                 510

Ala Arg

<210> SEQ ID NO 83
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv9 linked to SLT-1A variant 2

<400> SEQUENCE: 83

Met Asp Ile Val Met Thr Gln Thr Pro Leu Ser Leu Pro Val Thr Pro
1               5                   10                  15

Gly Glu Pro Ala Ser Ile Ser Cys Arg Ser Ser Lys Ser Leu Leu His
            20                  25                  30

Ser Asn Gly Ile Thr Tyr Leu Tyr Trp Tyr Leu Gln Lys Pro Gly Gln
        35                  40                  45

Ser Pro Gln Leu Leu Ile Tyr Gln Met Ser Asn Leu Val Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Ala Gln
                85                  90                  95

Asn Leu Glu Leu Pro Tyr Thr Phe Gly Gly Gly Thr Lys Val Glu Ile
            100                 105                 110

Lys Gly Ser Thr Ser Gly Ser Gly Lys Pro Gly Ser Gly Glu Gly Ser
        115                 120                 125

Gln Val Gln Leu Val Gln Ser Gly Ala Glu Val Lys Lys Pro Gly Ser
    130                 135                 140

Ser Val Lys Val Ser Cys Lys Ala Ser Gly Tyr Ala Phe Ser Tyr Ser
145                 150                 155                 160

Trp Ile Asn Trp Val Arg Gln Ala Pro Gly Gln Gly Leu Glu Trp Met
                165                 170                 175

Gly Arg Ile Phe Pro Gly Asp Gly Asp Thr Asp Tyr Asn Gly Lys Phe
            180                 185                 190

Lys Gly Arg Val Thr Ile Thr Ala Asp Lys Ser Thr Ser Thr Ala Tyr
        195                 200                 205
```

```
Met Glu Leu Ser Ser Leu Arg Ser Glu Asp Thr Ala Val Tyr Tyr Cys
        210                 215                 220

Ala Arg Asn Val Phe Asp Gly Tyr Trp Leu Val Tyr Trp Gly Gln Gly
225                 230                 235                 240

Thr Leu Val Thr Val Ser Ser Glu Phe Pro Lys Pro Ser Thr Pro Pro
                245                 250                 255

Gly Ser Ser Gly Gly Ala Pro Lys Glu Phe Thr Leu Asp Phe Ser Thr
                260                 265                 270

Ala Lys Thr Tyr Val Asp Ser Leu Asn Val Ile Arg Ser Ala Ile Gly
        275                 280                 285

Thr Pro Leu Gln Thr Ile Ser Ser Gly Gly Thr Ser Leu Leu Met Ile
        290                 295                 300

Asp Ser Gly Ser Gly Asp Asn Leu Phe Ala Val Asp Val Arg Gly Ile
305                 310                 315                 320

Asp Pro Glu Glu Gly Arg Phe Asn Asn Leu Arg Leu Ile Val Glu Arg
                325                 330                 335

Asn Asn Leu Tyr Val Thr Gly Phe Val Asn Arg Thr Asn Asn Val Phe
                340                 345                 350

Tyr Arg Phe Ala Asp Phe Ser His Val Thr Phe Pro Gly Thr Thr Ala
        355                 360                 365

Val Thr Leu Ser Gly Asp Ser Ser Tyr Thr Thr Leu Gln Arg Val Ala
        370                 375                 380

Gly Ile Ser Arg Thr Gly Met Gln Ile Asn Arg His Ser Leu Thr Thr
385                 390                 395                 400

Ser Tyr Leu Asp Leu Met Ser His Ser Gly Thr Ser Leu Thr Gln Ser
                405                 410                 415

Val Ala Arg Ala Met Leu Arg Phe Val Thr Val Thr Ala Glu Ala Leu
        420                 425                 430

Arg Phe Arg Gln Ile Gln Arg Gly Phe Arg Thr Thr Leu Asp Asp Leu
        435                 440                 445

Ser Gly Arg Ser Tyr Val Met Thr Ala Glu Asp Val Asp Leu Thr Leu
        450                 455                 460

Asn Trp Gly Arg Leu Ser Ser Val Leu Pro Asp Tyr His Gly Gln Asp
465                 470                 475                 480

Ser Val Arg Val Gly Arg Ile Ser Phe Gly Ser Ile Asn Ala Ile Leu
                485                 490                 495

Gly Ser Val Ala Leu Ile Leu Asn Ser His His His Ala Ser Arg Val
                500                 505                 510

Ala Arg

<210> SEQ ID NO 84
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv10 linked to SLT-1A variant 1

<400> SEQUENCE: 84

Met Gln Ala Tyr Leu Gln Gln Ser Gly Ala Glu Leu Val Arg Pro Gly
1               5                   10                  15

Ala Ser Val Lys Met Ser Cys Lys Ala Ser Gly Tyr Thr Phe Thr Ser
                20                  25                  30
```

Tyr Asn Met His Trp Val Lys Gln Thr Pro Arg Gln Gly Leu Glu Trp
                35                  40                  45

Ile Gly Ala Ile Tyr Pro Gly Asn Gly Asp Thr Ser Tyr Asn Gln Lys
 50                  55                  60

Phe Lys Gly Lys Ala Thr Leu Thr Val Asp Lys Ser Ser Ser Thr Ala
 65                  70                  75                  80

Tyr Met Gln Leu Ser Ser Leu Thr Ser Glu Asp Ser Ala Val Tyr Phe
                 85                  90                  95

Cys Ala Arg Val Val Tyr Ser Asn Ser Tyr Trp Tyr Phe Asp Val
                100                 105                 110

Trp Gly Thr Gly Thr Thr Val Thr Val Ser Gly Ser Thr Ser Gly Ser
                115                 120                 125

Gly Lys Pro Gly Ser Gly Glu Gly Ser Gln Ile Val Leu Ser Gln Ser
130                 135                 140

Pro Ala Ile Leu Ser Ala Ser Pro Gly Glu Lys Val Thr Met Thr Cys
145                 150                 155                 160

Arg Ala Ser Ser Ser Val Ser Tyr Met His Trp Tyr Gln Gln Lys Pro
                165                 170                 175

Gly Ser Ser Pro Lys Pro Trp Ile Tyr Ala Pro Ser Asn Leu Ala Ser
                180                 185                 190

Gly Val Pro Ala Arg Phe Ser Gly Ser Gly Ser Gly Thr Ser Tyr Ser
                195                 200                 205

Leu Thr Ile Ser Arg Val Glu Ala Glu Asp Ala Ala Thr Tyr Tyr Cys
                210                 215                 220

Gln Gln Trp Ser Phe Asn Pro Pro Thr Phe Gly Ala Gly Thr Lys Leu
225                 230                 235                 240

Glu Leu Lys Glu Phe Pro Lys Pro Ser Thr Pro Pro Gly Ser Ser Gly
                245                 250                 255

Gly Ala Pro Lys Glu Phe Thr Leu Asp Phe Ser Thr Ala Lys Thr Tyr
                260                 265                 270

Val Asp Ser Leu Asn Val Ile Arg Ser Ala Ile Gly Thr Pro Leu Gln
                275                 280                 285

Thr Ile Ser Ser Gly Gly Thr Ser Leu Leu Met Ile Asp Ser Gly Ser
                290                 295                 300

Gly Asp Asn Leu Phe Ala Val Asp Val Arg Gly Ile Asp Pro Glu Glu
305                 310                 315                 320

Gly Arg Phe Asn Asn Leu Arg Leu Ile Val Glu Arg Asn Asn Leu Tyr
                325                 330                 335

Val Thr Gly Phe Val Asn Arg Thr Asn Asn Val Phe Tyr Arg Phe Ala
                340                 345                 350

Asp Phe Ser His Val Thr Phe Pro Gly Thr Thr Ala Val Thr Leu Ser
                355                 360                 365

Gly Asp Ser Ser Tyr Thr Thr Leu Gln Arg Val Ala Gly Ile Ser Arg
                370                 375                 380

Thr Gly Met Gln Ile Asn Arg His Ser Leu Thr Thr Ser Tyr Leu Asp
385                 390                 395                 400

Leu Met Ser His Ser Gly Thr Ser Leu Thr Gln Ser Val Ala Arg Ala
                405                 410                 415

Met Leu Arg Phe Val Thr Val Thr Ala Glu Ala Leu Arg Phe Arg Gln
                420                 425                 430

Ile Gln Arg Gly Phe Arg Thr Thr Leu Asp Asp Leu Ser Gly Arg Ser
                435                 440                 445

Tyr Val Met Thr Ala Glu Asp Val Asp Leu Thr Leu Asn Trp Gly Arg

```
                450                 455                 460
Leu Ser Ser Val Leu Pro Asp Tyr His Gly Gln Asp Ser Val Arg Val
465                 470                 475                 480

Gly Arg Ile Ser Phe Gly Ser Ile Asn Ala Ile Leu Gly Ser Val Ala
                485                 490                 495

Leu Ile Leu Asn Cys His His His Ala Ser Arg Val Ala Arg
                500                 505                 510

<210> SEQ ID NO 85
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv10 linked to SLT-1A variant 2

<400> SEQUENCE: 85

Met Gln Ala Tyr Leu Gln Gln Ser Gly Ala Glu Leu Val Arg Pro Gly
1               5                   10                  15

Ala Ser Val Lys Met Ser Cys Lys Ala Ser Gly Tyr Thr Phe Thr Ser
                20                  25                  30

Tyr Asn Met His Trp Val Lys Gln Thr Pro Arg Gln Gly Leu Glu Trp
            35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Phe
                85                  90                  95

Cys Ala Arg Val Val Tyr Tyr Ser Asn Ser Tyr Trp Tyr Phe Asp Val
                100                 105                 110

Trp Gly Thr Gly Thr Thr Val Thr Val Ser Gly Ser Thr Ser Gly Ser
            115                 120                 125

Gly Lys Pro Gly Ser Gly Glu Gly Ser Gln Ile Val Leu Ser Gln Ser
    130                 135                 140

Pro Ala Ile Leu Ser Ala Ser Pro Gly Glu Lys Val Thr Met Thr Cys
145                 150                 155                 160

Arg Ala Ser Ser Ser Val Ser Tyr Met His Trp Tyr Gln Gln Lys Pro
                165                 170                 175

Gly Ser Ser Pro Lys Pro Trp Ile Tyr Ala Pro Ser Asn Leu Ala Ser
            180                 185                 190

Gly Val Pro Ala Arg Phe Ser Gly Ser Gly Ser Gly Thr Ser Tyr Ser
    195                 200                 205

Leu Thr Ile Ser Arg Val Glu Ala Glu Asp Ala Ala Thr Tyr Tyr Cys
210                 215                 220

Gln Gln Trp Ser Phe Asn Pro Pro Thr Phe Gly Ala Gly Thr Lys Leu
                225                 230                 235                 240

Glu Leu Lys Glu Phe Pro Lys Pro Ser Thr Pro Pro Gly Ser Ser Gly
            245                 250                 255

Gly Ala Pro Lys Glu Phe Thr Leu Asp Phe Ser Thr Ala Lys Thr Tyr
    260                 265                 270

Val Asp Ser Leu Asn Val Ile Arg Ser Ala Ile Gly Thr Pro Leu Gln
        275                 280                 285

Thr Ile Ser Ser Gly Gly Thr Ser Leu Leu Met Ile Asp Ser Gly Ser
```

```
                    290                 295                 300
Gly Asp Asn Leu Phe Ala Val Asp Val Arg Gly Ile Asp Pro Glu Glu
305                 310                 315                 320

Gly Arg Phe Asn Asn Leu Arg Leu Ile Val Glu Arg Asn Asn Leu Tyr
                    325                 330                 335

Val Thr Gly Phe Val Asn Arg Thr Asn Asn Val Phe Tyr Arg Phe Ala
                340                 345                 350

Asp Phe Ser His Val Thr Phe Pro Gly Thr Thr Ala Val Thr Leu Ser
                355                 360                 365

Gly Asp Ser Ser Tyr Thr Thr Leu Gln Arg Val Ala Gly Ile Ser Arg
370                 375                 380

Thr Gly Met Gln Ile Asn Arg His Ser Leu Thr Thr Ser Tyr Leu Asp
385                 390                 395                 400

Leu Met Ser His Ser Gly Thr Ser Leu Thr Gln Ser Val Ala Arg Ala
                405                 410                 415

Met Leu Arg Phe Val Thr Val Thr Ala Glu Ala Leu Arg Phe Arg Gln
                420                 425                 430

Ile Gln Arg Gly Phe Arg Thr Thr Leu Asp Asp Leu Ser Gly Arg Ser
                435                 440                 445

Tyr Val Met Thr Ala Glu Asp Val Asp Leu Thr Leu Asn Trp Gly Arg
450                 455                 460

Leu Ser Ser Val Leu Pro Asp Tyr His Gly Gln Asp Ser Val Arg Val
465                 470                 475                 480

Gly Arg Ile Ser Phe Gly Ser Ile Asn Ala Ile Leu Gly Ser Val Ala
                485                 490                 495

Leu Ile Leu Asn Ser His His His Ala Ser Arg Val Ala Arg
                500                 505                 510

<210> SEQ ID NO 86
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv11 linked to SLT-1A variant 1

<400> SEQUENCE: 86

Met Gln Ile Val Leu Ser Gln Ser Pro Ala Ile Leu Ser Ala Ser Pro
1               5                   10                  15

Gly Glu Lys Val Thr Met Thr Cys Arg Ala Ser Ser Ser Val Ser Tyr
                20                  25                  30

Met His Trp Tyr Gln Gln Lys Pro Gly Ser Ser Pro Lys Pro Trp Ile
            35                  40                  45

Tyr Ala Pro Ser Asn Leu Ala Ser Gly Val Pro Ala Arg Phe Ser Gly
        50                  55                  60

Ser Gly Ser Gly Thr Ser Tyr Ser Leu Thr Ile Ser Arg Val Glu Ala
65                  70                  75                  80

Glu Asp Ala Ala Thr Tyr Tyr Cys Gln Gln Trp Ser Phe Asn Pro Pro
                85                  90                  95

Thr Phe Gly Ala Gly Thr Lys Leu Glu Leu Lys Gly Ser Thr Ser Gly
                100                 105                 110

Ser Gly Lys Pro Gly Ser Gly Glu Gly Ser Gln Ala Tyr Leu Gln Gln
            115                 120                 125

Ser Gly Ala Glu Leu Val Arg Pro Gly Ala Ser Val Lys Met Ser Cys
```

Lys Ala Ser Gly Tyr Thr Phe Thr Ser Tyr Asn Met His Trp Val Lys
145                 150                 155                 160

Gln Thr Pro Arg Gln Gly Leu Glu Trp Ile Gly Ala Ile Tyr Pro Gly
            165                 170                 175

Asn Gly Asp Thr Ser Tyr Asn Gln Lys Phe Lys Gly Lys Ala Thr Leu
            180                 185                 190

Thr Val Asp Lys Ser Ser Ser Thr Ala Tyr Met Gln Leu Ser Ser Leu
            195                 200                 205

Thr Ser Glu Asp Ser Ala Val Tyr Phe Cys Ala Arg Val Val Tyr Tyr
            210                 215                 220

Ser Asn Ser Tyr Trp Tyr Phe Asp Val Trp Gly Thr Gly Thr Thr Val
225                 230                 235                 240

Thr Val Ser Glu Phe Pro Lys Pro Ser Thr Pro Pro Gly Ser Ser Gly
            245                 250                 255

Gly Ala Pro Lys Glu Phe Thr Leu Asp Phe Ser Thr Ala Lys Thr Tyr
            260                 265                 270

Val Asp Ser Leu Asn Val Ile Arg Ser Ala Ile Gly Thr Pro Leu Gln
            275                 280                 285

Thr Ile Ser Ser Gly Gly Thr Ser Leu Leu Met Ile Asp Ser Gly Ser
            290                 295                 300

Gly Asp Asn Leu Phe Ala Val Asp Val Arg Gly Ile Asp Pro Glu Glu
305                 310                 315                 320

Gly Arg Phe Asn Asn Leu Arg Leu Ile Val Glu Arg Asn Asn Leu Tyr
            325                 330                 335

Val Thr Gly Phe Val Asn Arg Thr Asn Asn Val Phe Tyr Arg Phe Ala
            340                 345                 350

Asp Phe Ser His Val Thr Phe Pro Gly Thr Thr Ala Val Thr Leu Ser
            355                 360                 365

Gly Asp Ser Ser Tyr Thr Thr Leu Gln Arg Val Ala Gly Ile Ser Arg
            370                 375                 380

Thr Gly Met Gln Ile Asn Arg His Ser Leu Thr Thr Ser Tyr Leu Asp
385                 390                 395                 400

Leu Met Ser His Ser Gly Thr Ser Leu Thr Gln Ser Val Ala Arg Ala
            405                 410                 415

Met Leu Arg Phe Val Thr Val Thr Ala Glu Ala Leu Arg Phe Arg Gln
            420                 425                 430

Ile Gln Arg Gly Phe Arg Thr Thr Leu Asp Asp Leu Ser Gly Arg Ser
            435                 440                 445

Tyr Val Met Thr Ala Glu Asp Val Asp Leu Thr Leu Asn Trp Gly Arg
            450                 455                 460

Leu Ser Ser Val Leu Pro Asp Tyr His Gly Gln Asp Ser Val Arg Val
465                 470                 475                 480

Gly Arg Ile Ser Phe Gly Ser Ile Asn Ala Ile Leu Gly Ser Val Ala
            485                 490                 495

Leu Ile Leu Asn Cys His His His Ala Ser Arg Val Ala Arg
            500                 505                 510

<210> SEQ ID NO 87
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: alphaCD20-scFv11 linked to SLT-1A variant 2

<400> SEQUENCE: 87

```
Met Gln Ile Val Leu Ser Gln Ser Pro Ala Ile Leu Ser Ala Ser Pro
1               5                   10                  15

Gly Glu Lys Val Thr Met Thr Cys Arg Ala Ser Ser Val Ser Tyr
            20                  25                  30

Met His Trp Tyr Gln Gln Lys Pro Gly Ser Ser Pro Lys Pro Trp Ile
            35                  40                  45

Tyr Ala Pro Ser Asn Leu Ala Ser Gly Val Pro Ala Arg Phe Ser Gly
        50                  55                  60

Ser Gly Ser Gly Thr Ser Tyr Ser Leu Thr Ile Ser Arg Val Glu Ala
65                  70                  75                  80

Glu Asp Ala Ala Thr Tyr Tyr Cys Gln Gln Trp Ser Phe Asn Pro Pro
                85                  90                  95

Thr Phe Gly Ala Gly Thr Lys Leu Glu Leu Lys Gly Ser Thr Ser Gly
            100                 105                 110

Ser Gly Lys Pro Gly Ser Gly Glu Gly Ser Gln Ala Tyr Leu Gln Gln
        115                 120                 125

Ser Gly Ala Glu Leu Val Arg Pro Gly Ala Ser Val Lys Met Ser Cys
130                 135                 140

Lys Ala Ser Gly Tyr Thr Phe Thr Ser Tyr Asn Met His Trp Val Lys
145                 150                 155                 160

Gln Thr Pro Arg Gln Gly Leu Glu Trp Ile Gly Ala Ile Tyr Pro Gly
                165                 170                 175

Asn Gly Asp Thr Ser Tyr Asn Gln Lys Phe Lys Gly Lys Ala Thr Leu
            180                 185                 190

Thr Val Asp Lys Ser Ser Ser Thr Ala Tyr Met Gln Leu Ser Ser Leu
        195                 200                 205

Thr Ser Glu Asp Ser Ala Val Tyr Phe Cys Ala Arg Val Val Tyr Tyr
210                 215                 220

Ser Asn Ser Tyr Trp Tyr Phe Asp Val Trp Gly Thr Gly Thr Thr Val
225                 230                 235                 240

Thr Val Ser Glu Phe Pro Lys Pro Ser Thr Pro Pro Gly Ser Ser Gly
                245                 250                 255

Gly Ala Pro Lys Glu Phe Thr Leu Asp Phe Ser Thr Ala Lys Thr Tyr
            260                 265                 270

Val Asp Ser Leu Asn Val Ile Arg Ser Ala Ile Gly Thr Pro Leu Gln
        275                 280                 285

Thr Ile Ser Ser Gly Gly Thr Ser Leu Leu Met Ile Asp Ser Gly Ser
290                 295                 300

Gly Asp Asn Leu Phe Ala Val Asp Val Arg Gly Ile Asp Pro Glu Glu
305                 310                 315                 320

Gly Arg Phe Asn Asn Leu Arg Leu Ile Val Glu Arg Asn Asn Leu Tyr
                325                 330                 335

Val Thr Gly Phe Val Asn Arg Thr Asn Asn Val Phe Tyr Arg Phe Ala
            340                 345                 350

Asp Phe Ser His Val Thr Phe Pro Gly Thr Thr Ala Val Thr Leu Ser
        355                 360                 365

Gly Asp Ser Ser Tyr Thr Thr Leu Gln Arg Val Ala Gly Ile Ser Arg
370                 375                 380

Thr Gly Met Gln Ile Asn Arg His Ser Leu Thr Thr Ser Tyr Leu Asp
385                 390                 395                 400
```

-continued

```
Leu Met Ser His Ser Gly Thr Ser Leu Thr Gln Ser Val Ala Arg Ala
            405                 410                 415

Met Leu Arg Phe Val Thr Val Thr Ala Glu Ala Leu Arg Phe Arg Gln
        420                 425                 430

Ile Gln Arg Gly Phe Arg Thr Thr Leu Asp Asp Leu Ser Gly Arg Ser
        435                 440                 445

Tyr Val Met Thr Ala Glu Asp Val Asp Leu Thr Leu Asn Trp Gly Arg
    450                 455                 460

Leu Ser Ser Val Leu Pro Asp Tyr His Gly Gln Asp Ser Val Arg Val
465                 470                 475                 480

Gly Arg Ile Ser Phe Gly Ser Ile Asn Ala Ile Leu Gly Ser Val Ala
                485                 490                 495

Leu Ile Leu Asn Ser His His His Ala Ser Arg Val Ala Arg
                500                 505                 510
```

<210> SEQ ID NO 88
<211> LENGTH: 364
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: alphaCD20-FN3 linked to SLT-1A variant 1

<400> SEQUENCE: 88

```
Ala Ser Val Ser Asp Val Pro Arg Asp Leu Glu Val Val Ala Ala Thr
1               5                   10                  15

Pro Thr Ser Leu Leu Ile Ser Trp Cys Arg Gln Arg Cys Ala Asp Ser
            20                  25                  30

Tyr Arg Ile Thr Tyr Gly Glu Thr Gly Gly Asn Ser Pro Val Gln Glu
        35                  40                  45

Phe Thr Val Pro Gly Ser Trp Lys Thr Ala Thr Ile Ser Gly Leu Lys
    50                  55                  60

Pro Gly Val Asp Tyr Thr Ile Thr Val Tyr Val Val Thr His Tyr Tyr
65                  70                  75                  80

Gly Trp Asp Arg Tyr Ser His Pro Ile Ser Ile Asn Tyr Arg Thr Gly
                85                  90                  95

Ser Glu Phe Pro Lys Pro Ser Thr Pro Pro Gly Ser Ser Gly Gly Ala
            100                 105                 110

Pro Lys Glu Phe Thr Leu Asp Phe Ser Thr Ala Lys Thr Tyr Val Asp
        115                 120                 125

Ser Leu Asn Val Ile Arg Ser Ala Ile Gly Thr Pro Leu Gln Thr Ile
    130                 135                 140

Ser Ser Gly Gly Thr Ser Leu Leu Met Ile Asp Ser Gly Ser Gly Asp
145                 150                 155                 160

Asn Leu Phe Ala Val Asp Val Arg Gly Ile Asp Pro Glu Glu Gly Arg
                165                 170                 175

Phe Asn Asn Leu Arg Leu Ile Val Glu Arg Asn Asn Leu Tyr Val Thr
            180                 185                 190

Gly Phe Val Asn Arg Thr Asn Asn Val Phe Tyr Arg Phe Ala Asp Phe
        195                 200                 205

Ser His Val Thr Phe Pro Gly Thr Thr Ala Val Thr Leu Ser Gly Asp
    210                 215                 220

Ser Ser Tyr Thr Thr Leu Gln Arg Val Ala Gly Ile Ser Arg Thr Gly
225                 230                 235                 240
```

```
Met Gln Ile Asn Arg His Ser Leu Thr Thr Ser Tyr Leu Asp Leu Met
                245                 250                 255

Ser His Ser Gly Thr Ser Leu Thr Gln Ser Val Ala Arg Ala Met Leu
            260                 265                 270

Arg Phe Val Thr Val Thr Ala Glu Ala Leu Arg Phe Arg Gln Ile Gln
        275                 280                 285

Arg Gly Phe Arg Thr Thr Leu Asp Asp Leu Ser Gly Arg Ser Tyr Val
    290                 295                 300

Met Thr Ala Glu Asp Val Asp Leu Thr Leu Asn Trp Gly Arg Leu Ser
305                 310                 315                 320

Ser Val Leu Pro Asp Tyr His Gly Gln Asp Ser Val Arg Val Gly Arg
                325                 330                 335

Ile Ser Phe Gly Ser Ile Asn Ala Ile Leu Gly Ser Val Ala Leu Ile
            340                 345                 350

Leu Asn Ser His His His Ala Ser Arg Val Ala Arg
        355                 360

<210> SEQ ID NO 89
<211> LENGTH: 373
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-FN3 linked to SLT-1A variant 2

<400> SEQUENCE: 89

Ala Ser Val

Thr Thr Ala Val Thr Leu Ser Gly Asp Ser Ser Tyr Thr Thr Leu Gln
225                 230                 235                 240

Arg Val Ala Gly Ile Ser Arg Thr Gly Met Gln Ile Asn Arg His Ser
            245                 250                 255

Leu Thr Thr Ser Tyr Leu Asp Leu Met Ser His Ser Gly Thr Ser Leu
        260                 265                 270

Thr Gln Ser Val Ala Arg Ala Met Leu Arg Phe Val Thr Val Thr Ala
    275                 280                 285

Glu Ala Leu Arg Phe Arg Gln Ile Gln Arg Gly Phe Arg Thr Thr Leu
290                 295                 300

Asp Asp Leu Ser Gly Arg Ser Tyr Val Met Thr Ala Glu Asp Val Asp
305                 310                 315                 320

Leu Thr Leu Asn Trp Gly Arg Leu Ser Ser Val Leu Pro Asp Tyr His
            325                 330                 335

Gly Gln Asp Ser Val Arg Val Gly Arg Ile Ser Phe Gly Ser Ile Asn
        340                 345                 350

Ala Ile Leu Gly Ser Val Ala Leu Ile Leu Asn Ser His His His Ala
    355                 360                 365

Ser Arg Val Ala Arg
    370

<210> SEQ ID NO 90
<211> LENGTH: 771
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv1 linked to SLT-1A and with
      chitin binding domain variant 1

<400> SEQUENCE: 90

Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Gln Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ala Gln Leu Arg Pro Asn Tyr Trp Tyr Phe Asp Val Trp
            100                 105                 110

Gly Ala Gly Thr Thr Val Thr Val Ser Ser Gly Gly Gly Gly Ser Gly
        115                 120                 125

Gly Gly Gly Ser Gly Gly Gly Ser Gly Gly Gly Gly Ser Gly Gly
    130                 135                 140

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
                165                 170                 175

Ser Tyr Met His Trp Tyr Gln Gln Lys Pro Gly Ser Ser Pro Lys Pro

```
                180             185                 190
Trp Ile Tyr Ala Thr Ser Asn Leu Ala Ser Gly Val Pro Ala Arg Phe
            195                 200             205
Ser Gly Ser Gly Ser Gly Thr Ser Tyr Ser Leu Thr Ile Ser Arg Val
            210                 215             220
Glu Ala Glu Asp Ala Ala Thr Tyr Tyr Cys Gln Gln Trp Ile Ser Asn
225             230                 235             240
Pro Pro Thr Phe Gly Ala Gly Thr Lys Leu Glu Leu Lys Gly Gly Gly
                245                 250             255
Gly Ser Gly Gly Lys Glu Phe Thr Leu Asp Phe Ser Thr Ala Lys Thr
            260                 265             270
Tyr Val Asp Ser Leu Asn Val Ile Arg Ser Ala Ile Gly Thr Pro Leu
            275                 280             285
Gln Thr Ile Ser Ser Gly Gly Thr Ser Leu Leu Met Ile Asp Ser Gly
            290                 295             300
Ser Gly Asp Asn Leu Phe Ala Val Asp Val Arg Gly Ile Asp Pro Glu
305             310                 315             320
Glu Gly Arg Phe Asn Asn Leu Arg Leu Ile Val Glu Arg Asn Asn Leu
                325                 330             335
Tyr Val Thr Gly Phe Val Asn Arg Thr Asn Asn Val Phe Tyr Arg Phe
                340                 345             350
Ala Asp Phe Ser His Val Thr Phe Pro Gly Thr Thr Ala Val Thr Leu
            355                 360             365
Ser Gly Asp Ser Ser Tyr Thr Thr Leu Gln Arg Val Ala Gly Ile Ser
            370                 375             380
Arg Thr Gly Met Gln Ile Asn Arg His Ser Leu Thr Thr Ser Tyr Leu
385                 390             395             400
Asp Leu Met Ser His Ser Gly Thr Ser Leu Thr Gln Ser Val Ala Arg
                405             410             415
Ala Met Leu Arg Phe Val Thr Val Thr Ala Glu Ala Leu Arg Phe Arg
                420                 425             430
Gln Ile Gln Arg Gly Phe Arg Thr Thr Leu Asp Asp Leu Ser Gly Arg
                435                 440             445
Ser Tyr Val Met Thr Ala Glu Asp Val Asp Leu Thr Leu Asn Trp Gly
            450                 455             460
Arg Leu Ser Ser Val Leu Pro Asp Tyr His Gly Gln Asp Ser Val Arg
465                 470                 475             480
Val Gly Arg Ile Ser Phe Gly Ser Ile Asn Ala Ile Leu Gly Ser Val
                485                 490             495
Ala Leu Ile Leu Asn Cys His His Ala Ser Arg Val Ala Arg Cys
            500             505                 510
Ile Thr Gly Asp Ala Leu Val Ala Leu Pro Glu Gly Glu Ser Val Arg
            515                 520             525
Ile Ala Asp Ile Val Pro Gly Ala Arg Pro Asn Ser Asp Asn Ala Ile
            530                 535             540
Asp Leu Lys Val Leu Asp Arg His Gly Asn Pro Val Leu Ala Asp Arg
545                 550             555                 560
Leu Phe His Ser Gly Glu His Pro Val Tyr Thr Val Arg Thr Val Glu
                565                 570             575
Gly Leu Arg Val Thr Gly Thr Ala Asn His Pro Leu Leu Cys Leu Val
            580                 585             590
Asp Val Ala Gly Val Pro Thr Leu Leu Trp Lys Leu Ile Asp Glu Ile
            595                 600             605
```

-continued

```
Lys Pro Gly Asp Tyr Ala Val Ile Gln Arg Ser Ala Phe Ser Val Asp
    610                 615                 620

Cys Ala Gly Phe Ala Arg Gly Lys Pro Glu Phe Ala Pro Thr Thr Tyr
625                 630                 635                 640

Thr Val Gly Val Pro Gly Leu Val Arg Phe Leu Glu Ala His His Arg
                645                 650                 655

Asp Pro Asp Ala Gln Ala Ile Ala Asp Glu Leu Thr Asp Gly Arg Phe
            660                 665                 670

Tyr Tyr Ala Lys Val Ala Ser Val Thr Asp Ala Gly Val Gln Pro Val
        675                 680                 685

Tyr Ser Leu Arg Val Asp Thr Ala Asp His Ala Phe Ile Thr Asn Gly
    690                 695                 700

Phe Val Ser His Ala Thr Gly Leu Thr Gly Leu Asn Ser Gly Leu Thr
705                 710                 715                 720

Thr Asn Pro Gly Val Ser Ala Trp Gln Val Asn Thr Ala Tyr Thr Ala
                725                 730                 735

Gly Gln Leu Val Thr Tyr Asn Gly Lys Thr Tyr Lys Cys Leu Gln Pro
            740                 745                 750

His Thr Ser Leu Ala Gly Trp Glu Pro Ser Asn Val Pro Ala Leu Trp
        755                 760                 765

Gln Leu Gln
    770

<210> SEQ ID NO 91
<211> LENGTH: 771
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv1 linked to SLT-1A and with
      chitin binding domain variant 2

<400> SEQUENCE: 91

Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Gln Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ala Gln Leu Arg Pro Asn Tyr Trp Tyr Phe Asp Val Trp
            100                 105                 110

Gly Ala Gly Thr Thr Val Thr Val Ser Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
```

```
            165                 170                 175
Ser Tyr Met His Trp Tyr Gln Gln Lys Pro Gly Ser Ser Pro Lys Pro
            180                 185                 190

Trp Ile Tyr Ala Thr Ser Asn Leu Ala Ser Gly Val Pro Ala Arg Phe
            195                 200                 205

Ser Gly Ser Gly Ser Gly Thr Ser Tyr Ser Leu Thr Ile Ser Arg Val
            210                 215                 220

Glu Ala Glu Asp Ala Ala Thr Tyr Tyr Cys Gln Gln Trp Ile Ser Asn
225                 230                 235                 240

Pro Pro Thr Phe Gly Ala Gly Thr Lys Leu Glu Leu Lys Gly Gly Gly
                    245                 250                 255

Gly Ser Gly Gly Lys Glu Phe Thr Leu Asp Phe Ser Thr Ala Lys Thr
                    260                 265                 270

Tyr Val Asp Ser Leu Asn Val Ile Arg Ser Ala Ile Gly Thr Pro Leu
                    275                 280                 285

Gln Thr Ile Ser Ser Gly Gly Thr Ser Leu Leu Met Ile Asp Ser Gly
            290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                    325                 330                 335

Tyr Val Thr Gly Phe Val Asn Arg Thr Asn Asn Val Phe Tyr Arg Phe
                    340                 345                 350

Ala Asp Phe Ser His Val Thr Phe Pro Gly Thr Thr Ala Val Thr Leu
                    355                 360                 365

Ser Gly Asp Ser Ser Tyr Thr Thr Leu Gln Arg Val Ala Gly Ile Ser
            370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                    405                 410                 415

Ala Met Leu Arg Phe Val Thr Val Thr Ala Glu Ala Leu Arg Phe Arg
                    420                 425                 430

Gln Ile Gln Arg Gly Phe Arg Thr Thr Leu Asp Asp Leu Ser Gly Arg
            435                 440                 445

Ser Tyr Val Met Thr Ala Glu Asp Val Asp Leu Thr Leu Asn Trp Gly
            450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                    485                 490                 495

Ala Leu Ile Leu Asn Ser His His Ala Ser Arg Val Ala Arg Cys
                    500                 505                 510

Ile Thr Gly Asp Ala Leu Val Ala Leu Pro Glu Gly Glu Ser Val Arg
            515                 520                 525

Ile Ala Asp Ile Val Pro Gly Ala Arg Pro Asn Ser Asp Asn Ala Ile
            530                 535                 540

Asp Leu Lys Val Leu Asp Arg His Gly Asn Pro Val Leu Ala Asp Arg
545                 550                 555                 560

Leu Phe His Ser Gly Glu His Pro Val Tyr Thr Val Arg Thr Val Glu
                    565                 570                 575

Gly Leu Arg Val Thr Gly Thr Ala Asn His Pro Leu Leu Cys Leu Val
                    580                 585                 590
```

```
Asp Val Ala Gly Val Pro Thr Leu Leu Trp Lys Leu Ile Asp Glu Ile
        595                 600                 605

Lys Pro Gly Asp Tyr Ala Val Ile Gln Arg Ser Ala Phe Ser Val Asp
    610                 615                 620

Cys Ala Gly Phe Ala Arg Gly Lys Pro Glu Phe Ala Pro Thr Thr Tyr
625                 630                 635                 640

Thr Val Gly Val Pro Gly Leu Val Arg Phe Leu Glu Ala His His Arg
                645                 650                 655

Asp Pro Asp Ala Gln Ala Ile Ala Asp Glu Leu Thr Asp Gly Arg Phe
            660                 665                 670

Tyr Tyr Ala Lys Val Ala Ser Val Thr Asp Ala Gly Val Gln Pro Val
        675                 680                 685

Tyr Ser Leu Arg Val Asp Thr Ala Asp His Ala Phe Ile Thr Asn Gly
    690                 695                 700

Phe Val Ser His Ala Thr Gly Leu Thr Gly Leu Asn Ser Gly Leu Thr
705                 710                 715                 720

Thr Asn Pro Gly Val Ser Ala Trp Gln Val Asn Thr Ala Tyr Thr Ala
                725                 730                 735

Gly Gln Leu Val Thr Tyr Asn Gly Lys Thr Tyr Lys Cys Leu Gln Pro
            740                 745                 750

His Thr Ser Leu Ala Gly Trp Glu Pro Ser Asn Val Pro Ala Leu Trp
        755                 760                 765

Gln Leu Gln
    770

<210> SEQ ID NO 92
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A and with
      chitin binding domain variant 1

<400> SEQUENCE: 92

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
        115                 120                 125

Gly Ser Gly Lys Pro Gly Ser Gly Glu Gly Ser Gln Ile Val Leu Ser
    130                 135                 140

Gln Ser Pro Thr Ile Leu Ser Ala Ser Pro Gly Glu Lys Val Thr Met
```

-continued

```
            145                 150                 155                 160
Thr Cys Arg Ala Ser Ser Val Ser Tyr Met Asp Trp Tyr Gln Gln
                    165                 170                 175
Lys Pro Gly Ser Ser Pro Lys Pro Trp Ile Tyr Ala Thr Ser Asn Leu
                180                 185                 190
Ala Ser Gly Val Pro Ala Arg Phe Ser Gly Ser Gly Ser Gly Thr Ser
                195                 200                 205
Tyr Ser Leu Thr Ile Ser Arg Val Glu Ala Glu Asp Ala Ala Thr Tyr
            210                 215                 220
Tyr Cys Gln Gln Trp Ile Ser Asn Pro Pro Thr Phe Gly Ala Gly Thr
225                 230                 235                 240
Lys Leu Glu Leu Lys Glu Phe Pro Lys Pro Ser Thr Pro Pro Gly Ser
                245                 250                 255
Ser Gly Gly Ala Pro Lys Glu Phe Thr Leu Asp Phe Ser Thr Ala Lys
                260                 265                 270
Thr Tyr Val Asp Ser Leu Asn Val Ile Arg Ser Ala Ile Gly Thr Pro
                275                 280                 285
Leu Gln Thr Ile Ser Ser Gly Gly Thr Ser Leu Leu Met Ile Asp Ser
            290                 295                 300
Gly Ser Gly Asp Asn Leu Phe Ala Val Asp Val Arg Gly Ile Asp Pro
305                 310                 315                 320
Glu Glu Gly Arg Phe Asn Asn Leu Arg Leu Ile Val Glu Arg Asn Asn
                325                 330                 335
Leu Tyr Val Thr Gly Phe Val Asn Arg Thr Asn Asn Val Phe Tyr Arg
                340                 345                 350
Phe Ala Asp Phe Ser His Val Thr Phe Pro Gly Thr Thr Ala Val Thr
                355                 360                 365
Leu Ser Gly Asp Ser Ser Tyr Thr Thr Leu Gln Arg Val Ala Gly Ile
            370                 375                 380
Ser Arg Thr Gly Met Gln Ile Asn Arg His Ser Leu Thr Thr Ser Tyr
385                 390                 395                 400
Leu Asp Leu Met Ser His Ser Gly Thr Ser Leu Thr Gln Ser Val Ala
                405                 410                 415
Arg Ala Met Leu Arg Phe Val Thr Val Thr Ala Glu Ala Leu Arg Phe
                420                 425                 430
Arg Gln Ile Gln Arg Gly Phe Arg Thr Thr Leu Asp Asp Leu Ser Gly
            435                 440                 445
Arg Ser Tyr Val Met Thr Ala Glu Asp Val Asp Leu Thr Leu Asn Trp
            450                 455                 460
Gly Arg Leu Ser Ser Val Leu Pro Asp Tyr His Gly Gln Asp Ser Val
465                 470                 475                 480
Arg Val Gly Arg Ile Ser Phe Gly Ser Ile Asn Ala Ile Leu Gly Ser
                485                 490                 495
Val Ala Leu Ile Leu Asn Cys His His His Ala Ser Arg Val Ala Arg
                500                 505                 510
Cys Ile Thr Gly Asp Ala Leu Val Ala Leu Pro Glu Gly Glu Ser Val
            515                 520                 525
Arg Ile Ala Asp Ile Val Pro Gly Ala Arg Pro Asn Ser Asp Asn Ala
            530                 535                 540
Ile Asp Leu Lys Val Leu Asp Arg His Gly Asn Pro Val Leu Ala Asp
545                 550                 555                 560
Arg Leu Phe His Ser Gly Glu His Pro Val Tyr Thr Val Arg Thr Val
                565                 570                 575
```

-continued

Glu Gly Leu Arg Val Thr Gly Thr Ala Asn His Pro Leu Leu Cys Leu
            580                 585                 590

Val Asp Val Ala Gly Val Pro Thr Leu Leu Trp Lys Leu Ile Asp Glu
            595                 600                 605

Ile Lys Pro Gly Asp Tyr Ala Val Ile Gln Arg Ser Ala Phe Ser Val
610                 615                 620

Asp Cys Ala Gly Phe Ala Arg Gly Lys Pro Glu Phe Ala Pro Thr Thr
625                 630                 635                 640

Tyr Thr Val Gly Val Pro Gly Leu Val Arg Phe Leu Glu Ala His His
            645                 650                 655

Arg Asp Pro Asp Ala Gln Ala Ile Ala Asp Glu Leu Thr Asp Gly Arg
            660                 665                 670

Phe Tyr Tyr Ala Lys Val Ala Ser Val Thr Asp Ala Gly Val Gln Pro
            675                 680                 685

Val Tyr Ser Leu Arg Val Asp Thr Ala Asp His Ala Phe Ile Thr Asn
            690                 695                 700

Gly Phe Val Ser His Ala Thr Gly Leu Thr Gly Leu Asn Ser Gly Leu
705                 710                 715                 720

Thr Thr Asn Pro Gly Val Ser Ala Trp Gln Val Asn Thr Ala Tyr Thr
            725                 730                 735

Ala Gly Gln Leu Val Thr Tyr Asn Gly Lys Thr Tyr Lys Cys Leu Gln
            740                 745                 750

Pro His Thr Ser Leu Ala Gly Trp Glu Pro Ser Asn Val Pro Ala Leu
            755                 760                 765

Trp Gln Leu Gln
    770

<210> SEQ ID NO 93
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A and with
      chitin binding domain variant 2

<400> SEQUENCE: 93

Met Gln Val Gln Leu Gln Pro Gly Ala Glu Leu Val Lys Pro Gly
1               5                   10                  15

Ala Ser Val Lys Met Ser Cys Lys Thr Ser Gly Tyr Thr Phe Thr Ser
                20                  25                  30

Tyr Asn Val His Trp Val Lys Gln Thr Pro Gly Gln Gly Leu Glu Trp
            35                  40                  45

Ile Gly Ala Ile Tyr Pro Gly Asn Gly Asp Thr Ser Phe Asn Gln Lys
        50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
                100                 105                 110

Val Trp Gly Ala Gly Thr Thr Val Thr Val Ser Ser Gly Ser Thr Ser
            115                 120                 125

Gly Ser Gly Lys Pro Gly Ser Gly Glu Gly Ser Gln Ile Val Leu Ser

```
            130                 135                 140
Gln Ser Pro Thr Ile Leu Ser Ala Ser Pro Gly Glu Lys Val Thr Met
145                 150                 155                 160

Thr Cys Arg Ala Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
                180                 185                 190

Ala Ser Gly Val Pro Ala Arg Phe Ser Gly Ser Gly Ser Gly Thr Ser
                195                 200                 205

Tyr Ser Leu Thr Ile Ser Arg Val Glu Ala Glu Asp Ala Ala Thr Tyr
                210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255

Ser Gly Gly Ala Pro Lys Glu Phe Thr Leu Asp Phe Ser Thr Ala Lys
                260                 265                 270

Thr Tyr Val Asp Ser Leu Asn Val Ile Arg Ser Ala Ile Gly Thr Pro
                275                 280                 285

Leu Gln Thr Ile Ser Ser Gly Gly Thr Ser Leu Leu Met Ile Asp Ser
                290                 295                 300

Gly Ser Gly Asp Asn Leu Phe Ala Val Asp Val Arg Gly Ile Asp Pro
305                 310                 315                 320

Glu Glu Gly Arg Phe Asn Asn Leu Arg Leu Ile Val Glu Arg Asn Asn
                325                 330                 335

Leu Tyr Val Thr Gly Phe Val Asn Arg Thr Asn Asn Val Phe Tyr Arg
                340                 345                 350

Phe Ala Asp Phe Ser His Val Thr Phe Pro Gly Thr Thr Ala Val Thr
                355                 360                 365

Leu Ser Gly Asp Ser Ser Tyr Thr Thr Leu Gln Arg Val Ala Gly Ile
                370                 375                 380

Ser Arg Thr Gly Met Gln Ile Asn Arg His Ser Leu Thr Thr Ser Tyr
385                 390                 395                 400

Leu Asp Leu Met Ser His Ser Gly Thr Ser Leu Thr Gln Ser Val Ala
                405                 410                 415

Arg Ala Met Leu Arg Phe Val Thr Val Thr Ala Glu Ala Leu Arg Phe
                420                 425                 430

Arg Gln Ile Gln Arg Gly Phe Arg Thr Thr Leu Asp Asp Leu Ser Gly
                435                 440                 445

Arg Ser Tyr Val Met Thr Ala Glu Asp Val Asp Leu Thr Leu Asn Trp
                450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Ser His His Ala Ser Arg Val Ala Arg
                500                 505                 510

Cys Ile Thr Gly Asp Ala Leu Val Ala Leu Pro Glu Gly Glu Ser Val
                515                 520                 525

Arg Ile Ala Asp Ile Val Pro Gly Ala Arg Pro Asn Ser Asp Asn Ala
                530                 535                 540

Ile Asp Leu Lys Val Leu Asp Arg His Gly Asn Pro Val Leu Ala Asp
545                 550                 555                 560
```

```
Arg Leu Phe His Ser Gly Glu His Pro Val Tyr Thr Val Arg Thr Val
                565                 570                 575

Glu Gly Leu Arg Val Thr Gly Thr Ala Asn His Pro Leu Leu Cys Leu
            580                 585                 590

Val Asp Val Ala Gly Val Pro Thr Leu Leu Trp Lys Leu Ile Asp Glu
        595                 600                 605

Ile Lys Pro Gly Asp Tyr Ala Val Ile Gln Arg Ser Ala Phe Ser Val
    610                 615                 620

Asp Cys Ala Gly Phe Ala Arg Gly Lys Pro Glu Phe Ala Pro Thr Thr
625                 630                 635                 640

Tyr Thr Val Gly Val Pro Gly Leu Val Arg Phe Leu Glu Ala His His
                645                 650                 655

Arg Asp Pro Asp Ala Gln Ala Ile Ala Asp Glu Leu Thr Asp Gly Arg
            660                 665                 670

Phe Tyr Tyr Ala Lys Val Ala Ser Val Thr Asp Ala Gly Val Gln Pro
        675                 680                 685

Val Tyr Ser Leu Arg Val Asp Thr Ala Asp His Ala Phe Ile Thr Asn
    690                 695                 700

Gly Phe Val Ser His Ala Thr Gly Leu Thr Gly Leu Asn Ser Gly Leu
705                 710                 715                 720

Thr Thr Asn Pro Gly Val Ser Ala Trp Gln Val Asn Thr Ala Tyr Thr
                725                 730                 735

Ala Gly Gln Leu Val Thr Tyr Asn Gly Lys Thr Tyr Lys Cys Leu Gln
            740                 745                 750

Pro His Thr Ser Leu Ala Gly Trp Glu Pro Ser Asn Val Pro Ala Leu
        755                 760                 765

Trp Gln Leu Gln
    770

<210> SEQ ID NO 94
<211> LENGTH: 781
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A and with
      chitin binding domain variant 3

<400> SEQUENCE: 94

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
```

-continued

```
            115                 120                 125
Gly Ser Gly Lys Pro Gly Ser Gly Glu Gly Ser Gln Ile Val Leu Ser
            130                 135                 140
Gln Ser Pro Thr Ile Leu Ser Ala Ser Pro Gly Glu Lys Val Thr Met
145                 150                 155                 160
Thr Cys Arg Ala Ser Ser Ser Val Ser Tyr Met Asp Trp Tyr Gln Gln
                    165                 170                 175
Lys Pro Gly Ser Ser Pro Lys Pro Trp Ile Tyr Ala Thr Ser Asn Leu
                180                 185                 190
Ala Ser Gly Val Pro Ala Arg Phe Ser Gly Ser Gly Ser Gly Thr Ser
            195                 200                 205
Tyr Ser Leu Thr Ile Ser Arg Val Glu Ala Glu Asp Ala Ala Thr Tyr
        210                 215                 220
Tyr Cys Gln Gln Trp Ile Ser Asn Pro Pro Thr Phe Gly Ala Gly Thr
225                 230                 235                 240
Lys Leu Glu Leu Lys Glu Phe Pro Lys Pro Ser Thr Pro Pro Gly Ser
                    245                 250                 255
Ser Gly Gly Ala Pro Gly Ile Leu Gly Phe Val Phe Thr Leu Lys Glu
                260                 265                 270
Phe Thr Leu Asp Phe Ser Thr Ala Lys Thr Tyr Val Asp Ser Leu Asn
            275                 280                 285
Val Ile Arg Ser Ala Ile Gly Thr Pro Leu Gln Thr Ile Ser Ser Gly
        290                 295                 300
Gly Thr Ser Leu Leu Met Ile Asp Ser Gly Ser Gly Asp Asn Leu Phe
305                 310                 315                 320
Ala Val Asp Val Arg Gly Ile Asp Pro Glu Glu Gly Arg Phe Asn Asn
                    325                 330                 335
Leu Arg Leu Ile Val Glu Arg Asn Asn Leu Tyr Val Thr Gly Phe Val
                340                 345                 350
Asn Arg Thr Asn Asn Val Phe Tyr Arg Phe Ala Asp Phe Ser His Val
            355                 360                 365
Thr Phe Pro Gly Thr Thr Ala Val Thr Leu Ser Gly Asp Ser Ser Tyr
        370                 375                 380
Thr Thr Leu Gln Arg Val Ala Gly Ile Ser Arg Thr Gly Met Gln Ile
385                 390                 395                 400
Asn Arg His Ser Leu Thr Thr Ser Tyr Leu Asp Leu Met Ser His Ser
                    405                 410                 415
Gly Thr Ser Leu Thr Gln Ser Val Ala Arg Ala Met Leu Arg Phe Val
                420                 425                 430
Thr Val Thr Ala Glu Ala Leu Arg Phe Arg Gln Ile Gln Arg Gly Phe
            435                 440                 445
Arg Thr Thr Leu Asp Asp Leu Ser Gly Arg Ser Tyr Val Met Thr Ala
        450                 455                 460
Glu Asp Val Asp Leu Thr Leu Asn Trp Gly Arg Leu Ser Ser Val Leu
465                 470                 475                 480
Pro Asp Tyr His Gly Gln Asp Ser Val Arg Val Gly Arg Ile Ser Phe
                    485                 490                 495
Gly Ser Ile Asn Ala Ile Leu Gly Ser Val Ala Leu Ile Leu Asn Cys
                500                 505                 510
His His His Ala Ser Arg Val Ala Arg Cys Ile Thr Gly Asp Ala Leu
            515                 520                 525
Val Ala Leu Pro Glu Gly Glu Ser Val Arg Ile Ala Asp Ile Val Pro
        530                 535                 540
```

Gly Ala Arg Pro Asn Ser Asp Asn Ala Ile Asp Leu Lys Val Leu Asp
545                 550                 555                 560

Arg His Gly Asn Pro Val Leu Ala Asp Arg Leu Phe His Ser Gly Glu
                565                 570                 575

His Pro Val Tyr Thr Val Arg Thr Val Glu Gly Leu Arg Val Thr Gly
            580                 585                 590

Thr Ala Asn His Pro Leu Leu Cys Leu Val Asp Val Ala Gly Val Pro
        595                 600                 605

Thr Leu Leu Trp Lys Leu Ile Asp Glu Ile Lys Pro Gly Asp Tyr Ala
    610                 615                 620

Val Ile Gln Arg Ser Ala Phe Ser Val Asp Cys Ala Gly Phe Ala Arg
625                 630                 635                 640

Gly Lys Pro Glu Phe Ala Pro Thr Thr Tyr Thr Val Gly Val Pro Gly
                645                 650                 655

Leu Val Arg Phe Leu Glu Ala His His Arg Asp Pro Asp Ala Gln Ala
            660                 665                 670

Ile Ala Asp Glu Leu Thr Asp Gly Arg Phe Tyr Tyr Ala Lys Val Ala
        675                 680                 685

Ser Val Thr Asp Ala Gly Val Gln Pro Val Tyr Ser Leu Arg Val Asp
    690                 695                 700

Thr Ala Asp His Ala Phe Ile Thr Asn Gly Phe Val Ser His Ala Thr
705                 710                 715                 720

Gly Leu Thr Gly Leu Asn Ser Gly Leu Thr Thr Asn Pro Gly Val Ser
                725                 730                 735

Ala Trp Gln Val Asn Thr Ala Tyr Thr Ala Gly Gln Leu Val Thr Tyr
            740                 745                 750

Asn Gly Lys Thr Tyr Lys Cys Leu Gln Pro His Thr Ser Leu Ala Gly
        755                 760                 765

Trp Glu Pro Ser Asn Val Pro Ala Leu Trp Gln Leu Gln
    770                 775                 780

<210> SEQ ID NO 95
<211> LENGTH: 781
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A and with
      chitin binding domain variant 4

<400> SEQUENCE: 95

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp

-continued

```
                100                 105                 110
Val Trp Gly Ala Gly Thr Thr Val Thr Val Ser Ser Gly Ser Thr Ser
            115                 120                 125
Gly Ser Gly Lys Pro Gly Ser Gly Glu Gly Ser Gln Ile Val Leu Ser
            130                 135             140
Gln Ser Pro Thr Ile Leu Ser Ala Ser Pro Gly Glu Lys Val Thr Met
145                 150                 155                 160
Thr Cys Arg Ala Ser Ser Val Ser Tyr Met Asp Trp Tyr Gln Gln
                165                 170                 175
Lys Pro Gly Ser Ser Pro Lys Pro Trp Ile Tyr Ala Thr Ser Asn Leu
            180                 185                 190
Ala Ser Gly Val Pro Ala Arg Phe Ser Gly Ser Gly Ser Gly Thr Ser
            195                 200                 205
Tyr Ser Leu Thr Ile Ser Arg Val Glu Ala Glu Asp Ala Ala Thr Tyr
            210                 215                 220
Tyr Cys Gln Gln Trp Ile Ser Asn Pro Pro Thr Phe Gly Ala Gly Thr
225                 230                 235                 240
Lys Leu Glu Leu Lys Glu Phe Pro Lys Pro Ser Thr Pro Pro Gly Ser
                245                 250                 255
Ser Gly Gly Ala Pro Gly Ile Leu Gly Phe Val Phe Thr Leu Lys Glu
            260                 265                 270
Phe Thr Leu Asp Phe Ser Thr Ala Lys Thr Tyr Val Asp Ser Leu Asn
            275                 280                 285
Val Ile Arg Ser Ala Ile Gly Thr Pro Leu Gln Thr Ile Ser Ser Gly
            290                 295                 300
Gly Thr Ser Leu Leu Met Ile Asp Ser Gly Ser Gly Asp Asn Leu Phe
305                 310                 315                 320
Ala Val Asp Val Arg Gly Ile Asp Pro Glu Glu Gly Arg Phe Asn Asn
                325                 330                 335
Leu Arg Leu Ile Val Glu Arg Asn Asn Leu Tyr Val Thr Gly Phe Val
            340                 345                 350
Asn Arg Thr Asn Asn Val Phe Tyr Arg Phe Ala Asp Phe Ser His Val
            355                 360                 365
Thr Phe Pro Gly Thr Thr Ala Val Thr Leu Ser Gly Asp Ser Ser Tyr
            370                 375                 380
Thr Thr Leu Gln Arg Val Ala Gly Ile Ser Arg Thr Gly Met Gln Ile
385                 390                 395                 400
Asn Arg His Ser Leu Thr Thr Ser Tyr Leu Asp Leu Met Ser His Ser
                405                 410                 415
Gly Thr Ser Leu Thr Gln Ser Val Ala Arg Ala Met Leu Arg Phe Val
            420                 425                 430
Thr Val Thr Ala Glu Ala Leu Arg Phe Arg Gln Ile Gln Arg Gly Phe
            435                 440                 445
Arg Thr Thr Leu Asp Asp Leu Ser Gly Arg Ser Tyr Val Met Thr Ala
            450                 455                 460
Glu Asp Val Asp Leu Thr Leu Asn Trp Gly Arg Leu Ser Ser Val Leu
465                 470                 475                 480
Pro Asp Tyr His Gly Gln Asp Ser Val Arg Val Gly Arg Ile Ser Phe
                485                 490                 495
Gly Ser Ile Asn Ala Ile Leu Gly Ser Val Ala Leu Ile Leu Asn Ser
            500                 505                 510
His His His Ala Ser Arg Val Ala Arg Cys Ile Thr Gly Asp Ala Leu
            515                 520                 525
```

Val Ala Leu Pro Glu Gly Glu Ser Val Arg Ile Ala Asp Ile Val Pro
    530                 535                 540

Gly Ala Arg Pro Asn Ser Asp Asn Ala Ile Asp Leu Lys Val Leu Asp
545                 550                 555                 560

Arg His Gly Asn Pro Val Leu Ala Asp Arg Leu Phe His Ser Gly Glu
                565                 570                 575

His Pro Val Tyr Thr Val Arg Thr Val Glu Gly Leu Arg Val Thr Gly
            580                 585                 590

Thr Ala Asn His Pro Leu Leu Cys Leu Val Asp Val Ala Gly Val Pro
        595                 600                 605

Thr Leu Leu Trp Lys Leu Ile Asp Glu Ile Lys Pro Gly Asp Tyr Ala
    610                 615                 620

Val Ile Gln Arg Ser Ala Phe Ser Val Asp Cys Ala Gly Phe Ala Arg
625                 630                 635                 640

Gly Lys Pro Glu Phe Ala Pro Thr Thr Tyr Thr Val Gly Val Pro Gly
                645                 650                 655

Leu Val Arg Phe Leu Glu Ala His His Arg Asp Pro Asp Ala Gln Ala
            660                 665                 670

Ile Ala Asp Glu Leu Thr Asp Gly Arg Phe Tyr Tyr Ala Lys Val Ala
        675                 680                 685

Ser Val Thr Asp Ala Gly Val Gln Pro Val Tyr Ser Leu Arg Val Asp
    690                 695                 700

Thr Ala Asp His Ala Phe Ile Thr Asn Gly Phe Val Ser His Ala Thr
705                 710                 715                 720

Gly Leu Thr Gly Leu Asn Ser Gly Leu Thr Thr Asn Pro Gly Val Ser
                725                 730                 735

Ala Trp Gln Val Asn Thr Ala Tyr Thr Ala Gly Gln Leu Val Thr Tyr
            740                 745                 750

Asn Gly Lys Thr Tyr Lys Cys Leu Gln Pro His Thr Ser Leu Ala Gly
        755                 760                 765

Trp Glu Pro Ser Asn Val Pro Ala Leu Trp Gln Leu Gln
    770                 775                 780

<210> SEQ ID NO 96
<211> LENGTH: 782
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A and with
      chitin binding domain variant 5

<400> SEQUENCE: 96

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr

-continued

```
                85                  90                  95
Cys Ala Arg Ser Asn Tyr Tyr Gly Ser Ser Tyr Val Trp Phe Phe Asp
                100                 105                 110
Val Trp Gly Ala Gly Thr Thr Val Thr Val Ser Ser Gly Gly Gly Gly
            115                 120                 125
Ser Gly Gly Gly Gly Ser Gly Gly Gly Ser Gly Gly Gly Ser
        130                 135                 140
Gly Gly Gly Gly Ser Gln Ile Val Leu Ser Gln Ser Pro Thr Ile Leu
145                 150                 155                 160
Ser Ala Ser Pro Gly Glu Lys Val Thr Met Thr Cys Arg Ala Ser Ser
                165                 170                 175
Ser Val Ser Tyr Met Asp Trp Tyr Gln Gln Lys Pro Gly Ser Ser Pro
            180                 185                 190
Lys Pro Trp Ile Tyr Ala Thr Ser Asn Leu Ala Ser Gly Val Pro Ala
        195                 200                 205
Arg Phe Ser Gly Ser Gly Ser Gly Thr Ser Tyr Ser Leu Thr Ile Ser
    210                 215                 220
Arg Val Glu Ala Glu Asp Ala Ala Thr Tyr Tyr Cys Gln Gln Trp Ile
225                 230                 235                 240
Ser Asn Pro Pro Thr Phe Gly Ala Gly Thr Lys Leu Glu Leu Lys Glu
                245                 250                 255
Phe Pro Lys Pro Ser Thr Pro Pro Gly Ser Ser Gly Gly Ala Pro Lys
            260                 265                 270
Glu Phe Thr Leu Asp Phe Ser Thr Ala Lys Thr Tyr Val Asp Ser Leu
        275                 280                 285
Asn Val Ile Arg Ser Ala Ile Gly Thr Pro Leu Gln Thr Ile Ser Ser
    290                 295                 300
Gly Gly Thr Ser Leu Leu Met Ile Asp Ser Gly Ser Gly Asp Asn Leu
305                 310                 315                 320
Phe Ala Val Asp Val Arg Gly Ile Asp Pro Glu Glu Gly Arg Phe Asn
                325                 330                 335
Asn Leu Arg Leu Ile Val Glu Arg Asn Asn Leu Tyr Val Thr Gly Phe
            340                 345                 350
Val Asn Arg Thr Asn Asn Val Phe Tyr Arg Phe Ala Asp Phe Ser His
        355                 360                 365
Val Thr Phe Pro Gly Thr Thr Ala Val Thr Leu Ser Gly Asp Ser Ser
    370                 375                 380
Tyr Thr Thr Leu Gln Arg Val Ala Gly Ile Ser Arg Thr Gly Met Gln
385                 390                 395                 400
Ile Asn Arg His Ser Leu Thr Thr Ser Tyr Leu Asp Leu Met Ser His
                405                 410                 415
Ser Gly Thr Ser Leu Thr Gln Ser Val Ala Arg Ala Met Leu Arg Phe
            420                 425                 430
Val Thr Val Thr Ala Glu Ala Leu Arg Phe Arg Gln Ile Gln Arg Gly
        435                 440                 445
Phe Arg Thr Thr Leu Asp Asp Leu Ser Gly Arg Ser Tyr Val Met Thr
    450                 455                 460
Ala Glu Asp Val Asp Leu Thr Leu Asn Trp Gly Arg Leu Ser Ser Val
465                 470                 475                 480
Leu Pro Asp Tyr His Gly Gln Asp Ser Val Arg Val Gly Arg Ile Ser
                485                 490                 495
Phe Gly Ser Ile Asn Ala Ile Leu Gly Ser Val Ala Leu Ile Leu Asn
            500                 505                 510
```

Ser His His His Ala Ser Arg Val Ala Arg Cys Ile Thr Gly Asp Ala
            515                 520                 525

Leu Val Ala Leu Pro Glu Gly Glu Ser Val Arg Ile Ala Asp Ile Val
            530                 535                 540

Pro Gly Ala Arg Pro Asn Ser Asp Asn Ala Ile Asp Leu Lys Val Leu
545                 550                 555                 560

Asp Arg His Gly Asn Pro Val Leu Ala Asp Arg Leu Phe His Ser Gly
            565                 570                 575

Glu His Pro Val Tyr Thr Val Arg Thr Val Glu Gly Leu Arg Val Thr
            580                 585                 590

Gly Thr Ala Asn His Pro Leu Leu Cys Leu Val Asp Val Ala Gly Val
            595                 600                 605

Pro Thr Leu Leu Trp Lys Leu Ile Asp Glu Ile Lys Pro Gly Asp Tyr
            610                 615                 620

Ala Val Ile Gln Arg Ser Ala Phe Ser Val Asp Cys Ala Gly Phe Ala
625                 630                 635                 640

Arg Gly Lys Pro Glu Phe Ala Pro Thr Thr Tyr Thr Val Gly Val Pro
            645                 650                 655

Gly Leu Val Arg Phe Leu Glu Ala His His Arg Asp Pro Asp Ala Gln
            660                 665                 670

Ala Ile Ala Asp Glu Leu Thr Asp Gly Arg Phe Tyr Tyr Ala Lys Val
            675                 680                 685

Ala Ser Val Thr Asp Ala Gly Val Gln Pro Val Tyr Ser Leu Arg Val
            690                 695                 700

Asp Thr Ala Asp His Ala Phe Ile Thr Asn Gly Phe Val Ser His Ala
705                 710                 715                 720

Thr Gly Leu Thr Gly Leu Asn Ser Gly Leu Thr Thr Asn Pro Gly Val
            725                 730                 735

Ser Ala Trp Gln Val Asn Thr Ala Tyr Thr Ala Gly Gln Leu Val Thr
            740                 745                 750

Tyr Asn Gly Lys Thr Tyr Lys Cys Leu Gln Pro His Thr Ser Leu Ala
            755                 760                 765

Gly Trp Glu Pro Ser Asn Val Pro Ala Leu Trp Gln Leu Gln
            770                 775                 780

<210> SEQ ID NO 97
<211> LENGTH: 773
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv3 linked to SLT-1A and with
      chitin binding domain variant 1

<400> SEQUENCE: 97

Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Arg Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala

```
                65                  70                  75                  80
Tyr Met Gln Leu Ser Ser Leu Thr Ser Glu Asp Ser Ala Val Tyr Tyr
                        85                  90                  95
Cys Ala Arg Ser Thr Tyr Tyr Gly Gly Asp Trp Tyr Phe Asn Val Trp
                        100                 105                 110
Gly Ala Gly Thr Thr Val Thr Val Ser Ala Gly Ser Thr Ser Gly Ser
                        115                 120                 125
Gly Lys Pro Gly Ser Gly Glu Gly Ser Thr Lys Gly Gln Ile Val Leu
            130                 135                 140
Ser Gln Ser Pro Ala Ile Leu Ser Ala Ser Pro Gly Glu Lys Val Thr
145                 150                 155                 160
Met Thr Cys Arg Ala Ser Ser Val Ser Tyr Ile His Trp Phe Gln
                        165                 170                 175
Gln Lys Pro Gly Ser Ser Pro Lys Pro Trp Ile Tyr Ala Thr Ser Asn
            180                 185                 190
Leu Ala Ser Gly Val Pro Val Arg Phe Ser Gly Ser Gly Ser Gly Thr
                195                 200                 205
Ser Tyr Ser Leu Thr Ile Ser Arg Val Glu Ala Glu Asp Ala Ala Thr
            210                 215                 220
Tyr Tyr Cys Gln Gln Trp Thr Ser Asn Pro Pro Thr Phe Gly Gly Gly
225                 230                 235                 240
Thr Lys Leu Glu Ile Lys Glu Phe Pro Lys Pro Ser Thr Pro Pro Gly
                245                 250                 255
Ser Ser Gly Gly Ala Pro Lys Glu Phe Thr Leu Asp Phe Ser Thr Ala
                260                 265                 270
Lys Thr Tyr Val Asp Ser Leu Asn Val Ile Arg Ser Ala Ile Gly Thr
            275                 280                 285
Pro Leu Gln Thr Ile Ser Ser Gly Gly Thr Ser Leu Leu Met Ile Asp
            290                 295                 300
Ser Gly Ser Gly Asp Asn Leu Phe Ala Val Asp Val Arg Gly Ile Asp
305                 310                 315                 320
Pro Glu Glu Gly Arg Phe Asn Asn Leu Arg Leu Ile Val Glu Arg Asn
                325                 330                 335
Asn Leu Tyr Val Thr Gly Phe Val Asn Arg Thr Asn Asn Val Phe Tyr
                340                 345                 350
Arg Phe Ala Asp Phe Ser His Val Thr Phe Pro Gly Thr Thr Ala Val
            355                 360                 365
Thr Leu Ser Gly Asp Ser Ser Tyr Thr Thr Leu Gln Arg Val Ala Gly
        370                 375                 380
Ile Ser Arg Thr Gly Met Gln Ile Asn Arg His Ser Leu Thr Thr Ser
385                 390                 395                 400
Tyr Leu Asp Leu Met Ser His Ser Gly Thr Ser Leu Thr Gln Ser Val
                405                 410                 415
Ala Arg Ala Met Leu Arg Phe Val Thr Val Thr Ala Glu Ala Leu Arg
                420                 425                 430
Phe Arg Gln Ile Gln Arg Gly Phe Arg Thr Thr Leu Asp Asp Leu Ser
            435                 440                 445
Gly Arg Ser Tyr Val Met Thr Ala Glu Asp Val Asp Leu Thr Leu Asn
            450                 455                 460
Trp Gly Arg Leu Ser Ser Val Leu Pro Asp Tyr His Gly Gln Asp Ser
465                 470                 475                 480
Val Arg Val Gly Arg Ile Ser Phe Gly Ser Ile Asn Ala Ile Leu Gly
            485                 490                 495
```

Ser Val Ala Leu Ile Leu Asn Cys His His His Ala Ser Arg Val Ala
            500                 505                 510

Arg Cys Ile Thr Gly Asp Ala Leu Val Ala Leu Pro Glu Gly Glu Ser
            515                 520                 525

Val Arg Ile Ala Asp Ile Val Pro Gly Ala Arg Pro Asn Ser Asp Asn
            530                 535                 540

Ala Ile Asp Leu Lys Val Leu Asp Arg His Gly Asn Pro Val Leu Ala
545                 550                 555                 560

Asp Arg Leu Phe His Ser Gly Glu His Pro Val Tyr Thr Val Arg Thr
                565                 570                 575

Val Glu Gly Leu Arg Val Thr Gly Thr Ala Asn His Pro Leu Leu Cys
            580                 585                 590

Leu Val Asp Val Ala Gly Val Pro Thr Leu Leu Trp Lys Leu Ile Asp
            595                 600                 605

Glu Ile Lys Pro Gly Asp Tyr Ala Val Ile Gln Arg Ser Ala Phe Ser
            610                 615                 620

Val Asp Cys Ala Gly Phe Ala Arg Gly Lys Pro Glu Phe Ala Pro Thr
625                 630                 635                 640

Thr Tyr Thr Val Gly Val Pro Gly Leu Val Arg Phe Leu Glu Ala His
                645                 650                 655

His Arg Asp Pro Asp Ala Gln Ala Ile Ala Asp Glu Leu Thr Asp Gly
            660                 665                 670

Arg Phe Tyr Tyr Ala Lys Val Ala Ser Val Thr Asp Ala Gly Val Gln
            675                 680                 685

Pro Val Tyr Ser Leu Arg Val Asp Thr Ala Asp His Ala Phe Ile Thr
            690                 695                 700

Asn Gly Phe Val Ser His Ala Thr Gly Leu Thr Gly Leu Asn Ser Gly
705                 710                 715                 720

Leu Thr Thr Asn Pro Gly Val Ser Ala Trp Gln Val Asn Thr Ala Tyr
                725                 730                 735

Thr Ala Gly Gln Leu Val Thr Tyr Asn Gly Lys Thr Tyr Lys Cys Leu
            740                 745                 750

Gln Pro His Thr Ser Leu Ala Gly Trp Glu Pro Ser Asn Val Pro Ala
            755                 760                 765

Leu Trp Gln Leu Gln
    770

<210> SEQ ID NO 98
<211> LENGTH: 773
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv3 linked to SLT-1A and with
      chitin binding domain variant 2

<400> SEQUENCE: 98

Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Arg Gly Leu Glu Trp
        35                  40                  45

Ile Gly Ala Ile Tyr Pro Gly Asn Gly Asp Thr Ser Tyr Asn Gln Lys

```
                50              55              60
Phe Lys Gly Lys Ala Thr Leu Thr Ala Asp Lys Ser Ser Ser Thr Ala
 65                  70                  75                  80

Tyr Met Gln Leu Ser Ser Leu Thr Ser Glu Asp Ser Ala Val Tyr Tyr
                 85                  90                  95

Cys Ala Arg Ser Thr Tyr Tyr Gly Gly Asp Trp Tyr Phe Asn Val Trp
            100                 105                 110

Gly Ala Gly Thr Thr Val Thr Val Ser Ala Gly Ser Thr Ser Gly Ser
                115                 120                 125

Gly Lys Pro Gly Ser Gly Glu Gly Ser Thr Lys Gly Gln Ile Val Leu
        130                 135                 140

Ser Gln Ser Pro Ala Ile Leu Ser Ala Ser Pro Gly Glu Lys Val Thr
145                 150                 155                 160

Met Thr Cys Arg Ala Ser Ser Ser Val Ser Tyr Ile His Trp Phe Gln
            165                 170                 175

Gln Lys Pro Gly Ser Ser Pro Lys Pro Trp Ile Tyr Ala Thr Ser Asn
            180                 185                 190

Leu Ala Ser Gly Val Pro Val Arg Phe Ser Gly Ser Gly Ser Gly Thr
            195                 200                 205

Ser Tyr Ser Leu Thr Ile Ser Arg Val Glu Ala Glu Asp Ala Ala Thr
210                 215                 220

Tyr Tyr Cys Gln Gln Trp Thr Ser Asn Pro Pro Thr Phe Gly Gly Gly
225                 230                 235                 240

Thr Lys Leu Glu Ile Lys Glu Phe Pro Lys Pro Ser Thr Pro Pro Gly
                245                 250                 255

Ser Ser Gly Gly Ala Pro Lys Glu Phe Thr Leu Asp Phe Ser Thr Ala
            260                 265                 270

Lys Thr Tyr Val Asp Ser Leu Asn Val Ile Arg Ser Ala Ile Gly Thr
            275                 280                 285

Pro Leu Gln Thr Ile Ser Ser Gly Gly Thr Ser Leu Leu Met Ile Asp
        290                 295                 300

Ser Gly Ser Gly Asp Asn Leu Phe Ala Val Asp Val Arg Gly Ile Asp
305                 310                 315                 320

Pro Glu Glu Gly Arg Phe Asn Asn Leu Arg Leu Ile Val Glu Arg Asn
                325                 330                 335

Asn Leu Tyr Val Thr Gly Phe Val Asn Arg Thr Asn Asn Val Phe Tyr
            340                 345                 350

Arg Phe Ala Asp Phe Ser His Val Thr Phe Pro Gly Thr Thr Ala Val
            355                 360                 365

Thr Leu Ser Gly Asp Ser Ser Tyr Thr Thr Leu Gln Arg Val Ala Gly
        370                 375                 380

Ile Ser Arg Thr Gly Met Gln Ile Asn Arg His Ser Leu Thr Thr Ser
385                 390                 395                 400

Tyr Leu Asp Leu Met Ser His Ser Gly Thr Ser Leu Thr Gln Ser Val
                405                 410                 415

Ala Arg Ala Met Leu Arg Phe Val Thr Val Thr Ala Glu Ala Leu Arg
            420                 425                 430

Phe Arg Gln Ile Gln Arg Gly Phe Arg Thr Thr Leu Asp Asp Leu Ser
            435                 440                 445

Gly Arg Ser Tyr Val Met Thr Ala Glu Asp Val Asp Leu Thr Leu Asn
        450                 455                 460

Trp Gly Arg Leu Ser Ser Val Leu Pro Asp Tyr His Gly Gln Asp Ser
465                 470                 475                 480
```

-continued

```
Val Arg Val Gly Arg Ile Ser Phe Gly Ser Ile Asn Ala Ile Leu Gly
                485                 490                 495

Ser Val Ala Leu Ile Leu Asn Ser His His Ala Ser Arg Val Ala
            500                 505                 510

Arg Cys Ile Thr Gly Asp Ala Leu Val Ala Leu Pro Glu Gly Glu Ser
        515                 520                 525

Val Arg Ile Ala Asp Ile Val Pro Gly Ala Arg Pro Asn Ser Asp Asn
        530                 535                 540

Ala Ile Asp Leu Lys Val Leu Asp Arg His Gly Asn Pro Val Leu Ala
545                 550                 555                 560

Asp Arg Leu Phe His Ser Gly Glu His Pro Val Tyr Thr Val Arg Thr
                565                 570                 575

Val Glu Gly Leu Arg Val Thr Gly Thr Ala Asn His Pro Leu Leu Cys
            580                 585                 590

Leu Val Asp Val Ala Gly Val Pro Thr Leu Leu Trp Lys Leu Ile Asp
        595                 600                 605

Glu Ile Lys Pro Gly Asp Tyr Ala Val Ile Gln Arg Ser Ala Phe Ser
    610                 615                 620

Val Asp Cys Ala Gly Phe Ala Arg Gly Lys Pro Glu Phe Ala Pro Thr
625                 630                 635                 640

Thr Tyr Thr Val Gly Val Pro Gly Leu Val Arg Phe Leu Glu Ala His
                645                 650                 655

His Arg Asp Pro Asp Ala Gln Ala Ile Ala Asp Glu Leu Thr Asp Gly
            660                 665                 670

Arg Phe Tyr Tyr Ala Lys Val Ala Ser Val Thr Asp Ala Gly Val Gln
        675                 680                 685

Pro Val Tyr Ser Leu Arg Val Asp Thr Ala Asp His Ala Phe Ile Thr
    690                 695                 700

Asn Gly Phe Val Ser His Ala Thr Gly Leu Thr Gly Leu Asn Ser Gly
705                 710                 715                 720

Leu Thr Thr Asn Pro Gly Val Ser Ala Trp Gln Val Asn Thr Ala Tyr
                725                 730                 735

Thr Ala Gly Gln Leu Val Thr Tyr Asn Gly Lys Thr Tyr Lys Cys Leu
            740                 745                 750

Gln Pro His Thr Ser Leu Ala Gly Trp Glu Pro Ser Asn Val Pro Ala
        755                 760                 765

Leu Trp Gln Leu Gln
        770
```

```
<210> SEQ ID NO 99
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv4 linked to SLT-1A and with
      chitin binding domain

<400> SEQUENCE: 99

Met Glu Val Gln Leu Val Glu Ser Gly Gly Gly Leu Val Gln Pro Gly
1               5                   10                  15

Arg Ser Leu Arg Leu Ser Cys Ala Ala Ser Gly Phe Thr Phe Asn Asp
            20                  25                  30

Tyr Ala Met His Trp Val Arg Gln Ala Pro Gly Lys Gly Leu Glu Trp
```

```
                35                  40                  45
Val Ser Thr Ile Ser Trp Asn Ser Gly Ser Ile Gly Tyr Ala Asp Ser
 50                  55                  60
Val Lys Gly Arg Phe Thr Ile Ser Arg Asp Asn Ala Lys Lys Ser Leu
 65                  70                  75                  80
Tyr Leu Gln Met Asn Ser Leu Arg Ala Glu Asp Thr Ala Leu Tyr Tyr
                 85                  90                  95
Cys Ala Lys Asp Ile Gln Tyr Gly Asn Tyr Tyr Tyr Gly Met Asp Val
                100                 105                 110
Trp Gly Gln Gly Thr Thr Val Thr Val Ser Ser Gly Ser Thr Ser Gly
                115                 120                 125
Ser Gly Lys Pro Gly Ser Gly Glu Gly Ser Glu Ile Val Leu Thr Gln
    130                 135                 140
Ser Pro Ala Thr Leu Ser Leu Ser Pro Gly Glu Arg Ala Thr Leu Ser
145                 150                 155                 160
Cys Arg Ala Ser Gln Ser Val Ser Ser Tyr Leu Ala Trp Tyr Gln Gln
                165                 170                 175
Lys Pro Gly Gln Ala Pro Arg Leu Leu Ile Tyr Asp Ala Ser Asn Arg
                180                 185                 190
Ala Thr Gly Ile Pro Ala Arg Phe Ser Gly Ser Gly Ser Gly Thr Asp
                195                 200                 205
Phe Thr Leu Thr Ile Ser Ser Leu Glu Pro Glu Asp Phe Ala Val Tyr
    210                 215                 220
Tyr Cys Gln Gln Arg Ser Asn Trp Pro Ile Thr Phe Gly Gln Gly Thr
225                 230                 235                 240
Arg Leu Glu Ile Lys Glu Phe Pro Lys Pro Ser Thr Pro Pro Gly Ser
                245                 250                 255
Ser Gly Gly Ala Pro Lys Glu Phe Thr Leu Asp Phe Ser Thr Ala Lys
                260                 265                 270
Thr Tyr Val Asp Ser Leu Asn Val Ile Arg Ser Ala Ile Gly Thr Pro
                275                 280                 285
Leu Gln Thr Ile Ser Ser Gly Gly Thr Ser Leu Leu Met Ile Asp Ser
    290                 295                 300
Gly Ser Gly Asp Asn Leu Phe Ala Val Asp Val Arg Gly Ile Asp Pro
305                 310                 315                 320
Glu Glu Gly Arg Phe Asn Asn Leu Arg Leu Ile Val Glu Arg Asn Asn
                325                 330                 335
Leu Tyr Val Thr Gly Phe Val Asn Arg Thr Asn Asn Val Phe Tyr Arg
                340                 345                 350
Phe Ala Asp Phe Ser His Val Thr Phe Pro Gly Thr Thr Ala Val Thr
                355                 360                 365
Leu Ser Gly Asp Ser Ser Tyr Thr Thr Leu Gln Arg Val Ala Gly Ile
    370                 375                 380
Ser Arg Thr Gly Met Gln Ile Asn Arg His Ser Leu Thr Thr Ser Tyr
385                 390                 395                 400
Leu Asp Leu Met Ser His Ser Gly Thr Ser Leu Thr Gln Ser Val Ala
                405                 410                 415
Arg Ala Met Leu Arg Phe Val Thr Val Thr Ala Glu Ala Leu Arg Phe
                420                 425                 430
Arg Gln Ile Gln Arg Gly Phe Arg Thr Thr Leu Asp Asp Leu Ser Gly
                435                 440                 445
Arg Ser Tyr Val Met Thr Ala Glu Asp Val Asp Leu Thr Leu Asn Trp
    450                 455                 460
```

-continued

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Ser His His His Ala Ser Arg Val Ala Arg
            500                 505                 510

Cys Ile Thr Gly Asp Ala Leu Val Ala Leu Pro Glu Gly Glu Ser Val
            515                 520                 525

Arg Ile Ala Asp Ile Val Pro Gly Ala Arg Pro Asn Ser Asp Asn Ala
            530                 535                 540

Ile Asp Leu Lys Val Leu Asp Arg His Gly Asn Pro Val Leu Ala Asp
545                 550                 555                 560

Arg Leu Phe His Ser Gly Glu His Pro Val Tyr Thr Val Arg Thr Val
                565                 570                 575

Glu Gly Leu Arg Val Thr Gly Thr Ala Asn His Pro Leu Leu Cys Leu
                580                 585                 590

Val Asp Val Ala Gly Val Pro Thr Leu Leu Trp Lys Leu Ile Asp Glu
            595                 600                 605

Ile Lys Pro Gly Asp Tyr Ala Val Ile Gln Arg Ser Ala Phe Ser Val
            610                 615                 620

Asp Cys Ala Gly Phe Ala Arg Gly Lys Pro Glu Phe Ala Pro Thr Thr
625                 630                 635                 640

Tyr Thr Val Gly Val Pro Gly Leu Val Arg Phe Leu Glu Ala His His
                645                 650                 655

Arg Asp Pro Asp Ala Gln Ala Ile Ala Asp Glu Leu Thr Asp Gly Arg
                660                 665                 670

Phe Tyr Tyr Ala Lys Val Ala Ser Val Thr Asp Ala Gly Val Gln Pro
            675                 680                 685

Val Tyr Ser Leu Arg Val Asp Thr Ala Asp His Ala Phe Ile Thr Asn
            690                 695                 700

Gly Phe Val Ser His Ala Thr Gly Leu Thr Gly Leu Asn Ser Gly Leu
705                 710                 715                 720

Thr Thr Asn Pro Gly Val Ser Ala Trp Gln Val Asn Thr Ala Tyr Thr
                725                 730                 735

Ala Gly Gln Leu Val Thr Tyr Asn Gly Lys Thr Tyr Lys Cys Leu Gln
                740                 745                 750

Pro His Thr Ser Leu Ala Gly Trp Glu Pro Ser Asn Val Pro Ala Leu
            755                 760                 765

Trp Gln Leu Gln
    770

<210> SEQ ID NO 100
<211> LENGTH: 772
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv5 linked to SLT-1A and with
      chitin binding domain

<400> SEQUENCE: 100

Met Glu Ile Val Leu Thr Gln Ser Pro Ala Thr Leu Ser Leu Ser Pro
1               5                   10                  15

Gly Glu Arg Ala Thr Leu Ser Cys Arg Ala Ser Gln Ser Val Ser Ser

```
                20                  25                  30
Tyr Leu Ala Trp Tyr Gln Gln Lys Pro Gly Gln Ala Pro Arg Leu Leu
            35                  40                  45
Ile Tyr Asp Ala Ser Asn Arg Ala Thr Gly Ile Pro Ala Arg Phe Ser
        50                  55                  60
Gly Ser Gly Ser Gly Thr Asp Phe Thr Leu Thr Ile Ser Ser Leu Glu
65                  70                  75                  80
Pro Glu Asp Phe Ala Val Tyr Tyr Cys Gln Gln Arg Ser Asn Trp Pro
                85                  90                  95
Ile Thr Phe Gly Gln Gly Thr Arg Leu Glu Ile Lys Gly Ser Thr Ser
            100                 105                 110
Gly Ser Gly Lys Pro Gly Ser Gly Glu Gly Ser Glu Val Gln Leu Val
        115                 120                 125
Glu Ser Gly Gly Gly Leu Val Gln Pro Gly Arg Ser Leu Arg Leu Ser
130                 135                 140
Cys Ala Ala Ser Gly Phe Thr Phe Asn Asp Tyr Ala Met His Trp Val
145                 150                 155                 160
Arg Gln Ala Pro Gly Lys Gly Leu Glu Trp Val Ser Thr Ile Ser Trp
                165                 170                 175
Asn Ser Gly Ser Ile Gly Tyr Ala Asp Ser Val Lys Gly Arg Phe Thr
            180                 185                 190
Ile Ser Arg Asp Asn Ala Lys Lys Ser Leu Tyr Leu Gln Met Asn Ser
        195                 200                 205
Leu Arg Ala Glu Asp Thr Ala Leu Tyr Tyr Cys Ala Lys Asp Ile Gln
210                 215                 220
Tyr Gly Asn Tyr Tyr Tyr Gly Met Asp Val Trp Gly Gln Gly Thr Thr
225                 230                 235                 240
Val Thr Val Ser Ser Glu Phe Pro Lys Pro Ser Thr Pro Pro Gly Ser
                245                 250                 255
Ser Gly Gly Ala Pro Lys Glu Phe Thr Leu Asp Phe Ser Thr Ala Lys
            260                 265                 270
Thr Tyr Val Asp Ser Leu Asn Val Ile Arg Ser Ala Ile Gly Thr Pro
        275                 280                 285
Leu Gln Thr Ile Ser Ser Gly Gly Thr Ser Leu Leu Met Ile Asp Ser
290                 295                 300
Gly Ser Gly Asp Asn Leu Phe Ala Val Asp Val Arg Gly Ile Asp Pro
305                 310                 315                 320
Glu Glu Gly Arg Phe Asn Asn Leu Arg Leu Ile Val Glu Arg Asn Asn
                325                 330                 335
Leu Tyr Val Thr Gly Phe Val Asn Arg Thr Asn Asn Val Phe Tyr Arg
            340                 345                 350
Phe Ala Asp Phe Ser His Val Thr Phe Pro Gly Thr Thr Ala Val Thr
        355                 360                 365
Leu Ser Gly Asp Ser Ser Tyr Thr Thr Leu Gln Arg Val Ala Gly Ile
370                 375                 380
Ser Arg Thr Gly Met Gln Ile Asn Arg His Ser Leu Thr Thr Ser Tyr
385                 390                 395                 400
Leu Asp Leu Met Ser His Ser Gly Thr Ser Leu Thr Gln Ser Val Ala
                405                 410                 415
Arg Ala Met Leu Arg Phe Val Thr Val Thr Ala Glu Ala Leu Arg Phe
            420                 425                 430
Arg Gln Ile Gln Arg Gly Phe Arg Thr Thr Leu Asp Asp Leu Ser Gly
        435                 440                 445
```

```
Arg Ser Tyr Val Met Thr Ala Glu Asp Val Asp Leu Thr Leu Asn Trp
    450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Ser His His His Ala Ser Arg Val Ala Arg
                500                 505                 510

Cys Ile Thr Gly Asp Ala Leu Val Ala Leu Pro Glu Gly Glu Ser Val
                515                 520                 525

Arg Ile Ala Asp Ile Val Pro Gly Ala Arg Pro Asn Ser Asp Asn Ala
                530                 535                 540

Ile Asp Leu Lys Val Leu Asp Arg His Gly Asn Pro Val Leu Ala Asp
545                 550                 555                 560

Arg Leu Phe His Ser Gly Glu His Pro Val Tyr Thr Val Arg Thr Val
                565                 570                 575

Glu Gly Leu Arg Val Thr Gly Thr Ala Asn His Pro Leu Leu Cys Leu
                580                 585                 590

Val Asp Val Ala Gly Val Pro Thr Leu Leu Trp Lys Leu Ile Asp Glu
                595                 600                 605

Ile Lys Pro Gly Asp Tyr Ala Val Ile Gln Arg Ser Ala Phe Ser Val
                610                 615                 620

Asp Cys Ala Gly Phe Ala Arg Gly Lys Pro Glu Phe Ala Pro Thr Thr
625                 630                 635                 640

Tyr Thr Val Gly Val Pro Gly Leu Val Arg Phe Leu Glu Ala His His
                645                 650                 655

Arg Asp Pro Asp Ala Gln Ala Ile Ala Asp Glu Leu Thr Asp Gly Arg
                660                 665                 670

Phe Tyr Tyr Ala Lys Val Ala Ser Val Thr Asp Ala Gly Val Gln Pro
                675                 680                 685

Val Tyr Ser Leu Arg Val Asp Thr Ala Asp His Ala Phe Ile Thr Asn
690                 695                 700

Gly Phe Val Ser His Ala Thr Gly Leu Thr Gly Leu Asn Ser Gly Leu
705                 710                 715                 720

Thr Thr Asn Pro Gly Val Ser Ala Trp Gln Val Asn Thr Ala Tyr Thr
                725                 730                 735

Ala Gly Gln Leu Val Thr Tyr Asn Gly Lys Thr Tyr Lys Cys Leu Gln
                740                 745                 750

Pro His Thr Ser Leu Ala Gly Trp Glu Pro Ser Asn Val Pro Ala Leu
                755                 760                 765

Trp Gln Leu Gln
    770
```

<210> SEQ ID NO 101
<211> LENGTH: 771
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv6 linked to SLT-1A and with
      chitin binding domain

<400> SEQUENCE: 101

Met Gln Ile Val Leu Ser Gln Ser Pro Ala Ile Leu Ser Ala Ser Pro

-continued

```
1               5                   10                  15
Gly Glu Lys Val Thr Met Thr Cys Arg Ala Ser Ser Val Ser Tyr
            20                  25                  30

Met His Trp Tyr Gln Gln Lys Pro Gly Ser Ser Pro Lys Pro Trp Ile
            35                  40                  45

Tyr Ala Pro Ser Asn Leu Ala Ser Gly Val Pro Ala Arg Phe Ser Gly
            50                  55                  60

Ser Gly Ser Gly Thr Ser Tyr Ser Leu Thr Ile Ser Arg Val Glu Ala
65                  70                  75                  80

Glu Asp Ala Ala Thr Tyr Tyr Cys Gln Gln Trp Ser Phe Asn Pro Pro
                85                  90                  95

Thr Phe Gly Ala Gly Thr Lys Leu Glu Leu Lys Ser Gly Ser Thr Ser
                100                 105                 110

Gly Ser Gly Lys Pro Gly Ser Gly Glu Gly Ser Gln Ala Tyr Leu Gln
            115                 120                 125

Gln Ser Gly Ala Glu Leu Val Arg Pro Gly Ala Ser Val Lys Met Ser
            130                 135                 140

Cys Lys Ala Ser Gly Tyr Thr Phe Thr Ser Tyr Asn Met His Trp Val
145                 150                 155                 160

Lys Gln Thr Pro Arg Gln Gly Leu Glu Trp Ile Gly Ala Ile Tyr Pro
                165                 170                 175

Gly Asn Gly Asp Thr Ser Tyr Asn Gln Lys Phe Lys Gly Lys Ala Thr
                180                 185                 190

Leu Thr Val Asp Lys Ser Ser Ser Thr Ala Tyr Met Gln Leu Ser Ser
            195                 200                 205

Leu Thr Ser Glu Asp Ser Ala Val Tyr Phe Cys Ala Arg Val Val Tyr
210                 215                 220

Tyr Ser Asn Ser Tyr Trp Tyr Phe Asp Val Trp Gly Thr Gly Thr Thr
225                 230                 235                 240

Val Thr Val Ser Glu Phe Pro Lys Pro Ser Thr Pro Pro Gly Ser Ser
                245                 250                 255

Gly Gly Ala Pro Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
            275                 280                 285

Gln Thr Ile Ser Ser Gly Gly Thr Ser Leu Leu Met Ile Asp Ser Gly
            290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
                340                 345                 350

Ala Asp Phe Ser His Val Thr Phe Pro Gly Thr Thr Ala Val Thr Leu
                355                 360                 365

Ser Gly Asp Ser Ser Tyr Thr Thr Leu Gln Arg Val Ala Gly Ile Ser
            370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                405                 410                 415

Ala Met Leu Arg Phe Val Thr Val Thr Ala Glu Ala Leu Arg Phe Arg
            420                 425                 430
```

Gln Ile Gln Arg Gly Phe Arg Thr Thr Leu Asp Asp Leu Ser Gly Arg
            435                 440                 445

Ser Tyr Val Met Thr Ala Glu Asp Val Asp Leu Thr Leu Asn Trp Gly
        450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
            485                 490                 495

Ala Leu Ile Leu Asn Ser His His Ala Ser Arg Val Ala Arg Cys
        500                 505                 510

Ile Thr Gly Asp Ala Leu Val Ala Leu Pro Glu Gly Glu Ser Val Arg
            515                 520                 525

Ile Ala Asp Ile Val Pro Gly Ala Arg Pro Asn Ser Asp Asn Ala Ile
        530                 535                 540

Asp Leu Lys Val Leu Asp Arg His Gly Asn Pro Val Leu Ala Asp Arg
545                 550                 555                 560

Leu Phe His Ser Gly Glu His Pro Val Tyr Thr Val Arg Thr Val Glu
            565                 570                 575

Gly Leu Arg Val Thr Gly Thr Ala Asn His Pro Leu Leu Cys Leu Val
        580                 585                 590

Asp Val Ala Gly Val Pro Thr Leu Leu Trp Lys Leu Ile Asp Glu Ile
            595                 600                 605

Lys Pro Gly Asp Tyr Ala Val Ile Gln Arg Ser Ala Phe Ser Val Asp
        610                 615                 620

Cys Ala Gly Phe Ala Arg Gly Lys Pro Glu Phe Ala Pro Thr Thr Tyr
625                 630                 635                 640

Thr Val Gly Val Pro Gly Leu Val Arg Phe Leu Glu Ala His His Arg
            645                 650                 655

Asp Pro Asp Ala Gln Ala Ile Ala Asp Glu Leu Thr Asp Gly Arg Phe
        660                 665                 670

Tyr Tyr Ala Lys Val Ala Ser Val Thr Asp Ala Gly Val Gln Pro Val
            675                 680                 685

Tyr Ser Leu Arg Val Asp Thr Ala Asp His Ala Phe Ile Thr Asn Gly
        690                 695                 700

Phe Val Ser His Ala Thr Gly Leu Thr Gly Leu Asn Ser Gly Leu Thr
705                 710                 715                 720

Thr Asn Pro Gly Val Ser Ala Trp Gln Val Asn Thr Ala Tyr Thr Ala
            725                 730                 735

Gly Gln Leu Val Thr Tyr Asn Gly Lys Thr Tyr Lys Cys Leu Gln Pro
            740                 745                 750

His Thr Ser Leu Ala Gly Trp Glu Pro Ser Asn Val Pro Ala Leu Trp
        755                 760                 765

Gln Leu Gln
    770

<210> SEQ ID NO 102
<211> LENGTH: 771
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv7 linked to SLT-1A and with
      chitin binding domain -continued

```
<400> SEQUENCE: 102

Met Gln Ala Tyr Leu Gln Gln Ser Gly Ala Glu Leu Val Arg Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Arg Gln Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Val Asp Lys Ser Ser Ser Thr Ala
65                  70                  75                  80

Tyr Met Gln Leu Ser Ser Leu Thr Ser Glu Asp Ser Ala Val Tyr Phe
                85                  90                  95

Cys Ala Arg Val Val Tyr Tyr Ser Asn Ser Tyr Trp Tyr Phe Asp Val
            100                 105                 110

Trp Gly Thr Gly Thr Thr Val Thr Val Ser Gly Ser Thr Ser Gly Ser
        115                 120                 125

Gly Lys Pro Gly Ser Gly Glu Gly Ser Gln Ile Val Leu Ser Gln Ser
    130                 135                 140

Pro Ala Ile Leu Ser Ala Ser Pro Gly Glu Lys Val Thr Met Thr Cys
145                 150                 155                 160

Arg Ala Ser Ser Ser Val Ser Tyr Met His Trp Tyr Gln Gln Lys Pro
                165                 170                 175

Gly Ser Ser Pro Lys Pro Trp Ile Tyr Ala Pro Ser Asn Leu Ala Ser
            180                 185                 190

Gly Val Pro Ala Arg Phe Ser Gly Ser Gly Ser Gly Thr Ser Tyr Ser
        195                 200                 205

Leu Thr Ile Ser Arg Val Glu Ala Glu Asp Ala Ala Thr Tyr Tyr Cys
    210                 215                 220

Gln Gln Trp Ser Phe Asn Pro Pro Thr Phe Gly Ala Gly Thr Lys Leu
225                 230                 235                 240

Glu Leu Lys Ser Glu Phe Pro Lys Pro Ser Thr Pro Pro Gly Ser Ser
                245                 250                 255

Gly Gly Ala Pro Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
        275                 280                 285

Gln Thr Ile Ser Ser Gly Gly Thr Ser Leu Leu Met Ile Asp Ser Gly
    290                 295                 300

Ser Gly Asp Asn Leu Phe Ala Val Asp Val Arg Gly Ile Asp Pro Glu
305                 310                 315                 320

Glu Gly Arg Phe Asn Asn Leu Arg Leu Ile Val Glu Arg Asn Asn Leu
                325                 330                 335

Tyr Val Thr Gly Phe Val Asn Arg Thr Asn Asn Val Phe Tyr Arg Phe
            340                 345                 350

Ala Asp Phe Ser His Val Thr Phe Pro Gly Thr Thr Ala Val Thr Leu
        355                 360                 365

Ser Gly Asp Ser Ser Tyr Thr Thr Leu Gln Arg Val Ala Gly Ile Ser
    370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
                405                 410                 415
```

Ala Met Leu Arg Phe Val Thr Val Thr Ala Glu Ala Leu Arg Phe Arg
            420                 425                 430

Gln Ile Gln Arg Gly Phe Arg Thr Leu Asp Asp Leu Ser Gly Arg
        435                 440                 445

Ser Tyr Val Met Thr Ala Glu Asp Val Asp Leu Thr Leu Asn Trp Gly
450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Ser His His Ala Ser Arg Val Ala Arg Cys
            500                 505                 510

Ile Thr Gly Asp Ala Leu Val Ala Leu Pro Glu Gly Glu Ser Val Arg
        515                 520                 525

Ile Ala Asp Ile Val Pro Gly Ala Arg Pro Asn Ser Asp Asn Ala Ile
530                 535                 540

Asp Leu Lys Val Leu Asp Arg His Gly Asn Pro Val Leu Ala Asp Arg
545                 550                 555                 560

Leu Phe His Ser Gly Glu His Pro Val Tyr Thr Val Arg Thr Val Glu
                565                 570                 575

Gly Leu Arg Val Thr Gly Thr Ala Asn His Pro Leu Leu Cys Leu Val
            580                 585                 590

Asp Val Ala Gly Val Pro Thr Leu Leu Trp Lys Leu Ile Asp Glu Ile
        595                 600                 605

Lys Pro Gly Asp Tyr Ala Val Ile Gln Arg Ser Ala Phe Ser Val Asp
610                 615                 620

Cys Ala Gly Phe Ala Arg Gly Lys Pro Glu Phe Ala Pro Thr Thr Tyr
625                 630                 635                 640

Thr Val Gly Val Pro Gly Leu Val Arg Phe Leu Glu Ala His His Arg
                645                 650                 655

Asp Pro Asp Ala Gln Ala Ile Ala Asp Glu Leu Thr Asp Gly Arg Phe
            660                 665                 670

Tyr Tyr Ala Lys Val Ala Ser Val Thr Asp Ala Gly Val Gln Pro Val
        675                 680                 685

Tyr Ser Leu Arg Val Asp Thr Ala Asp His Ala Phe Ile Thr Asn Gly
690                 695                 700

Phe Val Ser His Ala Thr Gly Leu Thr Gly Leu Asn Ser Gly Leu Thr
705                 710                 715                 720

Thr Asn Pro Gly Val Ser Ala Trp Gln Val Asn Thr Ala Tyr Thr Ala
                725                 730                 735

Gly Gln Leu Val Thr Tyr Asn Gly Lys Thr Tyr Lys Cys Leu Gln Pro
            740                 745                 750

His Thr Ser Leu Ala Gly Trp Glu Pro Ser Asn Val Pro Ala Leu Trp
        755                 760                 765

Gln Leu Gln
    770

<210> SEQ ID NO 103
<211> LENGTH: 519
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: alphaCD20-scFv1 linked to StxA variant N

<400> SEQUENCE: 103

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Glu Phe Pro Lys Pro
                245                 250                 255

Ser Thr Pro Pro Gly Ser Ser Gly Gly Ala Pro Gln Val Gln Leu Val
            260                 265                 270

Gln Ser Gly Ala Glu Leu Val Lys Pro Gly Ala Ser Val Lys Met Ser
        275                 280                 285

Cys Lys Ala Ser Gly Tyr Thr Phe Thr Ser Tyr Asn Met His Trp Val
290                 295                 300

Lys Gln Thr Pro Gly Gln Gly Leu Glu Trp Ile Gly Ala Ile Tyr Pro
305                 310                 315                 320

Gly Asn Gly Asp Thr Ser Tyr Asn Gln Lys Phe Lys Gly Lys Ala Thr
                325                 330                 335

Leu Thr Ala Asp Lys Ser Ser Ser Thr Ala Tyr Met Gln Leu Ser Ser
            340                 345                 350

Leu Thr Ser Glu Asp Ser Ala Val Tyr Tyr Cys Ala Arg Ala Gln Leu
        355                 360                 365

Arg Pro Asn Tyr Trp Tyr Phe Asp Val Trp Gly Ala Gly Thr Thr Val
    370                 375                 380

Thr Val Ser Ser Gly Gly Gly Gly Ser Gly Gly Gly Ser Gly Gly
385                 390                 395                 400
```

Gly Gly Ser Gly Gly Gly Ser Gly Gly Gly Ser Asp Ile Val
                405             410             415

Leu Ser Gln Ser Pro Ala Ile Leu Ser Ala Ser Pro Gly Glu Lys Val
        420                 425                 430

Thr Met Thr Cys Arg Ala Ser Ser Val Ser Tyr Met His Trp Tyr
            435                 440                 445

Gln Gln Lys Pro Gly Ser Ser Pro Lys Pro Trp Ile Tyr Ala Thr Ser
    450                 455                 460

Asn Leu Ala Ser Gly Val Pro Ala Arg Phe Ser Gly Ser Gly Ser Gly
465                 470                 475                 480

Thr Ser Tyr Ser Leu Thr Ile Ser Arg Val Glu Ala Glu Asp Ala Ala
                485                 490                 495

Thr Tyr Tyr Cys Gln Gln Trp Ile Ser Asn Pro Pro Thr Phe Gly Ala
    500                 505                 510

Gly Thr Lys Leu Glu Leu Lys
        515

-continued

```
Ser Phe Gly Ser Ile Asn Ala Ile Leu Gly Ser Val Ala Leu Ile Leu
225                 230                 235                 240

Asn Cys His His His Ala Ser Arg Val Ala Arg Glu Phe Pro Lys Pro
                245                 250                 255

Ser Thr Pro Pro Gly Ser Ser Gly Gly Ala Pro Gln Val Gln Leu Gln
            260                 265                 270

Gln Pro Gly Ala Glu Leu Val Lys Pro Gly Ala Ser Val Lys Met Ser
        275                 280                 285

Cys Lys Thr Ser Gly Tyr Thr Phe Thr Ser Tyr Asn Val His Trp Val
    290                 295                 300

Lys Gln Thr Pro Gly Gln Gly Leu Glu Trp Ile Gly Ala Ile Tyr Pro
305                 310                 315                 320

Gly Asn Gly Asp Thr Ser Phe Asn Gln Lys Phe Lys Gly Lys Ala Thr
                325                 330                 335

Leu Thr Ala Asp Lys Ser Ser Ser Thr Val Tyr Met Gln Leu Ser Ser
            340                 345                 350

Leu Thr Ser Glu Asp Ser Ala Val Tyr Tyr Cys Ala Arg Ser Asn Tyr
        355                 360                 365

Tyr Gly Ser Ser Tyr Val Trp Phe Phe Asp Val Trp Gly Ala Gly Thr
    370                 375                 380

Thr Val Thr Val Ser Ser Gly Ser Thr Ser Gly Ser Gly Lys Pro Gly
385                 390                 395                 400

Ser Gly Glu Gly Ser Gln Ile Val Leu Ser Gln Ser Pro Thr Ile Leu
                405                 410                 415

Ser Ala Ser Pro Gly Glu Lys Val Thr Met Thr Cys Arg Ala Ser Ser
            420                 425                 430

Ser Val Ser Tyr Met Asp Trp Tyr Gln Gln Lys Pro Gly Ser Ser Pro
        435                 440                 445

Lys Pro Trp Ile Tyr Ala Thr Ser Asn Leu Ala Ser Gly Val Pro Ala
    450                 455                 460

Arg Phe Ser Gly Ser Gly Ser Gly Thr Ser Tyr Ser Leu Thr Ile Ser
465                 470                 475                 480

Arg Val Glu Ala Glu Asp Ala Ala Thr Tyr Tyr Cys Gln Gln Trp Ile
                485                 490                 495

Ser Asn Pro Pro Thr Phe Gly Ala Gly Thr Lys Leu Glu Leu Lys
            500                 505                 510
```

<210> SEQ ID NO 105
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv3 linked to SLT-1A variant N

<400> SEQUENCE: 105

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60
```

```
Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
                115                 120                 125

Gln Ile Asn Arg His Ser Leu Thr Thr Ser Tyr Leu Asp Leu Met Ser
                130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
                210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Glu Phe Pro Lys Pro
                245                 250                 255

Ser Thr Pro Pro Gly Ser Ser Gly Gly Ala Pro Gln Val Gln Leu Gln
                260                 265                 270

Gln Pro Gly Ala Glu Leu Val Lys Pro Gly Ala Ser Val Lys Met Ser
                275                 280                 285

Cys Lys Ala Ser Gly Tyr Thr Phe Thr Ser Tyr Asn Met His Trp Val
                290                 295                 300

Lys Gln Thr Pro Gly Arg Gly Leu Glu Trp Ile Gly Ala Ile Tyr Pro
305                 310                 315                 320

Gly Asn Gly Asp Thr Ser Tyr Asn Gln Lys Phe Lys Gly Lys Ala Thr
                325                 330                 335

Leu Thr Ala Asp Lys Ser Ser Ser Thr Ala Tyr Met Gln Leu Ser Ser
                340                 345                 350

Leu Thr Ser Glu Asp Ser Ala Val Tyr Tyr Cys Ala Arg Ser Thr Tyr
                355                 360                 365

Tyr Gly Gly Asp Trp Tyr Phe Asn Val Trp Gly Ala Gly Thr Thr Val
                370                 375                 380

Thr Val Ser Ala Gly Ser Thr Ser Gly Ser Gly Lys Pro Gly Ser Gly
385                 390                 395                 400

Glu Gly Ser Thr Lys Gly Gln Ile Val Leu Ser Gln Ser Pro Ala Ile
                405                 410                 415

Leu Ser Ala Ser Pro Gly Glu Lys Val Thr Met Thr Cys Arg Ala Ser
                420                 425                 430

Ser Ser Val Ser Tyr Ile His Trp Phe Gln Gln Lys Pro Gly Ser Ser
                435                 440                 445

Pro Lys Pro Trp Ile Tyr Ala Thr Ser Asn Leu Ala Ser Gly Val Pro
                450                 455                 460

Val Arg Phe Ser Gly Ser Gly Ser Gly Thr Ser Tyr Ser Leu Thr Ile
465                 470                 475                 480

Ser Arg Val Glu Ala Glu Asp Ala Ala Thr Tyr Tyr Cys Gln Gln Trp
```

```
                    485                 490                 495
Thr Ser Asn Pro Pro Thr Phe Gly Gly Gly Thr Lys Leu Glu Ile Lys
                500                 505                 510

<210> SEQ ID NO 106
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv4 linked to SLT-1A variant N

<400> SEQUENCE: 106

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His Ala Ser Arg Val Ala Arg Glu Phe Pro Lys Pro
                245                 250                 255

Ser Thr Pro Pro Gly Ser Ser Gly Gly Ala Pro Glu Val Gln Leu Val
            260                 265                 270

Glu Ser Gly Gly Gly Leu Val Gln Pro Gly Arg Ser Leu Arg Leu Ser
        275                 280                 285

Cys Ala Ala Ser Gly Phe Thr Phe Asn Asp Tyr Ala Met His Trp Val
    290                 295                 300

Arg Gln Ala Pro Gly Lys Gly Leu Glu Trp Val Ser Thr Ile Ser Trp
305                 310                 315                 320

Asn Ser Gly Ser Ile Gly Tyr Ala Asp Ser Val Lys Gly Arg Phe Thr
```

```
                    325                 330                 335
Ile Ser Arg Asp Asn Ala Lys Lys Ser Leu Tyr Leu Gln Met Asn Ser
                340                 345                 350
Leu Arg Ala Glu Asp Thr Ala Leu Tyr Tyr Cys Ala Lys Asp Ile Gln
                355                 360                 365
Tyr Gly Asn Tyr Tyr Gly Met Asp Val Trp Gly Gln Gly Thr Thr
    370                 375                 380
Val Thr Val Ser Ser Gly Ser Thr Ser Gly Ser Gly Lys Pro Gly Ser
385                 390                 395                 400
Gly Glu Gly Ser Glu Ile Val Leu Thr Gln Ser Pro Ala Thr Leu Ser
                405                 410                 415
Leu Ser Pro Gly Glu Arg Ala Thr Leu Ser Cys Arg Ala Ser Gln Ser
                420                 425                 430
Val Ser Ser Tyr Leu Ala Trp Tyr Gln Gln Lys Pro Gly Gln Ala Pro
                435                 440                 445
Arg Leu Leu Ile Tyr Asp Ala Ser Asn Arg Ala Thr Gly Ile Pro Ala
        450                 455                 460
Arg Phe Ser Gly Ser Gly Ser Gly Thr Asp Phe Thr Leu Thr Ile Ser
465                 470                 475                 480
Ser Leu Glu Pro Glu Asp Phe Ala Val Tyr Tyr Cys Gln Gln Arg Ser
                485                 490                 495
Asn Trp Pro Ile Thr Phe Gly Gln Gly Thr Arg Leu Glu Ile Lys
                500                 505                 510
```

<210> SEQ ID NO 107
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv5 linked to SLT-1A variant N

<400> SEQUENCE: 107

```
Lys Glu Phe Thr Leu Asp Phe Ser Thr Ala Lys Thr Tyr Val Asp Ser
1               5                   10                  15
Leu Asn Val Ile Arg Ser Ala Ile Gly Thr Pro Leu Gln Thr Ile Ser
                20                  25                  30
Ser Gly Gly Thr Ser Leu Leu Met Ile Asp Ser Gly Ser Gly Asp Asn
            35                  40                  45
Leu Phe Ala Val Asp Val Arg Gly Ile Asp Pro Glu Glu Gly Arg Phe
    50                  55                  60
Asn Asn Leu Arg Leu Ile Val Glu Arg Asn Asn Leu Tyr Val Thr Gly
65                  70                  75                  80
Phe Val Asn Arg Thr Asn Asn Val Phe Tyr Arg Phe Ala Asp Phe Ser
                85                  90                  95
His Val Thr Phe Pro Gly Thr Thr Ala Val Thr Leu Ser Gly Asp Ser
                100                 105                 110
Ser Tyr Thr Thr Leu Gln Arg Val Ala Gly Ile Ser Arg Thr Gly Met
            115                 120                 125
Gln Ile Asn Arg His Ser Leu Thr Thr Ser Tyr Leu Asp Leu Met Ser
        130                 135                 140
His Ser Gly Thr Ser Leu Thr Gln Ser Val Ala Arg Ala Met Leu Arg
145                 150                 155                 160
Phe Val Thr Val Thr Ala Glu Ala Leu Arg Phe Arg Gln Ile Gln Arg
```

```
                165                 170                 175
Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Glu Phe Pro Lys Pro
                245                 250                 255

Ser Thr Pro Pro Gly Ser Ser Gly Gly Ala Pro Glu Ile Val Leu Thr
            260                 265                 270

Gln Ser Pro Ala Thr Leu Ser Leu Ser Pro Gly Glu Arg Ala Thr Leu
        275                 280                 285

Ser Cys Arg Ala Ser Gln Ser Val Ser Ser Tyr Leu Ala Trp Tyr Gln
290                 295                 300

Gln Lys Pro Gly Gln Ala Pro Arg Leu Leu Ile Tyr Asp Ala Ser Asn
305                 310                 315                 320

Arg Ala Thr Gly Ile Pro Ala Arg Phe Ser Gly Ser Gly Ser Gly Thr
                325                 330                 335

Asp Phe Thr Leu Thr Ile Ser Ser Leu Glu Pro Glu Asp Phe Ala Val
            340                 345                 350

Tyr Tyr Cys Gln Gln Arg Ser Asn Trp Pro Ile Thr Phe Gly Gln Gly
        355                 360                 365

Thr Arg Leu Glu Ile Lys Gly Ser Thr Ser Gly Ser Gly Lys Pro Gly
    370                 375                 380

Ser Gly Glu Gly Ser Glu Val Gln Leu Val Glu Ser Gly Gly Gly Leu
385                 390                 395                 400

Val Gln Pro Gly Arg Ser Leu Arg Leu Ser Cys Ala Ala Ser Gly Phe
                405                 410                 415

Thr Phe Asn Asp Tyr Ala Met His Trp Val Arg Gln Ala Pro Gly Lys
            420                 425                 430

Gly Leu Glu Trp Val Ser Thr Ile Ser Trp Asn Ser Gly Ser Ile Gly
        435                 440                 445

Tyr Ala Asp Ser Val Lys Gly Arg Phe Thr Ile Ser Arg Asp Asn Ala
    450                 455                 460

Lys Lys Ser Leu Tyr Leu Gln Met Asn Ser Leu Arg Ala Glu Asp Thr
465                 470                 475                 480

Ala Leu Tyr Tyr Cys Ala Lys Asp Ile Gln Tyr Gly Asn Tyr Tyr Tyr
                485                 490                 495

Gly Met Asp Val Trp Gly Gln Gly Thr Thr Val Thr Val Ser Ser
            500                 505                 510

<210> SEQ ID NO 108
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv1 linked to SLT-1A variant K

<400> SEQUENCE: 108

Met Gln Val Gln Leu Val Gln Ser Gly Ala Glu Leu Val Lys Pro Gly
```

-continued

```
1               5                   10                  15
Ala Ser Val Lys Met Ser Cys Lys Ala Ser Gly Tyr Thr Phe Thr Ser
            20                  25                  30
Tyr Asn Met His Trp Val Lys Gln Thr Pro Gly Gln Gly Leu Glu Trp
            35                  40                  45
Ile Gly Ala Ile Tyr Pro Gly Asn Gly Asp Thr Ser Tyr Asn Gln Lys
            50                  55                  60
Phe Lys Gly Lys Ala Thr Leu Thr Ala Asp Lys Ser Ser Ser Thr Ala
65                  70                  75                  80
Tyr Met Gln Leu Ser Ser Leu Thr Ser Glu Asp Ser Ala Val Tyr Tyr
            85                  90                  95
Cys Ala Arg Ala Gln Leu Arg Pro Asn Tyr Trp Tyr Phe Asp Val Trp
            100                 105                 110
Gly Ala Gly Thr Thr Val Thr Val Ser Gly Gly Gly Gly Ser Gly
            115                 120                 125
Gly Gly Gly Ser Gly Gly Gly Ser Gly Gly Gly Ser Gly Gly
            130                 135                 140
Gly Gly Ser Asp Ile Val Leu Ser Gln Ser Pro Ala Ile Leu Ser Ala
145                 150                 155                 160
Ser Pro Gly Glu Lys Val Thr Met Thr Cys Arg Ala Ser Ser Ser Val
            165                 170                 175
Ser Tyr Met His Trp Tyr Gln Gln Lys Pro Gly Ser Ser Pro Lys Pro
            180                 185                 190
Trp Ile Tyr Ala Thr Ser Asn Leu Ala Ser Gly Val Pro Ala Arg Phe
            195                 200                 205
Ser Gly Ser Gly Ser Gly Thr Ser Tyr Ser Leu Thr Ile Ser Arg Val
            210                 215                 220
Glu Ala Glu Asp Ala Ala Thr Tyr Tyr Cys Gln Gln Trp Ile Ser Asn
225                 230                 235                 240
Pro Pro Thr Phe Gly Ala Gly Thr Lys Leu Glu Leu Lys Gly Gly Gly
            245                 250                 255
Gly Ser Gly Gly Lys Glu Phe Thr Leu Asp Phe Ser Thr Ala Lys Thr
            260                 265                 270
Tyr Val Asp Ser Leu Asn Val Ile Arg Ser Ala Ile Gly Thr Pro Leu
            275                 280                 285
Gln Thr Ile Ser Ser Gly Gly Thr Ser Leu Leu Met Ile Asp Ser Gly
            290                 295                 300
Ser Gly Asp Asn Leu Phe Ala Val Asp Val Arg Gly Ile Asp Pro Glu
305                 310                 315                 320
Glu Gly Arg Phe Asn Asn Leu Arg Leu Ile Val Glu Arg Asn Asn Leu
            325                 330                 335
Tyr Val Thr Gly Phe Val Asn Arg Thr Asn Asn Val Phe Tyr Arg Phe
            340                 345                 350
Ala Asp Phe Ser His Val Thr Phe Pro Gly Thr Thr Ala Val Thr Leu
            355                 360                 365
Ser Gly Asp Ser Ser Tyr Thr Thr Leu Gln Arg Val Ala Gly Ile Ser
            370                 375                 380
Arg Thr Gly Met Gln Ile Asn Arg His Ser Leu Thr Thr Ser Tyr Leu
385                 390                 395                 400
Asp Leu Met Ser His Ser Gly Thr Ser Leu Thr Gln Ser Val Ala Arg
            405                 410                 415
Ala Met Leu Arg Phe Val Thr Val Thr Ala Glu Ala Leu Arg Phe Arg
            420                 425                 430
```

```
Gln Ile Gln Arg Gly Phe Arg Thr Thr Leu Asp Asp Leu Ser Gly Arg
            435                 440                 445

Ser Tyr Val Met Thr Ala Glu Asp Val Asp Leu Thr Leu Asn Trp Gly
        450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                485                 490                 495

Ala Leu Ile Leu Asn Cys His His His Ala Ser Arg Val Ala Arg Lys
            500                 505                 510

Asp Glu Leu
        515

<210> SEQ ID NO 109
<211> LENGTH: 516
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A variant K

<400> SEQUENCE: 109

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Ser Thr Ser
        115                 120                 125

Gly Ser Gly Lys Pro Gly Ser Gly Glu Gly Ser Gln Ile Val Leu Ser
    130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
                165                 170                 175

Lys Pro Gly Ser Ser Pro Lys Pro Trp Ile Tyr Ala Thr Ser Asn Leu
            180                 185                 190

Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
    210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255
```

```
Ser Gly Gly Ala Pro Lys Glu Phe Thr Leu Asp Phe Ser Thr Ala Lys
            260                 265                 270

Thr Tyr Val Asp Ser Leu Asn Val Ile Arg Ser Ala Ile Gly Thr Pro
        275                 280                 285

Leu Gln Thr Ile Ser Ser Gly Thr Ser Leu Leu Met Ile Asp Ser
    290                 295                 300

Gly Ser Gly Asp Asn Leu Phe Ala Val Asp Val Arg Gly Ile Asp Pro
305                 310                 315                 320

Glu Glu Gly Arg Phe Asn Asn Leu Arg Leu Ile Val Glu Arg Asn Asn
                325                 330                 335

Leu Tyr Val Thr Gly Phe Val Asn Arg Thr Asn Asn Val Phe Tyr Arg
                340                 345                 350

Phe Ala Asp Phe Ser His Val Thr Phe Pro Gly Thr Thr Ala Val Thr
                355                 360                 365

Leu Ser Gly Asp Ser Ser Tyr Thr Thr Leu Gln Arg Val Ala Gly Ile
    370                 375                 380

Ser Arg Thr Gly Met Gln Ile Asn Arg His Ser Leu Thr Thr Ser Tyr
385                 390                 395                 400

Leu Asp Leu Met Ser His Ser Gly Thr Ser Leu Thr Gln Ser Val Ala
                405                 410                 415

Arg Ala Met Leu Arg Phe Val Thr Val Thr Ala Glu Ala Leu Arg Phe
                420                 425                 430

Arg Gln Ile Gln Arg Gly Phe Arg Thr Thr Leu Asp Asp Leu Ser Gly
            435                 440                 445

Arg Ser Tyr Val Met Thr Ala Glu Asp Val Asp Leu Thr Leu Asn Trp
        450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Cys His His Ala Ser Arg Val Ala Arg
                500                 505                 510

Lys Asp Glu Leu
        515

<210> SEQ ID NO 110
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv2 linked to SLT-1A variant K

<400> SEQUENCE: 110

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80
```

-continued

```
Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
               100                 105                 110

Val Trp Gly Ala Gly Thr Thr Val Thr Val Ser Ser Gly Ser Thr Ser
           115                 120                 125

Gly Ser Gly Lys Pro Gly Ser Gly Glu Gly Ser Gln Ile Val Leu Ser
130                 135                 140

Gln Ser Pro Thr Ile Leu Ser Ala Ser Pro Gly Glu Lys Val Thr Met
145                 150                 155                 160

Thr Cys Arg Ala Ser Ser Ser Val Ser Tyr Met Asp Trp Tyr Gln Gln
               165                 170                 175

Lys Pro Gly Ser Ser Pro Lys Pro Trp Ile Tyr Ala Thr Ser Asn Leu
           180                 185                 190

Ala Ser Gly Val Pro Ala Arg Phe Ser Gly Ser Gly Ser Gly Thr Ser
       195                 200                 205

Tyr Ser Leu Thr Ile Ser Arg Val Glu Ala Glu Asp Ala Ala Thr Tyr
       210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
               245                 250                 255

Ser Gly Gly Ala Pro Gly Ile Leu Gly Phe Val Phe Thr Leu Lys Glu
           260                 265                 270

Phe Thr Leu Asp Phe Ser Thr Ala Lys Thr Tyr Val Asp Ser Leu Asn
           275                 280                 285

Val Ile Arg Ser Ala Ile Gly Thr Pro Leu Gln Thr Ile Ser Ser Gly
       290                 295                 300

Gly Thr Ser Leu Leu Met Ile Asp Ser Gly Ser Gly Asp Asn Leu Phe
305                 310                 315                 320

Ala Val Asp Val Arg Gly Ile Asp Pro Glu Glu Gly Arg Phe Asn Asn
               325                 330                 335

Leu Arg Leu Ile Val Glu Arg Asn Asn Leu Tyr Val Thr Gly Phe Val
           340                 345                 350

Asn Arg Thr Asn Asn Val Phe Tyr Arg Phe Ala Asp Phe Ser His Val
       355                 360                 365

Thr Phe Pro Gly Thr Thr Ala Val Thr Leu Ser Gly Asp Ser Ser Tyr
       370                 375                 380

Thr Thr Leu Gln Arg Val Ala Gly Ile Ser Arg Thr Gly Met Gln Ile
385                 390                 395                 400

Asn Arg His Ser Leu Thr Thr Ser Tyr Leu Asp Leu Met Ser His Ser
               405                 410                 415

Gly Thr Ser Leu Thr Gln Ser Val Ala Arg Ala Met Leu Arg Phe Val
           420                 425                 430

Thr Val Thr Ala Glu Ala Leu Arg Phe Arg Gln Ile Gln Arg Gly Phe
       435                 440                 445

Arg Thr Thr Leu Asp Asp Leu Ser Gly Arg Ser Tyr Val Met Thr Ala
       450                 455                 460

Glu Asp Val Asp Leu Thr Leu Asn Trp Gly Arg Leu Ser Ser Val Leu
465                 470                 475                 480

Pro Asp Tyr His Gly Gln Asp Ser Val Arg Val Gly Arg Ile Ser Phe
               485                 490                 495
```

```
Gly Ser Ile Asn Ala Ile Leu Gly Ser Val Ala Leu Ile Leu Asn Cys
                500                 505                 510

His His His Ala Ser Arg Val Ala Arg Lys Asp Glu Leu
            515                 520                 525

<210> SEQ ID NO 111
<211> LENGTH: 526
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv7 linked to SLT-1A variant K

<400> SEQUENCE: 111

Met Gln Val Gln Leu Gln Gln Pro Gly Ala Glu Leu Val Lys Pro Gly
1               5                   10                  15

Ala Ser Val Lys Met Ser Cys Lys Thr Ser Gly Tyr Thr Phe Thr Ser
            20                  25                  30

Tyr Asn Val His Trp Val Lys Gln Thr Pro Gly Gln Gly Leu Glu Trp
        35                  40                  45

Ile Gly Ala Ile Tyr Pro Gly Asn Gly Asp Thr Ser Phe Asn Gln Lys
    50                  55                  60

Phe Lys Gly Lys Ala Thr Leu Thr Ala Asp Lys Ser Ser Ser Thr Val
65                  70                  75                  80

Tyr Met Gln Leu Ser Ser Leu Thr Ser Glu Asp Ser Ala Val Tyr Tyr
                85                  90                  95

Cys Ala Arg Ser Asn Tyr Tyr Gly Ser Ser Tyr Val Trp Phe Phe Asp
            100                 105                 110

Val Trp Gly Ala Gly Thr Thr Val Thr Val Ser Ser Gly Gly Gly Gly
        115                 120                 125

Ser Gly Gly Gly Gly Ser Gly Gly Gly Gly Ser Gly Gly Gly Gly Ser
    130                 135                 140

Gly Gly Gly Gly Ser Gln Ile Val Leu Ser Gln Ser Pro Thr Ile Leu
145                 150                 155                 160

Ser Ala Ser Pro Gly Glu Lys Val Thr Met Thr Cys Arg Ala Ser Ser
                165                 170                 175

Ser Val Ser Tyr Met Asp Trp Tyr Gln Gln Lys Pro Gly Ser Ser Pro
            180                 185                 190

Lys Pro Trp Ile Tyr Ala Thr Ser Asn Leu Ala Ser Gly Val Pro Ala
        195                 200                 205

Arg Phe Ser Gly Ser Gly Ser Gly Thr Ser Tyr Ser Leu Thr Ile Ser
    210                 215                 220

Arg Val Glu Ala Glu Asp Ala Ala Thr Tyr Tyr Cys Gln Gln Trp Ile
225                 230                 235                 240

Ser Asn Pro Pro Thr Phe Gly Ala Gly Thr Lys Leu Glu Leu Lys Glu
                245                 250                 255

Phe Pro Lys Pro Ser Thr Pro Pro Gly Ser Ser Gly Gly Ala Pro Lys
            260                 265                 270

Glu Phe Thr Leu Asp Phe Ser Thr Ala Lys Thr Tyr Val Asp Ser Leu
        275                 280                 285

Asn Val Ile Arg Ser Ala Ile Gly Thr Pro Leu Gln Thr Ile Ser Ser
    290                 295                 300

Gly Gly Thr Ser Leu Leu Met Ile Asp Ser Gly Ser Gly Asp Asn Leu
305                 310                 315                 320
```

```
Phe Ala Val Asp Val Arg Gly Ile Asp Pro Glu Glu Gly Arg Phe Asn
            325                 330                 335

Asn Leu Arg Leu Ile Val Glu Arg Asn Asn Leu Tyr Val Thr Gly Phe
        340                 345                 350

Val Asn Arg Thr Asn Asn Val Phe Tyr Arg Phe Ala Asp Phe Ser His
        355                 360                 365

Val Thr Phe Pro Gly Thr Thr Ala Val Thr Leu Ser Gly Asp Ser Ser
    370                 375                 380

Tyr Thr Thr Leu Gln Arg Val Ala Gly Ile Ser Arg Thr Gly Met Gln
385                 390                 395                 400

Ile Asn Arg His Ser Leu Thr Thr Ser Tyr Leu Asp Leu Met Ser His
                405                 410                 415

Ser Gly Thr Ser Leu Thr Gln Ser Val Ala Arg Ala Met Leu Arg Phe
            420                 425                 430

Val Thr Val Thr Ala Glu Ala Leu Arg Phe Arg Gln Ile Gln Arg Gly
        435                 440                 445

Phe Arg Thr Thr Leu Asp Asp Leu Ser Gly Arg Ser Tyr Val Met Thr
    450                 455                 460

Ala Glu Asp Val Asp Leu Thr Leu Asn Trp Gly Arg Leu Ser Ser Val
465                 470                 475                 480

Leu Pro Asp Tyr His Gly Gln Asp Ser Val Arg Val Gly Arg Ile Ser
                485                 490                 495

Phe Gly Ser Ile Asn Ala Ile Leu Gly Ser Val Ala Leu Ile Leu Asn
            500                 505                 510

Cys His His His Ala Ser Arg Val Ala Arg Lys Asp Glu Leu
        515                 520                 525

<210> SEQ ID NO 112
<211> LENGTH: 517
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: alphaCD20-scFv3 linked to StxA variant K

<400> SEQUENCE: 112

Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
            20                  25                  30

Tyr Asn Met His Trp Val Lys Gln Thr Pro Gly Arg Gly Leu Glu Trp
        35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ser Thr Tyr Tyr Gly Gly Asp Trp Tyr Phe Asn Val Trp
            100                 105                 110

Gly Ala Gly Thr Thr Val Thr Val Ser Ala Gly Ser Thr Ser Gly Ser
        115                 120                 125

Gly Lys Pro Gly Ser Gly Glu Gly Ser Thr Lys Gly Gln Ile Val Leu
    130                 135                 140
```

-continued

Ser Gln Ser Pro Ala Ile Leu Ser Ala Ser Pro Gly Glu Lys Val Thr
145                 150                 155                 160

Met Thr Cys Arg Ala Ser Ser Val Ser Tyr Ile His Trp Phe Gln
            165                 170                 175

Gln Lys Pro Gly Ser Ser Pro Lys Pro Trp Ile Tyr Ala Thr Ser Asn
            180                 185                 190

Leu Ala Ser Gly Val Pro Val Arg Phe Ser Gly Ser Gly Ser Gly Thr
            195                 200                 205

Ser Tyr Ser Leu Thr Ile Ser Arg Val Glu Ala Glu Asp Ala Ala Thr
210                 215                 220

Tyr Tyr Cys Gln Gln Trp Thr Ser Asn Pro Pro Thr Phe Gly Gly Gly
225                 230                 235                 240

Thr Lys Leu Glu Ile Lys Glu Phe Pro Lys Pro Ser Thr Pro Pro Gly
                245                 250                 255

Ser Ser Gly Gly Ala Pro Lys Glu Phe Thr Leu Asp Phe Ser Thr Ala
            260                 265                 270

Lys Thr Tyr Val Asp Ser Leu Asn Val Ile Arg Ser Ala Ile Gly Thr
            275                 280                 285

Pro Leu Gln Thr Ile Ser Ser Gly Gly Thr Ser Leu Leu Met Ile Asp
290                 295                 300

Ser Gly Thr Gly Asp Asn Leu Phe Ala Val Asp Val Arg Gly Ile Asp
305                 310                 315                 320

Pro Glu Glu Gly Arg Phe Asn Asn Leu Arg Leu Ile Val Glu Arg Asn
                325                 330                 335

Asn Leu Tyr Val Thr Gly Phe Val Asn Arg Thr Asn Asn Val Phe Tyr
            340                 345                 350

Arg Phe Ala Asp Phe Ser His Val Thr Phe Pro Gly Thr Thr Ala Val
            355                 360                 365

Thr Leu Ser Gly Asp Ser Ser Tyr Thr Thr Leu Gln Arg Val Ala Gly
370                 375                 380

Ile Ser Arg Thr Gly Met Gln Ile Asn Arg His Ser Leu Thr Thr Ser
385                 390                 395                 400

Tyr Leu Asp Leu Met Ser His Ser Gly Thr Ser Leu Thr Gln Ser Val
            405                 410                 415

Ala Arg Ala Met Leu Arg Phe Val Thr Val Thr Ala Glu Ala Leu Arg
            420                 425                 430

Phe Arg Gln Ile Gln Arg Gly Phe Arg Thr Thr Leu Asp Asp Leu Ser
            435                 440                 445

Gly Arg Ser Tyr Val Met Thr Ala Glu Asp Val Asp Leu Thr Leu Asn
            450                 455                 460

Trp Gly Arg Leu Ser Ser Val Leu Pro Asp Tyr His Gly Gln Asp Ser
465                 470                 475                 480

Val Arg Val Gly Arg Ile Ser Phe Gly Ser Ile Asn Ala Ile Leu Gly
            485                 490                 495

Ser Val Ala Leu Ile Leu Asn Cys His His Ala Ser Arg Val Ala
            500                 505                 510

Arg Lys Asp Glu Leu
        515

<210> SEQ ID NO 113
<211> LENGTH: 4
<212> TYPE: PRT
<213> ORGANISM: Unknown
<220> FEATURE:
<223> OTHER INFORMATION: Description of Unknown:

'KDEL' family motif peptide

<400> SEQUENCE: 113

Lys Asp Glu Leu
1

<210> SEQ ID NO 114
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 114

His Asp Glu Leu
1

<210> SEQ ID NO 115
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 115

Arg Asp Glu Leu
1

<210> SEQ ID NO 116
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 116

Trp Asp Glu Leu
1

<210> SEQ ID NO 117
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 117

Tyr Asp Glu Leu
1

<210> SEQ ID NO 118
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 118

His Glu Glu Leu
1

<210> SEQ ID NO 119

```
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 119

Lys Glu Glu Leu
1

<210> SEQ ID NO 120
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 120

Arg Glu Glu Leu
1

<210> SEQ ID NO 121
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 121

Lys Phe Glu Leu
1

<210> SEQ ID NO 122
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 122

Lys Ile Glu Leu
1

<210> SEQ ID NO 123
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 123

Asp Lys Glu Leu
1

<210> SEQ ID NO 124
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 124
```

Lys Lys Glu Leu
1

<210> SEQ ID NO 125
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 125

His Asn Glu Leu
1

<210> SEQ ID NO 126
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 126

His Thr Glu Leu
1

<210> SEQ ID NO 127
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 127

Lys Thr Glu Leu
1

<210> SEQ ID NO 128
<211> LENGTH: 4
<212> TYPE: PRT
<213> ORGANISM: Unknown
<220> FEATURE:
<223> OTHER INFORMATION: Description of Unknown:
      'KDEL' family motif peptide

<400> SEQUENCE: 128

His Val Glu Leu
1

<210> SEQ ID NO 129
<211> LENGTH: 6
<212> TYPE: PRT
<213> ORGANISM: Unknown
<220> FEATURE:
<223> OTHER INFORMATION: Description of Unknown:
      'KDEL' family motif peptide

<400> SEQUENCE: 129

Ala Leu Glu Asp Glu Leu
1               5

<210> SEQ ID NO 130
<211> LENGTH: 6
<212> TYPE: PRT
<213> ORGANISM: Unknown
<220> FEATURE:

```
<223> OTHER INFORMATION: Description of Unknown:
      'KDEL' family motif peptide

<400> SEQUENCE: 130

His Ala Glu Asp Glu Leu
1               5

<210> SEQ ID NO 131
<211> LENGTH: 6
<212> TYPE: PRT
<213> ORGANISM: Unknown
<220> FEATURE:
<223> OTHER INFORMATION: Description of Unknown:
      'KDEL' family motif peptide

<400> SEQUENCE: 131

His Leu Glu Asp Glu Leu
1               5

<210> SEQ ID NO 132
<211> LENGTH: 6
<212> TYPE: PRT
<213> ORGANISM: Unknown
<220> FEATURE:
<223> OTHER INFORMATION: Description of Unknown:
      'KDEL' family motif peptide

<400> SEQUENCE: 132

Lys Leu Glu Asp Glu Leu
1               5

<210> SEQ ID NO 133
<211> LENGTH: 6
<212> TYPE: PRT
<213> ORGANISM: Unknown
<220> FEATURE:
<223> OTHER INFORMATION: Description of Unknown:
      'KDEL' family motif peptide

<400> SEQUENCE: 133

Ile Arg Ser Asp Glu Leu
1               5

<210> SEQ ID NO 134
<211> LENGTH: 6
<212> TYPE: PRT
<213> ORGANISM: Unknown
<220> FEATURE:
<223> OTHER INFORMATION: Description of Unknown:
      'KDEL' family motif peptide

<400> SEQUENCE: 134

Glu Arg Ser Thr Glu Leu
1               5

<210> SEQ ID NO 135
<211> LENGTH: 6
<212> TYPE: PRT
<213> ORGANISM: Unknown
<220> FEATURE:
<223> OTHER INFORMATION: Description of Unknown:
      'KDEL' family motif peptide

<400> SEQUENCE: 135

Arg Pro Ser Thr Glu Leu
1               5
```

```
<210> SEQ ID NO 136
<211> LENGTH: 12
<212> TYPE: PRT
<213> ORGANISM: Unknown
<220> FEATURE:
<223> OTHER INFORMATION: Description of Unknown:
      'KDEL' family motif peptide

<400> SEQUENCE: 136

Lys Arg His Gln Ser Ala Asp Glu Asn Gln Glu Leu
1               5                   10

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ser Gly Gly Pro Glu
1               5

<210> SEQ ID NO 138
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (3)..(52)
<223> OTHER INFORMATION: This region may encompass 1 to 10 "Gly Gly Gly
      Gly Ser" and embodiments of "Gly Gly Gly Gly Ser" repeating units
<220> FEATURE:
<221> NAME/KEY: MISC_FEATURE
<222> LOCATION: (3)..(6)
<223> OTHER INFORMATION: This region may encompass 2 to 4 residues
<220> FEATURE:
<221> NAME/KEY: MISC_FEATURE
<222> LOCATION: (8)..(11)
<223> OTHER INFORMATION: This region may encompass 2 to 4 residues
<220> FEATURE:
<221> NAME/KEY: MISC_FEATURE
<222> LOCATION: (13)..(16)
<223> OTHER INFORMATION: This region may encompass 2 to 4 residues
<220> FEATURE:
<221> NAME/KEY: MISC_FEATURE
<222> LOCATION: (18)..(21)
<223> OTHER INFORMATION: This region may encompass 2 to 4 residues
<220> FEATURE:
<221> NAME/KEY: MISC_FEATURE
<222> LOCATION: (23)..(26)
<223> OTHER INFORMATION: This region may encompass 2 to 4 residues
<220> FEATURE:
<221> NAME/KEY: MISC_FEATURE
<222> LOCATION: (28)..(31)
<223> OTHER INFORMATION: This region may encompass 2 to 4 residues
<220> FEATURE:
<221> NAME/KEY: MISC_FEATURE
<222> LOCATION: (33)..(36)
<223> OTHER INFORMATION: This region may encompass 2 to 4 residues
<220> FEATURE:
<221> NAME/KEY: MISC_FEATURE
<222> LOCATION: (38)..(41)
<223> OTHER INFORMATION: This region may encompass 2 to 4 residues
<220> FEATURE:
<221> NAME/KEY: MISC_FEATURE
<222> LOCATION: (43)..(46)
<223> OTHER INFORMATION: This region may encompass 2 to 4 residues
<220> FEATURE:
<221> NAME/KEY: MISC_FEATURE
<222> LOCATION: (48)..(51)
```

<223> OTHER INFORMATION: This region may encompass 2 to 4 residues

<400> SEQUENCE: 138

Ala Met Gly Gly Gly Gly Ser Gly Gly Gly Ser Gly Gly Gly Gly
1               5                   10                  15

Ser Gly Gly Gly Gly Ser Gly Gly Gly Ser Gly Gly Gly Gly Ser
            20                  25                  30

Gly Gly Gly Gly Ser Gly Gly Gly Ser Gly Gly Gly Gly Ser Gly
        35                  40                  45

Gly Gly Gly Ser Ala Met
        50

<210> SEQ ID NO 139
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(210)
<223> OTHER INFORMATION: This sequence may encompass 1 to 30 "Gly Gly
      Gly Gly Gly Gly Ser" and embodiments of "Gly Gly Gly Gly Gly
      Gly Ser" repeating units
<220> FEATURE:
<221> NAME/KEY: MISC_FEATURE
<222> LOCATION: (1)..(6)
<223> OTHER INFORMATION: This region may encompass 1 to 6 residues
<220> FEATURE:
<221> NAME/KEY: MISC_FEATURE
<222> LOCATION: (8)..(13)
<223> OTHER INFORMATION: This region may encompass 1 to 6 residues
<220> FEATURE:
<221> NAME/KEY: MISC_FEATURE
<222> LOCATION: (15)..(20)
<223> OTHER INFORMATION: This region may encompass 1 to 6 residues
<220> FEATURE:
<221> NAME/KEY: MISC_FEATURE
<222> LOCATION: (22)..(27)
<223> OTHER INFORMATION: This region may encompass 1 to 6 residues
<220> FEATURE:
<221> NAME/KEY: MISC_FEATURE
<222> LOCATION: (29)..(34)
<223> OTHER INFORMATION: This region may encompass 1 to 6 residues
<220> FEATURE:
<221> NAME/KEY: MISC_FEATURE
<222> LOCATION: (36)..(41)
<223> OTHER INFORMATION: This region may encompass 1 to 6 residues
<220> FEATURE:
<221> NAME/KEY: MISC_FEATURE
<222> LOCATION: (43)..(48)
<223> OTHER INFORMATION: This region may encompass 1 to 6 residues
<220> FEATURE:
<221> NAME/KEY: MISC_FEATURE
<222> LOCATION: (50)..(55)
<223> OTHER INFORMATION: This region may encompass 1 to 6 residues
<220> FEATURE:
<221> NAME/KEY: MISC_FEATURE
<222> LOCATION: (57)..(62)
<223> OTHER INFORMATION: This region may encompass 1 to 6 residues
<220> FEATURE:
<221> NAME/KEY: MISC_FEATURE
<222> LOCATION: (64)..(69)
<223> OTHER INFORMATION: This region may encompass 1 to 6 residues
<220> FEATURE:
<221> NAME/KEY: MISC_FEATURE
<222> LOCATION: (71)..(76)
<223> OTHER INFORMATION: This region may encompass 1 to 6 residues
<220> FEATURE:
<221> NAME/KEY: MISC_FEATURE
<222> LOCATION: (78)..(83)
<223> OTHER INFORMATION: This region may encompass 1 to 6 residues
<220> FEATURE:

```
<221> NAME/KEY: MISC_FEATURE
<222> LOCATION: (85)..(90)
<223> OTHER INFORMATION: This region may encompass 1 to 6 residues
<220> FEATURE:
<221> NAME/KEY: MISC_FEATURE
<222> LOCATION: (92)..(97)
<223> OTHER INFORMATION: This region may encompass 1 to 6 residues
<220> FEATURE:
<221> NAME/KEY: MISC_FEATURE
<222> LOCATION: (99)..(104)
<223> OTHER INFORMATION: This region may encompass 1 to 6 residues
<220> FEATURE:
<221> NAME/KEY: MISC_FEATURE
<222> LOCATION: (106)..(111)
<223> OTHER INFORMATION: This region may encompass 1 to 6 residues
<220> FEATURE:
<221> NAME/KEY: MISC_FEATURE
<222> LOCATION: (113)..(118)
<223> OTHER INFORMATION: This region may encompass 1 to 6 residues
<220> FEATURE:
<221> NAME/KEY: MISC_FEATURE
<222> LOCATION: (120)..(125)
<223> OTHER INFORMATION: This region may encompass 1 to 6 residues
<220> FEATURE:
<221> NAME/KEY: MISC_FEATURE
<222> LOCATION: (127)..(132)
<223> OTHER INFORMATION: This region may encompass 1 to 6 residues
<220> FEATURE:
<221> NAME/KEY: MISC_FEATURE
<222> LOCATION: (134)..(139)
<223> OTHER INFORMATION: This region may encompass 1 to 6 residues
<220> FEATURE:
<221> NAME/KEY: MISC_FEATURE
<222> LOCATION: (141)..(146)
<223> OTHER INFORMATION: This region may encompass 1 to 6 residues
<220> FEATURE:
<221> NAME/KEY: MISC_FEATURE
<222> LOCATION: (148)..(153)
<223> OTHER INFORMATION: This region may encompass 1 to 6 residues
<220> FEATURE:
<221> NAME/KEY: MISC_FEATURE
<222> LOCATION: (155)..(160)
<223> OTHER INFORMATION: This region may encompass 1 to 6 residues
<220> FEATURE:
<221> NAME/KEY: MISC_FEATURE
<222> LOCATION: (162)..(167)
<223> OTHER INFORMATION: This region may encompass 1 to 6 residues
<220> FEATURE:
<221> NAME/KEY: MISC_FEATURE
<222> LOCATION: (169)..(174)
<223> OTHER INFORMATION: This region may encompass 1 to 6 residues
<220> FEATURE:
<221> NAME/KEY: MISC_FEATURE
<222> LOCATION: (176)..(181)
<223> OTHER INFORMATION: This region may encompass 1 to 6 residues
<220> FEATURE:
<221> NAME/KEY: MISC_FEATURE
<222> LOCATION: (183)..(188)
<223> OTHER INFORMATION: This region may encompass 1 to 6 residues
<220> FEATURE:
<221> NAME/KEY: MISC_FEATURE
<222> LOCATION: (190)..(195)
<223> OTHER INFORMATION: This region may encompass 1 to 6 residues
<220> FEATURE:
<221> NAME/KEY: MISC_FEATURE
<222> LOCATION: (197)..(202)
<223> OTHER INFORMATION: This region may encompass 1 to 6 residues
<220> FEATURE:
<221> NAME/KEY: MISC_FEATURE
<222> LOCATION: (204)..(209)
<223> OTHER INFORMATION: This region may encompass 1 to 6 residues

<400> SEQUENCE: 139

Gly Gly Gly Gly Gly Gly Ser Gly Gly Gly Gly Gly Ser Gly Gly
1               5                   10                  15

Gly Gly Gly Gly Ser Gly Gly Gly Gly Gly Ser Gly Gly Gly Gly
            20                  25                  30
```

-continued

Gly Gly Ser Gly Gly Gly Gly Gly Ser Gly Gly Gly Gly Gly
        35                  40                  45

Ser Gly Gly Gly Gly Gly Ser Gly Gly Gly Gly Gly Ser Gly
    50                  55                  60

Gly Gly Gly Gly Gly Ser Gly Gly Gly Gly Gly Ser Gly Gly
65                  70                  75                  80

Gly Gly Gly Ser Gly Gly Gly Gly Gly Ser Gly Gly Gly Gly
            85                  90                  95

Gly Ser Gly Gly Gly Gly Gly Ser Gly Gly Gly Gly Gly Ser
        100                 105                 110

Gly Gly Gly Gly Gly Ser Gly Gly Gly Gly Gly Ser Gly Gly
        115                 120                 125

Gly Gly Gly Gly Ser Gly Gly Gly Gly Gly Ser Gly Gly Gly
        130                 135                 140

Gly Gly Ser Gly Gly Gly Gly Gly Ser Gly Gly Gly Gly Gly
145                 150                 155                 160

Ser Gly Gly Gly Gly Gly Ser Gly Gly Gly Gly Gly Ser Gly
            165                 170                 175

Gly Gly Gly Gly Ser Gly Gly Gly Gly Gly Ser Gly Gly Gly
            180                 185                 190

Gly Gly Gly Ser Gly Gly Gly Gly Gly Ser Gly Gly Gly Gly
        195                 200                 205

Gly Ser
    210

<210> SEQ ID NO 140
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(210)
<223> OTHER INFORMATION: This sequence may encompass 1 to 30 "Ser Ser
      Ser Ser Ser Ser Gly" and embodiments of "Ser Ser Ser Ser Ser Ser
      Gly" repeating units
<220> FEATURE:
<221> NAME/KEY: MISC_FEATURE
<222> LOCATION: (1)..(6)
<223> OTHER INFORMATION: This region may encompass 1 to 6 residues
<220> FEATURE:
<221> NAME/KEY: MISC_FEATURE
<222> LOCATION: (8)..(13)
<223> OTHER INFORMATION: This region may encompass 1 to 6 residues
<220> FEATURE:
<221> NAME/KEY: MISC_FEATURE
<222> LOCATION: (15)..(20)
<223> OTHER INFORMATION: This region may encompass 1 to 6 residues
<220> FEATURE:
<221> NAME/KEY: MISC_FEATURE
<222> LOCATION: (22)..(27)
<223> OTHER INFORMATION: This region may encompass 1 to 6 residues
<220> FEATURE:
<221> NAME/KEY: MISC_FEATURE
<222> LOCATION: (29)..(34)
<223> OTHER INFORMATION: This region may encompass 1 to 6 residues
<220> FEATURE:
<221> NAME/KEY: MISC_FEATURE
<222> LOCATION: (36)..(41)
<223> OTHER INFORMATION: This region may encompass 1 to 6 residues
<220> FEATURE:
<221> NAME/KEY: MISC_FEATURE
<222> LOCATION: (43)..(48)
<223> OTHER INFORMATION: This region may encompass 1 to 6 residues -continued

```
<220> FEATURE:
<221> NAME/KEY: MISC_FEATURE
<222> LOCATION: (50)..(55)
<223> OTHER INFORMATION: This region may encompass 1 to 6 residues
<220> FEATURE:
<221> NAME/KEY: MISC_FEATURE
<222> LOCATION: (57)..(62)
<223> OTHER INFORMATION: This region may encompass 1 to 6 residues
<220> FEATURE:
<221> NAME/KEY: MISC_FEATURE
<222> LOCATION: (64)..(69)
<223> OTHER INFORMATION: This region may encompass 1 to 6 residues
<220> FEATURE:
<221> NAME/KEY: MISC_FEATURE
<222> LOCATION: (71)..(76)
<223> OTHER INFORMATION: This region may encompass 1 to 6 residues
<220> FEATURE:
<221> NAME/KEY: MISC_FEATURE
<222> LOCATION: (78)..(83)
<223> OTHER INFORMATION: This region may encompass 1 to 6 residues
<220> FEATURE:
<221> NAME/KEY: MISC_FEATURE
<222> LOCATION: (85)..(90)
<223> OTHER INFORMATION: This region may encompass 1 to 6 residues
<220> FEATURE:
<221> NAME/KEY: MISC_FEATURE
<222> LOCATION: (92)..(97)
<223> OTHER INFORMATION: This region may encompass 1 to 6 residues
<220> FEATURE:
<221> NAME/KEY: MISC_FEATURE
<222> LOCATION: (99)..(104)
<223> OTHER INFORMATION: This region may encompass 1 to 6 residues
<220> FEATURE:
<221> NAME/KEY: MISC_FEATURE
<222> LOCATION: (106)..(111)
<223> OTHER INFORMATION: This region may encompass 1 to 6 residues
<220> FEATURE:
<221> NAME/KEY: MISC_FEATURE
<222> LOCATION: (113)..(118)
<223> OTHER INFORMATION: This region may encompass 1 to 6 residues
<220> FEATURE:
<221> NAME/KEY: MISC_FEATURE
<222> LOCATION: (120)..(125)
<223> OTHER INFORMATION: This region may encompass 1 to 6 residues
<220> FEATURE:
<221> NAME/KEY: MISC_FEATURE
<222> LOCATION: (127)..(132)
<223> OTHER INFORMATION: This region may encompass 1 to 6 residues
<220> FEATURE:
<221> NAME/KEY: MISC_FEATURE
<222> LOCATION: (134)..(139)
<223> OTHER INFORMATION: This region may encompass 1 to 6 residues
<220> FEATURE:
<221> NAME/KEY: MISC_FEATURE
<222> LOCATION: (141)..(146)
<223> OTHER INFORMATION: This region may encompass 1 to 6 residues
<220> FEATURE:
<221> NAME/KEY: MISC_FEATURE
<222> LOCATION: (148)..(153)
<223> OTHER INFORMATION: This region may encompass 1 to 6 residues
<220> FEATURE:
<221> NAME/KEY: MISC_FEATURE
<222> LOCATION: (155)..(160)
<223> OTHER INFORMATION: This region may encompass 1 to 6 residues
<220> FEATURE:
<221> NAME/KEY: MISC_FEATURE
<222> LOCATION: (162)..(167)
<223> OTHER INFORMATION: This region may encompass 1 to 6 residues
<220> FEATURE:
<221> NAME/KEY: MISC_FEATURE
<222> LOCATION: (169)..(174)
<223> OTHER INFORMATION: This region may encompass 1 to 6 residues
<220> FEATURE:
<221> NAME/KEY: MISC_FEATURE
<222> LOCATION: (176)..(181)
<223> OTHER INFORMATION: This region may encompass 1 to 6 residues
<220> FEATURE:
<221> NAME/KEY: MISC_FEATURE
<222> LOCATION: (183)..(188)
```

<223> OTHER INFORMATION: This region may encompass 1 to 6 residues
<220> FEATURE:
<221> NAME/KEY: MISC_FEATURE
<222> LOCATION: (190)..(195)
<223> OTHER INFORMATION: This region may encompass 1 to 6 residues
<220> FEATURE:
<221> NAME/KEY: MISC_FEATURE
<222> LOCATION: (197)..(202)
<223> OTHER INFORMATION: This region may encompass 1 to 6 residues
<220> FEATURE:
<221> NAME/KEY: MISC_FEATURE
<222> LOCATION: (204)..(209)
<223> OTHER INFORMATION: This region may encompass 1 to 6 residues

<400> SEQUENCE: 140

```
Ser Ser Ser Ser Ser Gly Ser Ser Ser Ser Ser Gly Ser Ser
1               5                   10                  15

Ser Ser Ser Ser Gly Ser Ser Ser Ser Ser Gly Ser Ser Ser
            20                  25                  30

Ser Ser Gly Ser Ser Ser Ser Ser Gly Ser Ser Ser Ser Ser
        35                  40                  45

Gly Ser Ser Ser Ser Ser Gly Ser Ser Ser Ser Ser Gly Ser
    50                  55                  60

Ser Ser Ser Ser Gly Ser Ser Ser Ser Ser Gly Ser Ser Ser
65                  70                  75                  80

Ser Ser Ser Gly Ser Ser Ser Ser Ser Gly Ser Ser Ser Ser
            85                  90                  95

Ser Gly Ser Ser Ser Ser Ser Gly Ser Ser Ser Ser Ser Gly
        100                 105                 110

Ser Ser Ser Ser Ser Gly Ser Ser Ser Ser Ser Gly Ser Ser
        115                 120                 125

Ser Ser Ser Ser Gly Ser Ser Ser Ser Ser Gly Ser Ser Ser
    130                 135                 140

Ser Ser Gly Ser Ser Ser Ser Ser Gly Ser Ser Ser Ser Ser
145                 150                 155                 160

Gly Ser Ser Ser Ser Ser Gly Ser Ser Ser Ser Ser Gly Ser
                165                 170                 175

Ser Ser Ser Ser Gly Ser Ser Ser Ser Ser Gly Ser Ser Ser
            180                 185                 190

Ser Ser Ser Gly Ser Ser Ser Ser Ser Gly Ser Ser Ser Ser
        195                 200                 205

Ser Gly
    210
```

<210> SEQ ID NO 141
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1 to 30 "Gly Gly
      Gly Gly Ser" repeating units

<400> SEQUENCE: 141

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30
```

Gly Gly Ser Gly Gly Gly Ser Gly Gly Gly Ser Gly Gly Gly
            35                  40                  45

Gly Ser Gly Gly Gly Gly Ser Gly Gly Gly Ser Gly Gly Gly
    50                  55                  60

Ser Gly Gly Gly Ser Gly Gly Gly Ser Gly Gly Gly Gly Ser
65                  70                  75                  80

Gly Gly Gly Gly Ser Gly Gly Gly Ser Gly Gly Gly Ser Gly
                85                  90                  95

Gly Gly Ser Gly Gly Gly Ser Gly Gly Gly Ser Gly Gly Gly
            100                 105                 110

Gly Gly Ser Gly Gly Gly Ser Gly Gly Gly Ser Gly Gly Gly
            115                 120                 125

Gly Ser Gly Gly Gly Ser Gly Gly Gly Ser Gly Gly Gly Gly
    130                 135                 140

Ser Gly Gly Gly Gly Ser
145                 150

<210> SEQ ID NO 142
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1 to 30 residues

<400> SEQUENCE: 142

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
                20                  25                  30

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Lys Ser Ser Gly Ser Gly Ser Glu Ser Lys Ser
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Ser Thr Ser Gly Ser Gly Lys Ser Ser Glu Gly Lys Gly
1               5                   10

<210> SEQ ID NO 145
<211> LENGTH: 18
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 145

Gly Ser Thr Ser Gly Ser Gly Lys Ser Ser Glu Gly Ser Gly Ser Thr
1               5                   10                  15

Lys Gly

<210> SEQ ID NO 146
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Ser Thr Ser Gly Ser Gly Lys Ser Ser Glu Gly Lys Gly
1               5                   10

<210> SEQ ID NO 147
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Ser Thr Ser Gly Ser Gly Lys Pro Gly Ser Gly Glu Gly Ser Thr
1               5                   10                  15

Lys Gly

<210> SEQ ID NO 148
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Glu Gly Lys Ser Ser Gly Ser Gly Ser Glu Ser Lys Glu Phe
1               5                   10

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ser Arg Ser Ser Gly
1               5

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150
```

```
Ser Gly Ser Ser Cys
1               5

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Any amino acid

<400> SEQUENCE: 151

Arg Xaa Xaa Arg
1

<210> SEQ ID NO 152
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Met Gly Arg Ser Gly Gly Gly Cys Ala Gly Asn Arg Val Gly Ser
1               5                   10                  15

Ser Leu Ser Cys Gly Gly Leu Asn Leu Gln Ala Met
            20                  25

<210> SEQ ID NO 153
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gly Gly Gly Ser
1

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Gly Gly Gly Ser
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Gly Gly Gly Ser Gly Gly Gly
```

```
<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gly Gly Ser Gly Gly Gly Gly
1               5

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gly Gly Gly Gly Ser Gly Gly Gly Gly Ser Gly Gly Gly Gly Ser
1               5                   10                  15

<210> SEQ ID NO 158
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gly Ser Thr Ser Gly Gly Gly Ser Gly Gly Gly Ser Gly Gly Gly Gly
1               5                   10                  15

Ser Ser

<210> SEQ ID NO 159
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Gly Ser Thr Ser Gly Ser Gly Lys Pro Gly Ser Ser Glu Gly Ser Thr
1               5                   10                  15

Lys Gly
```